(12) United States Patent
Shin et al.

(10) Patent No.: US 10,655,187 B2
(45) Date of Patent: May 19, 2020

(54) GENETIC MARKER FOR EARLY BREAST CANCER PROGNOSIS PREDICTION AND DIAGNOSIS, AND USE THEREOF

(71) Applicant: GENCURIX INC., Seoul (KR)

(72) Inventors: Young Kee Shin, Seoul (KR); Young-Deug Kim, Incheon (KR); En Sel Oh, Seoul (KR); Jun Young Choi, Gwangmyeong-si (KR); Sang Rea Cho, Seoul (KR)

(73) Assignee: GENCURIX INC., Seoul (KR)

( * ) Notice: Subject to any disclaimer, the term of this patent is extended or adjusted under 35 U.S.C. 154(b) by 0 days.

(21) Appl. No.: 16/155,220

(22) Filed: Oct. 9, 2018

(65) Prior Publication Data

US 2019/0040473 A1 Feb. 7, 2019

Related U.S. Application Data

(63) Continuation-in-part of application No. 14/886,948, filed on Oct. 19, 2015, now abandoned, which is a continuation of application No. PCT/KR2014/003384, filed on Apr. 18, 2014.

(30) Foreign Application Priority Data

Apr. 18, 2013 (KR) .......................... 10-2013-0043160

(51) Int. Cl.
| | | |
|---|---|---|
| C07H 21/04 | (2006.01) | |
| C12Q 1/68 | (2018.01) | |
| C12Q 1/6886 | (2018.01) | |

(52) U.S. Cl.
CPC ...... *C12Q 1/6886* (2013.01); *C12Q 2600/118* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| | | | | |
|---|---|---|---|---|
| 8,557,525 B1* | 10/2013 | Wang | .................... | C12Q 1/6886 435/194 |
| 2006/0246470 A1* | 11/2006 | Fuqua | .................. | C12Q 1/6886 435/6.16 |
| 2010/0113297 A1* | 5/2010 | Lidereau | .............. | C12Q 1/6886 506/9 |

FOREIGN PATENT DOCUMENTS

| | | |
|---|---|---|
| KR | 10-2012-0079295 | 7/2012 |
| KR | 10-1183522 | 9/2012 |
| WO | 2012/093821 | 7/2012 |

OTHER PUBLICATIONS

Pawitan et al. (Breast Cancer Research, vol. 7, R953-964, 2005) (Year: 2005).*
Lee et al. (J. of Biochemistry and Molecular Biology, vol. 40, No. 2, pp. 226-231, Mar. 2007). (Year: 2007).*
Chang, H.Y., et al., "Gene Expression Signature of Fibroblast Serum Response Predicts Human Cancer Progression: Similarities between Tumors and Wounds", PLoS Biology, Feb. 2004, pp. 0206-0214, vol. 2, Issue 2.
Marc J. Van De Vijver, M.D., Ph.D, et al., "A Gene-Expression Signature As a Predictor of Survival in Breast Cancer", The New England Journal of Medicine, Dec. 19, 2002, pp. 1999-2009, vol. 347, No. 25.
Laura J. Van'T Veer, et al., "Gene Expression Profiling Predicts Clinical Outcome of Breast Cancer", Macmillan Magazines Ltd, Jan. 31, 2002, pp. 530-536, vol. 415.
Yixin Wang, et al., "Gene-Expression Profiles to Predict Distant Metastasis of Lymph-Node-Negative Primary Breast Cancer", The Lancet, Feb. 19, 2005, pp. 671-679, vol. 365.
Marc Buyse, et al., "Validation and Clinical Utility of a 70-Gene Prognostic Signature for Women Wth Node-Negative Breast Cancer", Journal of the National Cancer Institute, Sep. 6, 2006, pp. 1183-1192, vol. 98, No. 17.
Soonmyung Paik, et al., "Development and Clinical Utility of a 21-Gene Recurrence Score Prognostic Assay in Patients with Early Breast Cancer Treated with Tamoxifen", The Oncologist, 2007, pp. 631-635, vol. 12.
Soonmyung Paik, M.D., et al., "A Multigene Assay to Predict Recurrence of Tamoxifen-Treated, Node-Negative Breast Cancer", The New England Journal of Medicine, Dec. 30, 2004, pp. 2817-2826.
Christos Sotiriou, et al., "Gene Expression Profiling in Breast Cancer: Understanding the Molecular Basis of Histologic Grade to Improve Prognosis", Journal of the National Cancer Institute, Feb. 15, 2006, pp. 261-272, vol. 98.

(Continued)

*Primary Examiner* — Jeanine A Goldberg
(74) *Attorney, Agent, or Firm* — H.C. Park & Associates, PLC

(57) ABSTRACT

The present invention relates to a gene for predicting or diagnosing the prognosis of early-stage breast cancer and to a use thereof, and more specifically relates to a genetic marker for predicting or diagnosing the prognosis of breast cancer, including TRBC1 (T cell receptor beta constant 1), BTN3A2 (butyrophilin, subfamily 3, member A2) or HLA-DPA1 (major histocompatibility complex, class II, DP alpha 1) for providing information necessary for predicting or diagnosing the prognosis of a breast cancer patient. The genetic marker of the present invention allows the prediction or diagnosis of the prognosis of a breast cancer patient, and can therefore advantageously be used for the purpose of providing a direction as to the future course of breast cancer treatment, including a decision on whether anticancer therapy is necessary.

3 Claims, 30 Drawing Sheets

(56) References Cited

OTHER PUBLICATIONS

Yudi Pawitan, et al., "Gene Expression Profiling Spares Early Breast Cancer Patients from Adjuvant Therapy: Derived and Validated in Two Population-based Chohorts", Breast Cancer Research, 2005, pp. R953-R964, vol. 7, No. 6.

Lance D. Miller, et al., "An Expression Signature for p53 Status in Human Breast Cancer Predicts Mutation Status, Transcriptional Effects, and Patient Survival", PNAS, Sep. 20, 2005, pp. 13550 13555, vol. 102, No. 38.

Andrea H. Bild, et al. "Oncogenic Pathway Signatures in Human Cancers as a Guide to Targeted Therapies", Nature, Jan. 19, 2006, pp. 353-357, vol. 439.

Andrew E. Teschedorff, et al. "A Consensus Prognostic Gene Expression Classifier for ER Positive Breast Cancer", Genome Biology, Oct. 31, 2006, vol. 7.

Christine Desmedt, et al. "Strong Time Dependence of the 76-Gene Prognostic Signature for Node-Negative Breast Cancer Patients in the TRANSBIG Multicenter Independent Validation Series", American Association for Cancer Research, Sep. 30, 2015, pp. 3207-3214.

Tony E. Godfrey, et al. "Quantitative mRNA Expression Analysis from Formalin-Fixed, Paraffin-Embedded Tissues Using 5' Nuclease Quantitative Reverse Transcription-Polymerase Chain Reaction", Journal of Molecular Diagnostics, May 2000, pp. 84-91, vol. 2, No. 2.

Katja Specht, et al. "Quantitative Gene Expression Analysis in Microdissected Archival Formalin-Fixed and Paraffin-Embedded Tumor Tissue", American Journal of Patbology, Feb. 2001, vol. 158, No. 2.

Christian A. Heid, et al. "Real Time Quantitative PCR", Genome Methods, Sep. 30, 2015, Published by Cold Spring Harbor Laboratory Press, Jun. 3, 1996, pp. 986-994.

Cecile Le Page, et al. "BTN3A2 Expression in Epithelial Ovarian Cancer is Associated with Higher Tumor Infiltrating T Cells and a Better Prognosis" PLoS One, Jun. 2012, pp. 1-12, vol. 7.

Stavropoulos et al. (PNAS, vol. 98, No. 18, pp. 10232-10237, Aug. 2001). (Year: 2001).

LePage et al, (Cancer Epidemiol Biomarkers Prev, vol. 17, No. 4, pp. 913-920, Apr. 2008).

Non-Final Office Action dated May 19, 2017, issued in U.S. Appl. No. 14/886,948.

Non-Final Office Action dated Oct. 12, 2017, issued in U.S. Appl. No. 14/886,948.

Final Office Action dated Apr. 10, 2018, issued in U.S. Appl. No. 14/886,948.

\* cited by examiner

C-indices of BTN3A2, RRM2, and Combination thereof

GENETIC MARKER FOR EARLY BREAST CANCER PROGNOSIS PREDICTION AND DIAGNOSIS, AND USE THEREOF

CROSS-REFERENCE TO RELATED APPLICATIONS

This application is a continuation-in-part of U.S. application Ser. No. 14/886,948, filed on Oct. 19, 2015, which is a continuation of International Application PCT/KR2014/003384, filed on Apr. 18, 2014, which claims priority from and the benefit of Korean Patent Application No. 10-2013-0043160, filed on Apr. 18, 2013, which is hereby incorporated by reference for all purposes as if fully set forth herein.

BACKGROUND

1. Field

The present invention relates to a gene for early-stage breast cancer prognosis prediction and diagnosis and a use thereof, and more specifically, to a genetic marker for early-stage breast cancer prognosis prediction and diagnosis, of TRBC1 (T cell receptor beta constant 1), BTN3A2 (butyrophilin, subfamily 3, member A2), or HLA-DPA1 (major histocompatibility complex, class II, DP alpha 1), for providing information necessary for the prognosis prediction and diagnosis of a breast cancer patient, and to a use thereof.

2. Discussion of the Background

As human genome information has been actively utilized, cancer research has focused on the establishment of mechanisms at the genome level. Particularly, cancer cell characteristics can be identified in a macroscopic view, based on information about expression patterns of tens of thousands of genes or on the increase or decrease in the number of genes using microarrays. This analysis of the genome-level information is very innovative in understanding organic and complicated life phenomena, and will be more commonly used. Specifically, in cases of complex diseases such as cancer, the analysis of a small number of particular genes is likely to obtain narrow results, and it is important to capture large behavior patterns with respect to the occurrence and development of cancer, and thus genome information analysis is absolutely necessary. As described above, most of the genome information that is a basis for cancer research is created using genome chips such as a microarray, and technologies that can obtain a lot of information at once are evolving day by day. In spite of the disadvantages of high costs, research using microarrays is being actively developed, so the amount of related information is explosively increasing. Since the mid-2000s, such genome information has started to be collected and made into a database, and secondary and tertiary analysis using the information thus obtained is becoming a focal point for the research of life phenomena.

Tens of thousands of probes indicating approximately 20,000 to 30,000 genes are embedded in general expression gene chips, and more than one million probes are often embedded in microarrays that measure precise information, such as SNP. Methods using these microarrays are very efficient since they are relatively simple and standardized and a large amount of information can be obtained at once in a short time, but analyzing the obtained results is a key point as well as being a difficult bottleneck. Comprehensive analysis for tens of thousands of genes incomparable to existing analysis for a small number of genes must be supported by a broad knowledge of the genome as well as statistical analysis techniques, so useful information can be eventually obtained. Besides, high-performance computing equipment capable of storing and analyzing large amounts of information are needed, and the related computational techniques are also needed. Meanwhile, it is difficult to perform for the researchers who are familiar with conventional biological research ranges and experimental methods, and thus, the methods cannot be favorably utilized even though genome information increases at an extraordinary rate in Korea. Considering the domestic situation with respect to capital and technology research that are insufficient compared with North America and Europe, actively utilizing known genome information should be at the head of bioinformatics. Genome analysis has been actively introduced in the research of, particularly, cancers, and a considerable amount of related-information has been accumulated.

Breast cancer is frequently detected in the early stage since self-diagnosis is possible and the importance of self-diagnosis is highly publicized. It was difficult to determine whether early-stage breast cancer patients should be allowed to receive anticancer treatments after surgery. It is possible to roughly predict a prognosis through pathological observation, but the observation result is difficult to normalize and quantify, and the reliability on prognosis prediction is low, and thus, most of early-stage breast cancer patients are recommended to receive anticancer treatments in actual clinical practice. Due to the nature of anticancer treatments, they are very expensive, while the patients suffer from very serious pains. It is estimated that more than half of early-stage breast cancer patients do not need to receive anticancer treatments. Therefore, if unnecessary anticancer treatments are reduced by analyzing the characteristics of the early-stage breast cancer to predict prognosis of patient, it may be a great help to increase the quality of life of the patients. As the information about tens of thousands of breast cancer gene expression patterns is obtained at once using microarrays, research for classifying breast cancer types at the molecular level and establishing mechanisms of cancer occurrence and development are being actively conducted. It is important to predict the prognosis of the early-stage breast cancer patients in clinical practice. The work of identifying genes for prognosis prediction using microarrays has already started in the early 2000s. Although research that uses microarrays is expensive, a significant number of breast cancer tissue expression profiles have been produced and available to researchers. Starting from the identifying of 70 prognosis prediction genes by analyzing the early-stage breast cancer tissues and survival data of 78 patients followed up for 10 years in 2002, a dozen genes for prognosis prediction genes were then published, and among these genes, several genes have already been commercialized and used in clinical practice (Chang, H. Y., et al., Gene expression signature of fibroblast serum response predicts human cancer progression: similarities between tumors and wounds. PLoSBiol 2(2): p. E7(2004); van de Vijver, M. J., et al., A gene-expression signature as a predictor of survival in breast cancer. N Engl J Med 347(25):1999-2009(2002); van 't Veer, L. J., et al., Gene expression profiling predicts clinical outcome of breast cancer. Nature 415(6871): 530-536(2002); Wang, Y., et al., Gene-expression profiles to predict distant metastasis of lymph-node-negative primary breast cancer. Lancet 365(9460): 671-679(2005); Buyse, M., et al., Validation and clinical utility of a 70-gene prognostic signature for women with node-negative breast cancer. J Natl Cancer Inst, 98(17):1183-92(2006); Paik, S., Development and clinical utility of a 21-gene recurrence score prognostic assay in patients with early-stage breast cancer treated with tamoxifen. Oncologist 12(6):631-635(2007); Paik, S., et al., A multigene assay to predict recurrence of tamoxifen-treated, node-negative breast cancer. N Engl J Med 351(27):2817-2826(2004); Sotiriou, C., et al., Gene expression profiling in breast cancer: understanding the molecular basis of histologic grade to improve prognosis. J Natl Cancer Inst 98(4):262-72(2006); Pawitan, Y., et al., Gene expression profiling spares early-stage breast cancer patients from adjuvant therapy: derived and validated in two population-based cohorts. Breast Cancer Res 7(6):R953-964 (2005); Miller, L. D., et al., An expression signature for p53 status in human breast cancer predicts mutation status, transcriptional effects, and patient survival. Proc Natl Acad Sci USA, 102(38):13550-13555(2005); Bild, A. H., et al., Oncogenic pathway signatures in human cancers as a guide to targeted therapies. Nature 439(7074):353-357(2006); Teschendorff, A. E., et al., A consensus prognostic gene expression classifier for ER positive breast cancer. Genome Biol 7(10):R101(2006); Desmedt, C., et al., Strong time dependence of the 76-gene prognostic signature for node-negative breast cancer patients in the TRANSBIG multicenter independent validation series. Clin Cancer Res 13(11): 3207-3214(2007)). Representative examples thereof are MammaPrint (Agendia) and Oncotype DX (Genomic Health), which are being currently used in clinical practice. However, they have been used as one of the references for prognosis (van de Vijver, M. J., et al., A gene-expression signature as a predictor of survival in breast cancer. N Engl J Med 347(25):1999-2009(2002); Paik, S., et al., A multigene assay to predict recurrence of tamoxifen-treated, node-negative breast cancer. N Engl J Med 351(27):2817-2826(2004)).

Throughout the entire specification, many research papers and patent documents are referenced and their citations are disclosed. The disclosure of cited papers and patent documents are entirely incorporated by reference into the present specification, and the level of the technical field within which the present invention falls, and details of the present invention are explained more clearly.

SUMMARY

The present inventors have endeavored to develop a gene diagnosis system capable of predicting the prognosis of the early-stage breast cancer patient and determining whether anticancer treatment is performed on the early-stage breast cancer patient by using an FFPE sample of the tissue containing cancer cells of the patient. As a result, the present inventors have identified genes associated with prognosis prediction by collecting and analyzing microarray data and clinical information, which are obtained from the early-stage breast cancer tissue; selected genes and sets thereof, which are suitable for the application to the FFPE sample, among the identified genes; and validated utility of the selected genes and gene sets, thereby completing the present invention.

Therefore, an aspect of the present invention is to provide a genetic marker for predicting or diagnosing the prognosis of a breast cancer patient, and a use thereof.

Another aspect of the present invention is to provide a novel method for predicting or diagnosing the prognosis of a breast cancer patient.

Still another aspect of the present invention is to provide a kit for predicting or diagnosing the prognosis of a breast cancer patient.

Still another aspect of the present invention is to provide a method for calculating a breast cancer prognosis predictive value in order to provide information necessary for predicting or diagnosing the prognosis of a breast cancer patient, the method comprising isolating mRNA from a patient sample, measuring the gene expression level, normalizing the gene expression level, and calculating a predictive value.

In accordance with an aspect of the present invention, there is provided a genetic marker for predicting or diagnosing the prognosis of a breast cancer patient and a use thereof.

In accordance with another aspect of the present invention, there is provided a novel method for predicting or diagnosing the prognosis of a breast cancer patient.

In accordance with still another aspect of the present invention, there is provided a kit for predicting or diagnosing the prognosis of a breast cancer patient.

In accordance with still another aspect of the present invention, there is provided a method for calculating a predictive value of the prognosis of breast cancer to provide information necessary for predicting or diagnosing the prognosis of a breast cancer patient, the method comprising isolating mRNA from a patient sample, measuring a gene expression level, normalizing the gene expression level, and calculating a predictive value.

In accordance with still another aspect of the present invention, there is provided a primer pair for at least one gene selected from the group consisting of T cell receptor beta constant 1 (TRBC1), butyrophilin, subfamily 3, member A2 (BTN3A2), and major histocompatibility complex, class II, DP alpha 1 (HLA-DPA1), wherein the primer pair is capable of amplifying a target gene through PCR amplification.

In accordance with still another aspect of the present invention, there is provided a use of a primer pair for preparing an agent for predicting the prognosis of breast cancer, wherein the primer pair is for at least one gene selected from the group consisting of TRBC1, BTN3A2, and HLA-DPA1, and wherein the primer pair is capable of amplifying a target gene through PCR amplification.

In accordance with further aspect of the present invention, there is provided a method for diagnosing a prognosis of breast cancer and treating breast cancer in a breast cancer patient, the method comprising the steps of:

collecting a sample from the breast cancer patient;

isolating mRNA from the sample of the breast cancer patient;

measuring a first mRNA expression level for the mRNA of at least one i-gene selected from the group consisting of BTN3A2 (butyrophilin, subfamily 3, member A2), T cell receptor beta constant 1 (TRBC1), and major histocompatibility complex, class II, DP alpha 1 (HLA-DPA1), and a second mRNA expression level for the mRNA of at least one p-gene selected from the group consisting of the p-genes of the following Table 1;

normalizing the first and second mRNA expression levels to determine a normalized value;

diagnosing the prognosis of breast cancer patient by using the determined normalized value of the first and second mRNA expression levels, wherein an overexpression of the i-gene indicates a good prognosis of breast cancer, while an overexpression of the p-gene indicates a poor prognosis of breast cancer; and treating the diagnosed breast cancer patient by administering at least one of an anti-cancer agent, a surgery and a radiation therapy.

TABLE 1

List of p-genes

| No. | Gene ID | Gene Name |
|---|---|---|
| 1 | APITD1 | apoptosis-inducing, TAF9-like domain 1 |
| 2 | BID | BH3 interacting domain death agonist |
| 3 | BUB1B | BUB1 mitotic checkpoint serine/threonine kinase B |
| 4 | BUB1 | BUB1 mitotic checkpoint serine/threonine kinase |
| 5 | CKS1B | CDC28 protein kinase regulatory subunit 1B |
| 6 | CKS2 | CDC28 protein kinase regulatory subunit 2 |
| 7 | DLGAP5 | discs, large (Drosophila) homolog-associated protein 5 |
| 8 | POLA1 | polymerase (DNA directed), alpha 1, catalytic subunit |
| 9 | POLA2 | polymerase (DNA directed), alpha 2, accessory subunit |
| 10 | DSCC1 | DNA replication and sister chromatid cohesion 1 |
| 11 | DNA2 | DNA replication helicase/nuclease 2 |
| 12 | E2F8 | E2F transcription factor 8 |
| 13 | ERCC6L | excision repair cross-complementation group 6-like |
| 14 | FBXO5 | F-box protein 5 |
| 15 | FANCI | Fanconi anemia, complementation group I |
| 16 | GADD45GIP1 | growth arrest and DNA-damage-inducible, gamma interacting protein 1 |
| 17 | GINS1 | GINS complex subunit 1 (Psf1 homolog) |
| 18 | GINS2 | GINS complex subunit 2 (Psf2 homolog) |
| 19 | MAD2L1 | MAD2 mitotic arrest deficient-like 1 (yeast) |
| 20 | MAD2L1BP | MAD2L1 binding protein |
| 21 | MIS18A | MIS18 kinetochore protein A |
| 22 | MYBL2 | v-myb avian myeloblastosis viral oncogene homolog-like 2 |
| 23 | NAA50 | N(alpha)-acetyltransferase 50, NatE catalytic subunit |
| 24 | NEK2 | NIMA-related kinase 2 |
| 25 | NSL1 | NSL1, MIS12 kinetochore complex component |
| 26 | PBK | PDZ binding kinase |
| 27 | RAB11A | RAB11A, member RAS oncogene family |
| 28 | RAD51C | RAD51 paralog C |
| 29 | RAD54B | RAD54 homolog B (S. cerevisiae) |
| 30 | RANBP1 | RAN binding protein 1 |
| 31 | RALA | v-ral simian leukemia viral oncogene homolog A (ras related) |
| 32 | RACGAP1 | Rac GTPase activating protein 1 |
| 33 | SSNA1 | Sjogren syndrome nuclear autoantigen 1 |
| 34 | STAMBP | STAM binding protein |
| 35 | SSSCA1 | Sjogren syndrome/scleroderma autoantigen 1 |
| 36 | TAF2 | TAF2 RNA polymerase II, TATA box binding protein (TBP)-associated factor, 150 kDa |
| 37 | TIPIN | TIMELESS interacting protein |
| 38 | TIPRL | TOR signaling pathway regulator |
| 39 | TRIAP1 | TP53 regulated inhibitor of apoptosis 1 |
| 40 | TTK | TTK protein kinase |
| 41 | ZWINT | ZW10 interacting kinetochore protein |
| 42 | ASPM | asp (abnormal spindle) homolog, microcephaly associated (Drosophila) |
| 43 | AURKA | aurora kinase A |
| 44 | AURKB | aurora kinase B |
| 45 | BRD7 | bromodomain containing 7 |
| 46 | CSNK2A1 | casein kinase 2, alpha 1 polypeptide |
| 47 | CDC20 | cell division cycle 20 |
| 48 | CDC25C | cell division cycle 25C |
| 49 | CENPA | centromere protein A |
| 50 | CENPE | centromere protein E, 312 kDa |
| 51 | CENPF | centromere protein F, 350/400 kDa |
| 52 | CENPI | centromere protein I |
| 53 | CENPM | centromere protein M |
| 54 | CENPN | centromere protein N |
| 55 | CENPU | centromere protein U |
| 56 | CEP55 | centrosomal protein 55 kDa |
| 57 | CHEK1 | checkpoint kinase 1 |
| 58 | CDT1 | chromatin licensing and DNA replication factor 1 |
| 59 | C11orf80 | chromosome 11 open reading frame 80 |
| 60 | CCNA2 | cyclin A2 |

TABLE 1-continued

List of p-genes

| No. | Gene ID | Gene Name |
|---|---|---|
| 61 | CCNB1 | cyclin B1 |
| 62 | CCNB2 | cyclin B2 |
| 63 | CCNE2 | cyclin E2 |
| 64 | CDK1 | cyclin-dependent kinase 1 |
| 65 | CDKN3 | cyclin-dependent kinase inhibitor 3 |
| 66 | CKAP5 | cytoskeleton associated protein 5 |
| 67 | DTL | denticleless E3 ubiquitin protein ligase homolog (Drosophila) |
| 68 | DCTN2 | dynactin 2 (p50) |
| 69 | DYNLT1 | dynein, light chain, Tctex-type 1 |
| 70 | ECD | ecdysoneless homolog (Drosophila) |
| 71 | ECT2 | epithelial cell transforming 2 |
| 72 | EIF4G1 | eukaryotic translation initiation factor 4 gamma, 1 |
| 73 | EIF4EBP1 | eukaryotic translation initiation factor 4E binding protein 1 |
| 74 | EZR | ezrin |
| 75 | FEN1 | flap structure-specific endonuclease 1 |
| 76 | FOXM1 | forkhead box M1 |
| 77 | GSK3B | glycogen synthase kinase 3 beta |
| 78 | HMGN5 | high mobility group nucleosome binding domain 5 |
| 79 | INTS7 | integrator complex subunit 7 |
| 80 | KIF11 | kinesin family member 11 |
| 81 | KIF14 | kinesin family member 14 |
| 82 | KIF20A | kinesin family member 20A |
| 83 | KIF23 | kinesin family member 23 |
| 84 | KIF2C | kinesin family member 2C |
| 85 | KIF4A | kinesin family member 4A |
| 86 | KIFC1 | kinesin family member C1 |
| 87 | MIF | macrophage migration inhibitory factor (glycosylation-inhibiting factor) |
| 88 | MELK | maternal embryonic leucine zipper kinase |
| 89 | MED1 | mediator complex subunit 1 |
| 90 | MCM10 | minichromosome maintenance complex component 10 |
| 91 | MCM2 | minichromosome maintenance complex component 2 |
| 92 | MCM6 | minichromosome maintenance complex component 6 |
| 93 | MAP2K1 | mitogen-activated protein kinase kinase 1 |
| 94 | MSH6 | mutS homolog 6 |
| 95 | MLF1 | myeloid leukemia factor 1 |
| 96 | NCAPG | non-SMC condensin I complex, subunit G |
| 97 | NUSAP1 | nucleolar and spindle associated protein 1 |
| 98 | NUP155 | nucleoporin 155 kDa |
| 99 | NUP93 | nucleoporin 93 kDa |
| 100 | ORC4 | origin recognition complex, subunit 4 |
| 101 | ORC5 | origin recognition complex, subunit 5 |
| 102 | PIN1 | peptidylprolyl cis/trans isomerase, NIMA-interacting 1 |
| 103 | PIK3R4 | phosphoinositide-3-kinase, regulatory subunit 4 |
| 104 | PTTG1 | pituitary tumor-transforming 1 |
| 105 | PTTG3P | pituitary tumor-transforming 3, pseudogene |
| 106 | PLK1 | polo-like kinase 1 |
| 107 | PLK4 | polo-like kinase 4 |
| 108 | PRIM1 | primase, DNA, polypeptide 1 (49 kDa) |
| 109 | PA2G4 | proliferation-associated 2G4, 38 kDa |
| 110 | LEPREL4 | leprecan-like 4 |
| 111 | PSMC3 | proteasome (prosome, macropain) 26S subunit, ATPase, 3 |
| 112 | PSMC6 | proteasome (prosome, macropain) 26S subunit, ATPase, 6 |
| 113 | PSMD10 | proteasome (prosome, macropain) 26S subunit, non-ATPase, 10 |
| 114 | PSMD12 | proteasome (prosome, macropain) 26S subunit, non-ATPase, 12 |
| 115 | PSMD14 | proteasome (prosome, macropain) 26S subunit, non-ATPase, 14 |
| 116 | PSMD2 | proteasome (prosome, macropain) 26S subunit, non-ATPase, 2 |
| 117 | PSMD3 | proteasome (prosome, macropain) 26S subunit, non-ATPase, 3 |
| 118 | PSMD4 | proteasome (prosome, macropain) 26S subunit, non-ATPase, 4 |
| 119 | PSMD6 | proteasome (prosome, macropain) 26S subunit, non-ATPase, 6 |

TABLE 1-continued

List of p-genes

| No. | Gene ID | Gene Name |
|---|---|---|
| 120 | PSMD7 | proteasome (prosome, macropain) 26S subunit, non-ATPase, 7 |
| 121 | PSMA1 | proteasome (prosome, macropain) subunit, alpha type, 1 |
| 122 | PSMA2 | proteasome (prosome, macropain) subunit, alpha type, 2 |
| 123 | PSMA3 | proteasome (prosome, macropain) subunit, alpha type, 3 |
| 124 | PSMA4 | proteasome (prosome, macropain) subunit, alpha type, 4 |
| 125 | PSMA6 | proteasome (prosome, macropain) subunit, alpha type, 6 |
| 126 | PSMA7 | proteasome (prosome, macropain) subunit, alpha type, 7 |
| 127 | PSMB3 | proteasome (prosome, macropain) subunit, beta type, 3 |
| 128 | PSMB5 | proteasome (prosome, macropain) subunit, beta type, 5 |
| 129 | PSMB7 | proteasome (prosome, macropain) subunit, beta type, 7 |
| 130 | PRMT1 | protein arginine methyltransferase 1 |
| 131 | PPP2R3B | protein phosphatase 2, regulatory subunit B", beta |
| 132 | PPP3CA | protein phosphatase 3, catalytic subunit, alpha isozyme |
| 133 | PRC1 | protein regulator of cytokinesis 1 |
| 134 | RRM2 | ribonucleotide reductase M2 |
| 135 | RPS6KB1 | ribosomal protein S6 kinase, 70 kDa, polypeptide 1 |
| 136 | SPAG5 | sperm associated antigen 5 |
| 137 | SKA1 | spindle and kinetochore associated complex subunit 1 |
| 138 | STMN1 | stathmin 1 |
| 139 | SLBP | stem-loop binding protein |
| 140 | SMC2 | structural maintenance of chromosomes 2 |
| 141 | SMC4 | structural maintenance of chromosomes 4 |
| 142 | SMC5 | structural maintenance of chromosomes 5 |
| 143 | TERF1 | telomeric repeat binding factor (NIMA-interacting) 1 |
| 144 | TXNL4A | thioredoxin-like 4A |
| 145 | TRIP13 | thyroid hormone receptor interactor 13 |
| 146 | TOP2A | topoisomerase (DNA) II alpha 170 kDa |
| 147 | TFDP2 | transcription factor Dp-2 (E2F dimerization partner 2) |
| 148 | TACC3 | transforming, acidic coiled-coil containing protein 3 |
| 149 | TUBB3 | tubulin, beta 3 class III |
| 150 | TUBB4B | tubulin, beta 4B class IVb |
| 151 | TUBB | tubulin, beta class I |
| 152 | TSG101 | tumor susceptibility 101 |
| 153 | UBE2C | ubiquitin-conjugating enzyme E2C |
| 154 | UBE2L3 | ubiquitin-conjugating enzyme E2L 3 |
| 155 | UBE2S | ubiquitin-conjugating enzyme E2S |
| 156 | USP9X | ubiquitin specific peptidase 9, X-linked |
| 157 | VRK1 | vaccinia related kinase 1 |
| 158 | ZFHX3 | zinc finger homeobox 3 |
| 159 | ZWILCH | zwilch kinetochore protein |
| 160 | MMP11 | Matrix Metallopeptidase 11 |

In another aspect of the present invention, there is provided the above method wherein the i-gene is BTN3A2 (butyrophilin, subfamily 3, member A2).

In still another aspect of the present invention, there is provided the above method wherein the p-gene is selected from the group consisting of AURKA (Aurora Kinase A), CCNB2 (Cyclin B2), FOXM1 (Forkhead box protein M1), MMP11 (Matrix Metallopeptidase 11), PTTG1 (Pituitary Tumor-Transforming 1), RACGAP1 (Rac GTPase Activating Protein 1), RRM2 (Ribonucleotide Reductase M2), TOP2A (Topoisomerase II Alpha) and UBE2C (Ubiquitin-Conjugating Enzyme E2C).

In another aspect of the present invention, there is provided the above method wherein the step of measuring the expression levels is conducted through PCR amplification of a target gene.

In still another aspect of the present invention, there is provided the above method wherein the sample is a formalin-fixed paraffin-embedded (FFPE) sample of tissue containing cancer cells of the breast cancer patient.

In still further aspect of the present invention, there is provided the above method wherein the step of normalizing is conducted by calculating a ratio of a mean expression level of the gene with a mean expression level of at least one standard gene selected from the group consisting of CTBP1 (C-terminal-binding protein 1), TBP (TATA-binding protein), HMBS (hydroxymethylbilane synthase), CUL1 (cullin 1), and UBQLN1 (ubiquilin-1).

In accordance with further aspect of the present invention, there is provided a method for determining a predictive value of the prognosis of breast cancer to provide information necessary for predicting or diagnosing the prognosis of a breast cancer patient, the method comprising the steps of:

isolating mRNA from a sample of the breast cancer patient;

measuring a first mRNA expression level for the mRNA of at least one i-gene selected from the group consisting of BTN3A2 (butyrophilin, subfamily 3, member A2), T cell receptor beta constant 1 (TRBC1), and major histocompatibility complex, class II, DP alpha 1 (HLA-DPA1), and a second mRNA expression level for the mRNA of at least one p-gene selected from the group consisting of the p-genes of the Table 1;

normalizing the first and second mRNA expression levels to obtain normalized values;

inserting the normalized values into a pre-determined calculation formula to obtain a numerical predictive value; and determining the prognosis of breast cancer as being good or poor depending on the numerical predictive value.

In another aspect of the present invention, there is provided the above method wherein the i-gene is BTN3A2 (butyrophilin, subfamily 3, member A2).

In still another aspect of the present invention, there is provided the above method wherein the p-gene is selected from the group consisting of AURKA (Aurora Kinase A), CCNB2 (Cyclin B2), FOXM1 (Forkhead box protein M1), MMP11 (Matrix Metallopeptidase 11), PTTG1 (Pituitary Tumor-Transforming 1), RACGAP1 (Rac GTPase Activating Protein 1), RRM2 (Ribonucleotide Reductase M2), TOP2A (Topoisomerase II Alpha) and UBE2C (Ubiquitin-Conjugating Enzyme E2C).

In further another aspect of the present invention, there is provided the above method wherein an overexpression of the i-gene indicates a good prognosis of breast cancer, while an overexpression of the p-gene indicates a poor prognosis of breast cancer.

In still further aspect of the present invention, there is provided the above method wherein the step of measuring the expression levels is conducted through PCR amplification of a target gene.

In further aspect of the present invention, there is provided the above method wherein the sample is a formalin-fixed paraffin-embedded (FFPE) sample of a tissue containing cancer cells of a patient.

In another aspect of the present invention, there is provided the above method wherein the step of normalizing is conducted by calculating a ratio of a mean expression level of the gene with a mean expression level of at least one standard gene selected from the group consisting of CTBP1 (C-terminal-binding protein 1), TBP (TATA-binding protein), HMBS (hydroxymethylbilane synthase), CUL1 (cullin 1), and UBQLN1 (ubiquilin-1).

In still another aspect of the present invention, there is provided the above method wherein the breast cancer patient determined as poor prognosis is treated by administering at least one of an anti-cancer agent, a surgery and a radiation therapy.

In accordance with further aspect of the present invention, there is provided a method for predicting or diagnosing the prognosis of breast cancer in a breast cancer patient, the method comprising a step of using a plurality of primer pairs, wherein the plurality of the primer pairs comprises a primer pair for at least one i-gene selected from the group consisting of BTN3A2 (butyrophilin, subfamily 3, member A2), T cell receptor beta constant 1 (TRBC1), and major histocompatibility complex, class II, DP alpha 1 (HLA-DPA1), and a primer pair for at least one p-gene selected from the group consisting of the p-genes of the Table 1, wherein the primer pairs are selected to amplify the at least one i-gene and the at least one p-gene through PCR amplification.

In another aspect of the present invention, there is provided the above method wherein the i-gene is BTN3A2 (butyrophilin, subfamily 3, member A2).

In still another aspect of the present invention, there is provided the above method wherein the p-gene is selected from the group consisting of AURKA (Aurora Kinase A), CCNB2 (Cyclin B2), FOXM1 (Forkhead box protein M1), MMP11 (Matrix Metallopeptidase 11), PTTG1 (Pituitary Tumor-Transforming 1), RACGAP1 (Rac GTPase Activating Protein 1), RRM2 (Ribonucleotide Reductase M2), TOP2A (Topoisomerase II Alpha) and UBE2C (Ubiquitin-Conjugating Enzyme E2C).

In still further aspect of the present invention, there is provided the above method wherein the breast cancer patient diagnosed as poor prognosis is treated by administering at least one of an anti-cancer agent, a surgery and a radiation therapy.

Unless defined otherwise, all technical and scientific terms used herein have the same meanings as are commonly understood by a person skilled in the art. The following reference documents provide one of skills that have general definitions of many terms used herein: Singleton et al., DICTIONARY OF MICROBIOLOGY AND MOLECULAR BIOLOTY (2ded. 1994); THE CAMBRIDGE DICTIONARY OF SCIENCE AND TECHNOLOGY (Walker ed., 1988); and Hale & Marham, THE HARPER COLLINS DICTIONARY OF BIOLOGY

BRIEF DESCRIPTION OF THE DRAWINGS

FIG. 2A shows that prognostic indexes of all patients using the prognostic model (frozen samples) were divided into four and classified into four prognostic groups, and the separation of the observed survival probability of each prognostic group was verified. The observed survival probability was compared with the predicted survival probability. FIG. 2B shows that observed survival probabilities were compared with predicted survival probabilities using the prognostic models in overall patients. FIG. 2C shows that overall patients were divided into four groups with respect to the most influential p.mean, and then the concurrence between the observed survival probability and the predicted survival probability by the prognostic model (frozen samples) in each group was verified. FIG. 2D shows that the concurrence between the observed survival probability and the predicted survival probability with respect to 5-year survival probability was verified.

FIG. 3A shows validation results on the determination, and FIG. 3B shows validation results on the calibration of the overall time period of observation. FIG. 3C shows validation results on the calibration of 5-year survival probability.

FIG. 4A shows validation results on determination, and FIG. 4B shows validation results on calibration of the overall time period of observation. FIG. 4C shows validation results on the calibration of 5-year survival probability.

DETAILED DESCRIPTION OF THE ILLUSTRATED EMBODIMENTS

Figure 1A:
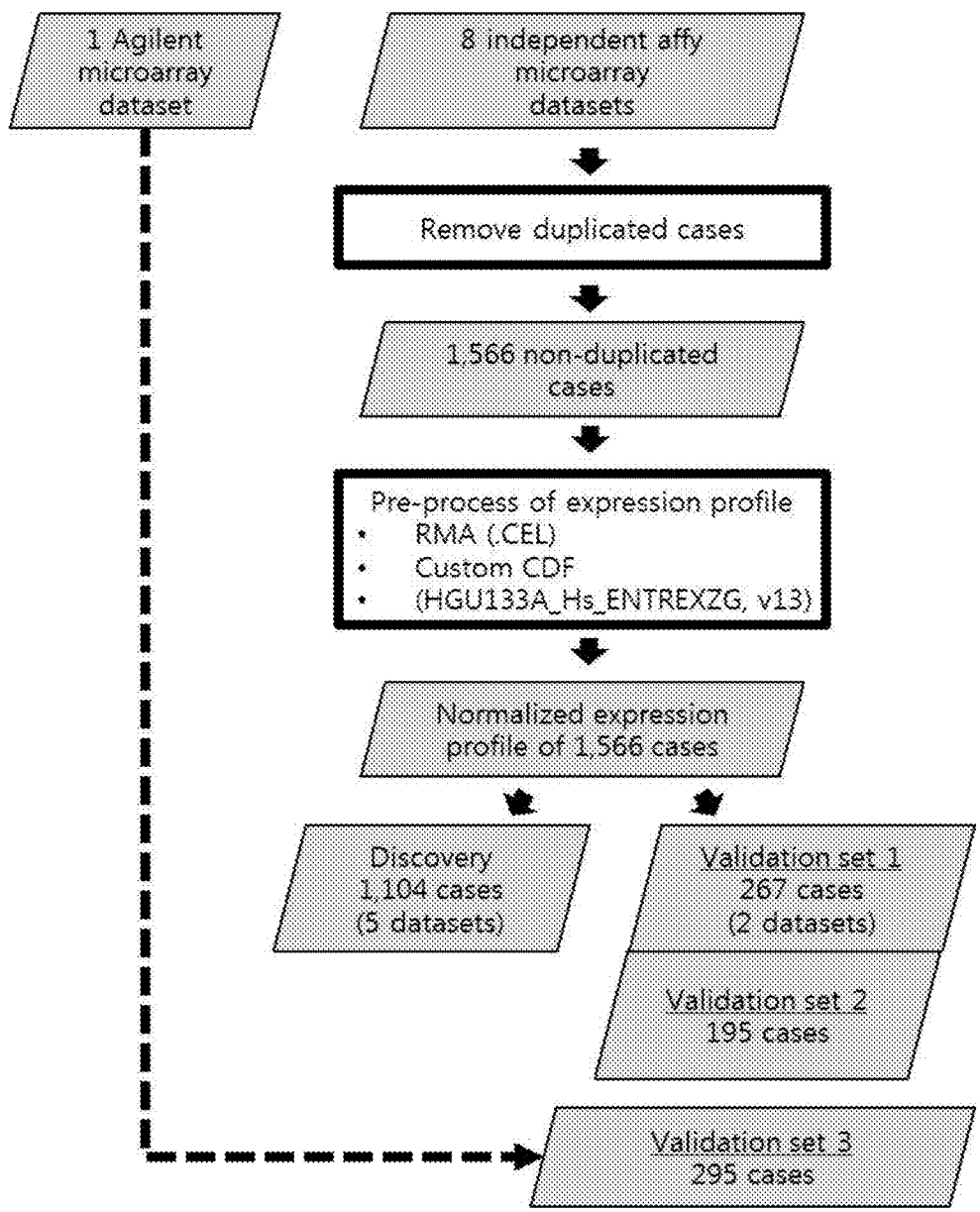
FIG. 1A schematically shows a normalization procedure by curation and pre-processing of microarray data of breast cancer tissue.
Figure 1B:
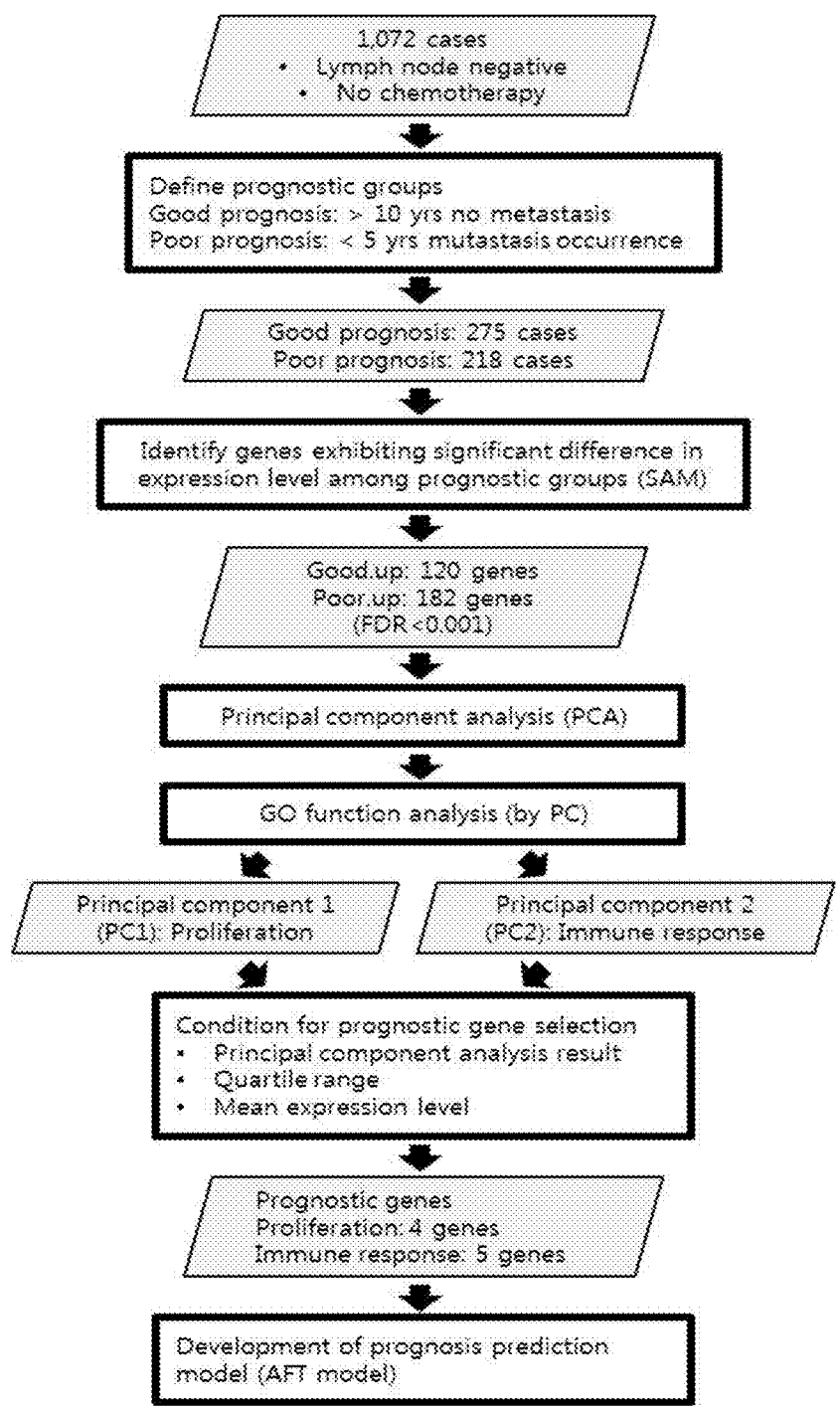
FIG. 1B schematically shows an identification procedure of prognostic genes in the discovery dataset.
Figure 2A:
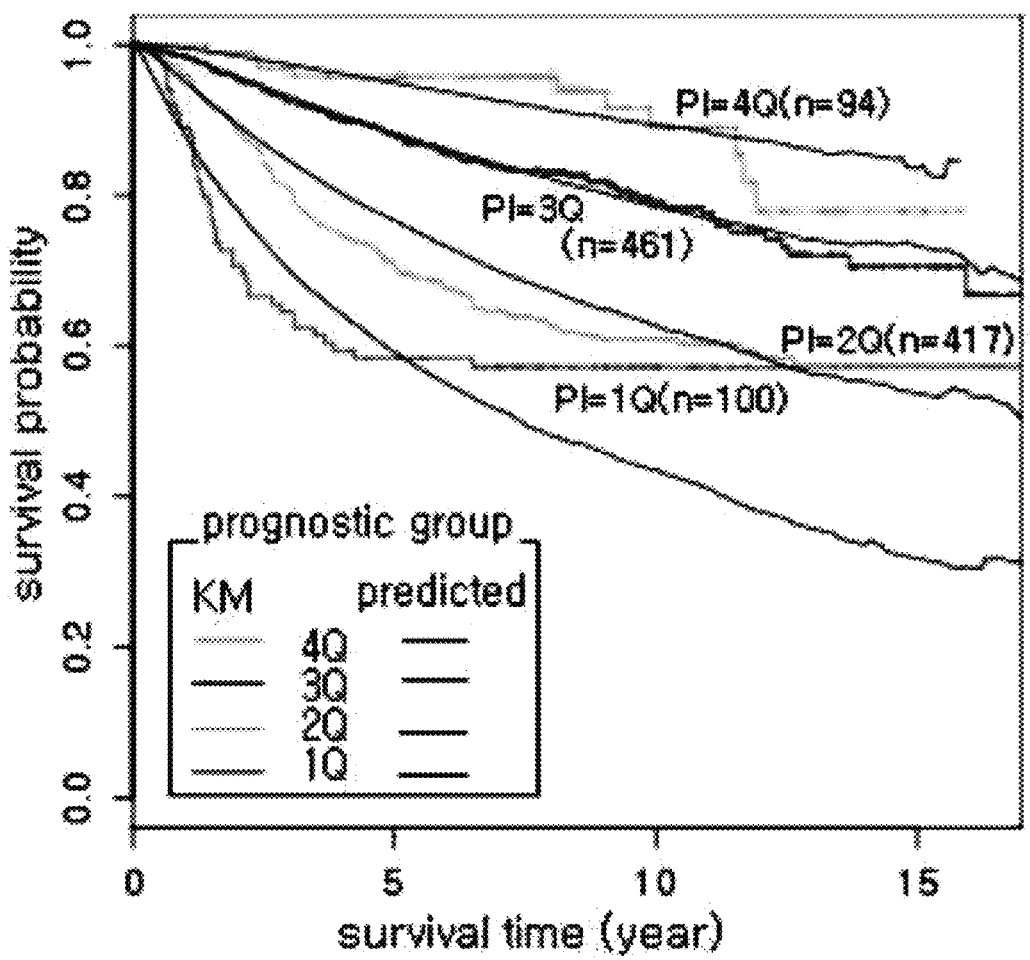
FIGS. 2A-2D show validation results of the prognostic model (frozen samples) in the discovery dataset.
Figure 2B:
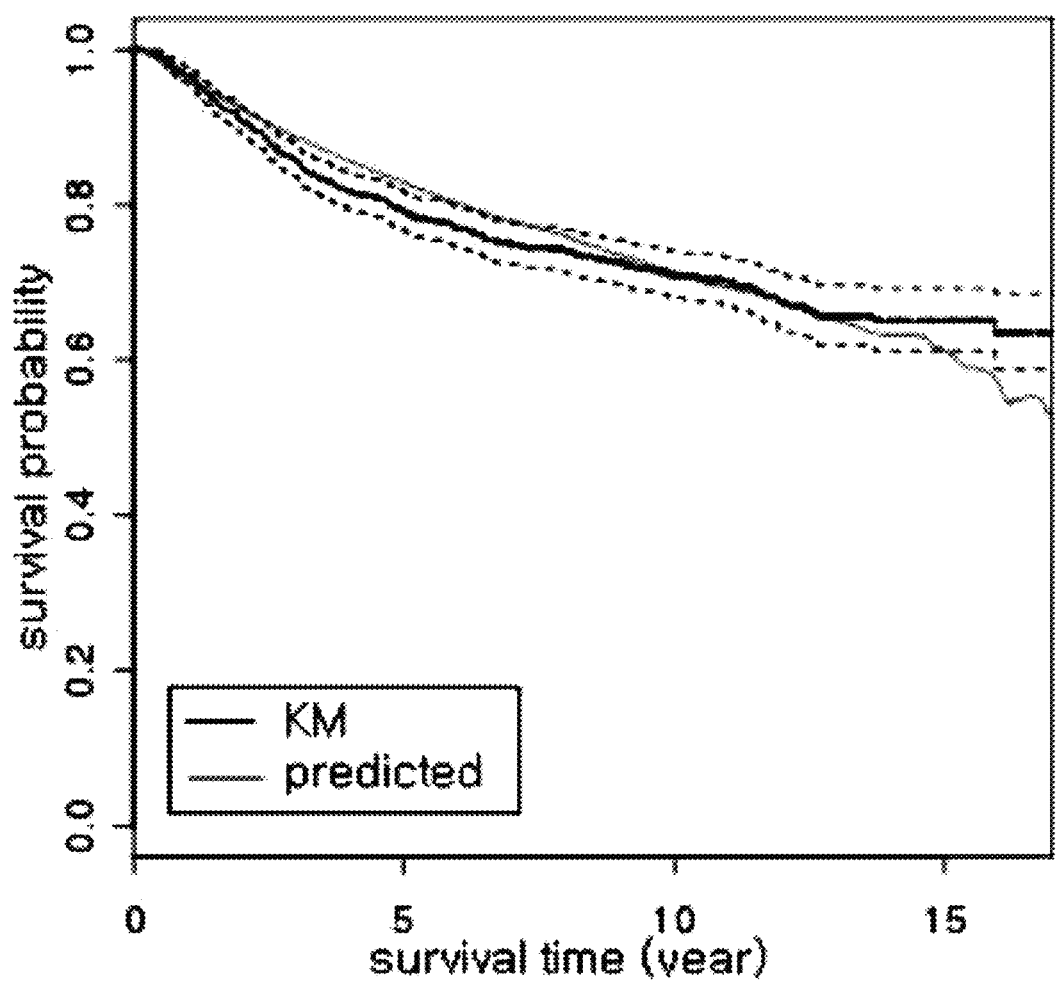
Figure 2C:
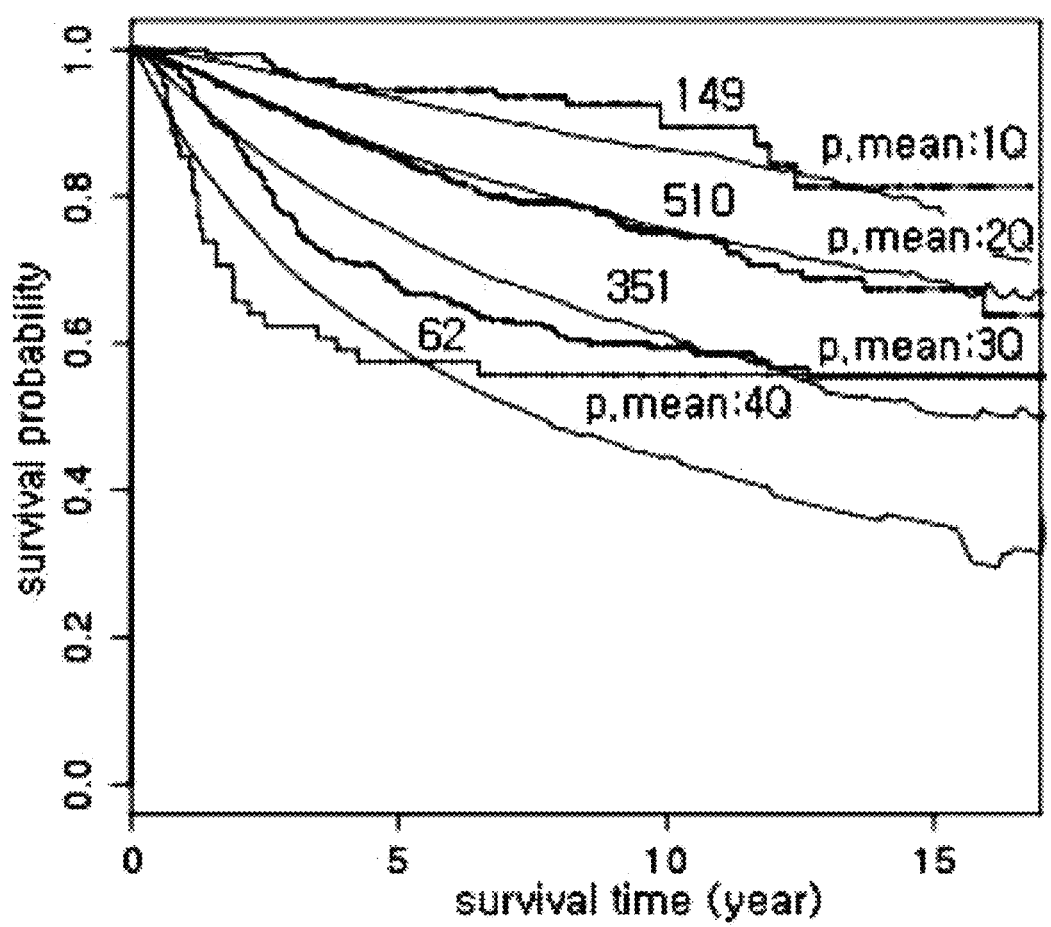
Figure 2D:
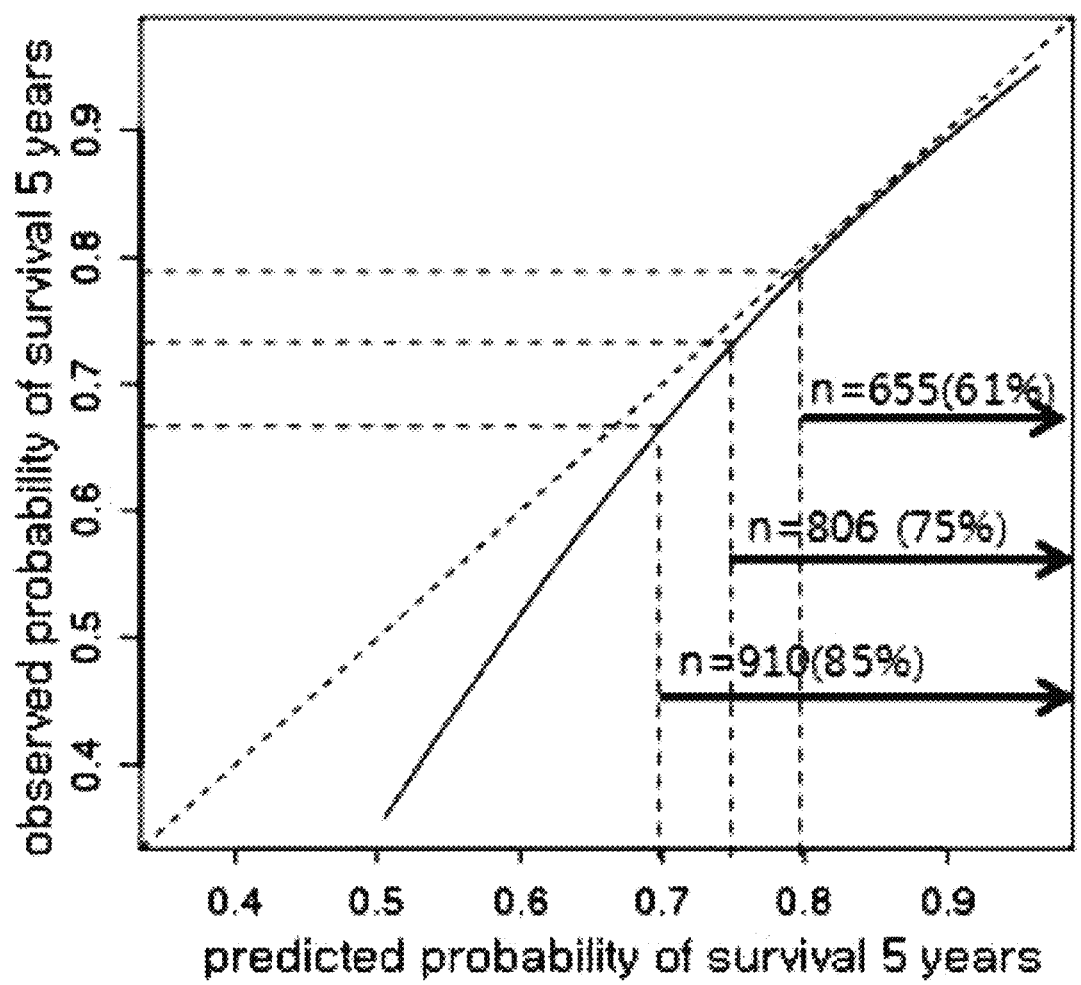
Figure 3A:
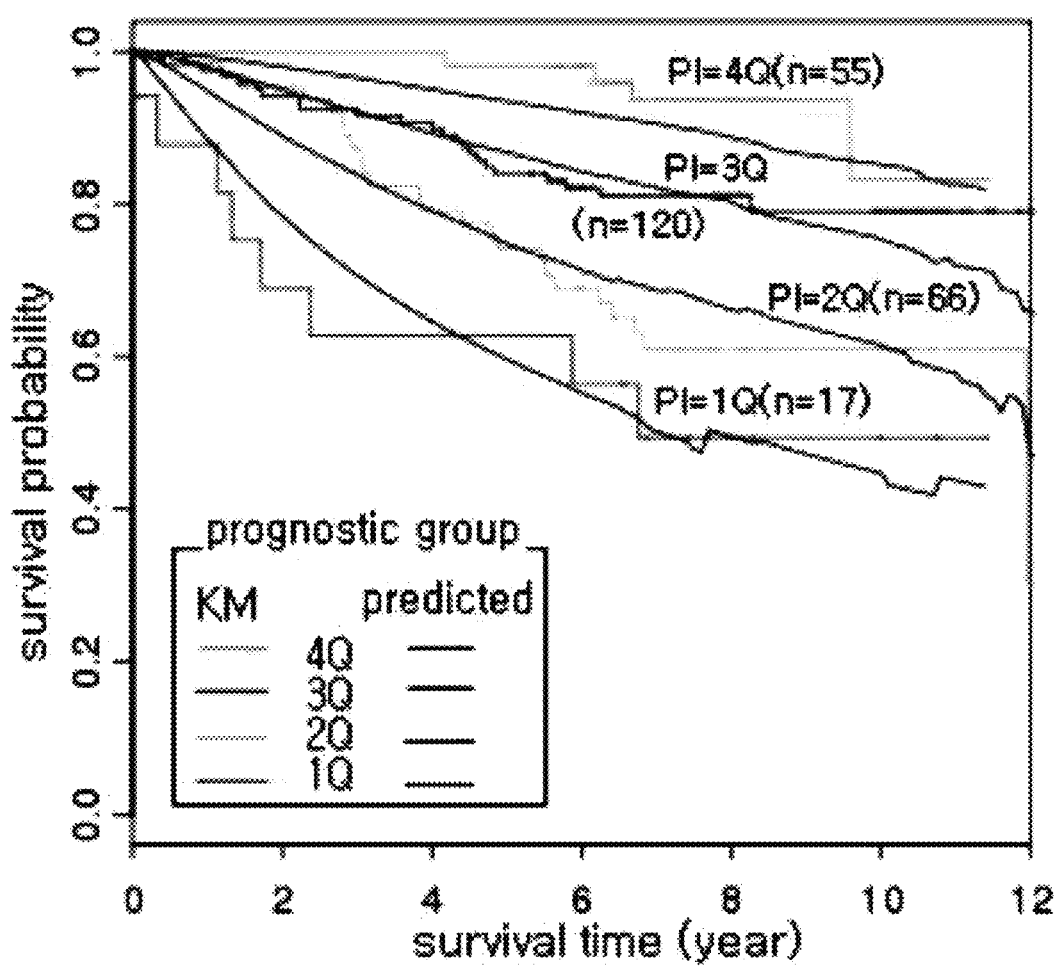
FIGS. 3A-3C show validation results of the prognostic model (frozen samples) in validation set 1. The validation method was the same as that in the discovery dataset.
Figure 3B:
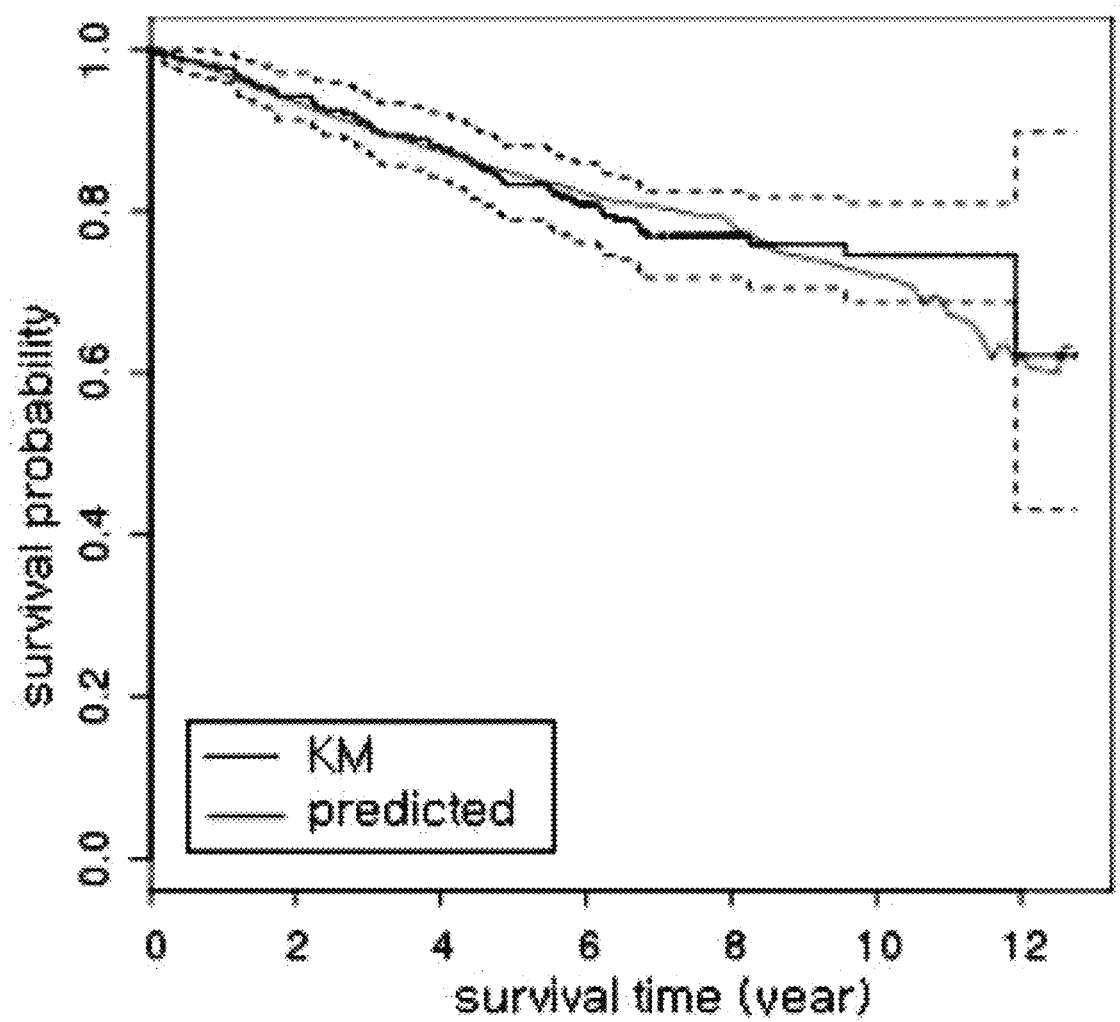
Figure 3C:
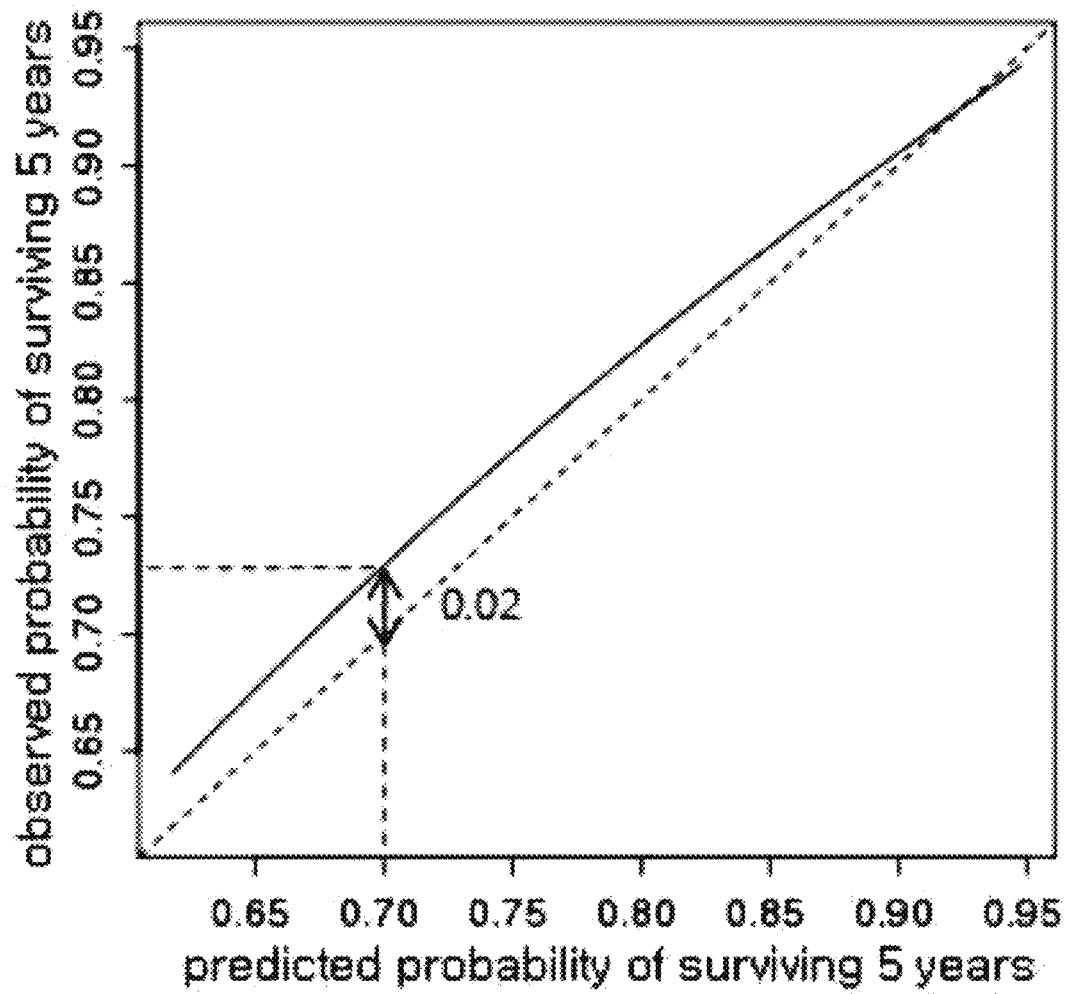
Figure 4A:
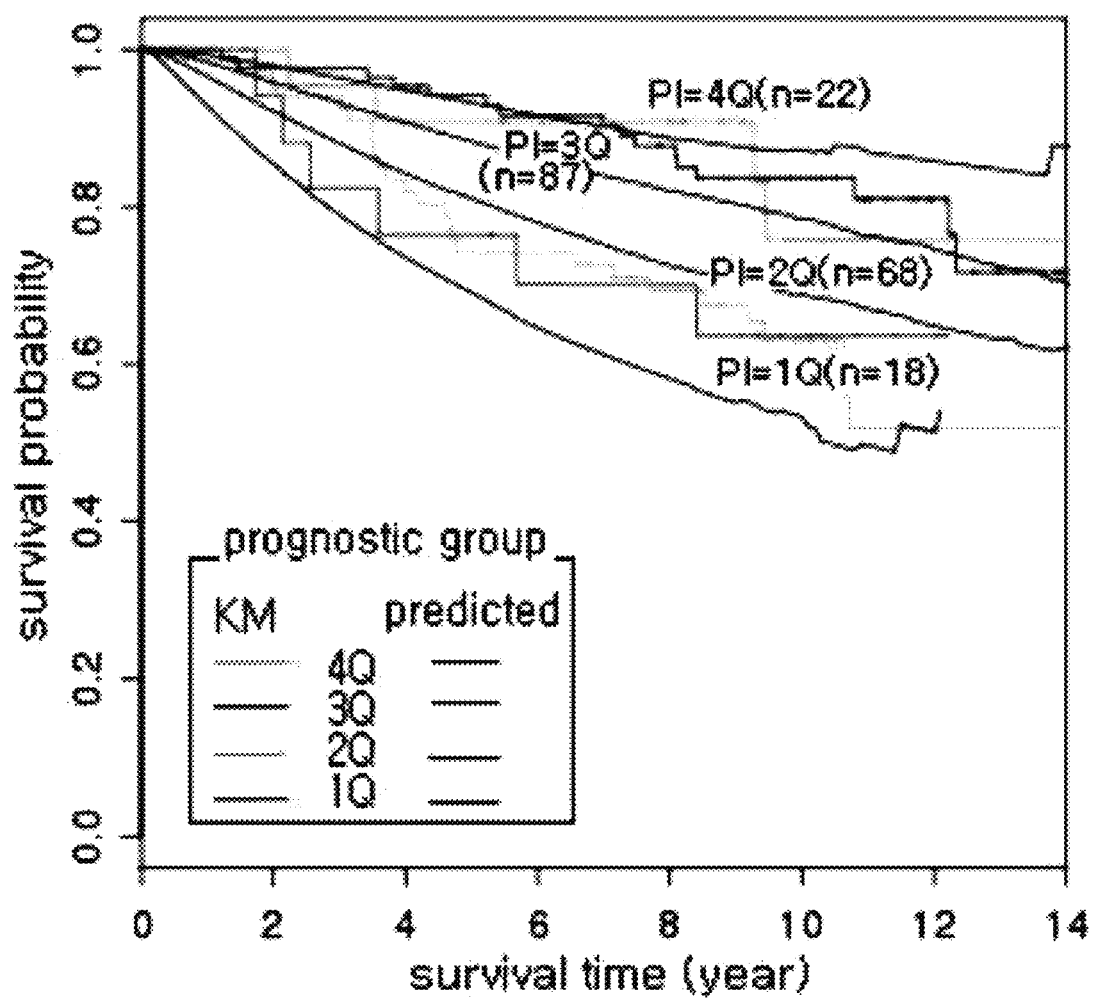
FIGS. 4A-4C show validation results of the prognostic model (frozen samples) in validation set 2. The validation method was the same as that in the discovery dataset.
Figure 4B:
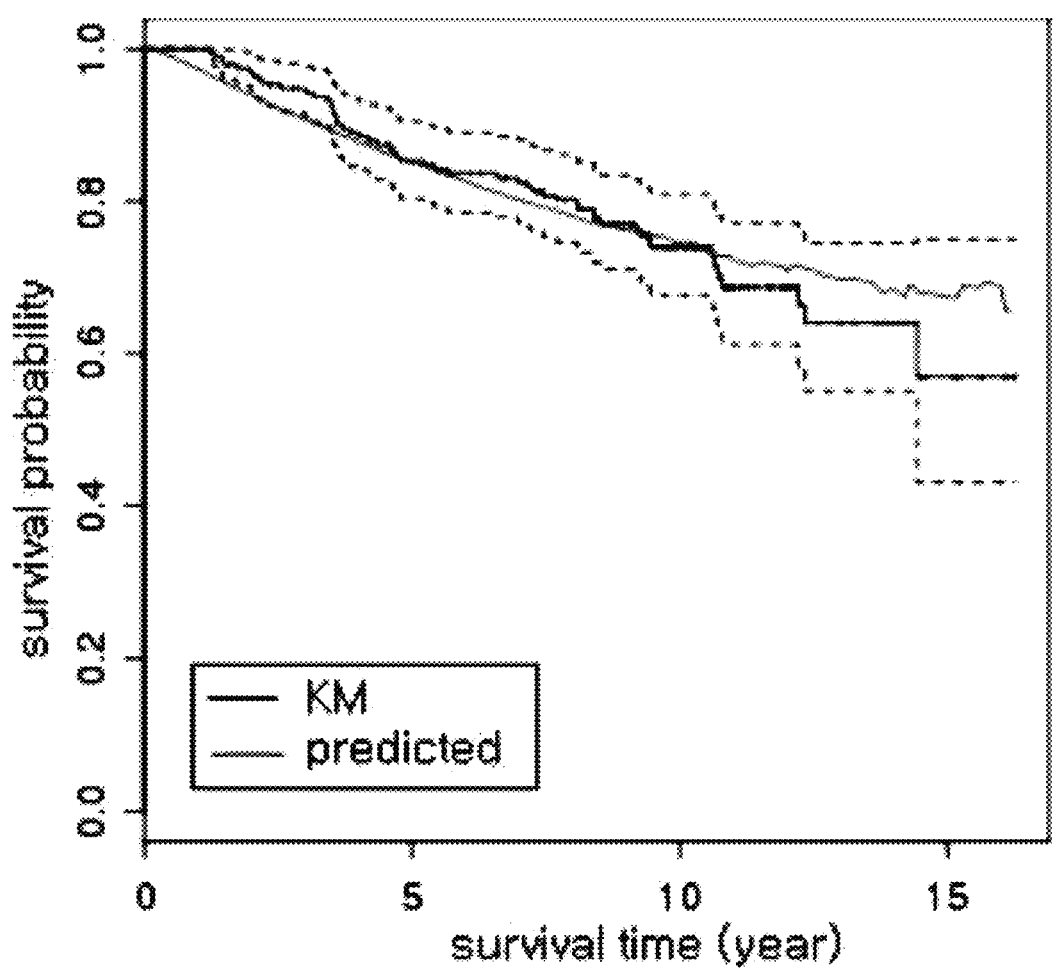
Figure 4C:
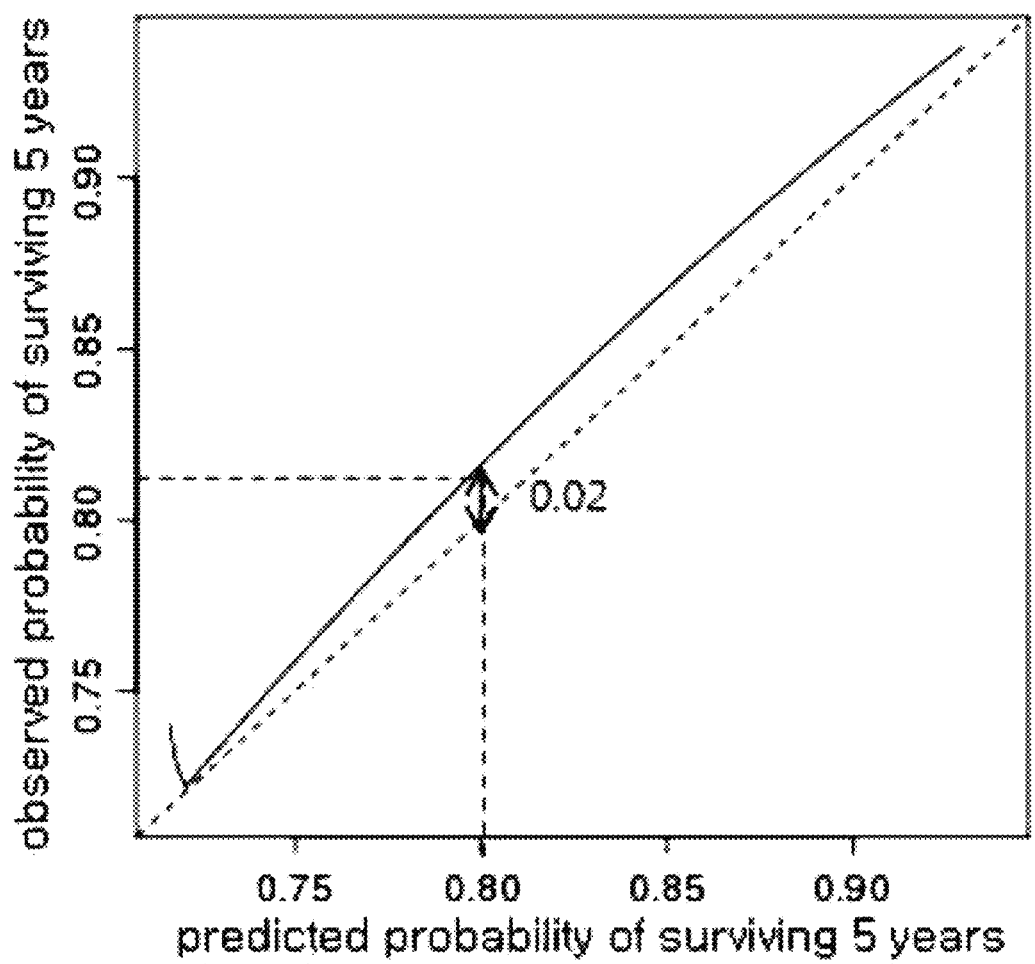
Figure 5:
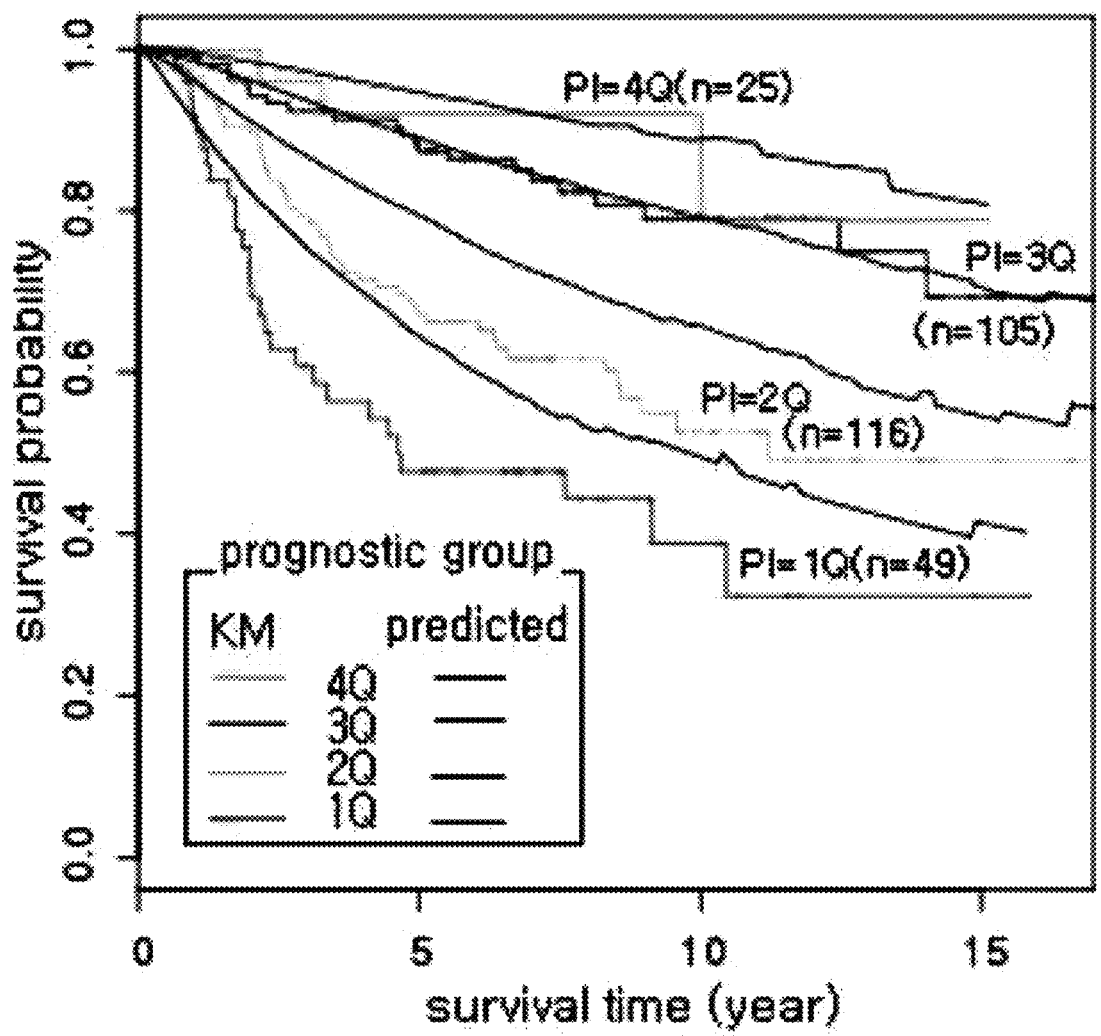
FIG. 5 shows validation results of the prognostic model (frozen samples) in validation set 3. The validation method was the same as that in the discovery dataset.
Figure 6A:
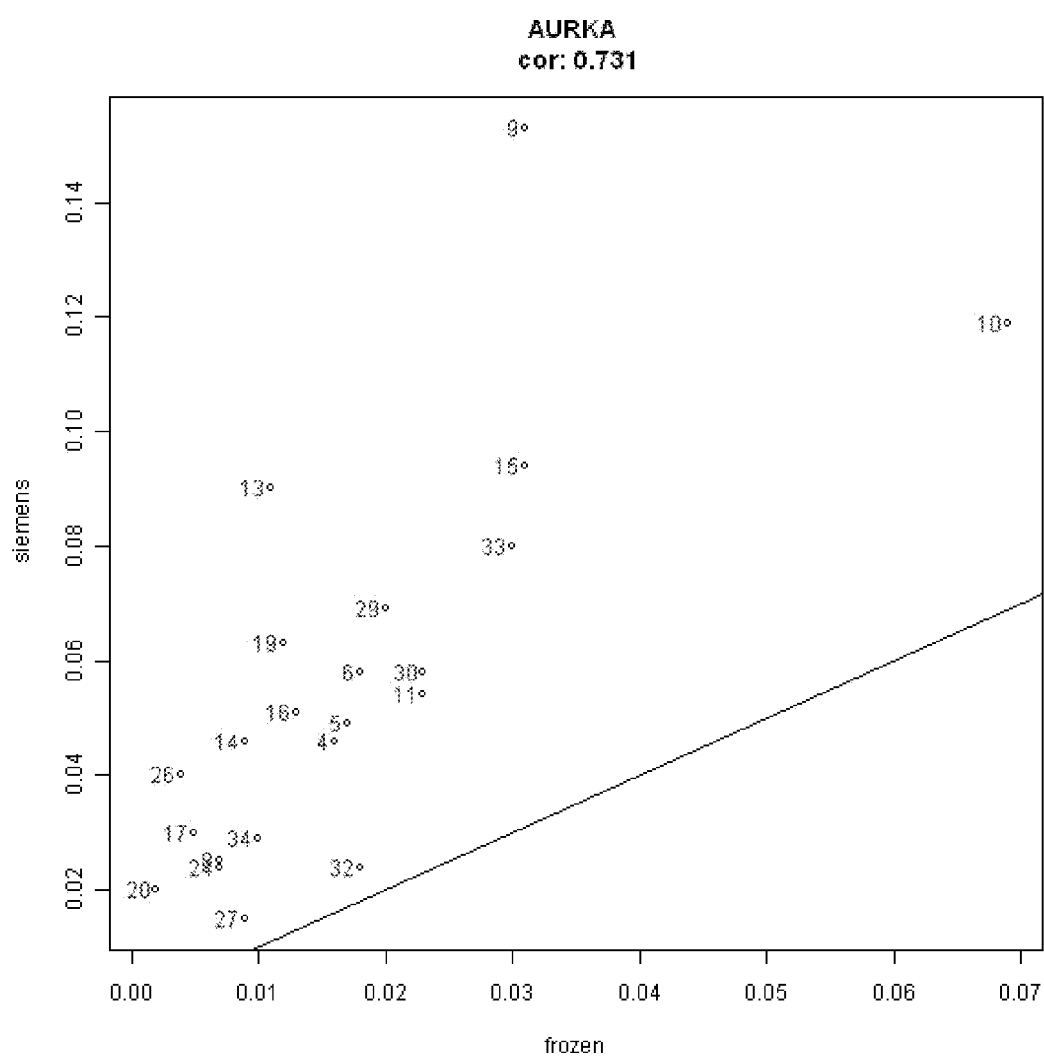
FIGS. 6A-6I show correlation measurement results between FFPE sample (siemens, vertical axis)/frozen sample (horizontal axis) with respect to selected p-gene, and gene names and correlation values (cor) are shown, respectively.
Figure 6B:
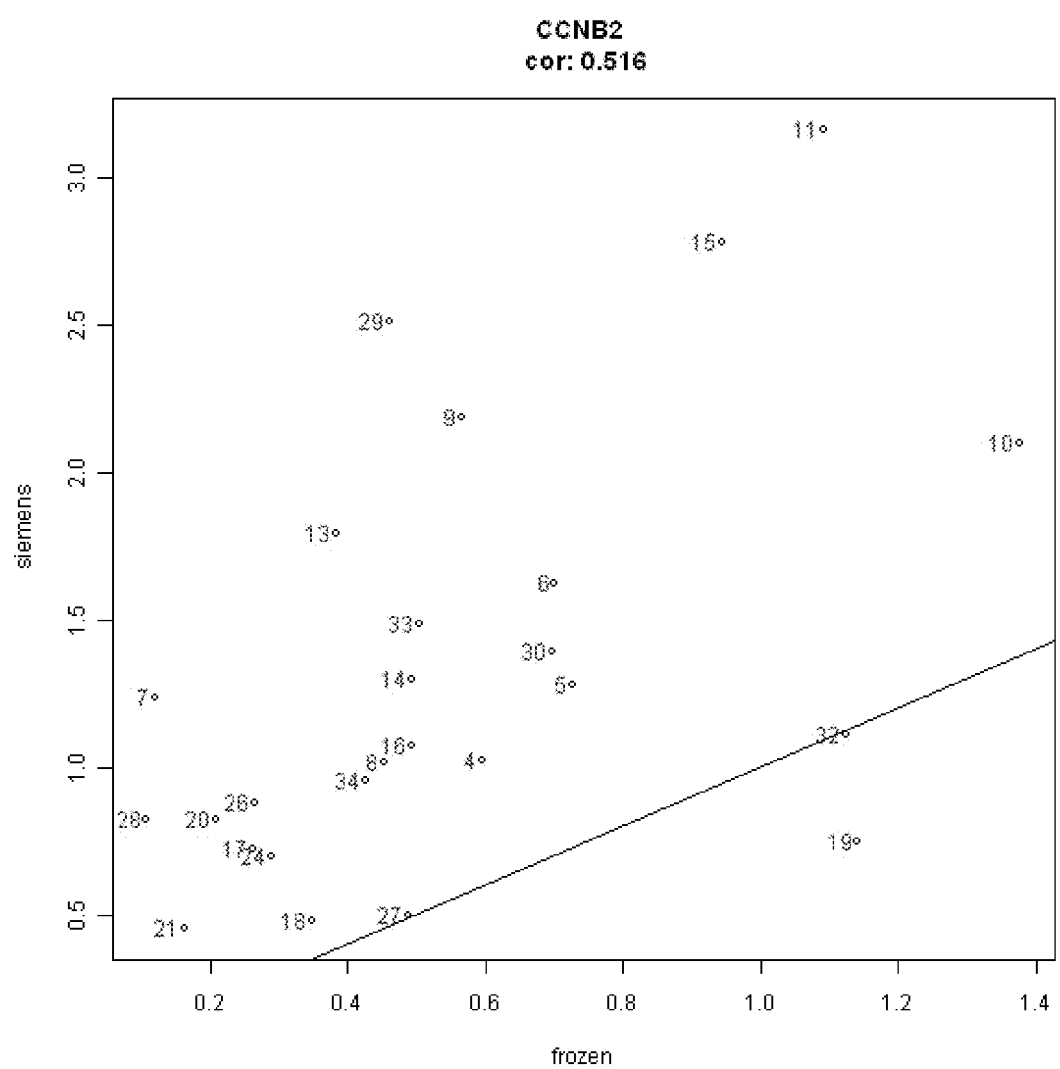
Figure 6C:
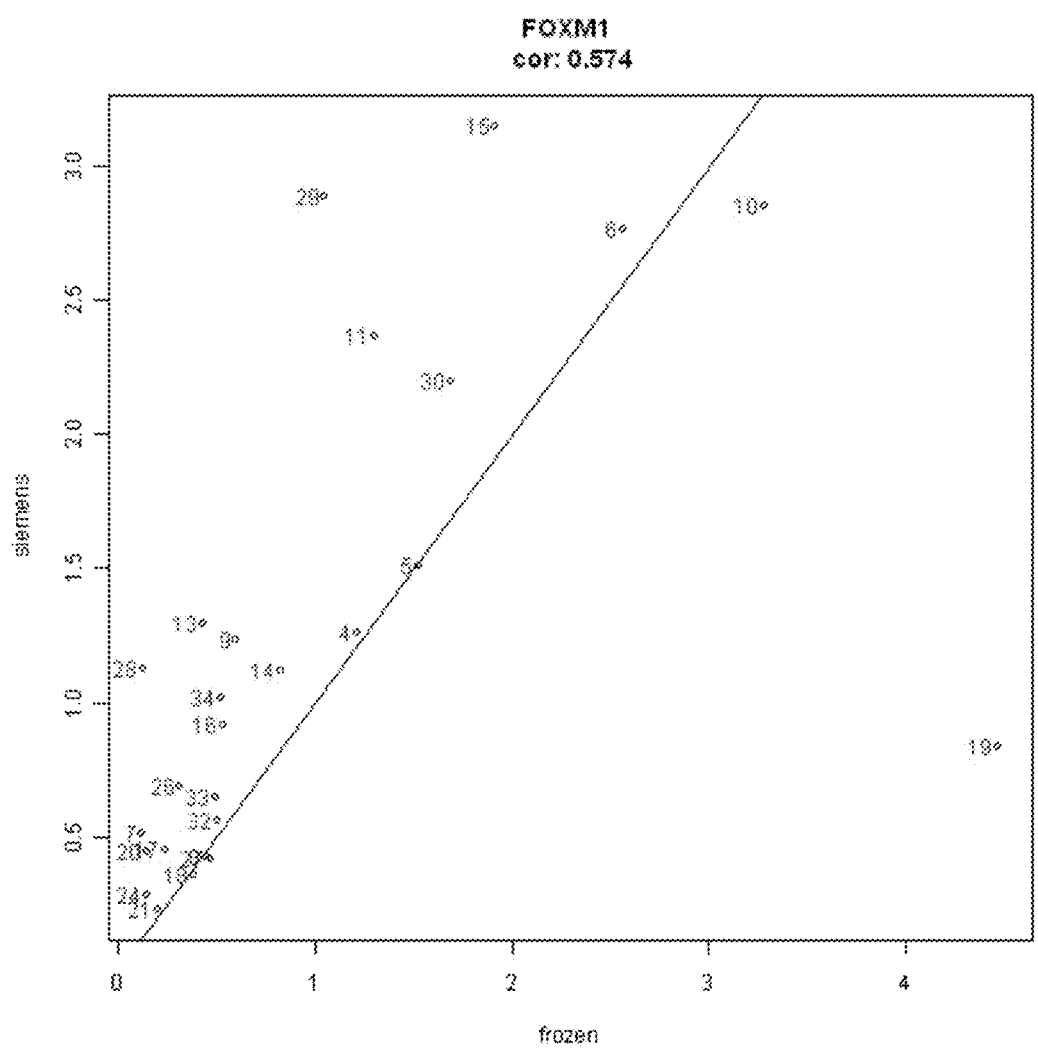
Figure 6D:
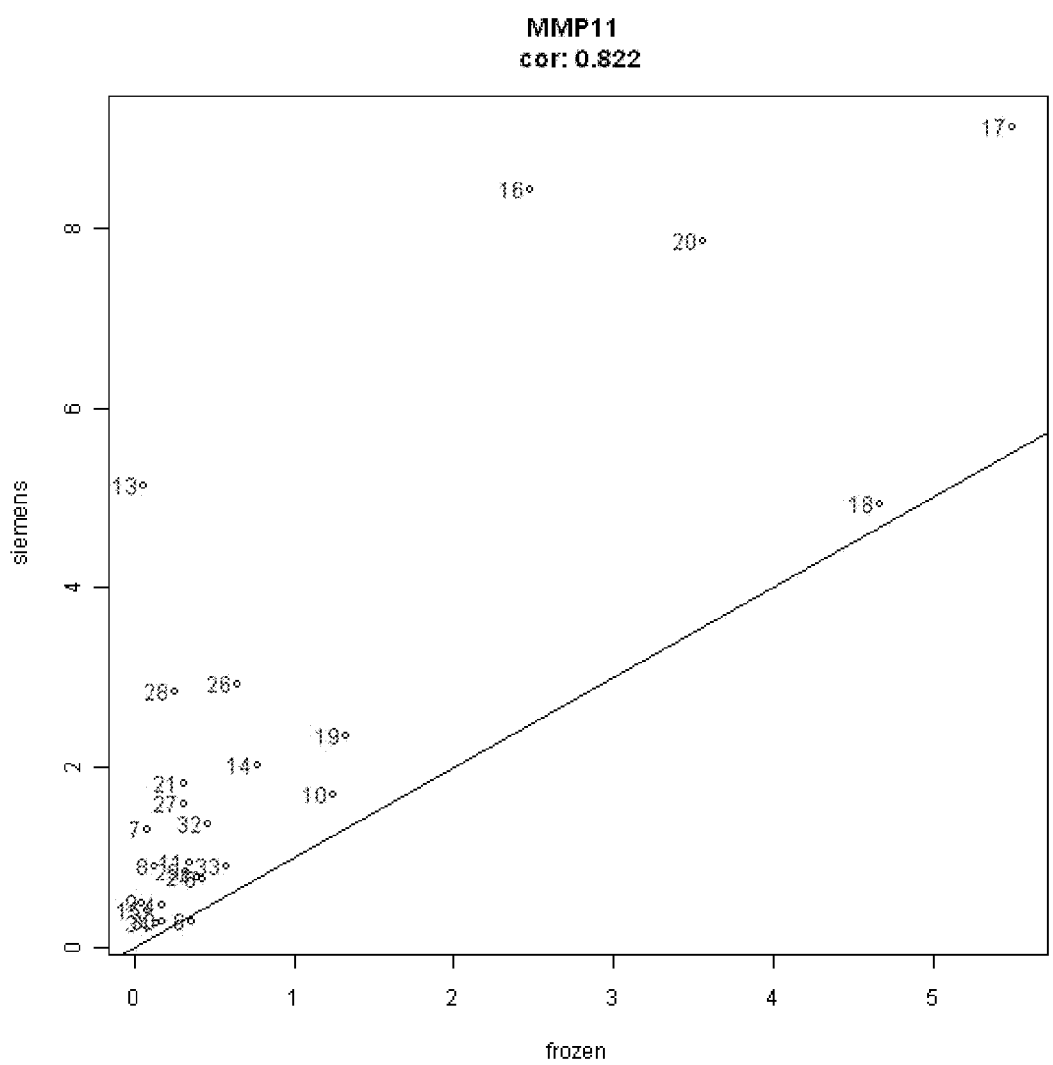
Figure 6E:
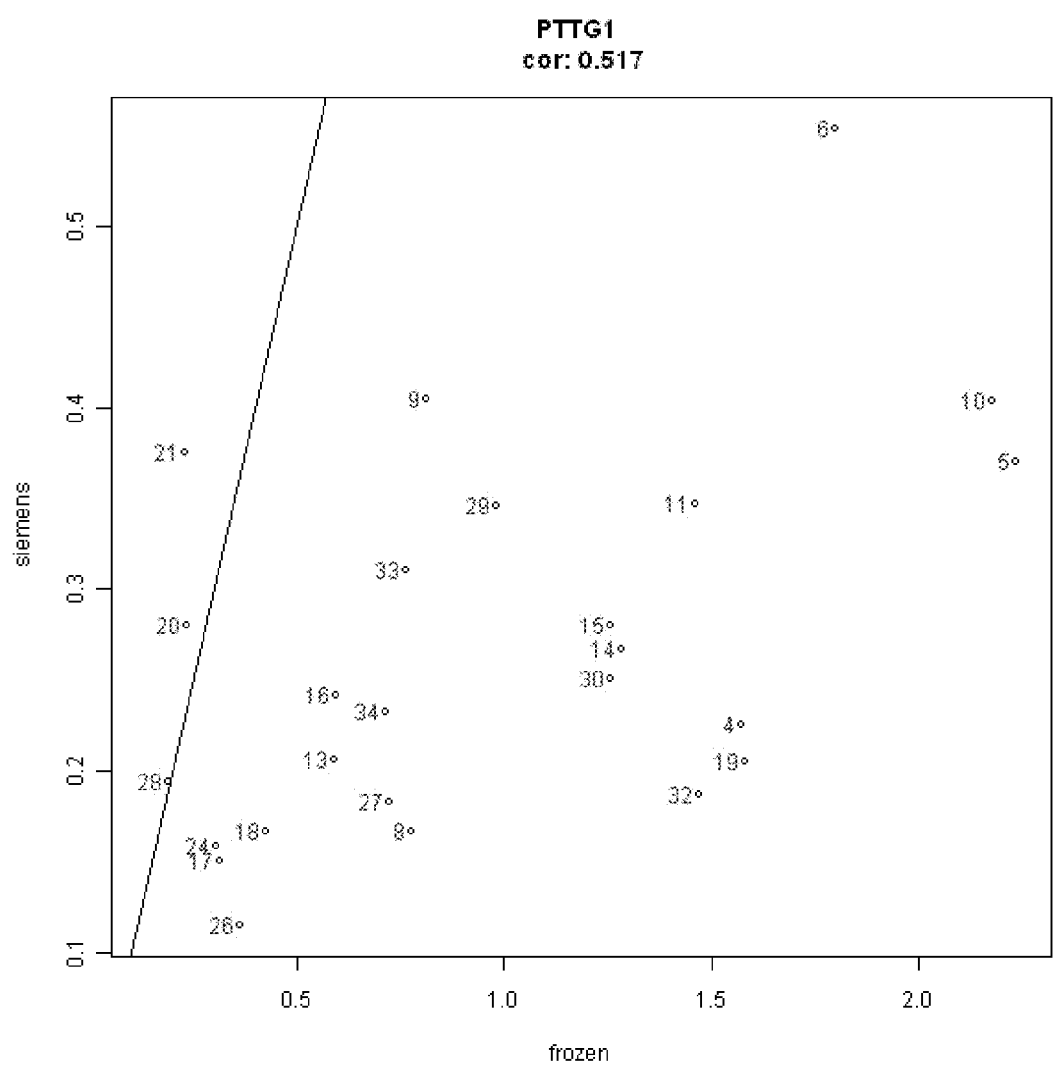
Figure 6F:
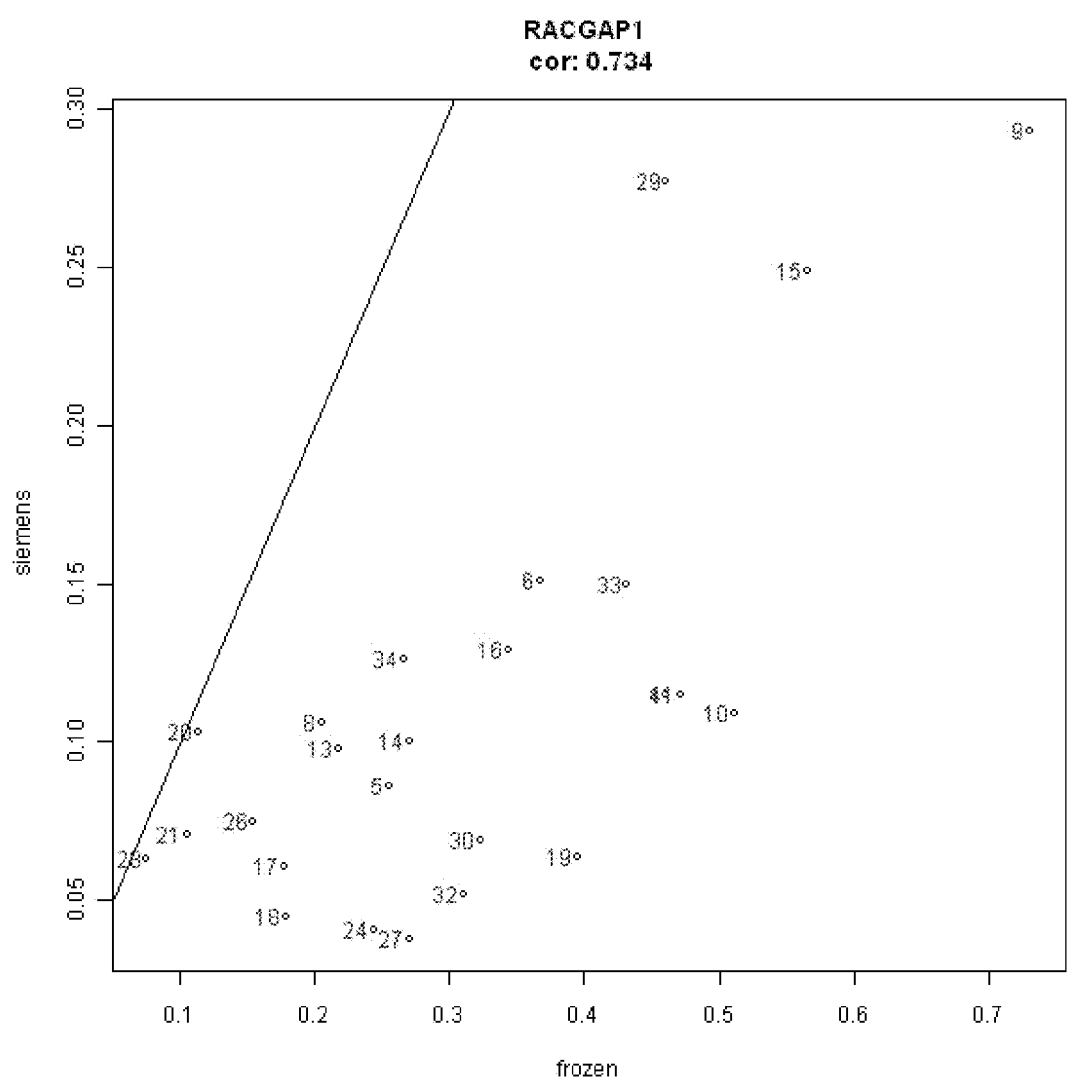
Figure 6G:
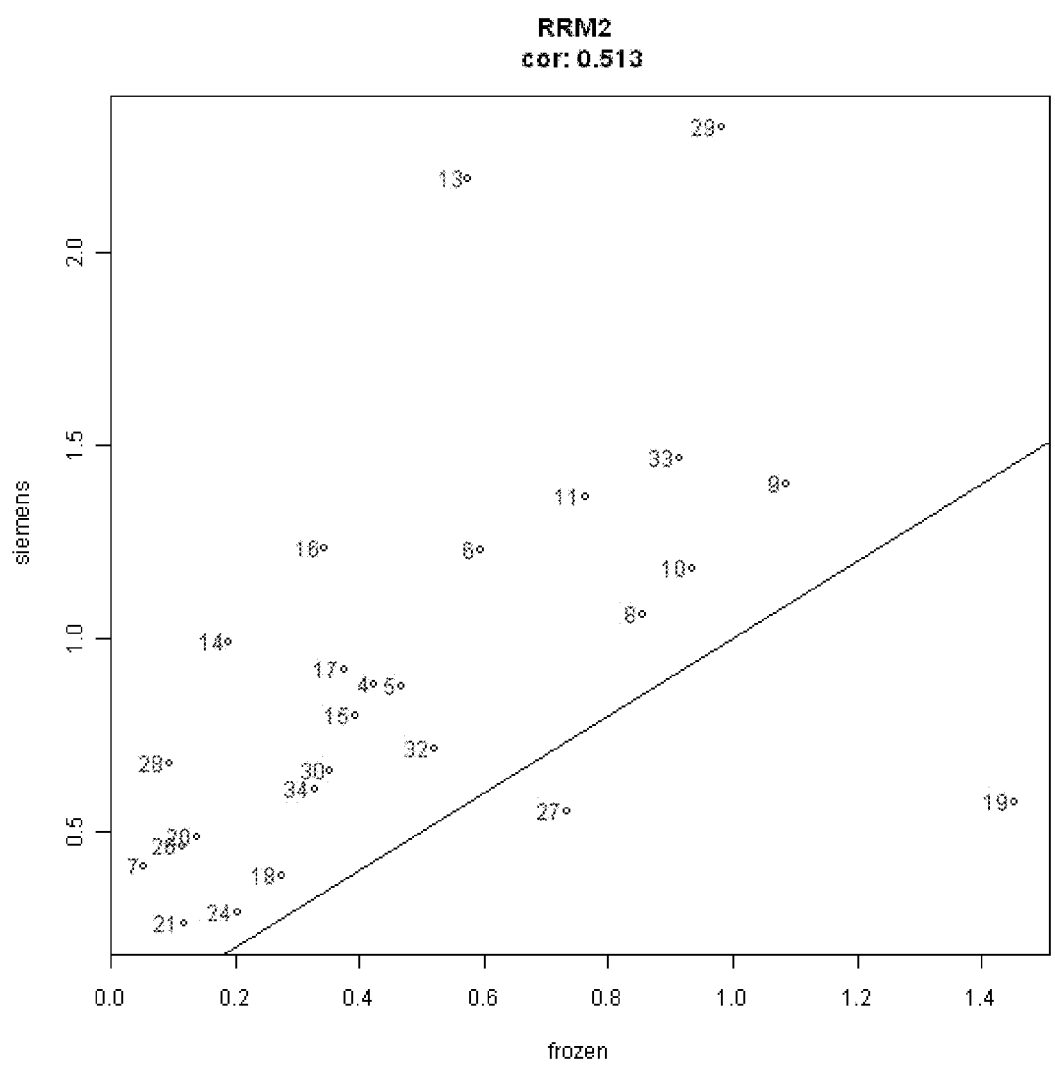
Figure 6H:
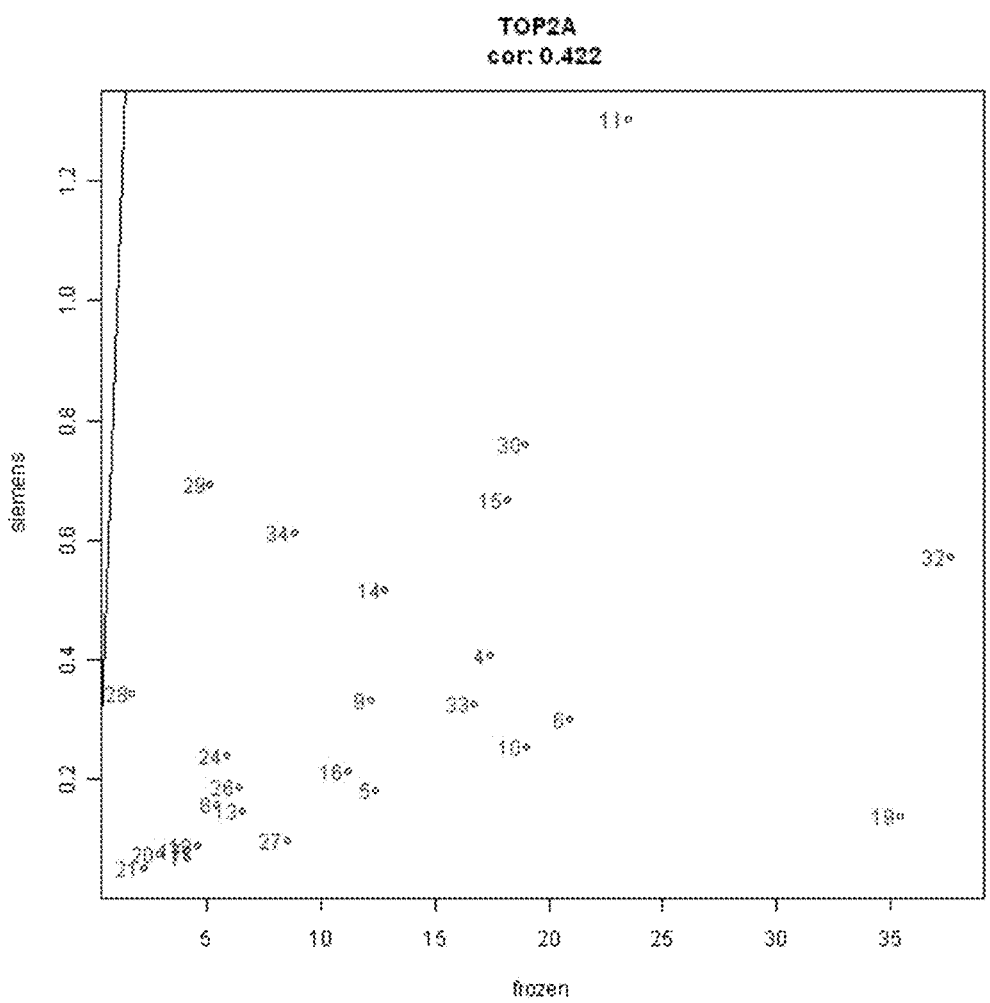
Figure 6I:
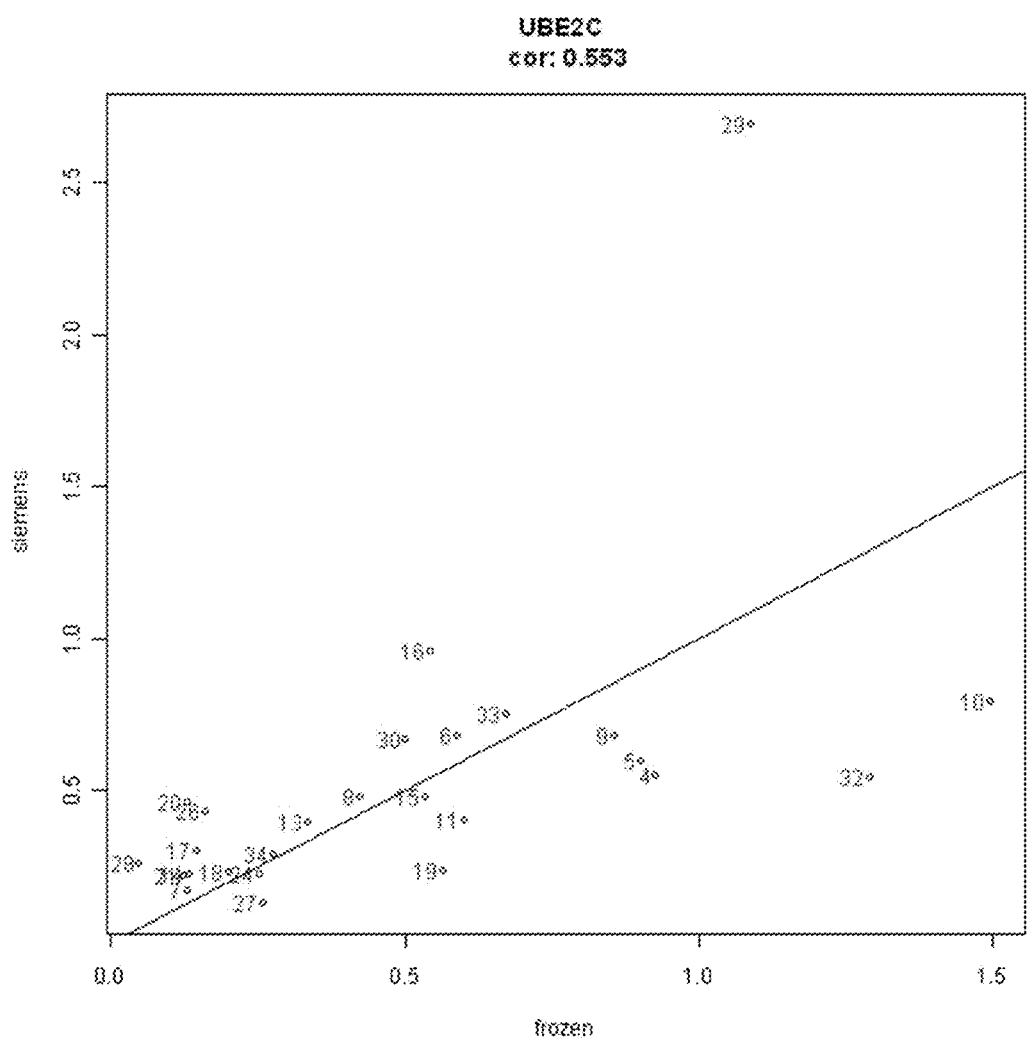
Figure 7A:
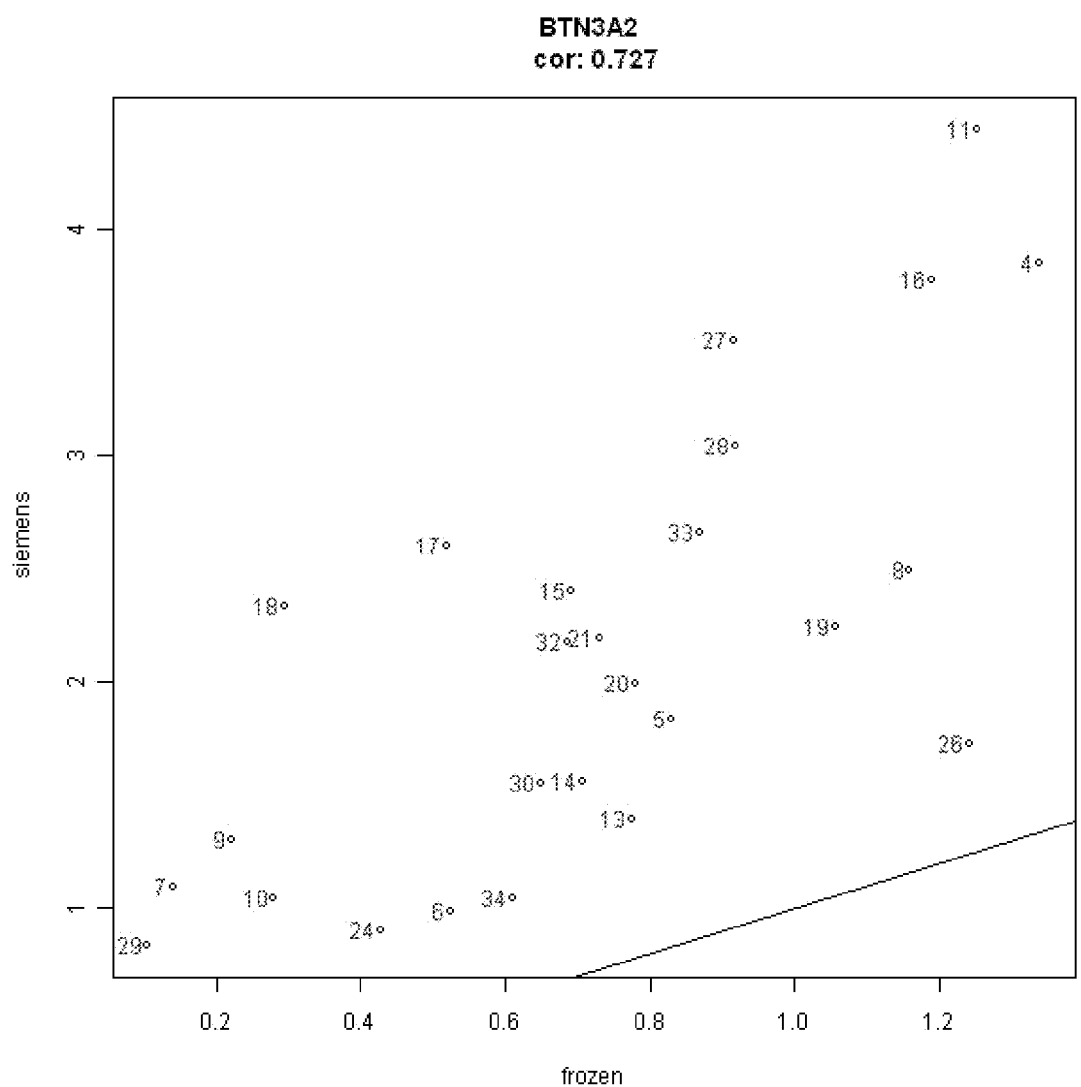
FIGS. 7A-7F show correlation measurement results between FFPE sample (siemens, vertical axis)/frozen sample (horizontal axis) with respect to selected i-gene, and gene names and correlation values (cor) are shown, respectively.
Figure 7B:
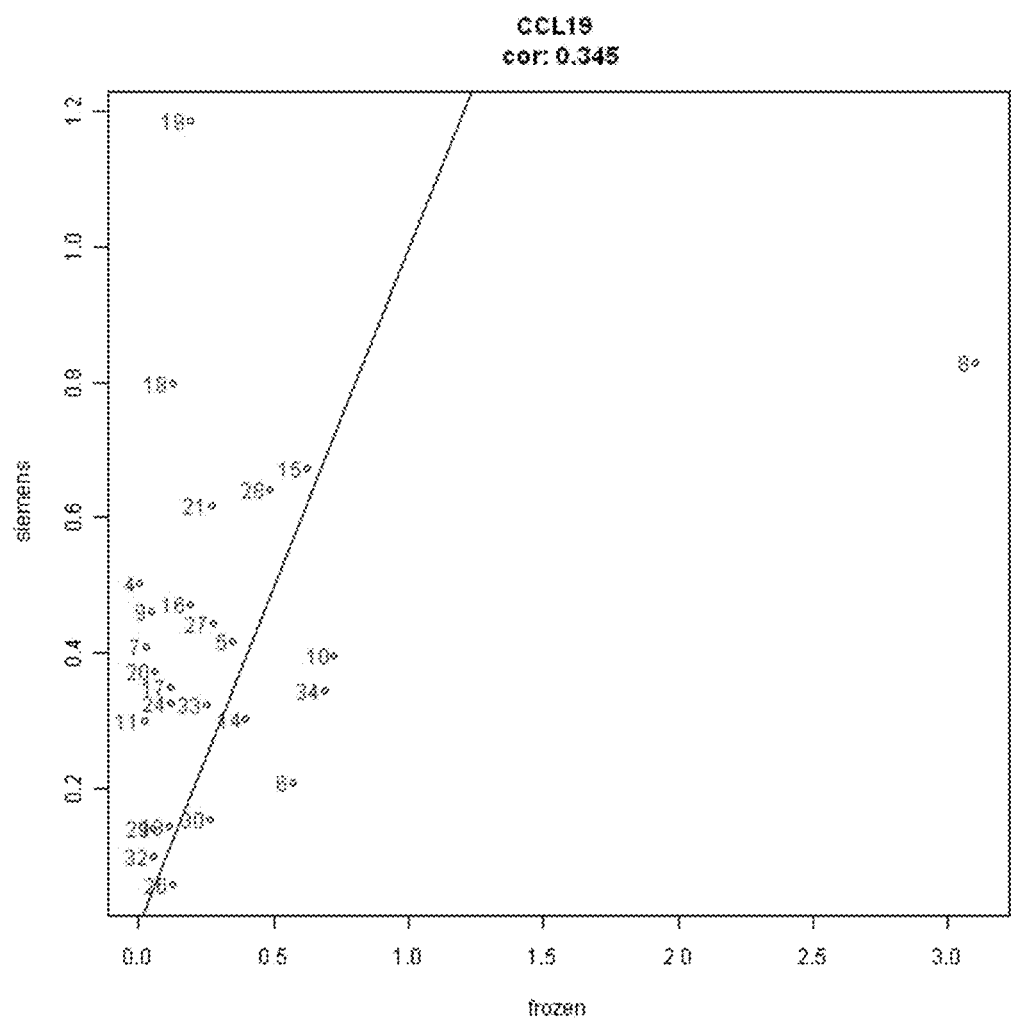
Figure 7C:
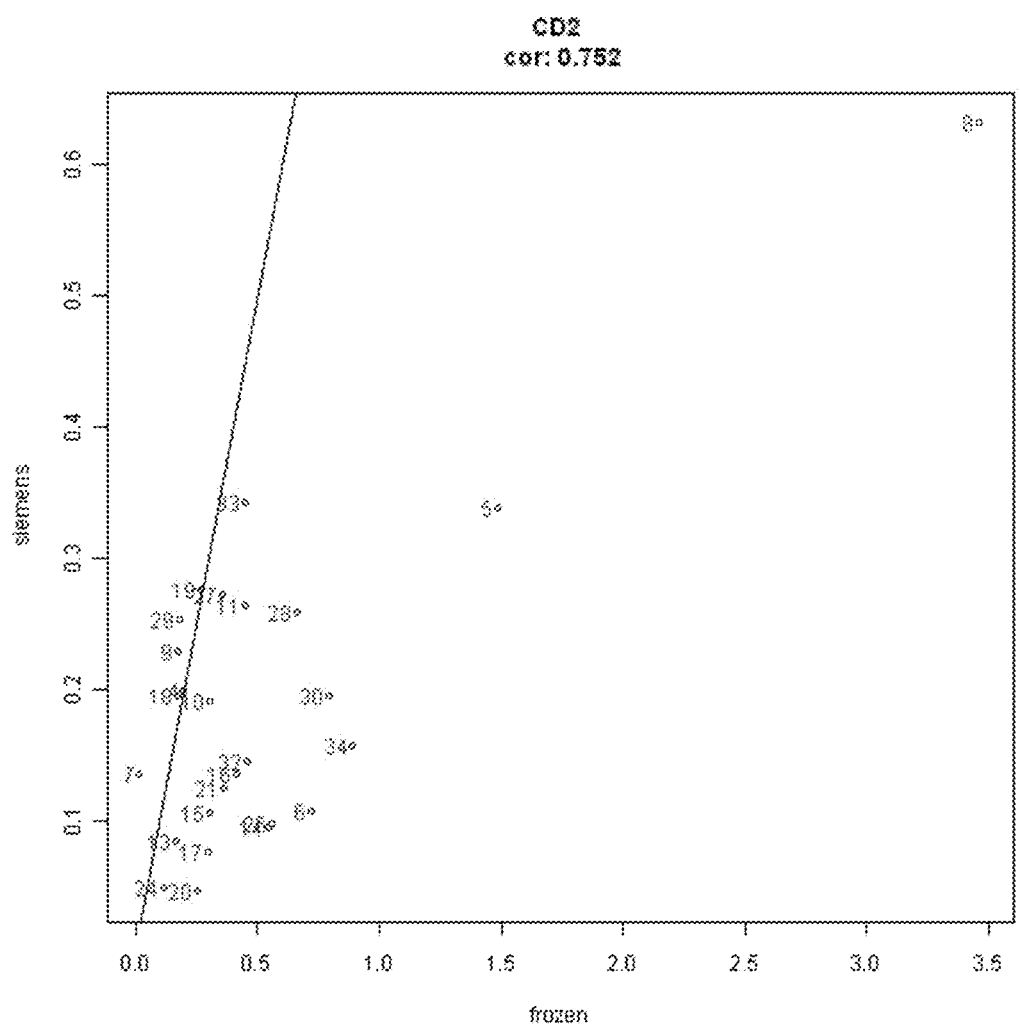
Figure 7D:
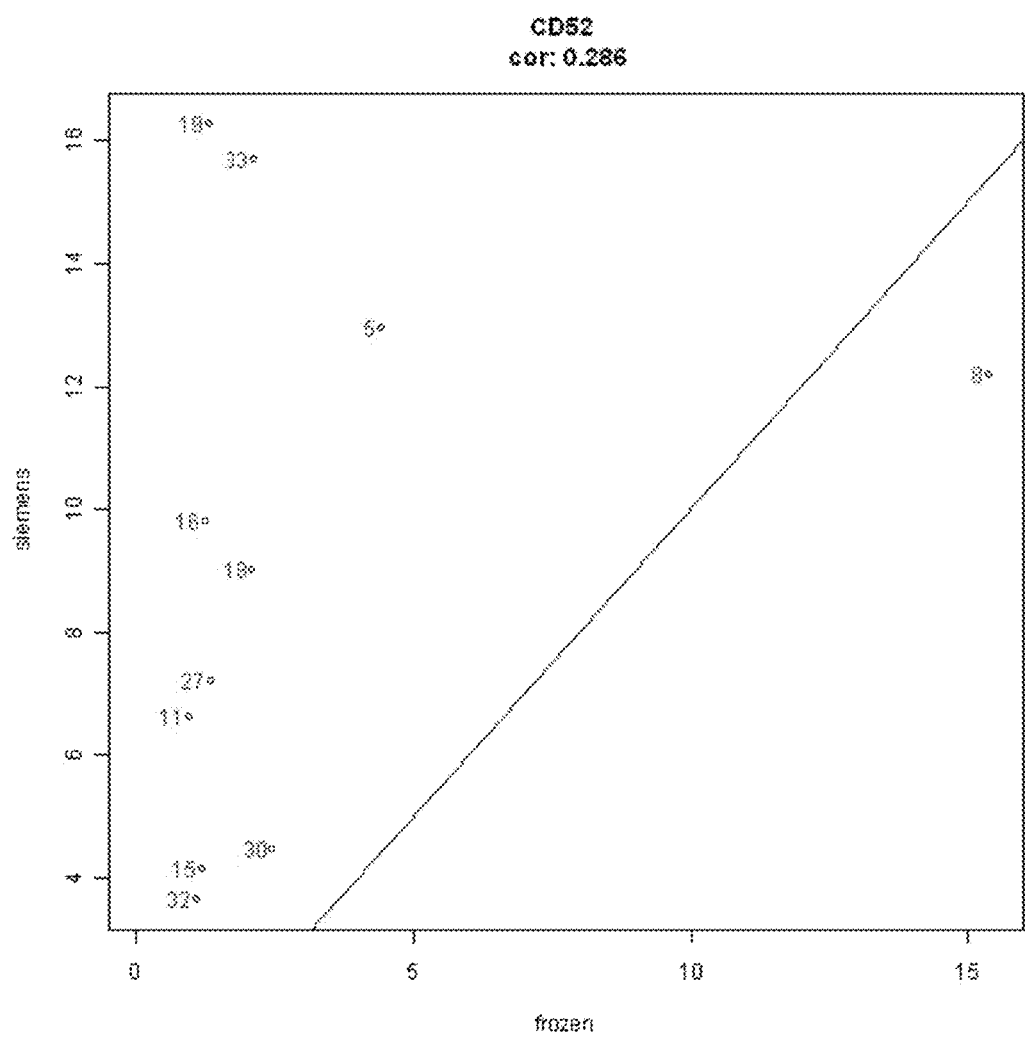
Figure 7E:
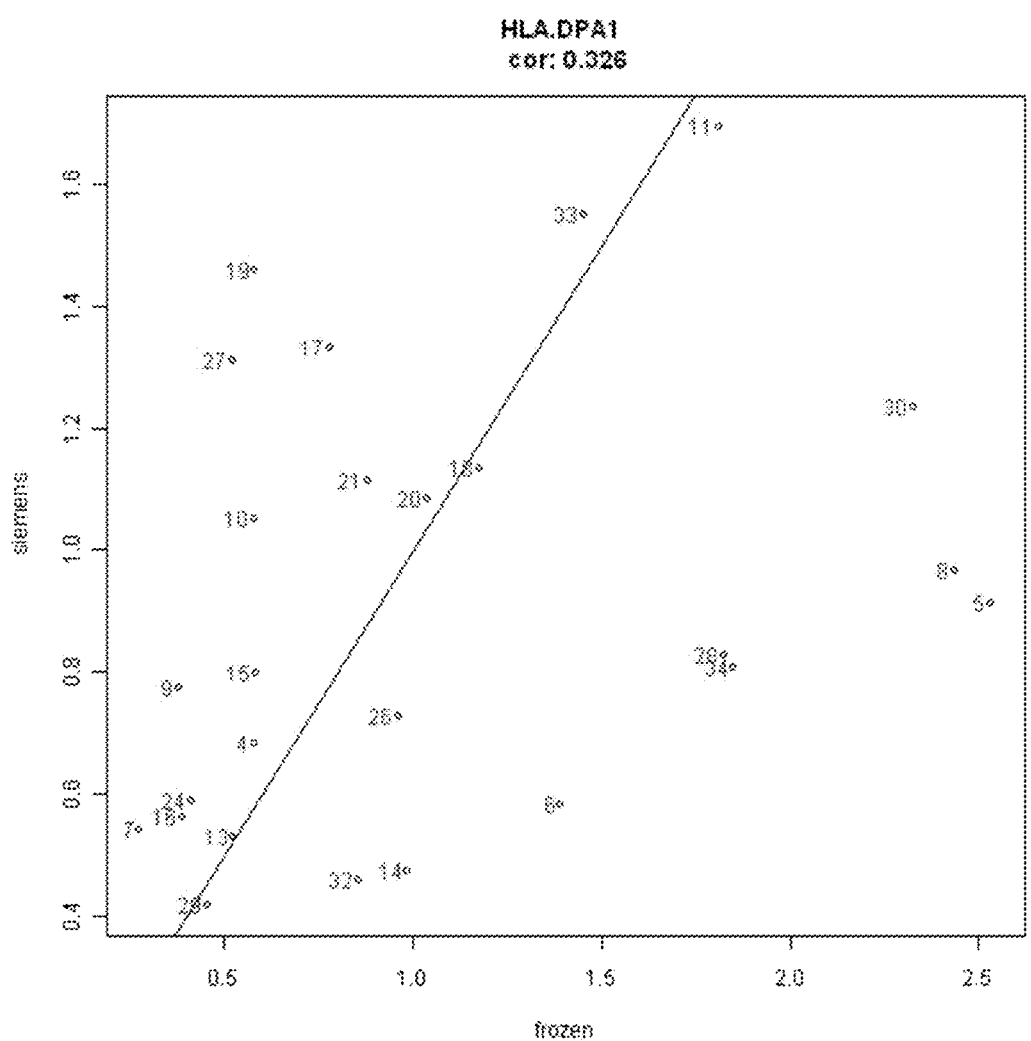
Figure 7F:
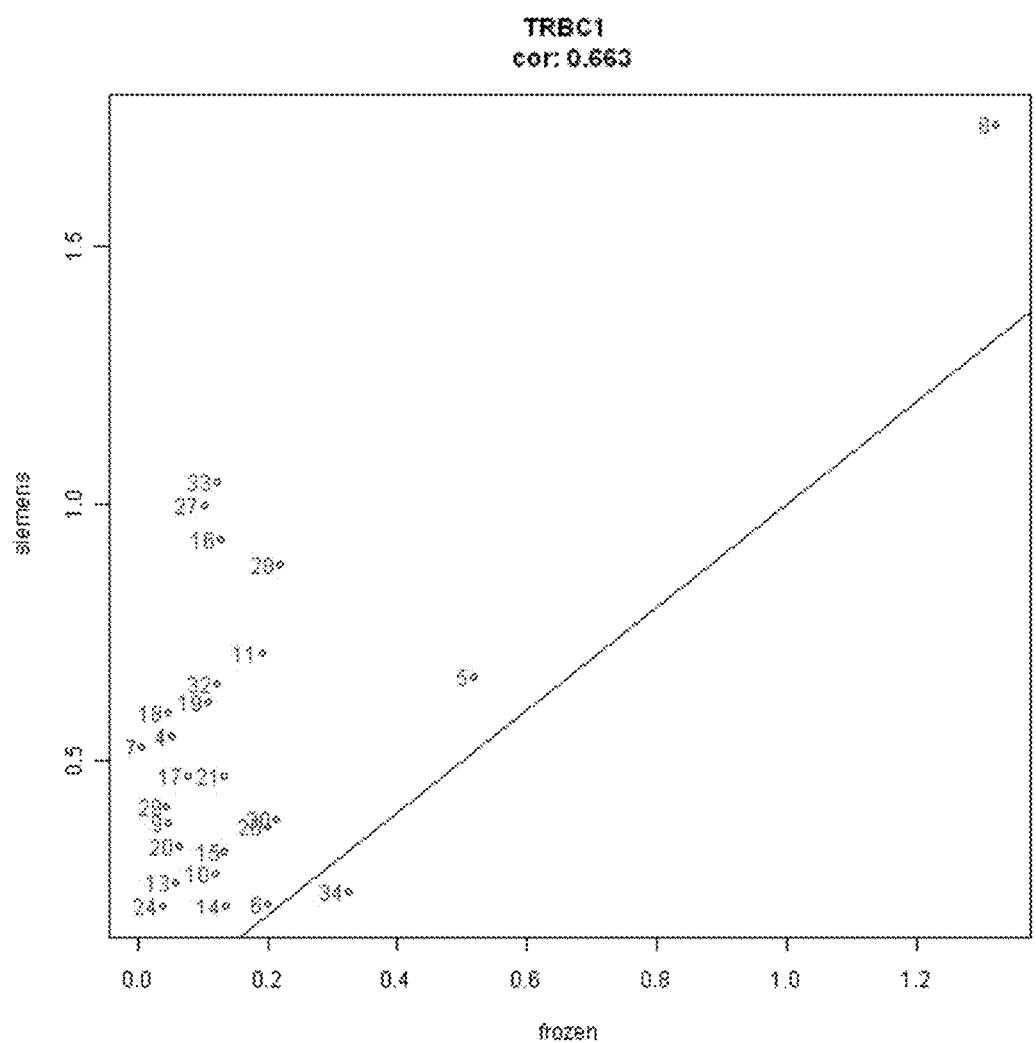

The present invention will be described in more detail.

The present invention provides a genetic marker for predicting or diagnosing the prognosis of a breast cancer patient and a use thereof. More specifically, the present invention provides a genetic marker of T cell receptor beta constant 1 (TRBC1), butyrophilin, subfamily 3, member A2 (BTN3A2), or major histocompatibility complex, class II, DP alpha 1 (HLA-DPA1), for predicting or diagnosing the prognosis of breast cancer, especially, early-stage breast cancer. In addition, the present invention provides a method for predicting the prognosis of breast cancer, the method comprising: (a) isolating mRNA from a sample; (b) measuring the mRNA expression level of at least one gene selected from the group consisting of T cell receptor beta constant 1 (TRBC1), butyrophilin, subfamily 3, member A2 (BTN3A2), and major histocompatibility complex, class II, DP alpha 1 (HLA-DPA1); and (c) normalizing the mRNA expression level of the gene, wherein the overexpression of the gene is determined as indicating good prognosis.

Herein, T cell receptor beta constant 1 (TRBC1), butyrophilin, subfamily 3, member A2 (BTN3A2), or major histocompatibility complex, class II, DP alpha 1 (HLA-DPA1) may serve as a genetic marker in the present invention. They may be used for predicting or diagnosing the prognosis of early-stage breast cancer by being independently selected, or by a combination of two or three genes. Each gene may be a sequence thereof known in the art or a sequence of the synonym thereof, and preferably a sequence thereof derived from a human being. More preferably, TRBC1 may be Genbank Accession No. BC030533.1; BTN3A2 may be Genbank Accession No. NM_007047.3; and HLA-DPA1 may be Genbank Accession No. NM_001242524.1, NM_001242525.1, or NM_033554.3. The synonym and the sequence of each gene may be searched in Genbank or Swissprot.

Herein, the breast cancer may be an invasive breast cancer, or breast cancer stage I, II, or III. Herein, the breast cancer may be estrogen receptor positive (ER+).

As used herein, the term "prognosis" refers to symptoms in the future or prospects of progress determined by disease diagnose. The prognosis in cancer patients generally means whether or not the cancer is metastatic within a certain period or the survival period after the occurrence of cancer or the surgical procedure. The prediction of prognosis (or the diagnosis of prognosis) presents clues for future direction of breast cancer treatment, especially, including whether chemotherapy treatment is performed on early-stage breast cancer patients, and thus is a very important clinical challenge. The prediction of prognosis includes predictions of the response of patients to disease therapeutic agents and therapeutic progress.

Herein, the sample may be a breast cancer tissue of a breast cancer patient. The breast cancer tissue may contain some normal cells, and may preferably be a formalin-fixed paraffin-embedded (FFPE) sample of the breast cancer tissue including cancer cells of the patient.

The marker for predicting or diagnosing the prognosis of breast cancer according to the present invention may be detected through polymerase chain reaction (PCR) amplification of a target gene. The detection of the target gene according to the present invention is preferably a detection of the expression level of the target gene, and more preferably a quantitative detection of the expression level of the target gene. For the detection of the expression level, the isolation of mRNA in the sample tissue and the synthesis of cDNA from the mRNA may be needed. For the isolation of mRNA, the isolation methods of mRNA from a sample, which are known in the art, may be employed, and since the sample is preferably an FFPE sample, the isolation methods of mRNA, which are appropriate for the FFPE sample, may be employed. For the synthesis of cDNA, the cDNA synthesis methods using mRNA as a template, which are known in the art, may be employed. Preferably, the detection of the marker for predicting or diagnosing the prognosis of breast cancer according to the present invention is a quantitative detection of the mRNA expression in the FFPE sample, and thus may be the detection by the isolation method of mRNA and the reverse transcription quantitative polymerase chain reaction (RT-qPCR) method with respect to the FFPE sample.

Herein, the detection may be a measurement of the mRNA expression level. The measurement of the expression level may be conducted using the methods known in the art, but may be conducted by an optical quantitative analysis system using a probe labeled with a reporter fluorescent dye and/or a quencher fluorescent dye. The measurement may be conducted using a commercially available system, for example, ABI PRISM 7700™ Sequence Detection System™, Roche Molecular BiochemicalsLightcycler, and an operating system affiliated therewith, such as software. The measurement data may be expressed as a measurement value or a threshold cycle (Ct or Cp). The point in which the measured fluorescent value is first recorded as being statistically significant is defined as the threshold cycle. The threshold cycle is inversely proportional to the value at the beginning in which targets of detection are present as a template of PCR, and thus the lower threshold cycle value indicates the presence of the quantitatively increased targets of detection.

Meanwhile, the present invention provides a composition for predicting or diagnosing the prognosis of breast cancer, the composition comprising a primer pair as an active ingredient, wherein the primer pair is for at least one gene selected from the group consisting of TRBC1, BTN3A2, and HLA-DPA1, and wherein the primer pair is capable of amplifying a target gene through PCR amplification.

As used herein, the term "primer" refers to an oligonucleotide, and the primer may act as an initial point of synthesis in the condition where the synthesis of the primer extension products that are complementary to a nucleic acid chain (template) is induced, that is, the presence of nucleotides and polymerases such as DNA polymerases, and appropriate temperature and pH. Preferably, the primer is deoxyribonucleotide, and has a single chain. The primer used herein may include naturally occurring dNMPs (that is, dAMP, dGMP, dCMP, and dTMP), modified nucleotides, or non-naturally occurring nucleotides. Also, the primer may include ribonucleotides.

The primer of the present invention may be an extension primer that is annealed to a target nucleic acid to form a sequence complementary to the target nucleic acid by template-dependent nucleic acid polymerase. The extension primer is extended to a site at which an immobilized probe is annealed, and thus occupies the site at which the probe is annealed.

The extension primer used herein includes a hybrid nucleotide sequence complementary to the first site of the target nucleic acid. The term "complementary" refers to being sufficiently complementary such that primers or probes are selectively hybridized with the target nucleic acid sequence under predetermined annealing or hybridizing conditions, encompassing the terms "substantially complementary" and "perfectly complementary", and means preferably "perfectly complementary". As used herein, the term "substantially complementary sequence" in conjunction with the primer sequence, means including the sequence that is partially un-identical to the sequence of the comparative target within the range in which the sequence is annealed to a particular sequence to serve as a primer, as well as the perfectly identical sequence.

The primer needs to be long enough to prime the synthesis of extension products in the presence of polymerases. The appropriate length of the primer varies depending on several factors, such as temperature, field of application, and primer source, but the primer generally has 15~30 nucleotides. Short primer molecules generally require lower temperatures in order to form sufficiently stable hybrid complexes together with templates. The term "annealing" or "priming" refers to the apposition of oligodeoxynucleotide or nucleic acid to the template nucleic acid, and the apposition enables the polymerase to polymerize nucleotides to form a nucleic acid molecule, which is complementary to the template nucleic acid or a portion thereof.

The sequences of primers do not need to have a perfectly complementary sequence to some sequences of templates.

The primers are good enough so long as they have sufficient complementarity within the scope in which they can perform their inherent actions through hybridization with the template. Therefore, the primer of the present invention does not need to have a perfectly complementary sequence to the foregoing nucleotide sequence as a template. The primers are good enough so long as they have sufficient complementarity within the scope in which they can perform their actions through hybridization with the gene sequence. This design of the primers may be easily carried out by a person skilled in the art with reference to the foregoing nucleotide sequences. For instance, the design of the primers may be carried out using computer programs for primer design (e.g., PRIMER 3 program).

The present invention provides a kit for predicting or diagnosing the prognosis of breast cancer, the kit comprising the primer pair. The kit of the present invention may further comprise tools and/or reagents known in the art which are used for PCR, RNA separation in samples, and cDNA synthesis, in addition to primer pairs allowing PCR amplification of TRBC1, BTN3A2, and/or HLA-DPA1. The kit of the present invention may further comprise, if necessary, tubes which are to be used to mix respective components, well plates, instruction manuals describing how to use, or the like.

The present invention provides a method for calculating a predictive value of the prognosis of breast cancer to provide information necessary for predicting or diagnosing the prognosis of a breast cancer patient, the method comprising:

(a) isolating mRNA from a sample;

(b) measuring the mRNA expression level of at least one gene selected from the group consisting of T cell receptor beta constant 1 (TRBC1), butyrophilin, subfamily 3, member A2 (BTN3A2), and major histocompatibility complex, class II, DP alpha 1 (HLA-DPA1);

(c) normalizing the mRNA expression level of the gene;

(d) inserting the normalized value into a predetermined calculation formula to calculate a numerical value; and (e) determining the breast cancer prognosis as being good(favorable) or poor(unfavorable) depending on the numerical value.

The present invention also provides a method for calculating a predictive value of the prognosis of breast cancer to provide information necessary for predicting or diagnosing the prognosis of a breast cancer patient, the method comprising:

(a) isolating mRNA from a sample of the breast cancer patient;

(b) measuring the mRNA expression level of at least one gene selected from the i-gene group consisting of TRBC1 (T cell receptor beta constant 1), BTN3A2 (butyrophilin, subfamily 3, member A2), and HLA-DPA1 (major histocompatibility complex, class II, DP alpha 1), and the mRNA expression level of at least one gene selected from the p-gene group consisting of AURKA (Aurora Kinase A), CCNB2 (Cyclin B2), FOXM1 (Forkhead box protein M1), MMP11 (Matrix Metallopeptidase 11), PTTG1 (Pituitary Tumor-Transforming 1), RACGAP1 (Rac GTPase Activating Protein 1), RRM2 (Ribonucleotide Reductase M2), TOP2A (Topoisomerase II Alpha) and UBE2C (Ubiquitin-Conjugating Enzyme E2C);

(c) normalizing the mRNA expression level of the gene; and (d) calculating a predictive value of the prognosis of breast cancer by combining the normalized value of the gene, wherein the predictive value indicates the prognosis of breast cancer as being good or poor.

Herein, the expression level of the target gene for detection needs to be normalized since the overall gene expression level may vary depending on the target patient or sample. The normalization is made through the difference in the expression of the gene, which can indicate the difference from the basic expression level, and preferably, the normalization may be carried out by measuring the expression levels of one to five genes selected from C-terminal-binding protein 1 (CTBP1), TATA-binding protein (TBP), hydroxymethylbilane synthase (HMBS), cullin 1 (CUL1), and ubiquilin-1 (UBQLN1) (or the mean of expression levels of selected multiple genes), and calculating the ratio thereof.

Meanwhile, the present invention provides a method for breast cancer prognosis prediction and diagnosis, the method comprising a step of using a primer pair to measure the mRNA expression level of a selected gene from a sample of a breast cancer patient, wherein the primer pair is for at least one gene selected from the group consisting of TRBC1, BTN3A2, and HLA-DPA1 and wherein the primer pair is capable of amplifying a target gene through PCR amplification.

Furthermore, the present invention provides a primer pair for at least one gene selected from the group consisting of TRBC1, BTN3A2, and HLA-DPA1, wherein the primer pair is capable of amplifying a target gene through PCR amplification.

Still furthermore, the present invention provides a use of a primer pair for preparing a preparation for predicting the prognosis of breast cancer, wherein the primer pair is for at least one gene selected from the group consisting of TRBC1, BTN3A2, and HLA-DPA1, and wherein the primer pair is capable of amplifying a target gene through PCR amplification.

Some embodiments of the present invention provide a method for diagnosing a prognosis of breast cancer and treating breast cancer in a breast cancer patient, the method comprising the steps of:

collecting a sample from the breast cancer patient;

isolating mRNA from the sample of the breast cancer patient;

measuring a first mRNA expression level for the mRNA of at least one i-gene selected from the group consisting of BTN3A2 (butyrophilin, subfamily 3, member A2), T cell receptor beta constant 1 (TRBC1), and major histocompatibility complex, class II, DP alpha 1 (HLA-DPA1), and a second mRNA expression level for the mRNA of at least one p-gene selected from the group consisting of the p-genes of the following Table 1;

normalizing the first and second mRNA expression levels to determine a normalized value;

diagnosing the prognosis of breast cancer patient by using the determined normalized value of the first and second mRNA expression levels, wherein an overexpression of the i-gene indicates a good prognosis of breast cancer, while an overexpression of the p-gene indicates a poor prognosis of breast cancer; and treating the diagnosed breast cancer patient by administering at least one of an anti-cancer agent, a surgery and a radiation therapy.

TABLE 1

List of p-genes

| No. | Gene ID | Gene Name |
|---|---|---|
| 1 | APITD1 | apoptosis-inducing, TAF9-like domain 1 |
| 2 | BID | BH3 interacting domain death agonist |
| 3 | BUB1B | BUB1 mitotic checkpoint serine/threonine kinase B |
| 4 | BUB1 | BUB1 mitotic checkpoint serine/threonine kinase |
| 5 | CKS1B | CDC28 protein kinase regulatory subunit 1B |
| 6 | CKS2 | CDC28 protein kinase regulatory subunit 2 |
| 7 | DLGAP5 | discs, large (Drosophila) homolog-associated protein 5 |
| 8 | POLA1 | polymerase (DNA directed), alpha 1, catalytic subunit |
| 9 | POLA2 | polymerase (DNA directed), alpha 2, accessory subunit |
| 10 | DSCC1 | DNA replication and sister chromatid cohesion 1 |
| 11 | DNA2 | DNA replication helicase/nuclease 2 |
| 12 | E2F8 | E2F transcription factor 8 |
| 13 | ERCC6L | excision repair cross-complementation group 6-like |
| 14 | FBXO5 | F-box protein 5 |
| 15 | FANCI | Fanconi anemia, complementation group I |
| 16 | GADD45GIP1 | growth arrest and DNA-damage-inducible, gamma interacting protein 1 |
| 17 | GINS1 | GINS complex subunit 1 (Psf1 homolog) |
| 18 | GINS2 | GINS complex subunit 2 (Psf2 homolog) |
| 19 | MAD2L1 | MAD2 mitotic arrest deficient-like 1 (yeast) |
| 20 | MAD2L1BP | MAD2L1 binding protein |
| 21 | MIS18A | MIS18 kinetochore protein A |
| 22 | MYBL2 | v-myb avian myeloblastosis viral oncogene homolog-like 2 |
| 23 | NAA50 | N(alpha)-acetyltransferase 50, NatE catalytic subunit |
| 24 | NEK2 | NIMA-related kinase 2 |
| 25 | NSL1 | NSL1, MIS12 kinetochore complex component |
| 26 | PBK | PDZ binding kinase |
| 27 | RAB11A | RAB11A, member RAS oncogene family |
| 28 | RAD51C | RAD51 paralog C |
| 29 | RAD54B | RAD54 homolog B (S. cerevisiae) |
| 30 | RANBP1 | RAN binding protein 1 |
| 31 | RALA | v-ral simian leukemia viral oncogene homolog A (ras related) |
| 32 | RACGAP1 | Rac GTPase activating protein 1 |
| 33 | SSNA1 | Sjogren syndrome nuclear autoantigen 1 |
| 34 | STAMBP | STAM binding protein |
| 35 | SSSCA1 | Sjogren syndrome/scleroderma autoantigen 1 |
| 36 | TAF2 | TAF2 RNA polymerase II, TATA box binding protein (TBP)-associated factor, 150 kDa |
| 37 | TIPIN | TIMELESS interacting protein |
| 38 | TIPRL | TOR signaling pathway regulator |
| 39 | TRIAP1 | TP53 regulated inhibitor of apoptosis 1 |
| 40 | TTK | TTK protein kinase |
| 41 | ZWINT | ZW10 interacting kinetochore protein |
| 42 | ASPM | asp (abnormal spindle) homolog, microcephaly associated (Drosophila) |
| 43 | AURKA | aurora kinase A |
| 44 | AURKB | aurora kinase B |
| 45 | BRD7 | bromodomain containing 7 |
| 46 | CSNK2A1 | casein kinase 2, alpha 1 polypeptide |
| 47 | CDC20 | cell division cycle 20 |
| 48 | CDC25C | cell division cycle 25C |
| 49 | CENPA | centromere protein A |
| 50 | CENPE | centromere protein E, 312 kDa |
| 51 | CENPF | centromere protein F, 350/400 kDa |
| 52 | CENPI | centromere protein I |
| 53 | CENPM | centromere protein M |
| 54 | CENPN | centromere protein N |
| 55 | CENPU | centromere protein U |
| 56 | CEP55 | centrosomal protein 55 kDa |
| 57 | CHEK1 | checkpoint kinase 1 |
| 58 | CDT1 | chromatin licensing and DNA replication factor 1 |
| 59 | C11orf80 | chromosome 11 open reading frame 80 |
| 60 | CCNA2 | cyclin A2 |
| 61 | CCNB1 | cyclin B1 |
| 62 | CCNB2 | cyclin B2 |
| 63 | CCNE2 | cyclin E2 |
| 64 | CDK1 | cyclin-dependent kinase 1 |
| 65 | CDKN3 | cyclin-dependent kinase inhibitor 3 |
| 66 | CKAP5 | cytoskeleton associated protein 5 |
| 67 | DTL | denticleless E3 ubiquitin protein ligase homolog (Drosophila) |
| 68 | DCTN2 | dynactin 2 (p50) |
| 69 | DYNLT1 | dynein, light chain, Tctex-type 1 |
| 70 | ECD | ecdysoneless homolog (Drosophila) |
| 71 | ECT2 | epithelial cell transforming 2 |
| 72 | EIF4G1 | eukaryotic translation initiation factor 4 gamma, 1 |
| 73 | EIF4EBP1 | eukaryotic translation initiation factor 4E binding protein 1 |
| 74 | EZR | ezrin |
| 75 | FEN1 | flap structure-specific endonuclease 1 |
| 76 | FOXM1 | forkhead box M1 |
| 77 | GSK3B | glycogen synthase kinase 3 beta |
| 78 | HMGN5 | high mobility group nucleosome binding domain 5 |
| 79 | INTS7 | integrator complex subunit 7 |
| 80 | KIF11 | kinesin family member 11 |
| 81 | KIF14 | kinesin family member 14 |
| 82 | KIF20A | kinesin family member 20A |
| 83 | KIF23 | kinesin family member 23 |
| 84 | KIF2C | kinesin family member 2C |
| 85 | KIF4A | kinesin family member 4A |
| 86 | KIFC1 | kinesin family member C1 |
| 87 | MIF | macrophage migration inhibitory factor (glycosylation-inhibiting factor) |
| 88 | MELK | maternal embryonic leucine zipper kinase |
| 89 | MED1 | mediator complex subunit 1 |
| 90 | MCM10 | minichromosome maintenance complex component 10 |
| 91 | MCM2 | minichromosome maintenance complex component 2 |
| 92 | MCM6 | minichromosome maintenance complex component 6 |
| 93 | MAP2K1 | mitogen-activated protein kinase kinase 1 |
| 94 | MSH6 | mutS homolog 6 |
| 95 | MLF1 | myeloid leukemia factor 1 |
| 96 | NCAPG | non-SMC condensin I complex, subunit G |
| 97 | NUSAP1 | nucleolar and spindle associated protein 1 |
| 98 | NUP155 | nucleoporin 155 kDa |
| 99 | NUP93 | nucleoporin 93 kDa |
| 100 | ORC4 | origin recognition complex, subunit 4 |
| 101 | ORC5 | origin recognition complex, subunit 5 |
| 102 | PIN1 | peptidylprolyl cis/trans isomerase, NIMA-interacting 1 |
| 103 | PIK3R4 | phosphoinositide-3-kinase, regulatory subunit 4 |
| 104 | PTTG1 | pituitary tumor-transforming 1 |
| 105 | PTTG3P | pituitary tumor-transforming 3, pseudogene |
| 106 | PLK1 | polo-like kinase 1 |
| 107 | PLK4 | polo-like kinase 4 |
| 108 | PRIM1 | primase, DNA, polypeptide 1 (49 kDa) |
| 109 | PA2G4 | proliferation-associated 2G4, 38 kDa |
| 110 | LEPREL4 | leprecan-like 4 |
| 111 | PSMC3 | proteasome (prosome, macropain) 26S subunit, ATPase, 3 |
| 112 | PSMC6 | proteasome (prosome, macropain) 26S subunit, ATPase, 6 |
| 113 | PSMD10 | proteasome (prosome, macropain) 26S subunit, non-ATPase, 10 |
| 114 | PSMD12 | proteasome (prosome, macropain) 26S subunit, non-ATPase, 12 |
| 115 | PSMD14 | proteasome (prosome, macropain) 26S subunit, non-ATPase, 14 |
| 116 | PSMD2 | proteasome (prosome, macropain) 26S subunit, non-ATPase, 2 |
| 117 | PSMD3 | proteasome (prosome, macropain) 26S subunit, non-ATPase, 3 |
| 118 | PSMD4 | proteasome (prosome, macropain) 26S subunit, non-ATPase, 4 |
| 119 | PSMD6 | proteasome (prosome, macropain) 26S subunit, non-ATPase, 6 |
| 120 | PSMD7 | proteasome (prosome, macropain) 26S subunit, non-ATPase, 7 |
| 121 | PSMA1 | proteasome (prosome, macropain) subunit, alpha type, 1 |
| 122 | PSMA2 | proteasome (prosome, macropain) subunit, alpha type, 2 |

TABLE 1-continued

List of p-genes

| No. | Gene ID | Gene Name |
|---|---|---|
| 123 | PSMA3 | proteasome (prosome, macropain) subunit, alpha type, 3 |
| 124 | PSMA4 | proteasome (prosome, macropain) subunit, alpha type, 4 |
| 125 | PSMA6 | proteasome (prosome, macropain) subunit, alpha type, 6 |
| 126 | PSMA7 | proteasome (prosome, macropain) subunit, alpha type, 7 |
| 127 | PSMB3 | proteasome (prosome, macropain) subunit, beta type, 3 |
| 128 | PSMB5 | proteasome (prosome, macropain) subunit, beta type, 5 |
| 129 | PSMB7 | proteasome (prosome, macropain) subunit, beta type, 7 |
| 130 | PRMT1 | protein arginine methyltransferase 1 |
| 131 | PPP2R3B | protein phosphatase 2, regulatory subunit B", beta |
| 132 | PPP3CA | protein phosphatase 3, catalytic subunit, alpha isozyme |
| 133 | PRC1 | protein regulator of cytokinesis 1 |
| 134 | RRM2 | ribonucleotide reductase M2 |
| 135 | RPS6KB1 | ribosomal protein S6 kinase, 70 kDa, polypeptide 1 |
| 136 | SPAG5 | sperm associated antigen 5 |
| 137 | SKA1 | spindle and kinetochore associated complex subunit 1 |
| 138 | STMN1 | stathmin 1 |
| 139 | SLBP | stem-loop binding protein |
| 140 | SMC2 | structural maintenance of chromosomes 2 |
| 141 | SMC4 | structural maintenance of chromosomes 4 |
| 142 | SMC5 | structural maintenance of chromosomes 5 |
| 143 | TERF1 | telomeric repeat binding factor (NIMA-interacting) 1 |
| 144 | TXNL4A | thioredoxin-like 4A |
| 145 | TRIP13 | thyroid hormone receptor interactor 13 |
| 146 | TOP2A | topoisomerase (DNA) II alpha 170 kDa |
| 147 | TFDP2 | transcription factor Dp-2 (E2F dimerization partner 2) |
| 148 | TACC3 | transforming, acidic coiled-coil containing protein 3 |
| 149 | TUBB3 | tubulin, beta 3 class III |
| 150 | TUBB4B | tubulin, beta 4B class IVb |
| 151 | TUBB | tubulin, beta class I |
| 152 | TSG101 | tumor susceptibility 101 |
| 153 | UBE2C | ubiquitin-conjugating enzyme E2C |
| 154 | UBE2L3 | ubiquitin-conjugating enzyme E2L 3 |
| 155 | UBE2S | ubiquitin-conjugating enzyme E2S |
| 156 | USP9X | ubiquitin specific peptidase 9, X-linked |
| 157 | VRK1 | vaccinia related kinase 1 |
| 158 | ZFHX3 | zinc finger homeobox 3 |
| 159 | ZWILCH | zwilch kinetochore protein |
| 160 | MMP11 | Matrix Metallopeptidase 11 |

In some exemplary embodiments of the present invention, the i-gene may be BTN3A2 (butyrophilin, subfamily 3, member A2).

In another exemplary embodiments of the present invention, the p-gene may be selected from the group consisting of AURKA (Aurora Kinase A), CCNB2 (Cyclin B2), FOXM1 (Forkhead box protein M1), MMP11 (Matrix Metallopeptidase 11), PTTG1 (Pituitary Tumor-Transforming 1), RACGAP1 (Rac GTPase Activating Protein 1), RRM2 (Ribonucleotide Reductase M2), TOP2A (Topoisomerase II Alpha) and UBE2C (Ubiquitin-Conjugating Enzyme E2C).

The steps of measuring mRNA expression levels of target genes and normalizing the measured mRNA expression levels are described above and well known in the art, while the step of treating the diagnosed breast cancer patient may be conducted by administering at least one of an anti-cancer agent, a surgery and a radiation therapy which is considered appropriate by one skilled in a cancer therapy.

The following references are made in the above-mentioned nucleotide and protein works (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press(1989); Deutscher, M., Guide to Protein Purification Methods Enzymology, vol. 182. Academic Press. Inc., San Diego, Calif. (1990); Ausubel et al., Current Protocols of Molecular Biology, John Wiley and Sons (1997); Rupp and Locker, Lab Invest. 56: A67 (1987); De Andres et al., BioTechniques 18: 42044 (1995); Held et al., Genome Research 6:986-994 (1996); T. E. Godfrey et al. J. Molec. Diagnostics 2: 84-91 (2000); K. Specht et al., Am. J. Pathol. 158: 419-29 (2001)).

Accordingly, the present invention provides a genetic marker for predicting or diagnosing the prognosis of early-stage breast cancer. The genetic marker of the present invention enables the prediction or diagnosis of the prognosis of a breast cancer patient, and thus can be favorably used to present clues for the future direction of breast cancer treatment, including the determination on whether anticancer treatment is needed.

Hereinafter, the present invention will be described in detail with reference to the following examples.

However, the following examples are merely for illustrating the present invention and are not intended to limit the scope of the present invention.

For examples in the present specification, the disclosures of Korean Patent Application Publication No. 10-2012-0079295 and PCT Publication No. WO2012093821A2 are entirely incorporated into the present specification by reference, and the level of the technical field to which the present pertain and the details of the present invention are explained more clearly.

Methods

Collection of Expression Profile in Early-Stage Breast Cancer Tissue

Expression profiles and clinical information obtained using frozen cancer tissues of early-stage breast cancer patients were collected from open database GEO (http://www.ncbi.nlm.nih.gov/geo). Each of a total nine independent expression profile sets was a relatively big dataset composed of 100 or more samples, and was made in order to conduct researches on prognosis of early-stage breast cancer patients (2, 4, 9, 10, 13, 25, 32, 33). Of these, eight datasets were made using microarray platform, Affymetrix U133A, and the other one dataset was manufactured using Agilent Hu25K. In most cases, important clinical information (age, sex, cancer size, cancer metastasis state, and degree of cancer differentiation) and survival information of patients were collected together. Of the eight datasets made by Affymetrix U133A, six datasets included survival information about distant metastasis (distant metastasis free survival), and the other two datasets included survival information about overall survival. Agilent data included survival information about distant metastasis. Survival analysis on the base of whether distant metastasis occurred or not was performed based on the facts that distant metastasis is the most decisive event in deciding prognosis, the distant metastasis is determined by unique characteristics of cancer, and the largest number of patients had information on the distant metastasis in the collected data. Through comparision of the collected information of all patients, the expression profiles of duplicated 186 cases were removed, and a total of 1,861 unique cases were researched. With respect to seven datasets made by the same platform (Affymetrix U133A), raw files (.CEL) of the expression profiles of corresponding patients were combined together, and then normalized. The normalization was conducted by the rma method (background correction: rma, normalization: quantile, summarization: medianpolish). For the normalization, custom CDF (http://brainarray.mbni.med.umich.edu/Brainarray/) ENTREZG version 13 developed by Manhong Dai et al., was used (34). After the normalization, the expression level of each probe was converted from the one-color expression level into, for example, the two-color expression level by subtracting the mean value of each probe in the discovery dataset. Of the total eight normalized dataset, five datasets were combined together, and then used as the discovery dataset, while two datasets were separately combined, and then used as validation dataset 1, and the other dataset was used as validation dataset 2. Agilent dataset was also used as validation dataset 3.

Prognosis of Patients and Definition of ER Status

In order to identify genes associated with prognosis of patients, the collected patients were classified into a good (favorable) prognostic group and a poor (unfavorable) prognostic group. In general clinical practice, five-year survival or metastasis information is used for such a classification. In other words, the prognosis is poor if metastasis or death occurs within five years, and the prognosis is good if metastasis or death does not occur within five years. The distribution of survival times of metastatic patients was investigated using patient information in the discovery dataset. About 73% or more of the metastatic patients had metastasis within 5 years, and less than 7% of them had metastasis after 10 years. Based on this fact, among patients in the discovery dataset, 217 patients who had metastasis within five years were classified as the "poor prognostic group", while 281 patients who had no metastasis for ten years or longer were classified as the "good prognostic group". As a result of classification, the median survival time of the good prognostic group was 2.4 years, while the median survival time of the poor prognostic group was 12.9 years. Error due to unreliable survival information could be minimized by clearly dividing the poor prognostic group and the good prognostic group. The expression or not of the estrogen receptor (ER) is the most commonly used criterion when breast cancer patients are classified by subtypes. In clinical practice, the breast cancer patients are classified into ER+ and ER− through ER immunohistochemistry (IHC) readout results by pathologists. Considering that about 200 patients had no ER IHC information in the collected discovery dataset, and the determination of ER IHC was made for each of five datasets constituting the discovery dataset, independently, the ER status was determined using the mRNA expression level of ESR1 gene in the expression profile for each patient. For the patients having ER IHC information, region of convergence (ROC) analysis was conducted using the ER IHC information and the ERS1 mRNA expression level. Through a comparison between the ER IHC results and the ERS1 mRNA expression level, the cutoff for ER status was determined at the point where the accuracy was highest (accuracy=0.88). The cases showing higher expression levels than the cutoff were classified as ER+, and the cases showing lower expression levels than the cutoff were classified as ER−. In the discovery dataset, 864 patients were designated as ER+ and 240 patients as ER−.

Selection of Prognostic Genes

The good prognosis group was defined as ER+, and the poor prognosis group was defined as ER− in the discovery dataset. 275 patients had good prognosis, while 218 patients had poor prognosis. Through significant analysis of microarray (SAM), genes showing a difference in the expression level among the prognostic groups were investigated. By using the q-value of the SAM analysis results, overexpressed genes in the good prognosis group and the poor prognosis group were selected. As a result of combining the selected genes, a total of 302 gene sets that were not duplicated have been made, and a cluster analysis for identifying expression patterns of these genes was conducted using the principal component analysis (PCA) method. Two principal components were selected, and in order to investigate biological functions related to each principal component, GO function analysis was performed for each cluster.

As a result of GO analysis, principal component 1 was shown to concentrate on the proliferation, whereas principal component 2 was shown to concentrate on the immune response. From genes belonging to two principal components involved in the proliferation and the immune response, genes showing the highest expression level between two prognosis groups were selected, respectively. The genes of the respective gene sets are named as p-gene in view of representing expression patterns of the proliferation and i-gene in view of representing expression patterns of the immune response, respectively.

Configuration of Prognostic Model Using Parametric Survival Analysis

Regression analysis in which expression levels of p-gene and i-gene were covariates was performed using the accelerated failure time (AFT) model of parametric survival models. Four p-genes were converted into p.mean by calculating the mean value for each patient, and five i-genes were also converted into i.mean by calculating the mean value of each patient before application. AFT model is specified as:

$$T_i = T_0 \exp(\beta_1 \chi_1 + \beta_2 \chi_2 + \ldots + \beta_q \chi_q) \varepsilon_i \qquad \text{Equation 1}$$

wherein, $T_i$ is the survival time of the i-th object; $T_0$ is the baseline survival time; $\chi_j$ is the vector of the covariates (j=1, 2, ..., q); $\beta$ is the coefficient of corresponding covariates; and $\varepsilon$ is the error. In this model, the covariates synergistically influence the baseline survival time, and thus this model is called the accelerated failure time (AFT) model in the industries in which this model is frequently used. The synergistic effect on the survival time, $\Phi = \beta_1 \chi_1 \chi_1 + \beta_2 \chi_2 + \ldots + \beta_q \chi_q$ is called the acceleration factor. Where the natural logarithm in Equation (1) is calculated, $$\log T_i = \log T_0 + \beta_1 \chi_1 + \beta_2 \chi_2 + \ldots + \beta_q \chi_q + \varepsilon^* \qquad \text{Equation 2}$$

Thus, the AFT model has the same form as the general linear regression model. However, since the dependent variable log T does not normally distribute and the survival analysis data always includes censored cases, which are not permitted in the linear regression model, Equation (2) cannot be processed like in the linear regression model. Since the distribution of $\varepsilon^*$ of Equation (2) may vary for different datasets, unlike where the normal distribution is assumed in the linear regression model, the practical statistical processing is inconvenient. In order to overcome this, log $T_0$ and $\varepsilon^*$ are modified, and expressed as follows:

$$\log T_i = \log T_0 + \beta_1 \chi_1 + \beta_2 \chi_2 + \ldots + \beta_q \chi_q + \sigma W \qquad \text{Equation 3}$$

wherein W follows the distribution of log T, and the variance thereof is fixed as the value of the normalized distribution. Here, $\sigma$ is the constant as the scale parameter, and the value thereof is determined depending on the dataset.

Various candidate prognostic models were fit to Weibull, loglogistic, and lognormal distributions, using AFT model, and then the most appropriate model was selected. For the risk distribution for AFT model, the hazard function, which can be obtained by creating the generation life table of survival information in the discovery dataset, was used. Since the hazard function obtained by the generation life table is shown to have a unimodal form, it was predicted that the Weibull, loglogistic, and lognormal distributions would be well appropriate. The final model was selected in consideration of Akaike's information criterion (AIC) and the R square (R2).

Validation of Prognostic Model

The performances of the selected model were assessed according to their "calibration" and "discrimination" aspects. "Calibration" is the degree of concurrence between the predicted survival probability produced by the prognostic model and the actually observed survival probability, and "Discrimination" is the ability of the prognostic model to correctly separate the given patient group into different prognostic groups. Herein, the actually observed survival probability refers to the value obtained by Kaplan-Meier method. The AFT-based prognostic model was used to obtain survival probabilities of all time zones for each patient. The survival probability predicted by the model was compared with the survival probability by Kaplan-Meier method. In order to obtain the predicted survival probabilities for the overall time period like in Kaplan-Meier, survival probability curves of all patients were obtained by calculating the mean survival probability for each time zone from 0 to 25 years by the 0.1 year unit. Together with the comparison of survival probability for the overall survival time, the 5-year survival probability was also compared. The 5-year predicted survival probability of patients produced by using the prognostic model in the given dataset was compared with, as the observed value, the 5-year survival probability calculated by using Hare which is the hazard regression analysis.

For "discrimination", the prognostic indexes of all patients in the given dataset were divided into four sections, and survival probabilities of patients for the respective sections were compared by the KM graph. The prognostic index is the dependent variable in the survival model. The more clearly the KM graphs of the four prognostic groups are separated, the better the discrimination power of the model.

Both "calibration" and "determination" for the discovery dataset and three independent validation datasets were investigated.

Important R packages used in statistical analysis are as below:
 affy: pre-processing of .CEL files using rma algorithm
 samr: identifying genes showing the difference in the expression level between prognostic groups
 GOstats: investigating function associated with selected gene set
 KMsurv: creating a life table using survival data of the discovery dataset
 rma: estimating coefficients of prognostic model using AFT model and conducting calibration on the model.

Selection of Gene Sets Applicable to FFPE Sample

RNA extracted from formalin-fixed paraffin embedded (FFPE) tissues and samples has not been accepted in the expression analysis due to many procedures causing the obstruction to RNA stability, such as immobilization causing cross-linking between tissues in the treatment process of tissues or samples. Herein, in order to develop a method for breast cancer prognosis prediction, suitable for FFPE samples, based on the actual breast cancer treatment procedure, gene sets were selected by placing a higher priority on genes having higher interqurtile ranges (IQR) and genes having higher mean expression levels in the order of higher degree of contribution, from p-genes (proliferation-related gene set) representing the expression pattern of proliferation and i-genes (immune response-related gene set) representing the expression pattern of the immune response, which were obtained according to the principal component analysis and function analysis with respect to the principal component analysis (GO function analysis or GO analysis).

As used herein, several genes having the same pattern in p-gene and i-gene were selected since the microarray data has a limitation in measuring accurate expression levels and the mean expression level for several genes rather than the expression level of one gene representing the pattern can represent the actual expression pattern better.

Measurement of Gene Correlation Between FFPE Sample and Frozen Sample and Selection of Genes 27 types of FFPE and frozen samples collected from the same patients were secured, and RNA was extracted from the FFPE or frozen samples by the RNA extraction method. The expression levels of 32 types of genes selected were measured by using the extracted RNA as a template.

The gene expression levels need to be normalized due to the difference thereof between individuals. Therefore, the expression levels of five genes selected as a normalization gene, that is, of C-terminal-binding protein 1 (CTBP1), TATA-binding protein (TBP), hydroxymethylbilane synthase (HMBS), cullin 1 (CUL1), and ubiquilin-1 (UBQLN1), were normalized, and then the gene expression correlation between FFPE sample and frozen sample was measured.

Based on the correlation measurement results and the expression level results for each gene, the genes that have a high correlation rate and various gene expression distributions between samples were finally selected as highly reliable genes for early-stage breast cancer prognosis prediction.

Results

Selection of Prognostic Genes for Prognostic Model

Five independent breast cancer datasets composed of expression profiles of early-stage breast cancer tissue were pooled into a discovery dataset of 1,104 samples. All patients did not receive chemotherapy, while most of them have little metastasis to axillary lymph nodes (N0 or N−), or have early-stage breast cancer (1st stage or 2nd stage). Among them, 1072 patients with information about distant metastasis were subjected to statistical analysis. In order to find genes associated with prognosis, expression profiles of the good prognostic group (having no metastasis for more than 10 years) and the poor prognostic group (having metastasis within 5 years) were compared. 182 genes showing high expression levels were selected from the good prognostic group, and 120 genes showing high expression levels were selected from the poor prognostic group (results not shown, FDR<0.001).

Principal component analysis was performed on the expression levels of the selected 302 genes. GO function analysis was performed on principal component 1 and principal component 2. Principal component 1 was definitely associated with the proliferation, while principal component 2 was strongly associated with the immune response. Based on this result, genes belonging to principal components 1 and 2 were selected, respective, and thus the prognostic model was allowed to reflect the two expression patterns.

Nine genes that were not only associated with the prognosis but also had the largest expression difference among the groups were selected. The gene selected from principal component 1 representing the proliferation is named p-gene, and the gene selected from principal 2 representing the immune response is named i-gene.

Comparison between ER+ Breast Cancer and ER– Breast Cancer

It is known that the expression or not of the estrogen receptor (ER) is closely associated with the occurrence and development of breast cancer. Two functions shown in the genes selected in association with prognosis, that is, proliferation and immune response are interestingly noticed in the mechanism of cancer. ER– breast cancer was compared with ER+ breast cancer using the selected 16 genes (p-genes and i-genes). In order to display the intensity of each function, the p-genes and i-genes were stratified into three stages (p1, p2, p3 or i1, i2, i3) according to the expression level. Here, p1 was a p-gene group showing the lowest expression level, and was assumed to make the slowest proliferation; p3 was a p-gene group showing the highest expression level, and was assumed to make the highest proliferation; and p2 was a p-gene group showing a moderate expression level, and was assumed to make a moderate level of proliferation. As used herein, it was an i-gene group showing the lowest expression level, and was assumed to make the weakest immune response; i3 was an i-gene group showing the highest expression level, and was assumed to make the strongest immune response; and i2 was considered to show a moderate expression level, and was assumed to do a moderate level of activity.

1,072 cases in the discovery dataset were classified according to the expression levels of p-gene and i-gene, and the intensity of each function according to the ER status was investigated. The proportion of p3 type indicating very active proliferation was higher in ER– breast cancer than in ER+ breast cancer. About 62% of ER– breast cancer cases showed very high p-gene expression levels (p3), while only 18% of ER+ breast cancer cases showed high p-gene expression levels, which supported the previously reported fact that ER– breast cancer tends to be more aggressive than ER+ breast cancer. About 35% of ER+ breast cancer cases showed weak p-genes (p1), while the proportion of p1 was only 9% in ER– breast cancer cases. The active immune response function is another characteristic of ER– breast cancer, and 38% or more of ER– breast cancer cases showed very high i-gene expression levels (i3). Whereas, only 21% of ER+ breast cancer cases showed high i-gene expression levels. It was observed that more active proliferation led to more active immune response in both ER+ and ER–, while ER– breast cancer showed a much more active immune response.

Besides, it was observed that the differentiation grade of the breast cancer was also closely related with the proliferation. Generally, poorly differentiated breast cancer (G3) showed a fast proliferation, whereas well-differentiated breast cancer (G1) showed a slow proliferation. It was observed that the prognosis of patients was also correlated with the proliferation. It was observed that more poor prognostic patients having metastasis within five years were concentrated in the group with a fast proliferation.

In summary, it was found that ER– breast cancer was more active than ER+ breast cancer in view of both the proliferation and the immune response, and it was supposed that the expression level of ER influences the mechanisms of occurrence and development of breast cancer.

Establishment of Prognostic Model

The AFT prognostic model of early-stage breast cancer patient metastasis was created using survival information of the discovery dataset and the selected p-genes and i-genes.

The generation life table on a yearly basis was created using the survival information of the discovery dataset, and the degree of hazard was roughly calculated.

Since the probability of death obtained by the generation life table is shown to have a unimodal form, it was predicted that the Weibull, loglogistic, and lognormal distributions would be well appropriate. The covariates to be included in the prognostic model are p.mean and i.mean. p.mean is the mean in the p-genes, and i.mean is the mean in the i-genes.

As a result of applying three models to the Weibull, loglogistic and lognormal distributions, the lognormal distribution was most appropriate. The final model following the lognormal distribution was selected using Akaikes information criterion (AIC).

$$\log(T) = -0.689 \times p.\text{mean} + 0.274 \times i.\text{mean} + 3.219 \quad \text{Equation 4}$$

According to the above estimated model, the p.mean, that is, the proliferation has a negative correlation (–0.689, p value=$2.47 \times e^{-17}$) with the survival time (T), and thus, more active proliferation shortens the survival time. On the contrary, the i.mean has a positive correlation (0.274, p value=$3.69 \times e^{-11}$) with the survival time, which indicates that a more active immune response lengthens the survival time. It could be concluded from the above estimated factors that proliferation plays a decisive role in the breast cancer prognosis, and more active proliferation leads to poor prognosis, while the immune response acts as a defense mechanism against fast proliferation.

Validation of Prognostic Model

The performances of the prognostic model, which was created using expression profiles for 1,072 early-stage breast cancer patients in the discovery dataset, were validated according to "calibration" and "discrimination" aspects. Here, the "calibration" is the degree of concurrence between the predicted survival probability produced through the model and the actually observed survival probability. The actually observed survival probability refers to the survival probability obtained using the Kaplan-Meier method. In addition, the "discrimination" is the ability of the model to correctly separate the patients into different prognostic groups. Validations for the two performances were performed on the discovery dataset developing the model and three independent validation datasets.

In the discovery dataset developing the prognostic model, the prognostic indexes (PI) were divided into four and classified into four prognostic groups. The survival probabilities observed in the four prognostic groups classified by the prognostic index were compared using the KM graph. As a result, it could be seen that four prognostic groups were very well classified, and the predicted survival probability corresponded well with the observed survival probability for each prognostic group.

The KM survival probability and the predicted survival probability produced by the prognostic model were compared with each other using the graph. The survival probabilities for all time zones of all patients were obtained in the prognostic model, and thus, in order to obtain the survival probability curve for the overall time period like the survival curve of KM, survival probability curves were drawn using the mean survival probability for each time zone (from 0 to 25 year, 0.1-year interval) of each patient. The predicted survival probability was slightly higher than the KM survival probability, but they are similar as a whole. In addition to the comparison of survival probability for the overall survival time, the comparison of 5-year survival probability was also conducted. The 5-year survival probability predicted by the model was similar to the actually observed 5-year survival probability. Particularly, as the predicted survival probability was higher, the concurrence between the predicted probability and the observed survival probability was stronger.

For more objective validation, the prognostic model was validated using three independent validation datasets. The first validation dataset was obtained by combining two datasets generated by Affymetrix U133A platform. The second validation dataset was the dataset generated by Affymetric U133A platform, and all were ER+ patients taking tamoxifen for five years. The third validation dataset was the dataset that was used to identify and validate 70 prognostic genes (currently, commercialized as MammaPrint) and generated by Agilent Hu25K platform. Validation datasets 1 and 2 were generated by the same platform as in the discovery dataset, Affymetrix U133A, and the expression levels thereof were normalized together with the discovery dataset. Validation datasets 1 and 2 were assessed in terms of calibration and discrimination aspects, while validation datasets 3 was assessed in terms of only the discrimination aspect due to the normalization of expression levels.

Selection of Gene Sets Applicable to FFPE Sample 32 types of genes were selected by placing a higher priority on genes having higher interqurtile ranges (IQR) and genes having higher mean expression levels in the order of higher degree of contribution, from 182 genes showing high expression levels in the good prognostic group and 120 genes showing high expression levels in the poor prognostic group in the discovery dataset of 1,104 samples.

Measurement of Gene Correlation Between FFPE Sample and Frozen Sample and Selection of Genes For the measurement of correlation between FFPE sample and frozen sample, samples that secure both FFPE sample and frozen sample from patients or their cancer tissues are needed. With respect to 27 pairs of FFPE and frozen samples thus obtained, the expression levels of 32 types of the selected genes and the correlation between FFPE and frozen samples were measured. Based on the measurement results, genes that have a high correlation rate and various gene expression distributions among samples were found 12 types in p-genes and 15 types in i-genes, which were selected as highly reliable genes for early-stage breast cancer prognosis prediction.

Among the selected genes above, 9 types of p-genes and 6 types of i-genes were selected as genes to be included in the kit for prognosis prediction.

The correlation measurement results for the respective genes are shown in FIGS. 6A-6I and 7A-7F. In each drawing, the solid line represents the equivalent value of the horizontal axis and the vertical axis (slope: 1, that is, the line that connects values of which the horizontal axis value is identical to the vertical axis value).

Meanwhile, among the respective genes, the expression levels of TRBC1, BTN3A2, and HLA-DPA1 were significantly different between the good prognostic group and the poor prognostic group. Through the above analysis, it could be concluded that the expression of TRBC1, BTN3A2, and HLA-DPA1 was significantly increased in the good prognostic group, verifying that their increased expression (overexpression) indicated good breast cancer prognosis.

Improvement in Predicting Prognosis of Breast Cancer Through Gene Combinations

The prognosis of each breast cancer patient is different among breast cancer patients, and the accurate prediction of the prognosis helps the patient to decide an appropriate treatment if needed. The purpose of this study was to investigate the gene expression in tissues of breast cancer patients after surgery so as to find a method for predicting a more accurate prognosis. For this purpose, the gene expression data collected from cancer tissues of early breast cancer patients (a total of 298 patients) was obtained from a public database GEO (http://www.ncbi.nlm.nih.gov/geo). The gene expression dataset as used in this experiment was obtained through microarray from 298 patients with ER+ breast cancer who had been treated with tamoxifen for 5 years after surgery.

For this purpose, RNA was extracted from cancer tissues of each patient and microarray experiment was performed according to the protocol of oligonucleotide microarray (U133A GeneChip; Affymetrix). The raw intensity values of the measured genes were normalized using MAS 5.0 (R/Bioconductor, www.bioconductor.org) and transformed into log 2 values. This dataset derived from this procedures was used to select a combination of genes which is capable of increasing a predictive performance of breast cancer prognosis through the combination of one of the i-genes, BTN3A2 gene and at least another prognostic genes.

Since the distant metastasis of breast cancer has a significant effect on the selection of the type of cancer therapy in comparison with its local or regional recurrence, Distant Metastasis Free Survival (DMFS) was designated as a primary endpoint in this analysis. As used herein, DMFS (Distant Metastasis Free Survival) means an interval between the surgery of a breast cancer patient and the diagnosis of a distant metastasis or death from any cause.

Figure 8:
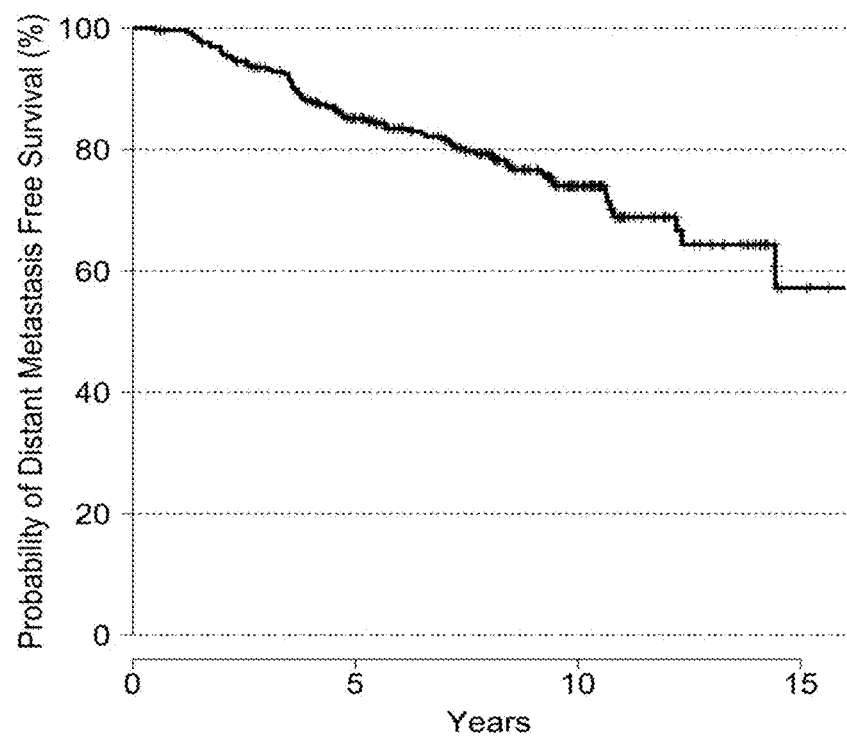
FIG. 8 shows a Kaplan-Meier plot of DIMES (Distant Metastasis Free Survival) over the course of 15 years for ER+ breast cancer patients who had been treated with tamoxifen for 5 years after surgery.

As shown in FIG. 8, it was found that the overall probability rate of DMFS (Distant Metastasis Free Survival) as determined by Kaplan-Meier estimation was 85.1% (81.0%-89.4%) within 5 years and 74.0% (68.5%-79.9%) within 10 years, respectively.

The C-index (concordance index) is an index for evaluating the accuracy of prediction in which the C-index of being closer to 1 is defined as being more accurate in prediction. The predictive accuracy of BTN3A2 gene for distant metastasis was found to be 0.55 through survival analysis.

Another prognosis-predictive indicator is a hazard ratio (HR) calculated via Cox's proportional hazard model. As for the risk of distant metastasis, when the hazard ratio is greater than 1, the risk of distant metastasis increases as the expression level of a target gene increases. On the contrary, when the hazard ratio is less than 1, the risk of distant metastasis decreases as the expression level of a target gene increases. With regard to BTN3A2 gene, its hazard ratio was found to be 0.82 (0.67-1.00), indicating that an increased expression of BTN3A2 gene is associated with a good prognosis.

TABLE 2

Prognostic Values of BTN3A2 gene

| Gene Name | C-Index | Hazard Ratio (HR) | |
| --- | --- | --- | --- |
| | | HR (95% C.I.) | p-value |
| BTN3A2 | 0.55 | 0.82 (0.67-1.00) | 0.046 |

Since BTN3A2 is known to be an immune-related gene, BTN3A2 gene was named 'i-gene' in this analysis. As shown in Table 2, these results suggest that BTN3A2 gene is a prognostic gene which can provide a statistically significant prognostic value.

Although BTN3A2 gene alone may provide a statistically significant prognostic value, the present inventors had sought to find a combination of BT3A2 gene and one or more another genes which leads to a more accurate prognosis prediction.

To determine the prognostic significance of another genes in combination with BTN3A2 gene, bivariate Cox analysis was conducted on BTN3A2 and a total of 13,268 another genes for predicting the probability of distant metastasis, respectively. Bivariate Cox analysis is used to determine whether each of two prognostic factors is an independent prognostic factor when the two prognostic factors are combined. Therefore, when each is confirmed as a significant (p-value<0.05) prognostic factor, the combination of the two factors is considered as a combination which may increase a prediction accuracy.

As a result of such bivariate Cox analysis, a total of 1,673 genes were found to be statistically significant (p-value<0.05) for predicting the probability of distant metastasis when used together with BTN3A2 gene. As used herein, those statistically significant genes are named as 'prognostic gene' as described above.

Further, among the prognostic 1,673 genes, a total of 1,635 genes as indicated in the following Table 3 were found to have a higher c-index (i.e., higher prediction accuracy) when used in combination with BTN3A2, in comparison with their single use.

Out of the 1,635 genes which have a higher c-index when used in combination with BTN3A2, a total of 848 genes were showed to be associated with a poor prognosis as their hazard ratio was greater than 1 in bivariate Cox analysis. Conversely, the hazard ratio of the remaining 786 genes was smaller than 1, respectively, indicating that they are associated with a good prognosis. For all of its combinations with each of the 1,635 genes, the hazard ratio of BTN3A2 was smaller than 1, indicating that BTN3A2 is associated with a good prognosis.

TABLE 3

1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
| --- | --- | --- | --- | --- | --- | --- | --- |
| 1 | A2M | 2 | alpha-2-macroglobulin | 0.81 | 0.044 | 0.56 | 0.003 |
| 2 | AAMDC | 28971 | adipogenesis associated, Mth938 domain containing | 0.79 | 0.025 | 1.33 | 0.014 |
| 3 | AATF | 26574 | apoptosis antagonizing transcription factor | 0.82 | 0.047 | 1.80 | 0.021 |
| 4 | ABAT | 18 | 4-aminobutyrate aminotransferase | 0.77 | 0.007 | 0.58 | 0.000 |
| 5 | ABCA1 | 19 | ATP-binding cassette, sub-family A (ABC1), member 1 | 0.79 | 0.015 | 1.89 | 0.005 |
| 6 | ABCA7 | 10347 | ATP-binding cassette, sub-family A (ABC1), member 7 | 0.79 | 0.026 | 0.63 | 0.028 |
| 7 | ABCB1 | 5243 | ATP-binding cassette, sub-family B (MDR/TAP), member 1 | 0.78 | 0.014 | 0.53 | 0.000 |
| 8 | ABCC1 | 4363 | ATP-binding cassette, sub-family C (CFTR/MRP), member 1 | 0.80 | 0.031 | 0.47 | 0.006 |
| 9 | ABCD4 | 5826 | ATP-binding cassette, sub-family D (ALD), member 4 | 0.81 | 0.039 | 0.35 | 0.000 |
| 10 | ABCE1 | 6059 | ATP-binding cassette, sub-family E (OABP), member 1 | 0.77 | 0.012 | 2.41 | 0.002 |
| 11 | ABCG1 | 9619 | ATP-binding cassette, sub-family G (WHITE), member 1 | 0.80 | 0.022 | 1.50 | 0.043 |
| 12 | ACACB | 32 | acetyl-CoA carboxylase beta | 0.78 | 0.017 | 0.60 | 0.005 |
| 13 | ACADVL | 37 | acyl-CoA dehydrogenase, very long chain | 0.77 | 0.014 | 0.51 | 0.004 |
| 14 | ACAT2 | 39 | acetyl-CoA acetyltransferase 2 | 0.78 | 0.011 | 2.01 | 0.004 |
| 15 | ACBD3 | 64746 | acyl-CoA binding domain containing 3 | 0.78 | 0.010 | 1.94 | 0.004 |
| 16 | ACBD4 | 79777 | acyl-CoA binding domain containing 4 | 0.78 | 0.006 | 0.52 | 0.001 |
| 17 | ACO1 | 48 | aconitase 1, soluble | 0.80 | 0.020 | 0.39 | 0.000 |
| 18 | ACOT13 | 55856 | acyl-CoA thioesterase 13 | 0.76 | 0.009 | 2.62 | 0.002 |
| 19 | ACOX1 | 51 | acyl-CoA oxidase 1, palmitoyl | 0.77 | 0.009 | 1.66 | 0.022 |
| 20 | ACTB | 60 | actin, beta | 0.77 | 0.011 | 0.52 | 0.010 |
| 21 | ACTG1 | 71 | actin, gamma 1 | 0.74 | 0.004 | 0.50 | 0.006 |
| 22 | ACTL6A | 86 | actin-like 6A | 0.81 | 0.042 | 2.28 | 0.003 |
| 23 | ACTR10 | 55860 | actin-related protein 10 homolog (S. cerevisiae) | 0.78 | 0.019 | 1.87 | 0.041 |
| 24 | ADAM2 | 2515 | ADAM metallopeptidase domain 2 | 0.79 | 0.023 | 1.22 | 0.021 |
| 25 | ADAMTS5 | 11096 | ADAM metallopeptidase with thrombospondin type 1 motif, 5 | 0.81 | 0.036 | 0.74 | 0.044 |
| 26 | ADCY9 | 115 | adenylate cyclase 9 | 0.81 | 0.020 | 0.51 | 0.001 |
| 27 | ADIPOR1 | 51094 | adiponectin receptor 1 | 0.81 | 0.040 | 2.14 | 0.002 |
| 28 | ADRA2A | 150 | adrenoceptor alpha 2A | 0.80 | 0.011 | 0.50 | 0.000 |
| 29 | ADSL | 158 | adenylosuccinate lyase | 0.77 | 0.011 | 2.67 | 0.004 |
| 30 | AGAP10 | 119016 | ArfGAP with GTPase domain, ankyrin repeat and PH domain 10 | 0.76 | 0.010 | 0.60 | 0.030 |
| 31 | AGAP11 | 119016 | ankyrin repeat and GTPase domain Arf GTPase activating protein 11 | 0.76 | 0.007 | 0.56 | 0.006 |
| 32 | AGBL2 | 79841 | ATP/GTP binding protein-like 2 | 0.79 | 0.015 | 0.59 | 0.020 |
| 33 | AGL | 178 | amylo-alpha-1, 6-glucosidase, 4-alpha-glucanotransferase | 0.79 | 0.022 | 1.28 | 0.035 |

TABLE 3-continued 1,635 prognostic genes for use in combination with BTN3A2 gene

| No. | Gene Symbol | GENE ID | Gene Name | BTN3A2 HR | p-value | prognostic gene HR | p-value |
|---|---|---|---|---|---|---|---|
| 34 | AHNAK | 79026 | AHNAK nucleoprotein | 0.76 | 0.005 | 0.60 | 0.009 |
| 35 | AHNAK2 | 113146 | AHNAK nucleoprotein 2 | 0.79 | 0.022 | 0.77 | 0.047 |
| 36 | AHSA2 | 130872 | AHA1, activator of heat shock 90 kDa protein ATPase homolog 2 (yeast) | 0.78 | 0.016 | 0.74 | 0.010 |
| 37 | AHSG | 197 | alpha-2-HS-glycoprotein | 0.77 | 0.012 | 1.50 | 0.001 |
| 38 | AK4 | 205 | adenylate kinase 4 | 0.80 | 0.028 | 0.67 | 0.016 |
| 39 | AK5 | 26289 | adenylate kinase 5 | 0.78 | 0.014 | 0.75 | 0.001 |
| 40 | AKAP11 | 11215 | A kinase (PRKA) anchor protein 11 | 0.81 | 0.043 | 0.56 | 0.010 |
| 41 | AKR7A2 | 8574 | aldo-keto reductase family 7, member A2 (aflatoxin aldehyde reductase) | 0.81 | 0.023 | 0.48 | 0.004 |
| 42 | ALDH18A1 | 5832 | aldehyde dehydrogenase 18 family, member A1 | 0.78 | 0.018 | 1.61 | 0.046 |
| 43 | ALDH1A2 | 8854 | aldehyde dehydrogenase 1 family, member A2 | 0.79 | 0.020 | 0.80 | 0.010 |
| 44 | ALDH6A1 | 4329 | aldehyde dehydrogenase 6 family, member A1 | 0.80 | 0.021 | 0.50 | 0.019 |
| 45 | ALMS1 | 7840 | Alstrom syndrome 1 | 0.78 | 0.011 | 0.72 | 0.048 |
| 46 | AMOTL2 | 51421 | angiomotin like 2 | 0.79 | 0.018 | 0.55 | 0.018 |
| 47 | AMT | 275 | aminomethyltransferase | 0.78 | 0.013 | 0.71 | 0.031 |
| 48 | ANGEL1 | 23357 | angel homolog 1 (Drosophila) | 0.77 | 0.016 | 0.59 | 0.039 |
| 49 | ANGPTL7 | 10218 | angiopoietin-like 7 | 0.78 | 0.017 | 0.78 | 0.038 |
| 50 | ANKRD10-IT1 | 100505494 | ANKRD10 intronic transcript 1 (non-protein coding) | 0.76 | 0.007 | 0.62 | 0.008 |
| 51 | ANKRD40 | 91369 | ankyrin repeat domain 40 | 0.77 | 0.014 | 1.26 | 0.048 |
| 52 | ANXA2 | 302 | annexin A2 | 0.77 | 0.012 | 1.93 | 0.018 |
| 53 | ANXA8 | 653145 | annexin A8 | 0.75 | 0.009 | 0.67 | 0.022 |
| 54 | AP1B1 | 162 | adaptor-related protein complex 1, beta 1 subunit | 0.79 | 0.021 | 1.63 | 0.045 |
| 55 | AP1M2 | 10053 | adaptor-related protein complex 1, mu 2 subunit | 0.82 | 0.048 | 1.57 | 0.024 |
| 56 | AP5M1 | 55745 | adaptor-related protein complex 5, mu 1 subunit | 0.78 | 0.011 | 1.69 | 0.020 |
| 57 | APITD1 | 378708 | apoptosis-inducing, TAF9-like domain 1 | 0.81 | 0.041 | 1.86 | 0.027 |
| 58 | APLP2 | 334 | amyloid beta (A4) precursor-like protein 2 | 0.81 | 0.024 | 0.67 | 0.033 |
| 59 | APOC1 | 341 | apolipoprotein C-I | 0.76 | 0.008 | 1.34 | 0.026 |
| 60 | APOC3 | 345 | apolipoprotein C-III | 0.77 | 0.015 | 1.62 | 0.000 |
| 61 | APOO | 79135 | apolipoprotein O | 0.74 | 0.007 | 2.27 | 0.000 |
| 62 | AQP1 | 358 | aquaporin 1 (Colton blood group) | 0.81 | 0.041 | 0.63 | 0.004 |
| 63 | AQP9 | 366 | aquaporin 9 | 0.77 | 0.007 | 1.33 | 0.001 |
| 64 | ARF1 | 375 | ADP-ribosylation factor 1 | 0.78 | 0.016 | 1.88 | 0.025 |
| 65 | ARGLU1 | 55082 | arginine and glutamate rich 1 | 0.79 | 0.026 | 0.58 | 0.001 |
| 66 | ARHGEF4 | 50649 | Rho guanine nucleotide exchange factor (GEF) 4 | 0.77 | 0.014 | 0.59 | 0.020 |
| 67 | ARHGEF5 | 7984 | Rho guanine nucleotide exchange factor (GEF) 5 | 0.82 | 0.049 | 0.76 | 0.040 |
| 68 | ARID4B | 23029 | AT rich interactive domain 4B (RBP1-like) | 0.78 | 0.011 | 1.57 | 0.029 |
| 69 | ARIH2 | 10425 | ariadne RBR E3 ubiquitin protein ligase 2 | 0.78 | 0.014 | 0.52 | 0.048 |
| 70 | ARMC1 | 55156 | armadillo repeat containing 1 | 0.81 | 0.043 | 1.75 | 0.001 |
| 71 | ARMC2-AS1 | 9551 | ARMC2 antisense RNA 1 | 0.80 | 0.026 | 1.83 | 0.043 |
| 72 | ARPC3 | 10094 | actin related protein 2/3 complex, subunit 3, 21 kDa | 0.78 | 0.012 | 1.60 | 0.039 |
| 73 | ARPC4 | 10093 | actin related protein 2/3 complex, subunit 4, 20 kDa | 0.78 | 0.014 | 0.68 | 0.003 |
| 74 | ARPC5L | 81873 | actin related protein 2/3 complex, subunit 5-like | 0.81 | 0.021 | 2.21 | 0.002 |
| 75 | ARPIN | 348110 | actin-related protein 2/3 complex inhibitor | 0.82 | 0.036 | 0.73 | 0.035 |
| 76 | ASAH1 | 427 | N-acylsphingosine amidohydrolase (acid ceramidase) 1 | 0.79 | 0.025 | 0.65 | 0.017 |
| 77 | ASAP1 | 50807 | ArfGAP with SH3 domain, ankyrin repeat and PH domain 1 | 0.80 | 0.020 | 2.14 | 0.002 |
| 78 | ASCC3 | 10973 | activating signal cointegrator 1 complex subunit 3 | 0.75 | 0.007 | 1.53 | 0.021 |
| 79 | ASH2L | 9070 | ash2 (absent, small, or homeotic)-like (Drosophila) | 0.81 | 0.037 | 1.80 | 0.003 |
| 80 | ASIC2 | 40 | acid-sensing (proton-gated) ion channel 2 | 0.82 | 0.046 | 1.24 | 0.045 |

TABLE 3-continued 1,635 prognostic genes for use in combination with BTN3A2 gene

| No. | Gene Symbol | GENE ID | Gene Name | BTN3A2 HR | p-value | prognostic gene HR | p-value |
|---|---|---|---|---|---|---|---|
| 81 | ASIC4 | 55515 | acid-sensing (proton-gated) ion channel family member 4 | 0.81 | 0.035 | 1.64 | 0.001 |
| 82 | ASL | 435 | argininosuccinate lyase | 0.80 | 0.024 | 1.67 | 0.030 |
| 83 | ASPM | 259266 | asp (abnormal spindle) homolog, microcephaly associated (*Drosophila*) | 0.79 | 0.011 | 1.32 | 0.002 |
| 84 | ASRGL1 | 80150 | asparaginase like 1 | 0.82 | 0.048 | 1.25 | 0.042 |
| 85 | ATAD2 | 29028 | ATPase family, AAA domain containing 2 | 0.80 | 0.022 | 1.39 | 0.004 |
| 86 | ATF6 | 22926 | activating transcription factor 6 | 0.80 | 0.022 | 1.76 | 0.018 |
| 87 | ATG101 | 60673 | autophagy related 101 | 0.80 | 0.038 | 1.84 | 0.035 |
| 88 | ATG5 | 9474 | autophagy related 5 | 0.74 | 0.003 | 2.16 | 0.002 |
| 89 | ATM | 472 | ATM serine/threonine kinase | 0.79 | 0.032 | 0.41 | 0.000 |
| 90 | ATOH1 | 474 | atonal homolog 1 (*Drosophila*) | 0.82 | 0.045 | 1.34 | 0.026 |
| 91 | ATP2A2 | 488 | ATPase, Ca++ transporting, cardiac muscle, slow twitch 2 | 0.82 | 0.050 | 1.99 | 0.008 |
| 92 | ATP5A1 | 498 | ATP synthase, H+ transporting, mitochondrial F1 complex, alpha subunit 1, cardiac muscle | 0.81 | 0.034 | 0.46 | 0.008 |
| 93 | ATP5C1 | 509 | ATP synthase, H+ transporting, mitochondrial F1 complex, gamma polypeptide 1 | 0.79 | 0.016 | 1.94 | 0.014 |
| 94 | ATP5H | 10476 | ATP synthase, H+ transporting, mitochondrial Fo complex, subunit d | 0.79 | 0.026 | 1.62 | 0.034 |
| 95 | ATP6V0B | 533 | ATPase, H+ transporting, lysosomal 21 kDa, V0 subunit b | 0.81 | 0.047 | 1.52 | 0.028 |
| 96 | ATP6V1E1 | 529 | ATPase, H+ transporting, lysosomal 31 kDa, V1 subunit E1 | 0.78 | 0.014 | 1.58 | 0.022 |
| 97 | ATP7B | 540 | ATPase, Cu++ transporting, beta polypeptide | 0.77 | 0.012 | 0.68 | 0.030 |
| 98 | ATP8B1 | 5205 | ATPase, aminophospholipid transporter, class I, type 8B, member 1 | 0.78 | 0.013 | 0.72 | 0.009 |
| 99 | AURKA | 6790 | aurora kinase A | 0.80 | 0.024 | 1.59 | 0.002 |
| 100 | AURKB | 9212 | aurora kinase B | 0.81 | 0.029 | 1.26 | 0.044 |
| 101 | AZGP1 | 563 | alpha-2-glycoprotein 1, zinc-binding | 0.79 | 0.020 | 0.80 | 0.031 |
| 102 | AZGP1 | 563 | alpha-2-glycoprotein 1, zinc-binding | 0.78 | 0.018 | 0.81 | 0.040 |
| 103 | AZIN1 | 51582 | antizyme inhibitor 1 | 0.79 | 0.024 | 1.86 | 0.000 |
| 104 | B3GALT4 | 8705 | UDP-Gal:betaGlcNAc beta 1,3-galactosyltransferase, polypeptide 4 | 0.81 | 0.035 | 1.50 | 0.035 |
| 105 | BANP | 54971 | BTG3 associated nuclear protein | 0.78 | 0.024 | 0.39 | 0.006 |
| 106 | BAP1 | 8314 | BRCA1 associated protein-1 (ubiquitin carboxy-terminal hydrolase) | 0.77 | 0.010 | 0.50 | 0.010 |
| 107 | BARX2 | 8538 | BARX homeobox 2 | 0.78 | 0.019 | 0.74 | 0.004 |
| 108 | BBOX1 | 8424 | butyrobetaine (gamma), 2-oxoglutarate dioxygenase (gamma-butyrobetaine hydroxylase) 1 | 0.81 | 0.043 | 0.86 | 0.029 |
| 109 | BBS1 | 582 | Bardet-Biedl syndrome 1 | 0.81 | 0.018 | 0.51 | 0.026 |
| 110 | BCAM | 4059 | basal cell adhesion molecule (Lutheran blood group) | 0.77 | 0.008 | 0.64 | 0.013 |
| 111 | BCAP29 | 55973 | B-cell receptor-associated protein 29 | 0.81 | 0.030 | 1.60 | 0.013 |
| 112 | BCAS2 | 10286 | breast carcinoma amplified sequence 2 | 0.79 | 0.017 | 1.64 | 0.034 |
| 113 | BCCIP | 56647 | BRCA2 and CDKN1A interacting protein | 0.77 | 0.013 | 1.37 | 0.017 |
| 114 | BCHE | 590 | butyrylcholinesterase | 0.79 | 0.016 | 0.84 | 0.043 |
| 115 | BET1 | 10282 | Bet1 golgi vesicular membrane trafficking protein | 0.80 | 0.026 | 1.66 | 0.047 |
| 116 | BICC1 | 80114 | BicC family RNA binding protein 1 | 0.80 | 0.026 | 0.52 | 0.025 |
| 117 | BID | 637 | BH3 interacting domain death agonist | 0.77 | 0.007 | 1.72 | 0.011 |
| 118 | BIK | 638 | BCL2-interacting killer (apoptosis-inducing) | 0.79 | 0.027 | 1.26 | 0.018 |
| 119 | BIN3 | 55909 | bridging integrator 3 | 0.77 | 0.012 | 0.44 | 0.001 |
| 120 | BIN3-IT1 | 80094 | BIN3 intronic transcript 1 (non-protein coding) | 0.81 | 0.031 | 0.67 | 0.001 |
| 121 | RDH5 | 100528022 | retinol dehydrogenase 5 (11-cis/9-cis) | 0.80 | 0.033 | 0.62 | 0.000 |
| 122 | BLZF1 | 8548 | basic leucine zipper nuclear factor 1 | 0.79 | 0.022 | 1.52 | 0.028 |
| 123 | BNC1 | 646 | basonuclin 1 | 0.77 | 0.012 | 0.83 | 0.041 |
| 124 | BOLA2 | 552900 | bolA family member 2 | 0.81 | 0.037 | 1.48 | 0.017 |
| 125 | BRD7 | 29117 | bromodomain containing 7 | 0.76 | 0.007 | 1.54 | 0.021 |
| 126 | BRIX1 | 55299 | BRX1, biogenesis of ribosomes, homolog (*S. cerevisiae*) | 0.80 | 0.028 | 1.45 | 0.044 |
| 127 | BSDC1 | 55108 | BSD domain containing 1 | 0.80 | 0.027 | 0.46 | 0.029 |
| 128 | BTF3 | 689 | basic transcription factor 3 | 0.78 | 0.014 | 0.46 | 0.003 |
| 129 | BTN1A1 | 696 | butyrophilin, subfamily 1, member A1 | 0.78 | 0.012 | 0.83 | 0.018 |

TABLE 3-continued 1,635 prognostic genes for use in combination with BTN3A2 gene

| | | | | BTN3A2 | | prognostic gene | |
|---|---|---|---|---|---|---|---|
| Gene No. | Gene Symbol | GENE ID | Gene Name | HR | p-value | HR | p-value |
| 130 | BUB1 | 699 | BUB1 mitotic checkpoint serine/threonine kinase | 0.78 | 0.014 | 1.73 | 0.005 |
| 131 | BUB1B | 701 | BUB1 mitotic checkpoint serine/threonine kinase B | 0.80 | 0.031 | 1.71 | 0.002 |
| 132 | BUD31 | 8896 | BUD31 homolog (S. cerevisiae) | 0.80 | 0.018 | 1.88 | 0.037 |
| 133 | BYSL | 705 | bystin-like | 0.76 | 0.009 | 1.51 | 0.017 |
| 134 | BZW1 | 9689 | basic leucine zipper and W2 domains 1 | 0.82 | 0.042 | 1.59 | 0.048 |
| 135 | BZW2 | 28969 | basic leucine zipper and W2 domains 2 | 0.82 | 0.048 | 1.58 | 0.006 |
| 136 | C11orf48 | 79081 | chromosome 11 open reading frame 48 | 0.77 | 0.010 | 1.56 | 0.018 |
| 137 | C11orf57 | 55216 | chromosome 11 open reading frame 57 | 0.77 | 0.013 | 0.44 | 0.037 |
| 138 | C11orf58 | 10944 | chromosome 11 open reading frame 58 | 0.79 | 0.023 | 1.86 | 0.036 |
| 139 | C11orf63 | 79864 | chromosome 11 open reading frame 63 | 0.79 | 0.019 | 0.74 | 0.001 |
| 140 | C11orf80 | 79703 | chromosome 11 open reading frame 80 | 0.82 | 0.039 | 1.31 | 0.004 |
| 141 | C12orf29 | 91298 | chromosome 12 open reading frame 29 | 0.81 | 0.033 | 1.42 | 0.026 |
| 142 | C14orf132 | 56967 | chromosome 14 open reading frame 132 | 0.80 | 0.024 | 0.74 | 0.040 |
| 143 | C16orf59 | 80178 | chromosome 16 open reading frame 59 | 0.81 | 0.034 | 1.29 | 0.021 |
| 144 | C16orf80 | 29105 | chromosome 16 open reading frame 80 | 0.76 | 0.008 | 1.58 | 0.037 |
| 145 | C17orf75 | 64149 | chromosome 17 open reading frame 75 | 0.79 | 0.024 | 1.33 | 0.020 |
| 146 | C18orf32 | 6139 | chromosome 18 open reading frame 32 | 0.81 | 0.044 | 0.58 | 0.015 |
| 147 | C19orf53 | 28974 | chromosome 19 open reading frame 53 | 0.78 | 0.017 | 1.72 | 0.025 |
| 148 | C19orf54 | 284325 | chromosome 19 open reading frame 54 | 0.80 | 0.029 | 0.54 | 0.000 |
| 149 | C1GALT1 | 56913 | core 1 synthase, glycoprotein-N-acetylgalactosamine 3-beta-galactosyltransferase 1 | 0.81 | 0.030 | 1.63 | 0.016 |
| 150 | C1orf21 | 81563 | chromosome 1 open reading frame 21 | 0.83 | 0.048 | 0.85 | 0.039 |
| 151 | C20orf24 | 55969 | chromosome 20 open reading frame 24 | 0.80 | 0.027 | 1.85 | 0.004 |
| 152 | C2orf43 | 60526 | chromosome 2 open reading frame 43 | 0.80 | 0.026 | 0.49 | 0.048 |
| 153 | TOMM7 | 201725 | translocase of outer mitochondrial membrane 7 homolog (yeast) | 0.80 | 0.025 | 0.44 | 0.002 |
| 154 | C5AR1 | 728 | complement component 5a receptor 1 | 0.80 | 0.023 | 1.44 | 0.032 |
| 155 | C7orf63 | 79846 | chromosome 7 open reading frame 63 | 0.79 | 0.024 | 0.82 | 0.018 |
| 156 | C9orf114 | 51490 | chromosome 9 open reading frame 114 | 0.80 | 0.023 | 1.72 | 0.029 |
| 157 | CA4 | 762 | carbonic anhydrase IV | 0.78 | 0.013 | 0.68 | 0.012 |
| 158 | CACNA1C | 775 | calcium channel, voltage-dependent, L type, alpha 1C subunit | 0.82 | 0.047 | 0.76 | 0.020 |
| 159 | CACNA1D | 776 | calcium channel, voltage-dependent, L type, alpha 1D subunit | 0.79 | 0.013 | 0.59 | 0.001 |
| 160 | CACNB2 | 783 | calcium channel, voltage-dependent, beta 2 subunit | 0.81 | 0.030 | 0.72 | 0.028 |
| 161 | CACNG1 | 786 | calcium channel, voltage-dependent, gamma subunit 1 | 0.83 | 0.043 | 1.45 | 0.000 |
| 162 | CACYBP | 27101 | calcyclin binding protein | 0.82 | 0.045 | 1.73 | 0.008 |
| 163 | CADM3-AS1 | 100131825 | CADM3 antisense RNA 1 | 0.78 | 0.011 | 0.68 | 0.031 |
| 164 | CADPS2 | 93664 | Ca++-dependent secretion activator 2 | 0.80 | 0.032 | 0.66 | 0.031 |
| 165 | CALCOCO1 | 57658 | calcium binding and coiled-coil domain 1 | 0.77 | 0.007 | 0.60 | 0.013 |
| 166 | CALML3 | 810 | calmodulin-like 3 | 0.73 | 0.006 | 0.65 | 0.003 |
| 167 | CAMKMT | 79823 | calmodulin-lysine N-methyltransferase | 0.81 | 0.036 | 0.73 | 0.037 |
| 168 | CAMKV | 79012 | CaM kinase-like vesicle-associated | 0.76 | 0.010 | 0.69 | 0.004 |
| 169 | CAMSAP1 | 157922 | calmodulin regulated spectrin-associated protein 1 | 0.82 | 0.036 | 2.34 | 0.031 |
| 170 | CAMSAP2 | 23271 | calmodulin regulated spectrin-associated protein family, member 2 | 0.81 | 0.040 | 1.67 | 0.021 |
| 171 | CAMTA2 | 23125 | calmodulin binding transcription activator 2 | 0.80 | 0.021 | 0.37 | 0.003 |
| 172 | CAND1 | 55832 | cullin-associated and neddylation-dissociated 1 | 0.80 | 0.022 | 1.71 | 0.014 |
| 173 | CAPN10 | 11132 | calpain 10 | 0.81 | 0.028 | 0.67 | 0.000 |
| 174 | CAPN15 | 6650 | calpain 15 | 0.80 | 0.038 | 0.59 | 0.026 |
| 175 | CAPRIN2 | 65981 | caprin family member 2 | 0.81 | 0.036 | 0.52 | 0.009 |
| 176 | CARD10 | 29775 | caspase recruitment domain family, member 10 | 0.79 | 0.018 | 0.64 | 0.004 |
| 177 | CASC1 | 55259 | cancer susceptibility candidate 1 | 0.80 | 0.024 | 0.75 | 0.003 |
| 178 | CASK | 8573 | calcium/calmodulin-dependent serine protein kinase (MAGUK family) | 0.82 | 0.044 | 1.54 | 0.034 |
| 179 | CASP2 | 835 | caspase 2, apoptosis-related cysteine peptidase | 0.76 | 0.009 | 0.60 | 0.032 |
| 180 | CASP3 | 836 | caspase 3, apoptosis-related cysteine peptidase | 0.77 | 0.008 | 2.03 | 0.016 |
| 181 | CASP5 | 838 | caspase 5, apoptosis-related cysteine peptidase | 0.80 | 0.038 | 1.26 | 0.044 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 182 | CAST | 831 | calpastatin | 0.81 | 0.046 | 0.59 | 0.022 |
| 183 | CATSPER2 | 117155 | cation channel, sperm associated 2 | 0.79 | 0.017 | 0.72 | 0.003 |
| 184 | CBX7 | 23492 | chromobox homolog 7 | 0.81 | 0.040 | 0.74 | 0.014 |
| 185 | CCBL1 | 883 | cysteine conjugate-beta lyase, cytoplasmic | 0.76 | 0.007 | 0.61 | 0.027 |
| 186 | CCDC101 | 112869 | coiled-coil domain containing 101 | 0.81 | 0.034 | 0.49 | 0.035 |
| 187 | CCDC132 | 55610 | coiled-coil domain containing 132 | 0.80 | 0.024 | 0.79 | 0.031 |
| 188 | CCDC176 | 80127 | coiled-coil domain containing 176 | 0.76 | 0.011 | 0.48 | 0.002 |
| 189 | CCDC59 | 29080 | coiled-coil domain containing 59 | 0.77 | 0.008 | 2.26 | 0.002 |
| 190 | CCNA2 | 890 | cyclin A2 | 0.82 | 0.043 | 1.70 | 0.006 |
| 191 | CCNB1 | 891 | cyclin B1 | 0.79 | 0.021 | 1.58 | 0.004 |
| 192 | CCNB2 | 9133 | cyclin B2 | 0.77 | 0.007 | 1.67 | 0.001 |
| 193 | CCNC | 892 | cyclin C | 0.80 | 0.021 | 1.68 | 0.043 |
| 194 | CCNE2 | 9134 | cyclin E2 | 0.80 | 0.027 | 2.07 | 0.000 |
| 195 | CCNO | 10309 | cyclin O | 0.80 | 0.026 | 0.80 | 0.027 |
| 196 | CCR6 | 1235 | chemokine (C-C motif) receptor 6 | 0.81 | 0.042 | 0.75 | 0.011 |
| 197 | CCT3 | 7203 | chaperonin containing TCP1, subunit 3 (gamma) | 0.76 | 0.010 | 2.35 | 0.001 |
| 198 | CCT5 | 22948 | chaperonin containing TCP1, subunit 5 (epsilon) | 0.79 | 0.015 | 1.73 | 0.008 |
| 199 | CCT6A | 908 | chaperonin containing TCP1, subunit 6A (zeta 1) | 0.78 | 0.010 | 2.45 | 0.000 |
| 200 | CD55 | 1604 | CD55 molecule, decay accelerating factor for complement (Cromer blood group) | 0.78 | 0.027 | 1.43 | 0.039 |
| 201 | CDC14B | 8555 | cell division cycle 14B | 0.74 | 0.006 | 0.48 | 0.004 |
| 202 | CDC20 | 991 | cell division cycle 20 | 0.78 | 0.011 | 1.32 | 0.019 |
| 203 | CDC25C | 995 | cell division cycle 25C | 0.80 | 0.038 | 1.70 | 0.011 |
| 204 | CDIPT | 10423 | CDP-diacylglycerol--inositol 3-phosphatidyltransferase | 0.79 | 0.028 | 0.63 | 0.012 |
| 205 | CDK1 | 983 | cyclin-dependent kinase 1 | 0.76 | 0.005 | 1.56 | 0.001 |
| 206 | CDK2AP2 | 10263 | cyclin-dependent kinase 2 associated protein 2 | 0.78 | 0.014 | 1.43 | 0.019 |
| 207 | CDK5RAP3 | 80279 | CDK5 regulatory subunit associated protein 3 | 0.78 | 0.015 | 0.63 | 0.023 |
| 208 | CDKN1C | 1028 | cyclin-dependent kinase inhibitor 1C (p57, Kip2) | 0.83 | 0.044 | 0.51 | 0.001 |
| 209 | CDKN3 | 1033 | cyclin-dependent kinase inhibitor 3 | 0.81 | 0.037 | 2.26 | 0.000 |
| 210 | CDO1 | 1036 | cysteine dioxygenase type 1 | 0.81 | 0.035 | 0.66 | 0.006 |
| 211 | CDT1 | 81620 | chromatin licensing and DNA replication factor 1 | 0.78 | 0.015 | 1.32 | 0.040 |
| 212 | CELA2A | 51032 | chymotrypsin-like elastase family, member 2A | 0.81 | 0.031 | 1.27 | 0.038 |
| 213 | CELSR2 | 1952 | cadherin, EGF LAG seven-pass G-type receptor 2 | 0.78 | 0.014 | 0.68 | 0.013 |
| 214 | CENPA | 1058 | centromere protein A | 0.73 | 0.002 | 2.00 | 0.000 |
| 215 | CENPBD1P1 | 65996 | CENPBD1 pseudogene 1 | 0.78 | 0.016 | 1.33 | 0.047 |
| 216 | CENPE | 1062 | centromere protein E, 312 kDa | 0.78 | 0.012 | 1.33 | 0.001 |
| 217 | CENPF | 1063 | centromere protein F, 350/400 kDa | 0.79 | 0.016 | 1.64 | 0.002 |
| 218 | CENPI | 2491 | centromere protein I | 0.81 | 0.030 | 1.50 | 0.040 |
| 219 | CENPM | 79019 | centromere protein M | 0.75 | 0.005 | 1.39 | 0.001 |
| 220 | CENPN | 55839 | centromere protein N | 0.78 | 0.006 | 1.50 | 0.001 |
| 221 | CENPU | 79682 | centromere protein U | 0.79 | 0.025 | 1.77 | 0.000 |
| 222 | CEP164 | 22897 | centrosomal protein 164 kDa | 0.74 | 0.003 | 0.51 | 0.002 |
| 223 | CEP55 | 55165 | centrosomal protein 55 kDa | 0.75 | 0.007 | 1.48 | 0.001 |
| 224 | CFHR4 | 10877 | complement factor H-related 4 | 0.79 | 0.020 | 1.40 | 0.014 |
| 225 | CFHR5 | 81494 | complement factor H-related 5 | 0.79 | 0.024 | 0.71 | 0.041 |
| 226 | CH25H | 9023 | cholesterol 25-hydroxylase | 0.81 | 0.042 | 0.77 | 0.027 |
| 227 | CHAC1 | 79094 | ChaC, cation transport regulator homolog 1 (*E. coli*) | 0.81 | 0.043 | 1.45 | 0.033 |
| 228 | CHD3 | 1107 | chromodomain helicase DNA binding protein 3 | 0.73 | 0.003 | 0.39 | 0.001 |
| 229 | CHEK1 | 1111 | checkpoint kinase 1 | 0.80 | 0.024 | 1.75 | 0.016 |
| 230 | CHL1 | 10752 | cell adhesion molecule L1-like | 0.81 | 0.041 | 0.86 | 0.040 |
| 231 | CHN1 | 1123 | chimerin 1 | 0.78 | 0.010 | 1.44 | 0.010 |
| 232 | CHRNB2 | 1141 | cholinergic receptor, nicotinic, beta 2 (neuronal) | 0.78 | 0.022 | 1.39 | 0.017 |
| 233 | CHRNB4 | 1143 | cholinergic receptor, nicotinic, beta 4 (neuronal) | 0.79 | 0.016 | 0.83 | 0.032 |
| 234 | CIC | 23152 | capicua transcriptional repressor | 0.78 | 0.015 | 0.65 | 0.023 |
| 235 | CIDEC | 63924 | cell death-inducing DFFA-like effector c | 0.82 | 0.037 | 0.61 | 0.009 |

TABLE 3-continued 1,635 prognostic genes for use in combination with BTN3A2 gene

| No. | Gene Symbol | GENE ID | Gene Name | BTN3A2 HR | BTN3A2 p-value | prognostic gene HR | prognostic gene p-value |
|---|---|---|---|---|---|---|---|
| 236 | CILP | 8483 | cartilage intermediate layer protein, nucleotide pyrophosphohydrolase | 0.81 | 0.042 | 0.80 | 0.026 |
| 237 | CIRBP | 1153 | cold inducible RNA binding protein | 0.75 | 0.004 | 0.47 | 0.000 |
| 238 | CKAP5 | 9793 | cytoskeleton associated protein 5 | 0.78 | 0.020 | 2.12 | 0.022 |
| 239 | CKS1B | 1163 | CDC28 protein kinase regulatory subunit 1B | 0.78 | 0.013 | 1.52 | 0.027 |
| 240 | CKS2 | 1164 | CDC28 protein kinase regulatory subunit 2 | 0.79 | 0.023 | 1.55 | 0.002 |
| 241 | CLCN7 | 1186 | chloride channel, voltage-sensitive 7 | 0.78 | 0.014 | 0.62 | 0.029 |
| 242 | CLDN8 | 9073 | claudin 8 | 0.82 | 0.038 | 0.64 | 0.000 |
| 243 | CLIP2 | 7461 | CAP-GLY domain containing linker protein 2 | 0.82 | 0.039 | 0.68 | 0.016 |
| 244 | CLK4 | 57396 | CDC-like kinase 4 | 0.80 | 0.023 | 0.56 | 0.005 |
| 245 | CLPB | 81570 | ClpB caseinolytic peptidase B homolog (E. coli) | 0.78 | 0.016 | 1.19 | 0.048 |
| 246 | CLPP | 8192 | caseinolytic mitochondrial matrix peptidase proteolytic subunit | 0.77 | 0.013 | 1.48 | 0.015 |
| 247 | CLPS | 1208 | colipase, pancreatic | 0.80 | 0.035 | 1.28 | 0.048 |
| 248 | CLUAP1 | 23059 | clusterin associated protein 1 | 0.82 | 0.027 | 0.43 | 0.010 |
| 249 | CLUHP3 | 100132341 | clustered mitochondria (cluA/CLU1) homolog pseudogene 3 | 0.82 | 0.046 | 0.61 | 0.000 |
| 250 | CMC2 | 56942 | C-x(9)-C motif containing 2 | 0.68 | 0.000 | 2.37 | 0.000 |
| 251 | CNIH4 | 29097 | cornichon family AMPA receptor auxiliary protein 4 | 0.77 | 0.011 | 1.73 | 0.002 |
| 252 | CNKSR1 | 10256 | connector enhancer of kinase suppressor of Ras 1 | 0.80 | 0.035 | 0.45 | 0.001 |
| 253 | CNN3 | 1266 | calponin 3, acidic | 0.83 | 0.045 | 0.64 | 0.002 |
| 254 | CNPY2 | 10330 | canopy FGF signaling regulator 2 | 0.75 | 0.007 | 1.73 | 0.025 |
| 255 | CNR1 | 1268 | cannabinoid receptor 1 (brain) | 0.75 | 0.008 | 0.63 | 0.005 |
| 256 | COL16A1 | 1307 | collagen, type XVI, alpha 1 | 0.82 | 0.039 | 0.62 | 0.002 |
| 257 | COL17A1 | 1308 | collagen, type XVII, alpha 1 | 0.81 | 0.031 | 0.73 | 0.005 |
| 258 | COL19A1 | 1310 | collagen, type XIX, alpha 1 | 0.77 | 0.014 | 1.28 | 0.038 |
| 259 | COL4A6 | 1288 | collagen, type IV, alpha 6 | 0.78 | 0.014 | 0.61 | 0.002 |
| 260 | COL7A1 | 1294 | collagen, type VII, alpha 1 | 0.81 | 0.035 | 0.76 | 0.048 |
| 261 | COMMD8 | 54951 | COMM domain containing 8 | 0.79 | 0.014 | 1.53 | 0.037 |
| 262 | COPB1 | 1315 | coatomer protein complex, subunit beta 1 | 0.80 | 0.024 | 2.57 | 0.005 |
| 263 | COPB2 | 9276 | coatomer protein complex, subunit beta 2 (beta prime) | 0.76 | 0.004 | 1.96 | 0.001 |
| 264 | COPS3 | 8533 | COP9 signalosome subunit 3 | 0.80 | 0.025 | 1.63 | 0.034 |
| 265 | COPS4 | 51138 | COP9 signalosome subunit 4 | 0.79 | 0.035 | 2.32 | 0.009 |
| 266 | COQ2 | 27235 | coenzyme Q2 4-hydroxybenzoate polyprenyltransferase | 0.79 | 0.013 | 1.67 | 0.013 |
| 267 | COQ3 | 51805 | coenzyme Q3 methyltransferase | 0.81 | 0.026 | 3.03 | 0.001 |
| 268 | CORO1C | 23603 | coronin, actin binding protein, 1C | 0.74 | 0.003 | 1.78 | 0.003 |
| 269 | COX17 | 10063 | COX17 cytochrome c oxidase copper chaperone | 0.78 | 0.017 | 1.75 | 0.001 |
| 270 | COX6B1 | 1340 | cytochrome c oxidase subunit VIb polypeptide 1 (ubiquitous) | 0.77 | 0.010 | 2.22 | 0.002 |
| 271 | COX7B | 1349 | cytochrome c oxidase subunit VIIb | 0.78 | 0.013 | 1.81 | 0.014 |
| 272 | CPEB1 | 64506 | cytoplasmic polyadenylation element binding protein 1 | 0.81 | 0.039 | 0.64 | 0.025 |
| 273 | CPNE3 | 8895 | copine III | 0.80 | 0.031 | 2.00 | 0.000 |
| 274 | CPSF6 | 11052 | cleavage and polyadenylation specific factor 6, 68 kDa | 0.77 | 0.010 | 2.50 | 0.008 |
| 275 | CREB3L2 | 64764 | cAMP responsive element binding protein 3-like 2 | 0.82 | 0.045 | 0.54 | 0.032 |
| 276 | CRELD1 | 78987 | cysteine-rich with EGF-like domains 1 | 0.82 | 0.044 | 0.54 | 0.042 |
| 277 | CRIM1 | 51232 | cysteine rich transmembrane BMP regulator 1 (chordin-like) | 0.80 | 0.025 | 0.73 | 0.028 |
| 278 | CRIPT | 9419 | cysteine-rich PDZ-binding protein | 0.78 | 0.016 | 1.42 | 0.024 |
| 279 | CRISP3 | 10321 | cysteine-rich secretory protein 3 | 0.79 | 0.019 | 1.08 | 0.043 |
| 280 | CRNKL1 | 51340 | crooked neck pre-mRNA splicing factor 1 | 0.80 | 0.033 | 1.50 | 0.041 |
| 281 | CROT | 54677 | carnitine O-octanoyltransferase | 0.79 | 0.024 | 0.60 | 0.002 |
| 282 | CRTAP | 10491 | cartilage associated protein | 0.78 | 0.012 | 0.39 | 0.001 |
| 283 | CRTC3 | 64784 | CREB regulated transcription coactivator 3 | 0.80 | 0.030 | 0.52 | 0.042 |
| 284 | CRYBA2 | 1412 | crystallin, beta A2 | 0.79 | 0.018 | 1.51 | 0.008 |
| 285 | CSAD | 51380 | cysteine sulfinic acid decarboxylase | 0.77 | 0.009 | 0.76 | 0.021 |
| 286 | CSH1 | 1442 | chorionic somatomammotropin hormone 1 (placental lactogen) | 0.80 | 0.037 | 1.45 | 0.007 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 287 | CSNK1G2 | 1455 | casein kinase 1, gamma 2 | 0.77 | 0.008 | 0.47 | 0.009 |
| 288 | CSNK2A1 | 1457 | casein kinase 2, alpha 1 polypeptide | 0.75 | 0.004 | 2.13 | 0.002 |
| 289 | CSNK2B | 1460 | casein kinase 2, beta polypeptide | 0.78 | 0.016 | 1.62 | 0.044 |
| 290 | CSRP1 | 1465 | cysteine and glycine-rich protein 1 | 0.80 | 0.021 | 0.60 | 0.011 |
| 291 | CSTF1 | 1477 | cleavage stimulation factor, 3' pre-RNA, subunit 1, 50 kDa | 0.76 | 0.007 | 1.63 | 0.005 |
| 292 | CTDSP1 | 58190 | CTD (carboxy-terminal domain, RNA polymerase II, polypeptide A) small phosphatase 1 | 0.78 | 0.013 | 0.49 | 0.006 |
| 293 | CTDSPL | 10217 | CTD (carboxy-terminal domain, RNA polymerase II, polypeptide A) small phosphatase-like | 0.80 | 0.014 | 0.54 | 0.005 |
| 294 | CTNNB1 | 1499 | catenin (cadherin-associated protein), beta 1, 88 kDa | 0.80 | 0.016 | 0.64 | 0.028 |
| 295 | CTNNBL1 | 56259 | catenin, beta like 1 | 0.78 | 0.013 | 1.64 | 0.021 |
| 296 | CTNND1 | 1500 | catenin (cadherin-associated protein), delta 1 | 0.81 | 0.024 | 0.47 | 0.008 |
| 297 | CTNS | 1497 | cystinosin, lysosomal cystine transporter | 0.81 | 0.041 | 0.35 | 0.003 |
| 298 | CTSA | 5476 | cathepsin A | 0.79 | 0.022 | 1.63 | 0.030 |
| 299 | CTSG | 1511 | cathepsin G | 0.79 | 0.024 | 0.78 | 0.028 |
| 300 | CTSV | 1515 | cathepsin V | 0.82 | 0.042 | 1.35 | 0.047 |
| 301 | CXCL10 | 3627 | chemokine (C-X-C motif) ligand 10 | 0.74 | 0.004 | 1.29 | 0.027 |
| 302 | CXCL11 | 6373 | chemokine (C-X-C motif) ligand 11 | 0.72 | 0.001 | 1.42 | 0.003 |
| 303 | CXCL9 | 4283 | chemokine (C-X-C motif) ligand 9 | 0.75 | 0.004 | 1.20 | 0.036 |
| 304 | CXorf40A | 91966 | chromosome X open reading frame 40A | 0.80 | 0.031 | 1.44 | 0.022 |
| 305 | CXorf40A | 91966 | chromosome X open reading frame 40A | 0.80 | 0.030 | 1.64 | 0.005 |
| 306 | CXorf40B | 541578 | chromosome X open reading frame 40B | 0.80 | 0.029 | 1.42 | 0.033 |
| 307 | CXXC1 | 30827 | CXXC finger protein 1 | 0.76 | 0.006 | 0.52 | 0.007 |
| 308 | CYCS | 54205 | cytochrome c, somatic | 0.82 | 0.032 | 1.80 | 0.005 |
| 309 | CYP4A11 | 1579 | cytochrome P450, family 4, subfamily A, polypeptide 11 | 0.77 | 0.010 | 0.76 | 0.014 |
| 310 | CYP4F8 | 11283 | cytochrome P450, family 4, subfamily F, polypeptide 8 | 0.78 | 0.025 | 0.89 | 0.019 |
| 311 | CYR61 | 3491 | cysteine-rich, angiogenic inducer, 61 | 0.82 | 0.041 | 0.79 | 0.026 |
| 312 | CYSLTR2 | 57105 | cysteinyl leukotriene receptor 2 | 0.77 | 0.010 | 0.80 | 0.024 |
| 313 | DAAM1 | 23002 | dishevelled associated activator of morphogenesis 1 | 0.81 | 0.036 | 1.90 | 0.002 |
| 314 | DAD1 | 1603 | defender against cell death 1 | 0.80 | 0.038 | 1.77 | 0.037 |
| 315 | DARS2 | 55157 | aspartyl-tRNA synthetase 2, mitochondrial | 0.82 | 0.050 | 1.75 | 0.024 |
| 316 | DBT | 1629 | dihydrolipoamide branched chain transacylase E2 | 0.76 | 0.008 | 0.69 | 0.016 |
| 317 | DCK | 1633 | deoxycytidine kinase | 0.77 | 0.007 | 1.70 | 0.004 |
| 318 | DCTN2 | 10540 | dynactin 2 (p50) | 0.77 | 0.012 | 1.85 | 0.015 |
| 319 | DCUN1D1 | 54165 | DCN1, defective in cullin neddylation 1, domain containing 1 | 0.77 | 0.010 | 2.50 | 0.003 |
| 320 | DDX17 | 10521 | DEAD (Asp-Glu-Ala-Asp) box helicase 17 | 0.77 | 0.009 | 0.55 | 0.013 |
| 321 | DDX23 | 9416 | DEAD (Asp-Glu-Ala-Asp) box polypeptide 23 | 0.76 | 0.009 | 1.70 | 0.006 |
| 322 | DDX39A | 10212 | DEAD (Asp-Glu-Ala-Asp) box polypeptide 39A | 0.80 | 0.017 | 1.92 | 0.005 |
| 323 | DDX49 | 54555 | DEAD (Asp-Glu-Ala-Asp) box polypeptide 49 | 0.78 | 0.015 | 1.76 | 0.032 |
| 324 | DDX5 | 1655 | DEAD (Asp-Glu-Ala-Asp) box helicase 5 | 0.79 | 0.022 | 0.59 | 0.030 |
| 325 | DERL1 | 79139 | derlin 1 | 0.74 | 0.003 | 1.89 | 0.000 |
| 326 | DGAT1 | 8694 | diacylglycerol O-acyltransferase 1 | 0.81 | 0.033 | 1.33 | 0.040 |
| 327 | DGKA | 1606 | diacylglycerol kinase, alpha 80 kDa | 0.79 | 0.029 | 0.51 | 0.010 |
| 328 | DHCR24 | 1718 | 24-dehydrocholesterol reductase | 0.79 | 0.015 | 0.66 | 0.013 |
| 329 | DHCR7 | 1717 | 7-dehydrocholesterol reductase | 0.80 | 0.030 | 1.40 | 0.011 |
| 330 | DHPS | 1725 | deoxyhypusine synthase | 0.78 | 0.018 | 1.47 | 0.017 |
| 331 | DHX9 | 1660 | DEAH (Asp-Glu-Ala-His) box helicase 9 | 0.80 | 0.028 | 2.07 | 0.025 |
| 332 | DIEXF | 27042 | digestive organ expansion factor homolog (zebrafish) | 0.82 | 0.049 | 2.16 | 0.013 |
| 333 | DKC1 | 1736 | dyskeratosis congenita 1, dyskerin | 0.81 | 0.040 | 1.78 | 0.026 |

TABLE 3-continued 1,635 prognostic genes for use in combination with BTN3A2 gene

| No. | Gene Symbol | GENE ID | Gene Name | BTN3A2 HR | p-value | prognostic gene HR | p-value |
|---|---|---|---|---|---|---|---|
| 334 | OBSCN | 84033 | obscurin, cytoskeletal calmodulin and titin-interacting RhoGEF | 0.77 | 0.010 | 0.76 | 0.005 |
| 335 | DLGAP5 | 9787 | discs, large (*Drosophila*) homolog-associated protein 5 | 0.75 | 0.004 | 1.76 | 0.000 |
| 336 | DNA2 | 1763 | DNA replication helicase/nuclease 2 | 0.81 | 0.034 | 1.49 | 0.047 |
| 337 | DNAAF1 | 123872 | dynein, axonemal, assembly factor 1 | 0.81 | 0.026 | 0.77 | 0.021 |
| 338 | DNAJB14 | 79982 | DnaJ (Hsp40) homolog, subfamily B, member 14 | 0.80 | 0.019 | 1.37 | 0.036 |
| 339 | DNAJC9 | 23234 | DnaJ (Hsp40) homolog, subfamily C, member 9 | 0.79 | 0.017 | 2.17 | 0.001 |
| 340 | DNM1 | 1759 | dynamin 1 | 0.80 | 0.028 | 0.77 | 0.043 |
| 341 | DOCK3 | 1795 | dedicator of cytokinesis 3 | 0.79 | 0.023 | 1.38 | 0.010 |
| 342 | DPP3 | 10072 | dipeptidyl-peptidase 3 | 0.77 | 0.015 | 1.35 | 0.017 |
| 343 | DPY19L4 | 286148 | dpy-19-like 4 (*C. elegans*) | 0.81 | 0.047 | 1.83 | 0.003 |
| 344 | LRRC37A2 | 474170 | leucine rich repeat containing 37, member A2 | 0.81 | 0.028 | 0.65 | 0.049 |
| 345 | DRG1 | 4733 | developmentally regulated GTP binding protein 1 | 0.78 | 0.018 | 2.02 | 0.007 |
| 346 | DSC3 | 1825 | desmocollin 3 | 0.77 | 0.017 | 0.68 | 0.019 |
| 347 | DSCC1 | 79075 | DNA replication and sister chromatid cohesion 1 | 0.80 | 0.021 | 1.93 | 0.000 |
| 348 | DSERG1 | 751816 | Down syndrome encephalopathy related protein 1 | 0.79 | 0.018 | 0.77 | 0.040 |
| 349 | DSG1 | 1828 | desmoglein 1 | 0.76 | 0.014 | 0.82 | 0.027 |
| 350 | DST | 667 | dystonin | 0.80 | 0.036 | 0.64 | 0.016 |
| 351 | DTL | 51514 | denticleless E3 ubiquitin protein ligase homolog (*Drosophila*) | 0.80 | 0.023 | 1.47 | 0.003 |
| 352 | DTX2 | 113878 | deltex 2, E3 ubiquitin ligase | 0.80 | 0.030 | 0.66 | 0.003 |
| 353 | DUSP6 | 1848 | dual specificity phosphatase 6 | 0.81 | 0.040 | 0.71 | 0.031 |
| 354 | DYNC2H1 | 79659 | dynein, cytoplasmic 2, heavy chain 1 | 0.82 | 0.041 | 0.52 | 0.004 |
| 355 | DYNLRB1 | 83658 | dynein, light chain, roadblock-type 1 | 0.81 | 0.035 | 1.62 | 0.017 |
| 356 | DYNLT1 | 6993 | dynein, light chain, Tctex-type 1 | 0.77 | 0.010 | 2.21 | 0.003 |
| 357 | DYRK2 | 8445 | dual-specificity tyrosine-(Y)-phosphorylation regulated kinase 2 | 0.78 | 0.009 | 1.91 | 0.008 |
| 358 | E2F8 | 79733 | E2F transcription factor 8 | 0.81 | 0.025 | 1.46 | 0.004 |
| 359 | EAF2 | 55840 | ELL associated factor 2 | 0.79 | 0.013 | 1.30 | 0.036 |
| 360 | EBAG9 | 9166 | estrogen receptor binding site associated, antigen, 9 | 0.79 | 0.022 | 1.48 | 0.008 |
| 361 | ECD | 11319 | ecdysoneless homolog (*Drosophila*) | 0.75 | 0.007 | 1.70 | 0.036 |
| 362 | ECHDC2 | 55268 | enoyl CoA hydratase domain containing 2 | 0.76 | 0.007 | 0.49 | 0.000 |
| 363 | ECT2 | 1894 | epithelial cell transforming 2 | 0.79 | 0.022 | 1.69 | 0.001 |
| 364 | EEF1A1 | 1915 | eukaryotic translation elongation factor 1 alpha 1 | 0.74 | 0.005 | 0.47 | 0.003 |
| 365 | EEF1E1 | 9521 | eukaryotic translation elongation factor 1 epsilon 1 | 0.78 | 0.015 | 2.06 | 0.004 |
| 366 | EEF1G | 1937 | eukaryotic translation elongation factor 1 gamma | 0.79 | 0.019 | 0.48 | 0.002 |
| 367 | EEF2 | 1938 | eukaryotic translation elongation factor 2 | 0.74 | 0.006 | 0.41 | 0.000 |
| 368 | EFCAB14 | 9813 | EF-hand calcium binding domain 14 | 0.79 | 0.023 | 0.46 | 0.026 |
| 369 | EFNA5 | 1946 | ephrin-A5 | 0.75 | 0.006 | 0.59 | 0.002 |
| 370 | EFR3A | 23167 | EFR3 homolog A (*S. cerevisiae*) | 0.80 | 0.033 | 1.59 | 0.037 |
| 371 | EFR3B | 22979 | EFR3 homolog B (*S. cerevisiae*) | 0.79 | 0.018 | 0.68 | 0.015 |
| 372 | EGF | 1950 | epidermal growth factor | 0.80 | 0.029 | 0.82 | 0.032 |
| 373 | EGFL8 | 9374 | EGF-like-domain, multiple 8 | 0.79 | 0.020 | 0.63 | 0.019 |
| 374 | EGFR | 1956 | epidermal growth factor receptor | 0.81 | 0.050 | 0.56 | 0.005 |
| 375 | EGR1 | 1958 | early growth response 1 | 0.79 | 0.019 | 0.67 | 0.001 |
| 376 | EGR3 | 1960 | early growth response 3 | 0.79 | 0.016 | 0.54 | 0.000 |
| 377 | EI24 | 9538 | etoposide induced 2.4 | 0.77 | 0.010 | 0.59 | 0.026 |
| 378 | EIF2S2 | 8894 | eukaryotic translation initiation factor 2, subunit 2 beta, 38 kDa | 0.76 | 0.008 | 1.54 | 0.018 |
| 379 | EIF3J | 8669 | eukaryotic translation initiation factor 3, subunit J | 0.79 | 0.022 | 1.70 | 0.028 |
| 380 | EIF3L | 51386 | eukaryotic translation initiation factor 3, subunit L | 0.81 | 0.035 | 0.62 | 0.026 |
| 381 | EIF4B | 1975 | eukaryotic translation initiation factor 4B | 0.80 | 0.021 | 0.54 | 0.012 |
| 382 | EIF4E2 | 9470 | eukaryotic translation initiation factor 4E family member 2 | 0.76 | 0.009 | 1.74 | 0.033 |
| 383 | EIF4EBP1 | 1978 | eukaryotic translation initiation factor 4E binding protein 1 | 0.77 | 0.010 | 1.45 | 0.003 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 384 | EIF4G1 | 1981 | eukaryotic translation initiation factor 4 gamma, 1 | 0.82 | 0.043 | 1.70 | 0.033 |
| 385 | EIF6 | 3692 | eukaryotic translation initiation factor 6 | 0.80 | 0.028 | 1.56 | 0.037 |
| 386 | ELAC1 | 55520 | elaC ribonuclease Z 1 | 0.81 | 0.035 | 0.73 | 0.028 |
| 387 | ELMO2 | 63916 | engulfment and cell motility 2 | 0.78 | 0.017 | 1.57 | 0.044 |
| 388 | ELOVL5 | 60481 | ELOVL fatty acid elongase 5 | 0.76 | 0.015 | 0.55 | 0.000 |
| 389 | EMC2 | 9694 | ER membrane protein complex subunit 2 | 0.80 | 0.035 | 2.07 | 0.000 |
| 390 | EMC9 | 51016 | ER membrane protein complex subunit 9 | 0.76 | 0.012 | 1.22 | 0.027 |
| 391 | EMG1 | 10436 | EMG1 N1-specific pseudouridine methyltransferase | 0.79 | 0.020 | 1.72 | 0.024 |
| 392 | EML3 | 256364 | echinoderm microtubule associated protein like 3 | 0.79 | 0.019 | 0.51 | 0.002 |
| 393 | ENOPH1 | 58478 | enolase-phosphatase 1 | 0.79 | 0.014 | 2.12 | 0.000 |
| 394 | ENOSF1 | 55556 | enolase superfamily member 1 | 0.79 | 0.020 | 0.67 | 0.028 |
| 395 | ENY2 | 56943 | enhancer of yellow 2 homolog (*Drosophila*) | 0.75 | 0.008 | 1.91 | 0.000 |
| 396 | EP400 | 57634 | E1A binding protein p400 | 0.80 | 0.027 | 0.40 | 0.023 |
| 397 | EPB41L2 | 2037 | erythrocyte membrane protein band 4.1-like 2 | 0.81 | 0.047 | 0.57 | 0.016 |
| 398 | EPRS | 2058 | glutamyl-prolyl-tRNA synthetase | 0.77 | 0.006 | 1.87 | 0.002 |
| 399 | ERBB2 | 2064 | v-erb-b2 avian erythroblastic leukemia viral oncogene homolog 2 | 0.81 | 0.048 | 1.30 | 0.024 |
| 400 | ERBB4 | 2066 | v-erb-b2 avian erythroblastic leukemia viral oncogene homolog 4 | 0.77 | 0.013 | 0.75 | 0.016 |
| 401 | ERCC6L | 54821 | excision repair cross-complementation group 6-like | 0.74 | 0.003 | 1.44 | 0.000 |
| 402 | ERO1L | 30001 | ERO1-like (*S. cerevisiae*) | 0.79 | 0.019 | 1.41 | 0.032 |
| 403 | ESRP1 | 54845 | epithelial splicing regulatory protein 1 | 0.80 | 0.024 | 1.77 | 0.002 |
| 404 | ETFA | 2108 | electron-transfer-flavoprotein, alpha polypeptide | 0.77 | 0.011 | 1.50 | 0.041 |
| 405 | ETV3 | 2117 | ets variant 3 | 0.80 | 0.021 | 0.71 | 0.044 |
| 406 | EXOC7 | 23265 | exocyst complex component 7 | 0.80 | 0.025 | 0.52 | 0.023 |
| 407 | EXOSC1 | 51013 | exosome component 1 | 0.80 | 0.027 | 0.83 | 0.033 |
| 408 | EXOSC4 | 54512 | exosome component 4 | 0.80 | 0.037 | 1.47 | 0.023 |
| 409 | EXT1 | 2131 | exostosin glycosyltransferase 1 | 0.74 | 0.004 | 2.05 | 0.001 |
| 410 | EZH1 | 2145 | enhancer of zeste 1 polycomb repressive complex 2 subunit | 0.79 | 0.017 | 0.39 | 0.001 |
| 411 | EZR | 7430 | ezrin | 0.82 | 0.041 | 1.73 | 0.011 |
| 412 | F8 | 2157 | coagulation factor VIII, procoagulant component | 0.81 | 0.043 | 0.57 | 0.033 |
| 413 | FABP1 | 2168 | fatty acid binding protein 1, liver | 0.81 | 0.037 | 1.34 | 0.036 |
| 414 | FABP6 | 2172 | fatty acid binding protein 6, ileal | 0.79 | 0.017 | 1.18 | 0.016 |
| 415 | FABP7 | 2173 | fatty acid binding protein 7, brain | 0.80 | 0.028 | 0.73 | 0.016 |
| 416 | FADD | 8772 | Fas (TNFRSF6)-associated via death domain | 0.78 | 0.021 | 1.57 | 0.005 |
| 417 | FAM120A | 23196 | family with sequence similarity 120A | 0.79 | 0.018 | 0.53 | 0.019 |
| 418 | FAM129A | 116496 | family with sequence similarity 129, member A | 0.81 | 0.035 | 0.78 | 0.034 |
| 419 | FAM131B | 9715 | family with sequence similarity 131, member B | 0.80 | 0.024 | 0.78 | 0.018 |
| 420 | FAM136A | 84908 | family with sequence similarity 136, member A | 0.80 | 0.027 | 1.83 | 0.048 |
| 421 | FAM160B2 | 64760 | family with sequence similarity 160, member B2 | 0.78 | 0.014 | 0.58 | 0.032 |
| 422 | FAM163A | 148753 | family with sequence similarity 163, member A | 0.80 | 0.025 | 1.46 | 0.004 |
| 423 | FAM171A1 | 221061 | family with sequence similarity 171, member A1 | 0.80 | 0.040 | 0.55 | 0.005 |
| 424 | FAM189A1 | 23359 | family with sequence similarity 189, member A1 | 0.80 | 0.020 | 0.74 | 0.015 |
| 425 | FAM189A2 | 9413 | family with sequence similarity 189, member A2 | 0.79 | 0.019 | 0.63 | 0.016 |
| 426 | FAM193B | 54540 | family with sequence similarity 193, member B | 0.77 | 0.015 | 0.65 | 0.030 |
| 427 | FAM47E | 8987 | family with sequence similarity 47, member E | 0.81 | 0.034 | 2.15 | 0.002 |
| 428 | FAM49B | 51571 | family with sequence similarity 49, member B | 0.73 | 0.003 | 2.04 | 0.001 |

TABLE 3-continued 1,635 prognostic genes for use in combination with BTN3A2 gene

| No. | Gene Symbol | GENE ID | Gene Name | BTN3A2 HR | BTN3A2 p-value | prognostic gene HR | prognostic gene p-value |
|---|---|---|---|---|---|---|---|
| 429 | FAM63A | 55793 | family with sequence similarity 63, member A | 0.77 | 0.010 | 0.65 | 0.017 |
| 430 | FAM96B | 51647 | family with sequence similarity 96, member B | 0.79 | 0.018 | 1.75 | 0.035 |
| 431 | FAM98A | 25940 | family with sequence similarity 98, member A | 0.74 | 0.004 | 1.87 | 0.016 |
| 432 | FANCI | 55215 | Fanconi anemia, complementation group I | 0.81 | 0.032 | 1.49 | 0.049 |
| 433 | FARP2 | 9855 | FERM, RhoGEF and pleckstrin domain protein 2 | 0.76 | 0.007 | 0.46 | 0.005 |
| 434 | FAU | 2197 | Finkel-Biskis-Reilly murine sarcoma virus (FBR-MuSV) ubiquitously expressed | 0.82 | 0.045 | 0.59 | 0.035 |
| 435 | FBP2 | 8789 | fructose-1,6-bisphosphatase 2 | 0.81 | 0.041 | 1.38 | 0.037 |
| 436 | FBXO5 | 26271 | F-box protein 5 | 0.74 | 0.005 | 1.49 | 0.012 |
| 437 | FCGBP | 8857 | Fc fragment of IgG binding protein | 0.79 | 0.016 | 0.82 | 0.006 |
| 438 | FDPS | 2224 | farnesyl diphosphate synthase | 0.80 | 0.022 | 1.66 | 0.024 |
| 439 | FEN1 | 2237 | flap structure-specific endonuclease 1 | 0.77 | 0.012 | 1.77 | 0.003 |
| 440 | FGB | 2244 | fibrinogen beta chain | 0.78 | 0.020 | 1.27 | 0.023 |
| 441 | FGF14 | 2259 | fibroblast growth factor 14 | 0.81 | 0.036 | 0.77 | 0.012 |
| 442 | FGF9 | 2254 | fibroblast growth factor 9 | 0.80 | 0.025 | 0.81 | 0.048 |
| 443 | FH | 2271 | fumarate hydratase | 0.80 | 0.032 | 1.74 | 0.013 |
| 444 | FIGF | 2277 | c-fos induced growth factor (vascular endothelial growth factor D) | 0.80 | 0.028 | 0.83 | 0.044 |
| 445 | FJX1 | 24147 | four jointed box 1 (Drosophila) | 0.80 | 0.027 | 1.25 | 0.042 |
| 446 | FKBP4 | 2288 | FK506 binding protein 4, 59 kDa | 0.80 | 0.036 | 2.11 | 0.000 |
| 447 | FLJ42627 | 645644 | uncharacterized LOC645644 | 0.78 | 0.011 | 0.63 | 0.030 |
| 448 | FLNA | 2316 | filamin A, alpha | 0.81 | 0.032 | 0.72 | 0.027 |
| 449 | FLRT2 | 23768 | fibronectin leucine rich transmembrane protein 2 | 0.81 | 0.043 | 0.67 | 0.022 |
| 450 | FLT3 | 2322 | fms-related tyrosine kinase 3 | 0.79 | 0.019 | 0.78 | 0.039 |
| 451 | FMO2 | 2327 | flavin containing monooxygenase 2 (non-functional) | 0.79 | 0.031 | 0.54 | 0.000 |
| 452 | FMO5 | 2330 | flavin containing monooxygenase 5 | 0.79 | 0.015 | 0.64 | 0.000 |
| 453 | FOCAD | 54914 | focadhesin | 0.82 | 0.044 | 0.59 | 0.032 |
| 454 | FOXI1 | 2299 | forkhead box I1 | 0.77 | 0.010 | 0.73 | 0.001 |
| 455 | FOXM1 | 2305 | forkhead box M1 | 0.78 | 0.015 | 1.42 | 0.002 |
| 456 | FPGS | 2356 | folylpolyglutamate synthase | 0.79 | 0.016 | 0.65 | 0.039 |
| 457 | FPR3 | 2359 | formyl peptide receptor 3 | 0.76 | 0.009 | 1.57 | 0.044 |
| 458 | FST | 10468 | follistatin | 0.80 | 0.029 | 0.68 | 0.024 |
| 459 | FTH1P5 | 2509 | ferritin, heavy polypeptide 1 pseudogene 5 | 0.81 | 0.036 | 0.62 | 0.023 |
| 460 | FUBP3 | 8939 | far upstream element (FUSE) binding protein 3 | 0.81 | 0.033 | 1.62 | 0.044 |
| 461 | FUT2 | 2524 | fucosyltransferase 2 (secretor status included) | 0.78 | 0.017 | 0.55 | 0.033 |
| 462 | FZD10 | 11211 | frizzled class receptor 10 | 0.77 | 0.012 | 0.69 | 0.002 |
| 463 | FZD4 | 8322 | frizzled class receptor 4 | 0.77 | 0.010 | 0.54 | 0.013 |
| 464 | G3BP2 | 9908 | GTPase activating protein (SH3 domain) binding protein 2 | 0.80 | 0.032 | 2.37 | 0.005 |
| 465 | GAA | 2548 | glucosidase, alpha; acid | 0.81 | 0.027 | 0.56 | 0.015 |
| 466 | GABRA1 | 2554 | gamma-aminobutyric acid (GABA) A receptor, alpha 1 | 0.81 | 0.046 | 1.49 | 0.022 |
| 467 | GABRB2 | 2561 | gamma-aminobutyric acid (GABA) A receptor, beta 2 | 0.80 | 0.026 | 0.77 | 0.041 |
| 468 | GABRB3 | 2562 | gamma-aminobutyric acid (GABA) A receptor, beta 3 | 0.79 | 0.021 | 0.84 | 0.031 |
| 469 | GABRD | 2563 | gamma-aminobutyric acid (GABA) A receptor, delta | 0.79 | 0.021 | 1.43 | 0.004 |
| 470 | GABRP | 2568 | gamma-aminobutyric acid (GABA) A receptor, pi | 0.81 | 0.032 | 0.81 | 0.001 |
| 471 | GADD45GIP1 | 90480 | growth arrest and DNA-damage-inducible, gamma interacting protein 1 | 0.77 | 0.008 | 1.64 | 0.002 |
| 472 | GAREM | 64762 | GRB2 associated, regulator of MAPK1 | 0.81 | 0.032 | 1.28 | 0.027 |
| 473 | GARS | 2617 | glycyl-tRNA synthetase | 0.81 | 0.025 | 2.24 | 0.005 |
| 474 | GAS2 | 2620 | growth arrest-specific 2 | 0.80 | 0.024 | 0.83 | 0.017 |
| 475 | GATA3 | 2625 | GATA binding protein 3 | 0.78 | 0.013 | 0.77 | 0.017 |
| 476 | GATAD1 | 57798 | GATA zinc finger domain containing 1 | 0.79 | 0.018 | 0.52 | 0.033 |
| 477 | GCH1 | 2643 | GTP cyclohydrolase 1 | 0.76 | 0.003 | 1.55 | 0.004 |
| 478 | GDF10 | 2662 | growth differentiation factor 10 | 0.78 | 0.015 | 0.79 | 0.019 |
| 479 | GFPT1 | 2673 | glutamine-fructose-6-phosphate transaminase 1 | 0.81 | 0.032 | 1.56 | 0.026 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 480 | GGA2 | 23062 | golgi-associated, gamma adaptin ear containing, ARF binding protein 2 | 0.77 | 0.008 | 0.40 | 0.002 |
| 481 | GGCX | 2677 | gamma-glutamyl carboxylase | 0.81 | 0.032 | 2.53 | 0.001 |
| 482 | GHITM | 27069 | growth hormone inducible transmembrane protein | 0.82 | 0.044 | 2.52 | 0.005 |
| 483 | GINS1 | 9837 | GINS complex subunit 1 (Psf1 homolog) | 0.82 | 0.044 | 1.42 | 0.014 |
| 484 | GINS2 | 51659 | GINS complex subunit 2 (Psf2 homolog) | 0.78 | 0.018 | 1.18 | 0.033 |
| 485 | GLB1L | 79411 | galactosidase, beta 1-like | 0.80 | 0.023 | 0.57 | 0.004 |
| 486 | GLI2 | 2736 | GLI family zinc finger 2 | 0.81 | 0.044 | 0.56 | 0.006 |
| 487 | GLI3 | 2737 | GLI family zinc finger 3 | 0.77 | 0.012 | 0.70 | 0.047 |
| 488 | GLO1 | 2739 | glyoxalase I | 0.81 | 0.040 | 1.84 | 0.003 |
| 489 | GLRX2 | 51022 | glutaredoxin 2 | 0.77 | 0.018 | 2.32 | 0.001 |
| 490 | GLRX5 | 51218 | glutaredoxin 5 | 0.77 | 0.017 | 1.30 | 0.042 |
| 491 | GLUL | 2752 | glutamate-ammonia ligase | 0.74 | 0.006 | 0.61 | 0.014 |
| 492 | GLYR1 | 84656 | glyoxylate reductase 1 homolog (*Arabidopsis*) | 0.79 | 0.010 | 0.55 | 0.017 |
| 493 | GMFB | 2764 | glia maturation factor, beta | 0.80 | 0.035 | 1.90 | 0.036 |
| 494 | GMNN | 51053 | geminin, DNA replication inhibitor | 0.77 | 0.010 | 1.52 | 0.013 |
| 495 | GMPS | 8833 | guanine monphosphate synthase | 0.79 | 0.020 | 1.64 | 0.009 |
| 496 | GNA11 | 2767 | guanine nucleotide binding protein (G protein), alpha 11 (Gq class) | 0.80 | 0.026 | 0.49 | 0.028 |
| 497 | GNAZ | 2781 | guanine nucleotide binding protein (G protein), alpha z polypeptide | 0.81 | 0.047 | 1.69 | 0.038 |
| 498 | GNB2L1 | 10399 | guanine nucleotide binding protein (G protein), beta polypeptide 2-like 1 | 0.82 | 0.047 | 0.56 | 0.013 |
| 499 | GNG12 | 55970 | guanine nucleotide binding protein (G protein), gamma 12 | 0.81 | 0.033 | 0.61 | 0.002 |
| 500 | GNL1 | 2794 | guanine nucleotide binding protein-like 1 | 0.80 | 0.027 | 0.68 | 0.046 |
| 501 | GNL2 | 29889 | guanine nucleotide binding protein-like 2 (nucleolar) | 0.80 | 0.022 | 1.60 | 0.042 |
| 502 | GNPTAB | 79158 | N-acetylglucosamine-1-phosphate transferase, alpha and beta subunits | 0.79 | 0.014 | 1.66 | 0.033 |
| 503 | GNRH1 | 2796 | gonadotropin-releasing hormone 1 (luteinizing-releasing hormone) | 0.78 | 0.009 | 0.74 | 0.000 |
| 504 | GOLGA6L4 | 374650 | golgin A6 family-like 4 | 0.78 | 0.017 | 0.73 | 0.018 |
| 505 | GOLGA8A | 23015 | golgin A8 family, member A | 0.79 | 0.018 | 0.79 | 0.017 |
| 506 | GOLGA8A | 23015 | golgin A8 family, member A | 0.79 | 0.015 | 0.66 | 0.002 |
| 507 | GOLT1B | 51026 | golgi transport 1B | 0.73 | 0.002 | 2.94 | 0.000 |
| 508 | GON4L | 54856 | gon-4-like (*C. elegans*) | 0.76 | 0.009 | 0.37 | 0.005 |
| 509 | GORASP1 | 64689 | golgi reassembly stacking protein 1, 65 kDa | 0.80 | 0.030 | 0.46 | 0.018 |
| 510 | GOT1 | 2805 | glutamic-oxaloacetic transaminase 1, soluble | 0.76 | 0.010 | 1.48 | 0.017 |
| 511 | GPN1 | 11321 | GPN-loop GTPase 1 | 0.78 | 0.011 | 1.86 | 0.016 |
| 512 | GPR153 | 387509 | G protein-coupled receptor 153 | 0.75 | 0.007 | 0.66 | 0.029 |
| 513 | GPR22 | 2845 | G protein-coupled receptor 22 | 0.81 | 0.039 | 0.80 | 0.025 |
| 514 | GPR35 | 2859 | G protein-coupled receptor 35 | 0.80 | 0.023 | 0.75 | 0.029 |
| 515 | GPRASP1 | 9737 | G protein-coupled receptor associated sorting protein 1 | 0.79 | 0.022 | 0.64 | 0.017 |
| 516 | GPRC5C | 55890 | G protein-coupled receptor, class C, group 5, member C | 0.79 | 0.020 | 1.41 | 0.034 |
| 517 | GPRIN2 | 9721 | G protein regulated inducer of neurite outgrowth 2 | 0.75 | 0.006 | 0.68 | 0.005 |
| 518 | GPX4 | 2879 | glutathione peroxidase 4 | 0.80 | 0.029 | 0.52 | 0.023 |
| 519 | GREB1L | 80000 | growth regulation by estrogen in breast cancer-like | 0.80 | 0.023 | 0.82 | 0.049 |
| 520 | GRK6 | 2870 | G protein-coupled receptor kinase 6 | 0.80 | 0.021 | 1.75 | 0.020 |
| 521 | GRSF1 | 2926 | G-rich RNA sequence binding factor 1 | 0.78 | 0.016 | 2.08 | 0.009 |
| 522 | GRWD1 | 83743 | glutamate-rich WD repeat containing 1 | 0.80 | 0.033 | 1.65 | 0.026 |
| 523 | GSK3B | 2932 | glycogen synthase kinase 3 beta | 0.79 | 0.017 | 1.99 | 0.003 |
| 524 | GSTM2 | 2946 | glutathione S-transferase mu 2 (muscle) | 0.79 | 0.016 | 0.75 | 0.047 |
| 525 | GSTM4 | 2948 | glutathione S-transferase mu 4 | 0.78 | 0.012 | 0.60 | 0.041 |
| 526 | GTF2A2 | 2958 | general transcription factor IIA, 2, 12 kDa | 0.79 | 0.017 | 1.73 | 0.041 |
| 527 | GTF2E1 | 2960 | general transcription factor II E, polypeptide 1, alpha 56 kDa | 0.79 | 0.026 | 1.91 | 0.036 |
| 528 | GTF2H5 | 404672 | general transcription factor IIH, polypeptide 5 | 0.80 | 0.028 | 2.02 | 0.011 |

TABLE 3-continued 1,635 prognostic genes for use in combination with BTN3A2 gene

| Gene No. | Gene Symbol | GENE ID | Gene Name | BTN3A2 HR | p-value | prognostic gene HR | p-value |
|---|---|---|---|---|---|---|---|
| 529 | GTF2IRD2B | 389524 | GTF2I repeat domain containing 2B | 0.77 | 0.011 | 0.67 | 0.010 |
| 530 | GTPBP4 | 23560 | GTP binding protein 4 | 0.79 | 0.017 | 2.05 | 0.007 |
| 531 | GUF1 | 60558 | GUF1 GTPase homolog (S. cerevisiae) | 0.82 | 0.046 | 2.03 | 0.009 |
| 532 | GUK1 | 2987 | guanylate kinase 1 | 0.79 | 0.017 | 1.77 | 0.016 |
| 533 | GYS2 | 2998 | glycogen synthase 2 (liver) | 0.77 | 0.014 | 0.84 | 0.030 |
| 534 | GZMB | 3002 | granzyme B (granzyme 2, cytotoxic T-lymphocyte-associated serine esterase 1) | 0.77 | 0.005 | 1.36 | 0.019 |
| 535 | H2AFV | 94239 | H2A histone family, member V | 0.80 | 0.015 | 3.04 | 0.000 |
| 536 | H2AFZ | 3015 | H2A histone family, member Z | 0.77 | 0.009 | 2.23 | 0.001 |
| 537 | HAB1 | 55547 | B1 for mucin | 0.82 | 0.039 | 1.53 | 0.037 |
| 538 | HAO1 | 54363 | hydroxyacid oxidase (glycolate oxidase) 1 | 0.76 | 0.008 | 0.81 | 0.015 |
| 539 | HAUS2 | 55142 | HAUS augmin-like complex, subunit 2 | 0.75 | 0.008 | 0.76 | 0.033 |
| 540 | HCCS | 3052 | holocytochrome c synthase | 0.80 | 0.034 | 2.95 | 0.003 |
| 541 | HCFC2 | 29915 | host cell factor C2 | 0.80 | 0.024 | 1.79 | 0.033 |
| 542 | HCG18 | 414777 | HLA complex group 18 (non-protein coding) | 0.79 | 0.018 | 0.82 | 0.022 |
| 543 | HDAC2 | 3066 | histone deacetylase 2 | 0.79 | 0.015 | 1.44 | 0.039 |
| 544 | HDAC5 | 10014 | histone deacetylase 5 | 0.80 | 0.021 | 0.72 | 0.043 |
| 545 | HDAC7 | 51564 | histone deacetylase 7 | 0.78 | 0.016 | 0.71 | 0.039 |
| 546 | HDDC2 | 51020 | HD domain containing 2 | 0.77 | 0.010 | 1.89 | 0.008 |
| 547 | HEATR6 | 63897 | HEAT repeat containing 6 | 0.78 | 0.015 | 1.79 | 0.001 |
| 548 | HFE | 3077 | hemochromatosis | 0.76 | 0.007 | 0.48 | 0.005 |
| 549 | HGD | 3081 | homogentisate 1,2-dioxygenase | 0.81 | 0.028 | 1.32 | 0.030 |
| 550 | HIP1 | 3092 | huntingtin interacting protein 1 | 0.81 | 0.038 | 0.49 | 0.005 |
| 551 | HIST1H1C | 3006 | histone cluster 1, H1c | 0.79 | 0.023 | 1.25 | 0.031 |
| 552 | HIST1H2AG | 8329 | histone cluster 1, H2ag | 0.77 | 0.011 | 1.36 | 0.017 |
| 553 | HIST1H2AJ | 8331 | histone cluster 1, H2aj | 0.79 | 0.024 | 1.47 | 0.046 |
| 554 | HIST1H2BB | 3018 | histone cluster 1, H2bb | 0.77 | 0.008 | 1.35 | 0.007 |
| 555 | HIST1H3C | 8352 | histone cluster 1, H3c | 0.80 | 0.023 | 1.61 | 0.001 |
| 556 | HIST1H4H | 8365 | histone cluster 1, H4h | 0.79 | 0.020 | 1.28 | 0.046 |
| 557 | HIST3H2A | 92815 | histone cluster 3, H2a | 0.81 | 0.034 | 1.28 | 0.027 |
| 558 | HJURP | 55355 | Holliday junction recognition protein | 0.79 | 0.023 | 1.36 | 0.049 |
| 559 | HK2 | 3099 | hexokinase 2 | 0.78 | 0.015 | 0.75 | 0.005 |
| 560 | HLTF | 6596 | helicase-like transcription factor | 0.82 | 0.038 | 1.79 | 0.005 |
| 561 | HMBOX1 | 79618 | homeobox containing 1 | 0.79 | 0.020 | 0.66 | 0.002 |
| 562 | HMGB2 | 3148 | high mobility group box 2 | 0.80 | 0.024 | 1.39 | 0.027 |
| 563 | HMGN5 | 79366 | high mobility group nucleosome binding domain 5 | 0.83 | 0.048 | 1.50 | 0.040 |
| 564 | HMHB1 | 57824 | histocompatibility (minor) HB-1 | 0.82 | 0.047 | 1.71 | 0.010 |
| 565 | HN1 | 51155 | hematological and neurological expressed 1 | 0.76 | 0.011 | 1.35 | 0.039 |
| 566 | HNRNPA1 | 3178 | heterogeneous nuclear ribonucleoprotein A1 | 0.79 | 0.026 | 0.52 | 0.007 |
| 567 | HNRNPA1 | 3178 | heterogeneous nuclear ribonucleoprotein A1 | 0.79 | 0.026 | 0.41 | 0.005 |
| 568 | HNRNPDL | 9987 | heterogeneous nuclear ribonucleoprotein D-like | 0.80 | 0.023 | 0.63 | 0.031 |
| 569 | HOXA10 | 3206 | homeobox A10 | 0.81 | 0.046 | 0.75 | 0.026 |
| 570 | HOXA4 | 3201 | homeobox A4 | 0.78 | 0.015 | 0.74 | 0.011 |
| 571 | HOXA5 | 3202 | homeobox A5 | 0.80 | 0.032 | 0.65 | 0.000 |
| 572 | HP | 3240 | haptoglobin | 0.80 | 0.036 | 0.78 | 0.023 |
| 573 | HPRT1 | 3251 | hypoxanthine phosphoribosyltransferase 1 | 0.77 | 0.009 | 1.83 | 0.003 |
| 574 | HS2ST1 | 9653 | heparan sulfate 2-O-sulfotransferase 1 | 0.77 | 0.012 | 1.48 | 0.042 |
| 575 | HSBP1 | 3281 | heat shock factor binding protein 1 | 0.77 | 0.011 | 1.65 | 0.021 |
| 576 | HSD17B10 | 3028 | hydroxysteroid (17-beta) dehydrogenase 10 | 0.80 | 0.030 | 1.56 | 0.044 |
| 577 | HSDL2 | 84263 | hydroxysteroid dehydrogenase like 2 | 0.79 | 0.022 | 1.51 | 0.030 |
| 578 | HSPA13 | 6782 | heat shock protein 70 kDa family, member 13 | 0.79 | 0.017 | 1.34 | 0.048 |
| 579 | HSPH1 | 10808 | heat shock 105 kDa/110 kDa protein 1 | 0.78 | 0.015 | 1.62 | 0.005 |
| 580 | HTATIP2 | 10553 | HIV-1 Tat interactive protein 2, 30 kDa | 0.74 | 0.002 | 1.91 | 0.000 |
| 581 | HTATSF1 | 27336 | HIV-1 Tat specific factor 1 | 0.80 | 0.022 | 1.58 | 0.033 |
| 582 | HTR1E | 3354 | 5-hydroxytryptamine (serotonin) receptor 1E, G protein-coupled | 0.77 | 0.016 | 0.77 | 0.007 |
| 583 | HTR3B | 9177 | 5-hydroxytryptamine (serotonin) receptor 3B, ionotropic | 0.77 | 0.013 | 0.80 | 0.013 |
| 584 | HUWE1 | 10075 | HECT, UBA and WWE domain containing 1, E3 ubiquitin protein ligase | 0.73 | 0.004 | 0.46 | 0.000 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 585 | HYPK | 10169 | huntingtin interacting protein K | 0.78 | 0.019 | 1.93 | 0.003 |
| 586 | IARS | 3376 | isoleucyl-tRNA synthetase | 0.82 | 0.036 | 1.84 | 0.014 |
| 587 | ICMT | 23463 | isoprenylcysteine carboxyl methyltransferase | 0.80 | 0.025 | 2.03 | 0.043 |
| 588 | ICT1 | 3396 | immature colon carcinoma transcript 1 | 0.77 | 0.015 | 1.83 | 0.003 |
| 589 | ID4 | 3400 | inhibitor of DNA binding 4, dominant negative helix-loop-helix protein | 0.81 | 0.039 | 0.75 | 0.009 |
| 590 | IDH2 | 3418 | isocitrate dehydrogenase 2 (NADP+), mitochondrial | 0.75 | 0.008 | 1.45 | 0.017 |
| 591 | IDH3A | 3419 | isocitrate dehydrogenase 3 (NAD+) alpha | 0.79 | 0.022 | 1.82 | 0.019 |
| 592 | IDI1 | 3422 | isopentenyl-diphosphate delta isomerase 1 | 0.78 | 0.010 | 2.00 | 0.000 |
| 593 | IDO1 | 3620 | indoleamine 2,3-dioxygenase 1 | 0.73 | 0.003 | 1.43 | 0.009 |
| 594 | IDUA | 3425 | iduronidase, alpha-L- | 0.77 | 0.011 | 0.66 | 0.044 |
| 595 | IER2 | 9592 | immediate early response 2 | 0.81 | 0.033 | 0.56 | 0.002 |
| 596 | IFIH1 | 64135 | interferon induced with helicase C domain 1 | 0.76 | 0.006 | 1.34 | 0.029 |
| 597 | IFIT5 | 24138 | interferon-induced protein with tetratricopeptide repeats 5 | 0.77 | 0.012 | 1.48 | 0.037 |
| 598 | IFT46 | 56912 | intraflagellar transport 46 homolog (*Chlamydomonas*) | 0.81 | 0.015 | 0.35 | 0.000 |
| 599 | IGH | 3492 | immunoglobulin heavy locus | 0.82 | 0.037 | 1.63 | 0.023 |
| 600 | IKBKB | 3551 | inhibitor of kappa light polypeptide gene enhancer in B-cells, kinase beta | 0.76 | 0.007 | 0.63 | 0.010 |
| 601 | IKZF1 | 10320 | IKAROS family zinc finger 1 (Ikaros) | 0.81 | 0.046 | 0.66 | 0.042 |
| 602 | IKZF2 | 22807 | IKAROS family zinc finger 2 (Helios) | 0.79 | 0.016 | 0.83 | 0.030 |
| 603 | IL11RA | 3590 | interleukin 11 receptor, alpha | 0.80 | 0.025 | 0.77 | 0.023 |
| 604 | IL1A | 3552 | interleukin 1, alpha | 0.77 | 0.011 | 0.59 | 0.008 |
| 605 | IL1RL2 | 8808 | interleukin 1 receptor-like 2 | 0.78 | 0.023 | 1.40 | 0.006 |
| 606 | IL5 | 3567 | interleukin 5 | 0.82 | 0.047 | 1.25 | 0.019 |
| 607 | IL6ST | 3572 | interleukin 6 signal transducer | 0.78 | 0.013 | 0.69 | 0.003 |
| 608 | ILF2 | 3608 | interleukin enhancer binding factor 2 | 0.76 | 0.007 | 1.75 | 0.012 |
| 609 | IMPA1 | 3612 | inositol(myo)-1(or 4)-monophosphatase 1 | 0.78 | 0.013 | 1.58 | 0.008 |
| 610 | INADL | 10207 | InaD-like (*Drosophila*) | 0.79 | 0.021 | 0.66 | 0.000 |
| 611 | INPP5D | 3635 | inositol polyphosphate-5-phosphatase, 145 kDa | 0.79 | 0.030 | 0.70 | 0.042 |
| 612 | INPP5K | 51763 | inositol polyphosphate-5-phosphatase K | 0.83 | 0.046 | 0.40 | 0.019 |
| 613 | INTS6 | 26512 | integrator complex subunit 6 | 0.78 | 0.012 | 1.46 | 0.041 |
| 614 | INTS7 | 25896 | integrator complex subunit 7 | 0.75 | 0.007 | 1.61 | 0.014 |
| 615 | INTS8 | 55656 | integrator complex subunit 8 | 0.78 | 0.016 | 1.54 | 0.012 |
| 616 | INTS9 | 55756 | integrator complex subunit 9 | 0.78 | 0.018 | 0.47 | 0.007 |
| 617 | IPO7 | 10527 | importin 7 | 0.80 | 0.023 | 1.94 | 0.026 |
| 618 | IQCK | 124152 | IQ motif containing K | 0.82 | 0.038 | 0.51 | 0.008 |
| 619 | IRAK3 | 11213 | interleukin-1 receptor-associated kinase 3 | 0.80 | 0.037 | 0.81 | 0.024 |
| 620 | IRF2BP1 | 26145 | interferon regulatory factor 2 binding protein 1 | 0.81 | 0.025 | 0.77 | 0.043 |
| 621 | ISG20 | 3669 | interferon stimulated exonuclease gene 20 kDa | 0.76 | 0.004 | 1.48 | 0.018 |
| 622 | ISOC2 | 79763 | isochorismatase domain containing 2 | 0.81 | 0.039 | 1.80 | 0.031 |
| 623 | ITGA10 | 8515 | integrin, alpha 10 | 0.77 | 0.011 | 0.67 | 0.047 |
| 624 | ITGA2 | 3673 | integrin, alpha 2 (CD49B, alpha 2 subunit of VLA-2 receptor) | 0.81 | 0.043 | 0.68 | 0.034 |
| 625 | ITGA7 | 3679 | integrin, alpha 7 | 0.81 | 0.045 | 0.85 | 0.044 |
| 626 | ITGA9 | 3680 | integrin, alpha 9 | 0.81 | 0.031 | 0.73 | 0.028 |
| 627 | ITIH4 | 3700 | inter-alpha-trypsin inhibitor heavy chain family, member 4 | 0.76 | 0.007 | 0.72 | 0.015 |
| 628 | IVD | 3712 | isovaleryl-CoA dehydrogenase | 0.83 | 0.049 | 0.56 | 0.030 |
| 629 | IVNS1ABP | 10625 | influenza virus NS1A binding protein | 0.79 | 0.015 | 1.79 | 0.017 |
| 630 | JADE2 | 23338 | jade family PHD finger 2 | 0.80 | 0.035 | 0.44 | 0.003 |
| 631 | JAG2 | 3714 | jagged 2 | 0.76 | 0.011 | 0.60 | 0.037 |
| 632 | JAM2 | 58494 | junctional adhesion molecule 2 | 0.82 | 0.041 | 0.62 | 0.022 |
| 633 | JMJD6 | 23210 | jumonji domain containing 6 | 0.77 | 0.010 | 2.24 | 0.005 |
| 634 | JMJD7-PLA2G4B | 8681 | JMJD7-PLA2G4B readthrough | 0.75 | 0.005 | 0.70 | 0.015 |
| 635 | JUN | 3725 | jun proto-oncogene | 0.82 | 0.042 | 0.61 | 0.002 |
| 636 | JUP | 3728 | junction plakoglobin | 0.78 | 0.024 | 0.78 | 0.011 |
| 637 | KANK1 | 23189 | KN motif and ankyrin repeat domains 1 | 0.79 | 0.027 | 0.51 | 0.003 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 638 | KANK2 | 25959 | KN motif and ankyrin repeat domains 2 | 0.80 | 0.028 | 0.63 | 0.044 |
| 639 | KANSL1L | 151050 | KAT8 regulatory NSL complex subunit 1-like | 0.80 | 0.019 | 1.38 | 0.017 |
| 640 | KANSL2 | 54934 | KAT8 regulatory NSL complex subunit 2 | 0.75 | 0.011 | 2.50 | 0.004 |
| 641 | KCMF1 | 56888 | potassium channel modulatory factor 1 | 0.77 | 0.005 | 3.20 | 0.002 |
| 642 | KCNC4 | 3749 | potassium voltage-gated channel, Shaw-related subfamily, member 4 | 0.78 | 0.013 | 0.79 | 0.029 |
| 643 | KCNG1 | 3755 | potassium voltage-gated channel, subfamily G, member 1 | 0.79 | 0.019 | 1.23 | 0.050 |
| 644 | KCNK1 | 3775 | potassium channel, subfamily K, member 1 | 0.81 | 0.040 | 1.23 | 0.022 |
| 645 | KCNMB1 | 3779 | potassium large conductance calcium-activated channel, subfamily M, beta member 1 | 0.79 | 0.018 | 0.61 | 0.007 |
| 646 | KCNS3 | 3790 | potassium voltage-gated channel, delayed-rectifier, subfamily S, member 3 | 0.80 | 0.033 | 0.68 | 0.016 |
| 647 | KDELR2 | 11014 | KDEL (Lys-Asp-Glu-Leu) endoplasmic reticulum protein retention receptor 2 | 0.80 | 0.031 | 1.71 | 0.019 |
| 648 | KEAP1 | 9817 | kelch-like ECH-associated protein 1 | 0.79 | 0.016 | 1.72 | 0.030 |
| 649 | KHDRBS3 | 10656 | KH domain containing, RNA binding, signal transduction associated 3 | 0.80 | 0.023 | 1.35 | 0.043 |
| 650 | KIAA0101 | 9768 | KIAA0101 | 0.78 | 0.012 | 1.56 | 0.004 |
| 651 | KIAA0391 | 5687 | KIAA0391 | 0.76 | 0.008 | 1.67 | 0.027 |
| 652 | KIAA0485 | 57235 | uncharacterized LOC57235 | 0.80 | 0.022 | 0.73 | 0.002 |
| 653 | KIAA0556 | 23247 | KIAA0556 | 0.73 | 0.003 | 0.48 | 0.006 |
| 654 | KIAA0753 | 9851 | KIAA0753 | 0.76 | 0.004 | 0.47 | 0.001 |
| 655 | KIAA0754 | 643314 | KIAA0754 | 0.80 | 0.023 | 0.84 | 0.004 |
| 656 | KIAA1024 | 23251 | KIAA1024 | 0.77 | 0.008 | 1.31 | 0.007 |
| 657 | KIF11 | 3832 | kinesin family member 11 | 0.78 | 0.012 | 1.61 | 0.003 |
| 658 | KIF13B | 23303 | kinesin family member 13B | 0.77 | 0.012 | 0.59 | 0.002 |
| 659 | KIF14 | 9928 | kinesin family member 14 | 0.78 | 0.013 | 1.73 | 0.001 |
| 660 | KIF20A | 10112 | kinesin family member 20A | 0.76 | 0.011 | 1.46 | 0.005 |
| 661 | KIF23 | 9493 | kinesin family member 23 | 0.79 | 0.021 | 1.22 | 0.028 |
| 662 | KIF2C | 11004 | kinesin family member 2C | 0.78 | 0.009 | 1.90 | 0.003 |
| 663 | KIF4A | 24137 | kinesin family member 4A | 0.79 | 0.016 | 1.73 | 0.003 |
| 664 | KIF5B | 3799 | kinesin family member 5B | 0.80 | 0.022 | 1.77 | 0.033 |
| 665 | KIFC1 | 3833 | kinesin family member C1 | 0.78 | 0.015 | 1.35 | 0.003 |
| 666 | KIT | 3815 | v-kit Hardy-Zuckerman 4 feline sarcoma viral oncogene homolog | 0.79 | 0.023 | 0.77 | 0.010 |
| 667 | KLF13 | 51621 | Kruppel-like factor 13 | 0.80 | 0.037 | 0.81 | 0.019 |
| 668 | KLF2 | 10365 | Kruppel-like factor 2 | 0.80 | 0.034 | 0.63 | 0.028 |
| 669 | KLHL7 | 55975 | kelch-like family member 7 | 0.78 | 0.010 | 1.57 | 0.036 |
| 670 | KMT2A | 4297 | lysine (K)-specific methyltransferase 2A | 0.81 | 0.048 | 0.33 | 0.000 |
| 671 | KMT2A | 4297 | lysine (K)-specific methyltransferase 2A | 0.81 | 0.029 | 0.79 | 0.020 |
| 672 | KPNA2 | 3838 | karyopherin alpha 2 (RAG cohort 1, importin alpha 1) | 0.79 | 0.021 | 1.44 | 0.038 |
| 673 | KPTN | 11133 | kaptin (actin binding protein) | 0.80 | 0.027 | 0.74 | 0.046 |
| 674 | KRAS | 3845 | Kirsten rat sarcoma viral oncogene homolog | 0.82 | 0.047 | 1.87 | 0.016 |
| 675 | KRR1 | 11103 | KRR1, small subunit (SSU) processome component, homolog (yeast) | 0.81 | 0.039 | 1.87 | 0.001 |
| 676 | KRT14 | 3861 | keratin 14 | 0.78 | 0.024 | 0.89 | 0.014 |
| 677 | KRT15 | 3866 | keratin 15 | 0.80 | 0.025 | 0.88 | 0.002 |
| 678 | KRT23 | 25984 | keratin 23 (histone deacetylase inducible) | 0.79 | 0.014 | 0.85 | 0.015 |
| 679 | KRT5 | 3852 | keratin 5 | 0.73 | 0.006 | 0.75 | 0.000 |
| 680 | KRT6B | 3854 | keratin 6B | 0.76 | 0.018 | 0.77 | 0.023 |
| 681 | LAGE3 | 8270 | L antigen family, member 3 | 0.79 | 0.022 | 1.47 | 0.010 |
| 682 | LAMA1 | 284217 | laminin, alpha 1 | 0.78 | 0.014 | 0.77 | 0.020 |
| 683 | LAMA3 | 3909 | laminin, alpha 3 | 0.81 | 0.027 | 0.81 | 0.002 |
| 684 | LAMB2 | 3913 | laminin, beta 2 (laminin S) | 0.78 | 0.011 | 0.55 | 0.001 |
| 685 | LAMP1 | 3916 | lysosomal-associated membrane protein 1 | 0.78 | 0.018 | 0.59 | 0.031 |
| 686 | LANCL1 | 10314 | LanC lantibiotic synthetase component C-like 1 (bacterial) | 0.82 | 0.050 | 0.60 | 0.042 |

TABLE 3-continued 1,635 prognostic genes for use in combination with BTN3A2 gene

| No. | Gene Symbol | GENE ID | Gene Name | BTN3A2 HR | BTN3A2 p-value | prognostic gene HR | prognostic gene p-value |
|---|---|---|---|---|---|---|---|
| 687 | LAPTM4A | 9741 | lysosomal protein transmembrane 4 alpha | 0.77 | 0.010 | 0.35 | 0.001 |
| 688 | LAPTM4B | 55353 | lysosomal protein transmembrane 4 beta | 0.80 | 0.036 | 1.34 | 0.012 |
| 689 | LDLR | 3949 | low density lipoprotein receptor | 0.79 | 0.019 | 1.60 | 0.002 |
| 690 | LDLRAP1 | 26119 | low density lipoprotein receptor adaptor protein 1 | 0.80 | 0.044 | 0.50 | 0.002 |
| 691 | LEPR | 3953 | leptin receptor | 0.81 | 0.036 | 0.54 | 0.008 |
| 692 | LEPREL1 | 55214 | leprecan-like 1 | 0.79 | 0.024 | 0.77 | 0.008 |
| 693 | LEPREL4 | 10609 | leprecan-like 4 | 0.79 | 0.029 | 1.30 | 0.046 |
| 694 | LEPROT | 54741 | leptin receptor overlapping transcript | 0.82 | 0.044 | 0.42 | 0.002 |
| 695 | LETMD1 | 25875 | LETM1 domain containing 1 | 0.77 | 0.006 | 0.44 | 0.001 |
| 696 | LGR4 | 55366 | leucine-rich repeat containing G protein-coupled receptor 4 | 0.80 | 0.021 | 1.32 | 0.015 |
| 697 | LGR5 | 8549 | leucine-rich repeat containing G protein-coupled receptor 5 | 0.81 | 0.034 | 0.77 | 0.027 |
| 698 | LHFP | 10186 | lipoma HMGIC fusion partner | 0.81 | 0.047 | 0.59 | 0.003 |
| 699 | LHX1 | 3975 | LIM homeobox 1 | 0.79 | 0.024 | 1.27 | 0.024 |
| 700 | LINC00472 | 79940 | long intergenic non-protein coding RNA 472 | 0.79 | 0.014 | 0.73 | 0.000 |
| 701 | LINC00965 | 349196 | long intergenic non-protein coding RNA 965 | 0.80 | 0.031 | 0.78 | 0.022 |
| 702 | LMAN1 | 3998 | lectin, mannose-binding, 1 | 0.78 | 0.014 | 1.41 | 0.012 |
| 703 | LMBR1L | 55716 | limb development membrane protein 1-like | 0.77 | 0.013 | 0.50 | 0.018 |
| 704 | LMF1 | 64788 | lipase maturation factor 1 | 0.77 | 0.009 | 0.58 | 0.013 |
| 705 | LMO7 | 4008 | LIM domain 7 | 0.78 | 0.015 | 0.75 | 0.000 |
| 706 | LOC100129361 | 100129361 | chromosome X open reading frame 69-like | 0.77 | 0.010 | 1.60 | 0.016 |
| 707 | LOC100505498 | 100505498 | uncharacterized LOC100505498 | 0.74 | 0.004 | 0.62 | 0.002 |
| 708 | LOC100505915 | 100505915 | uncharacterized LOC100505915 | 0.80 | 0.021 | 0.74 | 0.002 |
| 709 | LOC100506282 | 100506282 | uncharacterized LOC100506282 | 0.78 | 0.011 | 0.76 | 0.005 |
| 710 | LOC100506469 | 100506469 | uncharacterized LOC100506469 | 0.75 | 0.004 | 0.57 | 0.003 |
| 711 | LONP2 | 100507577 | Ion peptidase 2, peroxisomal | 0.78 | 0.019 | 0.48 | 0.000 |
| 712 | SIAH1 | 100507577 | siah E3 ubiquitin protein ligase 1 | 0.78 | 0.017 | 0.71 | 0.004 |
| 713 | SNORD14B | 100508408 | small nucleolar RNA, C/D box 14B | 0.81 | 0.040 | 0.42 | 0.004 |
| 714 | ZNF44 | 101060181 | zinc finger protein 44 | 0.76 | 0.008 | 0.58 | 0.017 |
| 715 | NPIPB5 | 101929910 | nuclear pore complex interacting protein family, member B5 | 0.77 | 0.007 | 0.76 | 0.003 |
| 716 | POLR3E | 101060521 | polymerase (RNA) III (DNA directed) polypeptide E (80 kD) | 0.81 | 0.022 | 0.43 | 0.001 |
| 717 | LOC101927792 | 101927792 | uncharacterized LOC101927792 | 0.80 | 0.028 | 1.22 | 0.041 |
| 718 | RSRP1 | 101928189 | arginine/serine-rich protein 1 | 0.79 | 0.027 | 0.69 | 0.024 |
| 719 | MFAP3L | 101928198 | microfibrillar-associated protein 3-like | 0.82 | 0.045 | 1.30 | 0.043 |
| 720 | SLC19A1 | 101928717 | solute carrier family 19 (folate transporter), member 1 | 0.79 | 0.023 | 1.46 | 0.033 |
| 721 | TPT1 | 101928826 | tumor protein, translationally-controlled 1 | 0.74 | 0.005 | 0.46 | 0.001 |
| 722 | SNX29 | 101929304 | sorting nexin 29 | 0.82 | 0.031 | 0.72 | 0.019 |
| 723 | RIF1 | 101929336 | replication timing regulatory factor 1 | 0.79 | 0.014 | 1.59 | 0.011 |
| 724 | SULT1A4 | 101929857 | sulfotransferase family, cytosolic, 1A, phenol-preferring, member 4 | 0.76 | 0.007 | 0.59 | 0.008 |
| 725 | NPIPB5 | 101929910 | nuclear pore complex interacting protein family, member B5 | 0.80 | 0.020 | 0.73 | 0.005 |
| 726 | PKD1P1 | 102724993 | polycystic kidney disease 1 (autosomal dominant) pseudogene 1 | 0.78 | 0.013 | 0.65 | 0.002 |
| 727 | PKD1P1 | 101930075 | polycystic kidney disease 1 (autosomal dominant) pseudogene 1 | 0.79 | 0.018 | 0.70 | 0.016 |
| 728 | PKD1 | 101930075 | polycystic kidney disease 1 (autosomal dominant) | 0.76 | 0.007 | 0.61 | 0.014 |
| 729 | PPP2R3B | 102725016 | protein phosphatase 2, regulatory subunit B'', beta | 0.83 | 0.049 | 1.24 | 0.022 |
| 730 | LOC155060 | 155060 | AI894139 pseudogene | 0.79 | 0.012 | 0.65 | 0.019 |
| 731 | LOC157562 | 157562 | uncharacterized LOC157562 | 0.77 | 0.015 | 1.38 | 0.004 |
| 732 | LOC202181 | 202181 | SUMO-interacting motifs containing 1 pseudogene | 0.79 | 0.018 | 0.83 | 0.015 |
| 733 | PDE4C | 729966 | phosphodiesterase 4C, cAMP-specific | 0.76 | 0.008 | 0.81 | 0.038 |
| 734 | LONRF1 | 91694 | LON peptidase N-terminal domain and ring finger 1 | 0.79 | 0.020 | 0.70 | 0.006 |
| 735 | LPCAT4 | 254531 | lysophosphatidylcholine acyltransferase 4 | 0.80 | 0.027 | 0.43 | 0.002 |

TABLE 3-continued 1,635 prognostic genes for use in combination with BTN3A2 gene

| Gene No. | Gene Symbol | GENE ID | Gene Name | BTN3A2 HR | p-value | prognostic gene HR | p-value |
|---|---|---|---|---|---|---|---|
| 736 | LPPR2 | 64748 | lipid phosphate phosphatase-related protein type 2 | 0.77 | 0.025 | 1.55 | 0.027 |
| 737 | LRIG1 | 26018 | leucine-rich repeats and immunoglobulin-like domains 1 | 0.81 | 0.020 | 0.65 | 0.004 |
| 738 | LRRC1 | 55227 | leucine rich repeat containing 1 | 0.80 | 0.027 | 1.50 | 0.028 |
| 739 | LRRC17 | 10234 | leucine rich repeat containing 17 | 0.83 | 0.049 | 0.71 | 0.016 |
| 740 | LRRC48 | 83450 | leucine rich repeat containing 48 | 0.81 | 0.030 | 0.54 | 0.003 |
| 741 | LRRC59 | 55379 | leucine rich repeat containing 59 | 0.78 | 0.013 | 1.78 | 0.001 |
| 742 | LRRFIP1 | 9208 | leucine rich repeat (in FLII) interacting protein 1 | 0.79 | 0.019 | 0.73 | 0.048 |
| 743 | LRRN3 | 54674 | leucine rich repeat neuronal 3 | 0.80 | 0.028 | 0.68 | 0.044 |
| 744 | LRRTM2 | 26045 | leucine rich repeat transmembrane neuronal 2 | 0.82 | 0.044 | 0.79 | 0.022 |
| 745 | LSM1 | 27257 | LSM1, U6 small nuclear RNA associated | 0.80 | 0.034 | 1.90 | 0.000 |
| 746 | LSM3 | 27258 | LSM3 homolog, U6 small nuclear RNA associated (*S. cerevisiae*) | 0.75 | 0.007 | 1.68 | 0.019 |
| 747 | LTBP3 | 4054 | latent transforming growth factor beta binding protein 3 | 0.79 | 0.026 | 0.55 | 0.000 |
| 748 | LTBP4 | 8425 | latent transforming growth factor beta binding protein 4 | 0.79 | 0.022 | 0.66 | 0.028 |
| 749 | LYRM4 | 57128 | LYR motif containing 4 | 0.74 | 0.007 | 1.70 | 0.027 |
| 750 | MAB21L1 | 4081 | mab-21-like 1 (*C. elegans*) | 0.82 | 0.046 | 0.79 | 0.010 |
| 751 | MACF1 | 23499 | microtubule-actin crosslinking factor 1 | 0.79 | 0.027 | 0.48 | 0.000 |
| 752 | MAD2L1 | 4085 | MAD2 mitotic arrest deficient-like 1 (yeast) | 0.77 | 0.009 | 1.57 | 0.001 |
| 753 | MAD2L1BP | 9587 | MAD2L1 binding protein | 0.79 | 0.017 | 2.01 | 0.021 |
| 754 | MAFK | 7975 | v-maf avian musculoaponeurotic fibrosarcoma oncogene homolog K | 0.77 | 0.011 | 1.29 | 0.015 |
| 755 | MAGED1 | 9500 | melanoma antigen family D, 1 | 0.78 | 0.012 | 1.56 | 0.014 |
| 756 | MAGOHB | 55110 | mago-nashi homolog B (*Drosophila*) | 0.78 | 0.016 | 1.23 | 0.031 |
| 757 | MAK | 4117 | male germ cell-associated kinase | 0.81 | 0.039 | 0.85 | 0.044 |
| 758 | MAN1C1 | 57134 | mannosidase, alpha, class 1C, member 1 | 0.80 | 0.022 | 0.56 | 0.018 |
| 759 | MAN2C1 | 4123 | mannosidase, alpha, class 2C, member 1 | 0.80 | 0.018 | 0.55 | 0.026 |
| 760 | MAOA | 4128 | monoamine oxidase A | 0.80 | 0.028 | 0.71 | 0.001 |
| 761 | MAOB | 4129 | monoamine oxidase B | 0.81 | 0.041 | 0.89 | 0.048 |
| 762 | MAP2K1 | 5604 | mitogen-activated protein kinase kinase 1 | 0.77 | 0.014 | 1.99 | 0.016 |
| 763 | MAP3K12 | 7786 | mitogen-activated protein kinase kinase kinase 12 | 0.77 | 0.008 | 0.61 | 0.004 |
| 764 | MAP3K13 | 9175 | mitogen-activated protein kinase kinase kinase 13 | 0.79 | 0.018 | 1.27 | 0.049 |
| 765 | MAP7D3 | 79649 | MAP7 domain containing 3 | 0.76 | 0.010 | 0.72 | 0.027 |
| 766 | MAPK1 | 5594 | mitogen-activated protein kinase 1 | 0.77 | 0.016 | 1.75 | 0.015 |
| 767 | MARCH2 | 51257 | membrane-associated ring finger (C3HC4) 2, E3 ubiquitin protein ligase | 0.83 | 0.039 | 0.51 | 0.005 |
| 768 | MARCH5 | 54708 | membrane-associated ring finger (C3HC4) 5 | 0.79 | 0.017 | 2.06 | 0.033 |
| 769 | MARCH8 | 220972 | membrane-associated ring finger (C3HC4) 8, E3 ubiquitin protein ligase | 0.81 | 0.033 | 0.55 | 0.002 |
| 770 | MARS | 4141 | methionyl-tRNA synthetase | 0.77 | 0.008 | 3.44 | 0.000 |
| 771 | MAST4 | 375449 | microtubule associated serine/threonine kinase family member 4 | 0.81 | 0.031 | 0.74 | 0.043 |
| 772 | MBD3 | 53615 | methyl-CpG binding domain protein 3 | 0.79 | 0.020 | 0.58 | 0.049 |
| 773 | MCAT | 27349 | malonyl CoA:ACP acyltransferase (mitochondrial) | 0.79 | 0.021 | 1.84 | 0.015 |
| 774 | MCL1 | 4170 | myeloid cell leukemia 1 | 0.81 | 0.045 | 0.59 | 0.021 |
| 775 | MCM10 | 55388 | minichromosome maintenance complex component 10 | 0.79 | 0.016 | 1.39 | 0.001 |
| 776 | MCM2 | 4171 | minichromosome maintenance complex component 2 | 0.81 | 0.028 | 1.53 | 0.012 |
| 777 | MCM6 | 4175 | minichromosome maintenance complex component 6 | 0.77 | 0.013 | 1.63 | 0.020 |
| 778 | MCUR1 | 63933 | mitochondrial calcium uniporter regulator 1 | 0.76 | 0.004 | 1.95 | 0.002 |
| 779 | ME3 | 10873 | malic enzyme 3, NADP(+)-dependent, mitochondrial | 0.78 | 0.020 | 0.69 | 0.002 |
| 780 | MEA1 | 4201 | male-enhanced antigen 1 | 0.80 | 0.030 | 1.66 | 0.044 |
| 781 | MED1 | 5469 | mediator complex subunit 1 | 0.78 | 0.012 | 1.40 | 0.003 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 782 | MED31 | 51003 | mediator complex subunit 31 | 0.80 | 0.020 | 0.66 | 0.022 |
| 783 | MELK | 9833 | maternal embryonic leucine zipper kinase | 0.78 | 0.010 | 1.54 | 0.003 |
| 784 | METTL2A | 55798 | methyltransferase like 2A | 0.80 | 0.027 | 1.44 | 0.040 |
| 785 | METTL5 | 29081 | methyltransferase like 5 | 0.79 | 0.019 | 2.03 | 0.012 |
| 786 | MGC12488 | 84786 | uncharacterized protein MGC12488 | 0.78 | 0.010 | 0.78 | 0.002 |
| 787 | MGP | 4256 | matrix Gla protein | 0.81 | 0.027 | 0.81 | 0.007 |
| 788 | MGRN1 | 23295 | mahogunin ring finger 1, E3 ubiquitin protein ligase | 0.80 | 0.029 | 0.56 | 0.035 |
| 789 | MIF | 4282 | macrophage migration inhibitory factor (glycosylation-inhibiting factor) | 0.78 | 0.026 | 1.67 | 0.003 |
| 790 | MINK1 | 50488 | misshapen-like kinase 1 | 0.80 | 0.035 | 0.53 | 0.005 |
| 791 | NELFE | 100302242 | negative elongation factor complex member E | 0.74 | 0.005 | 1.68 | 0.009 |
| 792 | UCK2 | 100500832 | uridine-cytidine kinase 2 | 0.75 | 0.007 | 1.69 | 0.004 |
| 793 | STMN1 | 100500808 | stathmin 1 | 0.74 | 0.005 | 1.82 | 0.010 |
| 794 | PDCD4 | 100616113 | programmed cell death 4 (neoplastic transformation inhibitor) | 0.82 | 0.046 | 0.81 | 0.026 |
| 795 | NDUFS8 | 102465669 | NADH dehydrogenase (ubiquinone) Fe—S protein 8, 23 kDa (NADH-coenzyme Q reductase) | 0.80 | 0.031 | 1.67 | 0.003 |
| 796 | NEAT1 | 693197 | nuclear paraspeckle assembly transcript 1 (non-protein coding) | 0.77 | 0.010 | 0.81 | 0.040 |
| 797 | NEIL1 | 693216 | nei endonuclease VIII-like 1 (*E. coli*) | 0.80 | 0.030 | 0.72 | 0.043 |
| 798 | PFDN6 | 102465501 | prefoldin subunit 6 | 0.80 | 0.037 | 2.05 | 0.006 |
| 799 | SEMA3B | 102465526 | sema domain, immunoglobulin domain (Ig), short basic domain, secreted, (semaphorin) 3B | 0.80 | 0.023 | 0.84 | 0.030 |
| 800 | QARS | 102465536 | glutaminyl-tRNA synthetase | 0.77 | 0.013 | 0.36 | 0.002 |
| 801 | MIS18A | 54069 | MIS18 kinetochore protein A | 0.81 | 0.029 | 1.86 | 0.033 |
| 802 | MKL2 | 57496 | MKL/myocardin-like 2 | 0.80 | 0.020 | 0.57 | 0.025 |
| 803 | MKNK2 | 2872 | MAP kinase interacting serine/threonine kinase 2 | 0.75 | 0.007 | 0.49 | 0.000 |
| 804 | MLF1 | 4291 | myeloid leukemia factor 1 | 0.80 | 0.027 | 1.39 | 0.041 |
| 805 | MLLT10 | 8028 | myeloid/lymphoid or mixed-lineage leukemia; translocated to, 10 | 0.75 | 0.010 | 0.52 | 0.049 |
| 806 | MLLT11 | 10962 | myeloid/lymphoid or mixed-lineage leukemia; translocated to, 11 | 0.79 | 0.019 | 1.42 | 0.023 |
| 807 | MLLT3 | 4300 | myeloid/lymphoid or mixed-lineage leukemia; translocated to, 3 | 0.78 | 0.018 | 0.55 | 0.006 |
| 808 | MLPH | 79083 | melanophilin | 0.76 | 0.008 | 0.73 | 0.013 |
| 809 | MMP1 | 4312 | matrix metallopeptidase 1 (interstitial collagenase) | 0.74 | 0.004 | 1.22 | 0.000 |
| 810 | MMP11 | 4320 | matrix metallopeptidase 11 (stromelysin 3) | 0.81 | 0.048 | 1.18 | 0.050 |
| 811 | MNT | 4335 | MAX network transcriptional repressor | 0.80 | 0.032 | 0.40 | 0.006 |
| 812 | MOK | 5891 | MOK protein kinase | 0.76 | 0.005 | 0.39 | 0.000 |
| 813 | MOSPD1 | 56180 | motile sperm domain containing 1 | 0.79 | 0.023 | 2.16 | 0.005 |
| 814 | MPRIP | 23164 | myosin phosphatase Rho interacting protein | 0.79 | 0.024 | 0.55 | 0.029 |
| 815 | MR1 | 3140 | major histocompatibility complex, class I-related | 0.79 | 0.029 | 0.53 | 0.033 |
| 816 | MRPL13 | 28998 | mitochondrial ribosomal protein L13 | 0.78 | 0.017 | 1.72 | 0.000 |
| 817 | MRPL15 | 29088 | mitochondrial ribosomal protein L15 | 0.79 | 0.025 | 1.90 | 0.000 |
| 818 | MRPL17 | 63875 | mitochondrial ribosomal protein L17 | 0.76 | 0.008 | 2.05 | 0.002 |
| 819 | MRPL18 | 29074 | mitochondrial ribosomal protein L18 | 0.77 | 0.011 | 2.21 | 0.001 |
| 820 | MRPL22 | 29093 | mitochondrial ribosomal protein L22 | 0.79 | 0.017 | 1.75 | 0.031 |
| 821 | MRPL23 | 6150 | mitochondrial ribosomal protein L23 | 0.79 | 0.022 | 1.51 | 0.025 |
| 822 | MRPL3 | 11222 | mitochondrial ribosomal protein L3 | 0.74 | 0.004 | 2.34 | 0.000 |
| 823 | MRPL35 | 51318 | mitochondrial ribosomal protein L35 | 0.73 | 0.005 | 1.21 | 0.022 |
| 824 | MRPL40 | 64976 | mitochondrial ribosomal protein L40 | 0.79 | 0.023 | 1.36 | 0.049 |
| 825 | MRPL41 | 64975 | mitochondrial ribosomal protein L41 | 0.83 | 0.050 | 1.28 | 0.049 |
| 826 | MRPL48 | 51642 | mitochondrial ribosomal protein L48 | 0.78 | 0.019 | 2.51 | 0.000 |
| 827 | MRPS10 | 55173 | mitochondrial ribosomal protein S10 | 0.81 | 0.038 | 1.96 | 0.010 |
| 828 | MRPS11 | 64963 | mitochondrial ribosomal protein S11 | 0.71 | 0.003 | 1.86 | 0.006 |
| 829 | MRPS12 | 6183 | mitochondrial ribosomal protein S12 | 0.77 | 0.015 | 1.48 | 0.028 |
| 830 | MRPS14 | 63931 | mitochondrial ribosomal protein S14 | 0.79 | 0.022 | 1.85 | 0.021 |
| 831 | MRPS16 | 51021 | mitochondrial ribosomal protein S16 | 0.75 | 0.006 | 1.65 | 0.007 |
| 832 | MRPS17 | 51373 | mitochondrial ribosomal protein S17 | 0.76 | 0.013 | 3.13 | 0.000 |
| 833 | MRPS18A | 55168 | mitochondrial ribosomal protein S18A | 0.81 | 0.035 | 1.87 | 0.019 |
| 834 | MRPS18C | 51023 | mitochondrial ribosomal protein S18C | 0.81 | 0.031 | 1.46 | 0.004 |
| 835 | MRPS22 | 56945 | mitochondrial ribosomal protein S22 | 0.79 | 0.015 | 5.21 | 0.000 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 836 | MRPS28 | 28957 | mitochondrial ribosomal protein S28 | 0.81 | 0.039 | 1.33 | 0.029 |
| 837 | MRPS33 | 51650 | mitochondrial ribosomal protein S33 | 0.79 | 0.017 | 1.65 | 0.027 |
| 838 | MRPS7 | 51081 | mitochondrial ribosomal protein S7 | 0.79 | 0.021 | 2.07 | 0.003 |
| 839 | MRS2 | 57380 | MRS2 magnesium transporter | 0.78 | 0.011 | 2.22 | 0.004 |
| 840 | MS4A5 | 64232 | membrane-spanning 4-domains, subfamily A, member 5 | 0.78 | 0.013 | 1.46 | 0.024 |
| 841 | MSH6 | 2956 | mutS homolog 6 | 0.76 | 0.008 | 2.86 | 0.001 |
| 842 | MSMO1 | 6307 | methylsterol monooxygenase 1 | 0.79 | 0.022 | 1.36 | 0.046 |
| 843 | MSR1 | 4481 | macrophage scavenger receptor 1 | 0.77 | 0.013 | 1.46 | 0.040 |
| 844 | MSRA | 4482 | methionine sulfoxide reductase A | 0.80 | 0.025 | 0.43 | 0.003 |
| 845 | MST1 | 4485 | macrophage stimulating 1 (hepatocyte growth factor-like) | 0.76 | 0.006 | 0.69 | 0.008 |
| 846 | MTA1 | 9112 | metastasis associated 1 | 0.79 | 0.015 | 0.50 | 0.001 |
| 847 | MTA2 | 9219 | metastasis associated 1 family, member 2 | 0.79 | 0.033 | 0.73 | 0.033 |
| 848 | MTCH2 | 23788 | mitochondrial carrier 2 | 0.75 | 0.005 | 2.43 | 0.002 |
| 849 | MTERF3 | 51001 | mitochondrial transcription termination factor 3 | 0.82 | 0.049 | 1.58 | 0.003 |
| 850 | MTFR1 | 9650 | mitochondrial fission regulator 1 | 0.80 | 0.026 | 1.50 | 0.004 |
| 851 | MTG1 | 92170 | mitochondrial ribosome-associated GTPase 1 | 0.80 | 0.034 | 0.49 | 0.003 |
| 852 | MTHFD2 | 10797 | methylenetetrahydrofolate dehydrogenase 2, methenyltetrahydrofolate cyclohydrolase | 0.76 | 0.005 | 2.59 | 0.000 |
| 853 | MTHFS | 10588 | 5,10-methenyltetrahydrofolate synthetase | 0.78 | 0.015 | 1.61 | 0.048 |
| 854 | MTM1 | 4534 | myotubularin 1 | 0.78 | 0.016 | 1.43 | 0.042 |
| 855 | MTMR2 | 8898 | myotubularin related protein 2 | 0.78 | 0.017 | 1.57 | 0.050 |
| 856 | MTPAP | 55149 | mitochondrial poly(A) polymerase | 0.80 | 0.028 | 2.25 | 0.022 |
| 857 | MTSS1 | 9788 | metastasis suppressor 1 | 0.82 | 0.032 | 1.86 | 0.001 |
| 858 | MTX1 | 4580 | metaxin 1 | 0.79 | 0.027 | 1.52 | 0.044 |
| 859 | MTX2 | 10651 | metaxin 2 | 0.79 | 0.022 | 1.82 | 0.049 |
| 860 | MUC7 | 4589 | mucin 7, secreted | 0.78 | 0.016 | 0.82 | 0.044 |
| 861 | MUM1 | 84939 | melanoma associated antigen (mutated) 1 | 0.82 | 0.037 | 0.52 | 0.001 |
| 862 | MUT | 4594 | methylmalonyl CoA mutase | 0.78 | 0.011 | 2.20 | 0.003 |
| 863 | MXD1 | 4084 | MAX dimerization protein 1 | 0.81 | 0.036 | 1.28 | 0.043 |
| 864 | MYBL2 | 4605 | v-myb avian myeloblastosis viral oncogene homolog-like 2 | 0.77 | 0.012 | 1.26 | 0.010 |
| 865 | MYH6 | 4624 | myosin, heavy chain 6, cardiac muscle, alpha | 0.79 | 0.019 | 1.24 | 0.001 |
| 866 | MYL12B | 103910 | myosin, light chain 12B, regulatory | 0.78 | 0.015 | 0.69 | 0.036 |
| 867 | MYL6 | 4637 | myosin, light chain 6, alkali, smooth muscle and non-muscle | 0.76 | 0.007 | 0.47 | 0.017 |
| 868 | MYNN | 55892 | myoneurin | 0.80 | 0.026 | 1.76 | 0.036 |
| 869 | MYO15B | 80022 | myosin XVB pseudogene | 0.76 | 0.009 | 0.55 | 0.010 |
| 870 | MYO1C | 4641 | myosin IC | 0.75 | 0.006 | 0.62 | 0.014 |
| 871 | MYO5A | 4644 | myosin VA (heavy chain 12, myoxin) | 0.79 | 0.017 | 2.02 | 0.012 |
| 872 | MYO5C | 55930 | myosin VC | 0.80 | 0.019 | 0.63 | 0.038 |
| 873 | MYOF | 26509 | myoferlin | 0.80 | 0.021 | 0.61 | 0.013 |
| 874 | MYOZ2 | 51778 | myozenin 2 | 0.82 | 0.040 | 1.30 | 0.006 |
| 875 | MZF1 | 7593 | myeloid zinc finger 1 | 0.76 | 0.010 | 0.48 | 0.007 |
| 876 | NAA10 | 8260 | N(alpha)-acetyltransferase 10, NatA catalytic subunit | 0.79 | 0.016 | 1.89 | 0.014 |
| 877 | NAA15 | 80155 | N(alpha)-acetyltransferase 15, NatA auxiliary subunit | 0.81 | 0.027 | 1.68 | 0.009 |
| 878 | NAA40 | 79829 | N(alpha)-acetyltransferase 40, NatD catalytic subunit | 0.77 | 0.007 | 0.57 | 0.018 |
| 879 | NAA50 | 80218 | N(alpha)-acetyltransferase 50, NatE catalytic subunit | 0.81 | 0.030 | 1.60 | 0.037 |
| 880 | NAA60 | 79903 | N(alpha)-acetyltransferase 60, NatF catalytic subunit | 0.78 | 0.014 | 0.55 | 0.036 |
| 881 | NAALAD2 | 10003 | N-acetylated alpha-linked acidic dipeptidase 2 | 0.80 | 0.024 | 0.72 | 0.000 |
| 882 | NAB1 | 4664 | NGFI-A binding protein 1 (EGR1 binding protein 1) | 0.81 | 0.047 | 0.49 | 0.009 |
| 883 | NACA | 4666 | nascent polypeptide-associated complex alpha subunit | 0.77 | 0.010 | 0.37 | 0.003 |
| 884 | NANS | 54187 | N-acetylneuraminic acid synthase | 0.79 | 0.013 | 1.59 | 0.016 |
| 885 | NAP1L2 | 4674 | nucleosome assembly protein 1-like 2 | 0.80 | 0.029 | 0.81 | 0.038 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 886 | NAPG | 8774 | N-ethylmaleimide-sensitive factor attachment protein, gamma | 0.79 | 0.015 | 2.48 | 0.004 |
| 887 | NARF | 26502 | nuclear prelamin A recognition factor | 0.79 | 0.018 | 1.48 | 0.041 |
| 888 | NAV2 | 89797 | neuron navigator 2 | 0.82 | 0.043 | 0.75 | 0.045 |
| 889 | NBPF1 | 55672 | neuroblastoma breakpoint family, member 1 | 0.81 | 0.041 | 0.66 | 0.050 |
| 890 | NBPF10 | 25832 | neuroblastoma breakpoint family, member 10 | 0.81 | 0.034 | 0.62 | 0.015 |
| 891 | NBR2 | 10230 | neighbor of BRCA1 gene 2 (non-protein coding) | 0.78 | 0.015 | 0.79 | 0.017 |
| 892 | NCAPG | 64151 | non-SMC condensin I complex, subunit G | 0.76 | 0.005 | 1.98 | 0.000 |
| 893 | NCOA1 | 8648 | nuclear receptor coactivator 1 | 0.77 | 0.008 | 0.41 | 0.003 |
| 894 | NCOR1 | 9611 | nuclear receptor corepressor 1 | 0.82 | 0.043 | 0.48 | 0.007 |
| 895 | NCSTN | 23385 | nicastrin | 0.78 | 0.019 | 0.52 | 0.021 |
| 896 | NDE1 | 54820 | nudE neurodevelopment protein 1 | 0.78 | 0.013 | 0.62 | 0.011 |
| 897 | NDP | 4693 | Norrie disease (pseudoglioma) | 0.77 | 0.011 | 0.78 | 0.014 |
| 898 | NDRG2 | 57447 | NDRG family member 2 | 0.76 | 0.009 | 0.64 | 0.004 |
| 899 | NDST2 | 8509 | N-deacetylase/N-sulfotransferase (heparan glucosaminyl) 2 | 0.82 | 0.047 | 0.74 | 0.023 |
| 900 | NDUFA3 | 4696 | NADH dehydrogenase (ubiquinone) 1 alpha subcomplex, 3, 9 kDa | 0.78 | 0.017 | 1.60 | 0.010 |
| 901 | NDUFA6 | 4700 | NADH dehydrogenase (ubiquinone) 1 alpha subcomplex, 6, 14 kDa | 0.76 | 0.010 | 1.80 | 0.002 |
| 902 | NDUFA7 | 4701 | NADH dehydrogenase (ubiquinone) 1 alpha subcomplex, 7, 14.5 kDa | 0.80 | 0.032 | 1.30 | 0.023 |
| 903 | NDUFA8 | 4702 | NADH dehydrogenase (ubiquinone) 1 alpha subcomplex, 8, 19 kDa | 0.73 | 0.002 | 2.26 | 0.000 |
| 904 | NDUFB3 | 4709 | NADH dehydrogenase (ubiquinone) 1 beta subcomplex, 3, 12 kDa | 0.79 | 0.018 | 4.97 | 0.000 |
| 905 | NDUFB5 | 4711 | NADH dehydrogenase (ubiquinone) 1 beta subcomplex, 5, 16 kDa | 0.74 | 0.004 | 2.54 | 0.001 |
| 906 | NDUFS1 | 4719 | NADH dehydrogenase (ubiquinone) Fe—S protein 1, 75 kDa | 0.78 | 0.012 | 2.31 | 0.000 |
| 907 | NDUFS3 | 4722 | NADH dehydrogenase (ubiquinone) Fe—S protein 3, 30 kDa | 0.79 | 0.019 | 1.93 | 0.014 |
| 908 | NEK2 | 4751 | NIMA-related kinase 2 | 0.80 | 0.026 | 1.45 | 0.003 |
| 909 | NEK3 | 4752 | NIMA-related kinase 3 | 0.80 | 0.035 | 0.61 | 0.043 |
| 910 | NEK9 | 91754 | NIMA-related kinase 9 | 0.83 | 0.043 | 0.42 | 0.001 |
| 911 | NELL1 | 4745 | NEL-like 1 (chicken) | 0.80 | 0.034 | 1.36 | 0.003 |
| 912 | NEU2 | 4759 | sialidase 2 (cytosolic sialidase) | 0.78 | 0.017 | 1.41 | 0.008 |
| 913 | NFATC2IP | 84901 | nuclear factor of activated T-cells, cytoplasmic, calcineurin-dependent 2 interacting protein | 0.76 | 0.013 | 0.42 | 0.001 |
| 914 | NFE2L1 | 4779 | nuclear factor, erythroid 2-like 1 | 0.77 | 0.013 | 0.49 | 0.006 |
| 915 | NFIB | 4781 | nuclear factor I/B | 0.81 | 0.041 | 0.79 | 0.037 |
| 916 | NFRKB | 4798 | nuclear factor related to kappaB binding protein | 0.76 | 0.007 | 0.37 | 0.000 |
| 917 | NFX1 | 4799 | nuclear transcription factor, X-box binding 1 | 0.79 | 0.016 | 0.30 | 0.001 |
| 918 | NHLH1 | 4807 | nescient helix loop helix 1 | 0.82 | 0.048 | 1.42 | 0.041 |
| 919 | NINL | 22981 | ninein-like | 0.79 | 0.014 | 0.55 | 0.010 |
| 920 | NIPSNAP3B | 55335 | nipsnap homolog 3B (C. elegans) | 0.78 | 0.013 | 0.76 | 0.038 |
| 921 | NISCH | 11188 | nischarin | 0.77 | 0.016 | 0.52 | 0.002 |
| 922 | NIT2 | 56954 | nitrilase family, member 2 | 0.80 | 0.026 | 1.71 | 0.037 |
| 923 | NKX2-5 | 1482 | NK2 homeobox 5 | 0.82 | 0.044 | 1.35 | 0.016 |
| 924 | NME1 | 4830 | NME/NM23 nucleoside diphosphate kinase 1 | 0.80 | 0.034 | 1.66 | 0.002 |
| 925 | NME5 | 8382 | NME/NM23 family member 5 | 0.79 | 0.018 | 0.73 | 0.022 |
| 926 | NMT2 | 9397 | N-myristoyltransferase 2 | 0.82 | 0.048 | 0.55 | 0.043 |
| 927 | NOL11 | 25926 | nucleolar protein 11 | 0.79 | 0.019 | 1.66 | 0.021 |
| 928 | NOL7 | 51406 | nucleolar protein 7, 27 kDa | 0.81 | 0.030 | 2.23 | 0.003 |
| 929 | NOL9 | 79707 | nucleolar protein 9 | 0.82 | 0.047 | 0.44 | 0.037 |
| 930 | NOP10 | 55505 | NOP10 ribonucleoprotein | 0.72 | 0.002 | 2.63 | 0.001 |
| 931 | NOP16 | 51491 | NOP16 nucleolar protein | 0.77 | 0.011 | 1.64 | 0.005 |
| 932 | NOS1 | 4842 | nitric oxide synthase 1 (neuronal) | 0.77 | 0.011 | 0.69 | 0.038 |
| 933 | NOTCH2 | 4853 | notch 2 | 0.81 | 0.040 | 0.56 | 0.029 |
| 934 | NOTCH2NL | 388677 | notch 2 N-terminal like | 0.82 | 0.044 | 0.79 | 0.040 |
| 935 | NOV | 4856 | nephroblastoma overexpressed | 0.77 | 0.011 | 0.63 | 0.015 |
| 936 | NPAS2 | 4862 | neuronal PAS domain protein 2 | 0.81 | 0.032 | 0.70 | 0.035 |
| 937 | NPC1L1 | 29881 | NPC1-like 1 | 0.78 | 0.024 | 1.48 | 0.001 |
| 938 | NPEPPS | 9520 | aminopeptidase puromycin sensitive | 0.81 | 0.027 | 0.57 | 0.022 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 939 | NPIPA1 | 9284 | nuclear pore complex interacting protein family, member A1 | 0.78 | 0.015 | 0.59 | 0.004 |
| 940 | NPIPA1 | 9284 | nuclear pore complex interacting protein family, member A1 | 0.78 | 0.011 | 0.79 | 0.005 |
| 941 | NPL | 80896 | N-acetylneuraminate pyruvate lyase (dihydrodipicolinate synthase) | 0.74 | 0.001 | 1.32 | 0.003 |
| 942 | NPR3 | 4883 | natriuretic peptide receptor 3 | 0.82 | 0.045 | 1.41 | 0.038 |
| 943 | NPY1R | 4886 | neuropeptide Y receptor Y1 | 0.82 | 0.034 | 0.88 | 0.011 |
| 944 | NPY5R | 4889 | neuropeptide Y receptor Y5 | 0.77 | 0.009 | 0.80 | 0.011 |
| 945 | NQO1 | 1728 | NAD(P)H dehydrogenase, quinone 1 | 0.79 | 0.020 | 1.35 | 0.009 |
| 946 | NRAS | 4893 | neuroblastoma RAS viral (v-ras) oncogene homolog | 0.78 | 0.012 | 1.58 | 0.050 |
| 947 | NRDE2 | 55051 | NRDE-2, necessary for RNA interference, domain containing | 0.81 | 0.019 | 0.50 | 0.000 |
| 948 | NRN1 | 51299 | neuritin 1 | 0.80 | 0.027 | 0.56 | 0.011 |
| 949 | NRXN1 | 9378 | neurexin 1 | 0.77 | 0.009 | 0.68 | 0.012 |
| 950 | NSDHL | 50814 | NAD(P) dependent steroid dehydrogenase -like | 0.78 | 0.016 | 1.59 | 0.015 |
| 951 | NSFL1C | 55968 | NSFL1 (p97) cofactor (p47) | 0.79 | 0.018 | 1.81 | 0.024 |
| 952 | NSL1 | 25936 | NSL1, MIS12 kinetochore complex component | 0.78 | 0.015 | 1.96 | 0.020 |
| 953 | NT5DC3 | 51559 | 5'-nucleotidase domain containing 3 | 0.76 | 0.007 | 0.57 | 0.013 |
| 954 | NT5E | 4907 | 5'-nucleotidase, ecto (CD73) | 0.76 | 0.011 | 1.30 | 0.045 |
| 955 | NTRK2 | 4915 | neurotrophic tyrosine kinase, receptor, type 2 | 0.80 | 0.022 | 0.48 | 0.000 |
| 956 | NUDT21 | 11051 | nudix (nucleoside diphosphate linked moiety X)-type motif 21 | 0.75 | 0.005 | 1.66 | 0.016 |
| 957 | NUMA1 | 4926 | nuclear mitotic apparatus protein 1 | 0.78 | 0.022 | 0.56 | 0.002 |
| 958 | NUP155 | 9631 | nucleoporin 155 kDa | 0.80 | 0.031 | 1.50 | 0.048 |
| 959 | NUP93 | 9688 | nucleoporin 93 kDa | 0.75 | 0.005 | 1.17 | 0.028 |
| 960 | NUS1 | 11049 | nuclear undecaprenyl pyrophosphate synthase 1 homolog (S. cerevisiae) | 0.79 | 0.019 | 1.59 | 0.028 |
| 961 | NUS1P3 | 11049 | nuclear undecaprenyl pyrophosphate synthase 1 homolog (S. cerevisiae) pseudogene 3 | 0.74 | 0.010 | 1.35 | 0.034 |
| 962 | NUSAP1 | 51203 | nucleolar and spindle associated protein 1 | 0.79 | 0.016 | 1.73 | 0.000 |
| 963 | NVL | 4931 | nuclear VCP-like | 0.76 | 0.009 | 1.20 | 0.038 |
| 964 | NXF1 | 10482 | nuclear RNA export factor 1 | 0.79 | 0.025 | 0.43 | 0.003 |
| 965 | NXF3 | 56000 | nuclear RNA export factor 3 | 0.81 | 0.038 | 1.26 | 0.033 |
| 966 | NXT2 | 55916 | nuclear transport factor 2-like export factor 2 | 0.79 | 0.019 | 1.80 | 0.013 |
| 967 | OGT | 8473 | O-linked N-acetylglucosamine (GlcNAc) transferase | 0.78 | 0.017 | 0.56 | 0.002 |
| 968 | OMD | 4958 | osteomodulin | 0.80 | 0.024 | 0.74 | 0.038 |
| 969 | OR5I1 | 10798 | olfactory receptor, family 5, subfamily I, member 1 | 0.78 | 0.014 | 0.79 | 0.035 |
| 970 | OR7E47P | 26628 | olfactory receptor, family 7, subfamily E, member 47 pseudogene | 0.79 | 0.025 | 1.27 | 0.030 |
| 971 | ORAI3 | 93129 | ORAI calcium release-activated calcium modulator 3 | 0.77 | 0.006 | 0.46 | 0.002 |
| 972 | ORC4 | 5000 | origin recognition complex, subunit 4 | 0.78 | 0.013 | 1.55 | 0.036 |
| 973 | ORC5 | 5001 | origin recognition complex, subunit 5 | 0.77 | 0.011 | 1.86 | 0.021 |
| 974 | ORMDL2 | 29095 | ORMDL sphingolipid biosynthesis regulator 2 | 0.77 | 0.010 | 2.27 | 0.000 |
| 975 | OS9 | 10956 | osteosarcoma amplified 9, endoplasmic reticulum lectin | 0.80 | 0.032 | 0.53 | 0.037 |
| 976 | OSBPL10 | 114884 | oxysterol binding protein-like 10 | 0.81 | 0.046 | 0.57 | 0.022 |
| 977 | OXR1 | 55074 | oxidation resistance 1 | 0.82 | 0.044 | 1.50 | 0.012 |
| 978 | P2RY2 | 5029 | purinergic receptor P2Y, G-protein coupled, 2 | 0.80 | 0.031 | 1.19 | 0.049 |
| 979 | PA2G4 | 5036 | proliferation-associated 2G4, 38 kDa | 0.82 | 0.043 | 2.15 | 0.007 |
| 980 | PAFAH1B3 | 5050 | platelet-activating factor acetylhydrolase 1b, catalytic subunit 3 (29 kDa) | 0.77 | 0.012 | 1.98 | 0.000 |
| 981 | PALM | 5064 | paralemmin | 0.79 | 0.013 | 0.55 | 0.031 |
| 982 | PALMD | 54873 | palmdelphin | 0.81 | 0.045 | 0.74 | 0.041 |
| 983 | PANX1 | 24145 | pannexin 1 | 0.78 | 0.011 | 2.19 | 0.021 |
| 984 | PARL | 55486 | presenilin associated, rhomboid-like | 0.78 | 0.014 | 2.17 | 0.016 |
| 985 | PARPBP | 55010 | PARP1 binding protein | 0.79 | 0.022 | 1.45 | 0.017 |
| 986 | PAX7 | 5081 | paired box 7 | 0.77 | 0.014 | 1.60 | 0.004 |
| 987 | PBK | 55872 | PDZ binding kinase | 0.78 | 0.012 | 1.55 | 0.001 |

TABLE 3-continued 1,635 prognostic genes for use in combination with BTN3A2 gene

| Gene No. | Gene Symbol | GENE ID | Gene Name | BTN3A2 HR | p-value | prognostic gene HR | p-value |
|---|---|---|---|---|---|---|---|
| 988 | PCDHB17 | 54661 | protocadherin beta 17 pseudogene | 0.80 | 0.027 | 1.32 | 0.027 |
| 989 | PCNXL2 | 80003 | pecanex-like 2 (*Drosophila*) | 0.81 | 0.049 | 0.53 | 0.006 |
| 990 | PCSK1N | 27344 | proprotein convertase subtilisin/kexin type 1 inhibitor | 0.80 | 0.026 | 1.22 | 0.032 |
| 991 | PCSK5 | 5125 | proprotein convertase subtilisin/kexin type 5 | 0.81 | 0.038 | 0.66 | 0.037 |
| 992 | PCTP | 58488 | phosphatidylcholine transfer protein | 0.77 | 0.011 | 1.17 | 0.046 |
| 993 | PDAP1 | 11333 | PDGFA associated protein 1 | 0.82 | 0.040 | 1.77 | 0.036 |
| 994 | PDCD10 | 11235 | programmed cell death 10 | 0.81 | 0.033 | 1.80 | 0.029 |
| 995 | PDCD5 | 9141 | programmed cell death 5 | 0.78 | 0.010 | 2.16 | 0.001 |
| 996 | PDCL | 5082 | phosducin-like | 0.77 | 0.014 | 2.29 | 0.008 |
| 997 | PDE2A | 5138 | phosphodiesterase 2A, cGMP-stimulated | 0.79 | 0.025 | 0.77 | 0.012 |
| 998 | PDE6D | 5147 | phosphodiesterase 6D, cGMP-specific, rod, delta | 0.78 | 0.013 | 1.38 | 0.039 |
| 999 | PDGFD | 80310 | platelet derived growth factor D | 0.81 | 0.031 | 0.60 | 0.003 |
| 1000 | PDHA1 | 5160 | pyruvate dehydrogenase (lipoamide) alpha 1 | 0.77 | 0.009 | 3.34 | 0.001 |
| 1001 | PDHX | 8050 | pyruvate dehydrogenase complex, component X | 0.80 | 0.025 | 1.60 | 0.032 |
| 1002 | PDLIM1 | 9124 | PDZ and LIM domain 1 | 0.75 | 0.010 | 0.69 | 0.005 |
| 1003 | PDZK1 | 5174 | PDZ domain containing 1 | 0.80 | 0.027 | 0.86 | 0.018 |
| 1004 | PEX13 | 5194 | peroxisomal biogenesis factor 13 | 0.77 | 0.015 | 1.33 | 0.039 |
| 1005 | PEX5L | 51555 | peroxisomal biogenesis factor 5-like | 0.80 | 0.028 | 0.80 | 0.020 |
| 1006 | PFDN1 | 5201 | prefoldin subunit 1 | 0.76 | 0.013 | 2.20 | 0.007 |
| 1007 | PFDN2 | 5202 | prefoldin subunit 2 | 0.76 | 0.008 | 1.94 | 0.002 |
| 1008 | PFDN4 | 5203 | prefoldin subunit 4 | 0.80 | 0.029 | 1.48 | 0.025 |
| 1009 | PGAM1 | 5223 | phosphoglycerate mutase 1 (brain) | 0.80 | 0.032 | 1.74 | 0.048 |
| 1010 | PGK1 | 5230 | phosphoglycerate kinase 1 | 0.79 | 0.020 | 2.35 | 0.001 |
| 1011 | PGM3 | 5238 | phosphoglucomutase 3 | 0.79 | 0.016 | 1.50 | 0.031 |
| 1012 | PHB | 5245 | prohibitin | 0.78 | 0.015 | 1.53 | 0.016 |
| 1013 | PHF20L1 | 51105 | PHD finger protein 20-like 1 | 0.81 | 0.034 | 1.84 | 0.011 |
| 1014 | PHKA2 | 5256 | phosphorylase kinase, alpha 2 (liver) | 0.80 | 0.022 | 0.48 | 0.021 |
| 1015 | PHKG2 | 5261 | phosphorylase kinase, gamma 2 (testis) | 0.78 | 0.009 | 0.56 | 0.009 |
| 1016 | PHTF2 | 57157 | putative homeodomain transcription factor 2 | 0.79 | 0.014 | 1.68 | 0.011 |
| 1017 | PI15 | 51050 | peptidase inhibitor 15 | 0.79 | 0.015 | 0.76 | 0.006 |
| 1018 | PIGL | 9487 | phosphatidylinositol glycan anchor biosynthesis, class L | 0.77 | 0.009 | 0.62 | 0.042 |
| 1019 | PIK3CA | 5290 | phosphatidylinositol-4,5-bisphosphate 3-kinase, catalytic subunit alpha | 0.79 | 0.015 | 1.48 | 0.027 |
| 1020 | PIK3CB | 5291 | phosphatidylinositol-4,5-bisphosphate 3-kinase, catalytic subunit beta | 0.79 | 0.019 | 1.80 | 0.009 |
| 1021 | PIK3R4 | 30849 | phosphoinositide-3-kinase, regulatory subunit 4 | 0.78 | 0.015 | 1.90 | 0.019 |
| 1022 | PIN1 | 5300 | peptidylprolyl cis/trans isomerase, NIMA-interacting 1 | 0.75 | 0.006 | 1.26 | 0.010 |
| 1023 | PIN1P1 | 5301 | peptidylprolyl cis/trans isomerase, NIMA-interacting 1 pseudogene 1 | 0.78 | 0.013 | 1.31 | 0.013 |
| 1024 | PIN4 | 5303 | protein (peptidylprolyl cis/trans isomerase) NIMA-interacting, 4 (parvulin) | 0.79 | 0.025 | 2.08 | 0.012 |
| 1025 | PIP | 5304 | prolactin-induced protein | 0.80 | 0.035 | 0.87 | 0.003 |
| 1026 | PIP4K2C | 79837 | phosphatidylinositol-5-phosphate 4-kinase, type II, gamma | 0.79 | 0.023 | 1.79 | 0.011 |
| 1027 | PIPOX | 51268 | pipecolic acid oxidase | 0.81 | 0.036 | 1.45 | 0.030 |
| 1028 | PIR | 8544 | pirin (iron-binding nuclear protein) | 0.78 | 0.012 | 1.47 | 0.004 |
| 1029 | PITRM1 | 10531 | pitrilysin metallopeptidase 1 | 0.80 | 0.019 | 1.93 | 0.030 |
| 1030 | PITX1 | 5307 | paired-like homeodomain 1 | 0.80 | 0.031 | 1.15 | 0.046 |
| 1031 | PKP4 | 8502 | plakophilin 4 | 0.80 | 0.028 | 0.54 | 0.020 |
| 1032 | PLA2G12A | 81579 | phospholipase A2, group XIIA | 0.81 | 0.049 | 2.68 | 0.000 |
| 1033 | PLA2G7 | 7941 | phospholipase A2, group VII (platelet-activating factor acetylhydrolase, plasma) | 0.76 | 0.004 | 1.39 | 0.012 |
| 1034 | PLAA | 9373 | phospholipase A2-activating protein | 0.77 | 0.012 | 1.61 | 0.028 |
| 1035 | PLAT | 5327 | plasminogen activator, tissue | 0.82 | 0.045 | 0.81 | 0.050 |
| 1036 | PLAUR | 5329 | plasminogen activator, urokinase receptor | 0.79 | 0.022 | 1.53 | 0.031 |
| 1037 | PLEKHF2 | 79666 | pleckstrin homology domain containing, family F (with FYVE domain) member 2 | 0.80 | 0.035 | 1.57 | 0.003 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1038 | PLEKHG3 | 26030 | pleckstrin homology domain containing, family G (with RhoGef domain) member 3 | 0.82 | 0.036 | 0.60 | 0.018 |
| 1039 | PLIN2 | 123 | perilipin 2 | 0.75 | 0.005 | 1.43 | 0.006 |
| 1040 | PLK1 | 5347 | polo-like kinase 1 | 0.81 | 0.037 | 1.53 | 0.020 |
| 1041 | PLK4 | 10733 | polo-like kinase 4 | 0.78 | 0.021 | 1.34 | 0.048 |
| 1042 | PLLP | 51090 | plasmolipin | 0.79 | 0.021 | 0.60 | 0.041 |
| 1043 | PLSCR3 | 57048 | phospholipid scramblase 3 | 0.77 | 0.012 | 0.55 | 0.009 |
| 1044 | PLSCR4 | 57088 | phospholipid scramblase 4 | 0.82 | 0.047 | 0.52 | 0.000 |
| 1045 | PMEL | 6490 | premelanosome protein | 0.77 | 0.010 | 0.71 | 0.008 |
| 1046 | PMP22 | 5376 | peripheral myelin protein 22 | 0.82 | 0.043 | 0.71 | 0.011 |
| 1047 | PMS2P8 | 729299 | postmeiotic segregation increased 2 pseudogene 8 | 0.77 | 0.011 | 0.62 | 0.017 |
| 1048 | PNISR | 25957 | PNN-interacting serine/arginine-rich protein | 0.80 | 0.036 | 0.69 | 0.021 |
| 1049 | PNLIPRP1 | 5407 | pancreatic lipase-related protein 1 | 0.77 | 0.013 | 0.74 | 0.022 |
| 1050 | PNMA2 | 10687 | paraneoplastic Ma antigen 2 | 0.78 | 0.014 | 0.67 | 0.010 |
| 1051 | PODNL1 | 79883 | podocan-like 1 | 0.77 | 0.009 | 0.74 | 0.002 |
| 1052 | PODXL2 | 50512 | podocalyxin-like 2 | 0.77 | 0.007 | 1.38 | 0.000 |
| 1053 | POLA1 | 5422 | polymerase (DNA directed), alpha 1, catalytic subunit | 0.79 | 0.017 | 1.91 | 0.018 |
| 1054 | POLA2 | 23649 | polymerase (DNA directed), alpha 2, accessory subunit | 0.74 | 0.006 | 1.41 | 0.010 |
| 1055 | POLD4 | 57804 | polymerase (DNA-directed), delta 4, accessory subunit | 0.76 | 0.008 | 1.37 | 0.002 |
| 1056 | POLR2A | 5430 | polymerase (RNA) II (DNA directed) polypeptide A, 220 kDa | 0.80 | 0.028 | 0.55 | 0.009 |
| 1057 | POLR2B | 5431 | polymerase (RNA) II (DNA directed) polypeptide B, 140 kDa | 0.79 | 0.021 | 2.50 | 0.011 |
| 1058 | POLR2J4 | 84820 | polymerase (RNA) II (DNA directed) polypeptide J4, pseudogene | 0.80 | 0.019 | 0.61 | 0.038 |
| 1059 | POLR2K | 5440 | polymerase (RNA) II (DNA directed) polypeptide K, 7.0 kDa | 0.78 | 0.017 | 1.85 | 0.000 |
| 1060 | POM121L9P | 29774 | POM121 transmembrane nucleoporin-like 9, pseudogene | 0.81 | 0.034 | 0.79 | 0.047 |
| 1061 | POMP | 51371 | proteasome maturation protein | 0.81 | 0.033 | 2.13 | 0.022 |
| 1062 | PON2 | 5445 | paraoxonase 2 | 0.77 | 0.017 | 0.66 | 0.045 |
| 1063 | POP1 | 10940 | processing of precursor 1, ribonuclease P/MRP subunit (S. cerevisiae) | 0.81 | 0.036 | 1.54 | 0.012 |
| 1064 | POP7 | 10248 | processing of precursor 7, ribonuclease P/MRP subunit (S. cerevisiae) | 0.81 | 0.030 | 2.40 | 0.000 |
| 1065 | POU2F3 | 25833 | POU class 2 homeobox 3 | 0.78 | 0.014 | 0.79 | 0.010 |
| 1066 | PP14571 | 100130449 | uncharacterized LOC100130449 | 0.81 | 0.045 | 1.18 | 0.033 |
| 1067 | PPA2 | 27068 | pyrophosphatase (inorganic) 2 | 0.78 | 0.017 | 1.58 | 0.046 |
| 1068 | PPEF1 | 5475 | protein phosphatase, EF-hand calcium binding domain 1 | 0.82 | 0.050 | 1.55 | 0.035 |
| 1069 | PPIEL | 728448 | peptidylprolyl isomerase E-like pseudogene | 0.81 | 0.030 | 0.71 | 0.011 |
| 1070 | PPL | 5493 | periplakin | 0.76 | 0.006 | 0.64 | 0.001 |
| 1071 | PPP1CA | 5499 | protein phosphatase 1, catalytic subunit, alpha isozyme | 0.76 | 0.010 | 1.45 | 0.008 |
| 1072 | PPP1R12B | 4660 | protein phosphatase 1, regulatory subunit 12B | 0.78 | 0.015 | 0.42 | 0.004 |
| 1073 | PPP1R14B | 26472 | protein phosphatase 1, regulatory (inhibitor) subunit 14B | 0.79 | 0.022 | 1.73 | 0.009 |
| 1074 | PPP1R2 | 5504 | protein phosphatase 1, regulatory (inhibitor) subunit 2 | 0.79 | 0.021 | 1.60 | 0.044 |
| 1075 | PPP2R3C | 55012 | protein phosphatase 2, regulatory subunit B", gamma | 0.78 | 0.014 | 1.91 | 0.033 |
| 1076 | PPP3CA | 5530 | protein phosphatase 3, catalytic subunit, alpha isozyme | 0.82 | 0.039 | 1.52 | 0.020 |
| 1077 | PPP3CB | 5532 | protein phosphatase 3, catalytic subunit, beta isozyme | 0.80 | 0.024 | 1.69 | 0.048 |
| 1078 | PPRC1 | 23082 | peroxisome proliferator-activated receptor gamma, coactivator-related 1 | 0.81 | 0.031 | 1.95 | 0.020 |
| 1079 | PQLC1 | 80148 | PQ loop repeat containing 1 | 0.79 | 0.016 | 0.45 | 0.002 |
| 1080 | PRAME | 23532 | preferentially expressed antigen in melanoma | 0.82 | 0.049 | 1.21 | 0.032 |
| 1081 | PRC1 | 9055 | protein regulator of cytokinesis 1 | 0.79 | 0.019 | 1.82 | 0.000 |
| 1082 | PRDM10 | 56980 | PR domain containing 10 | 0.79 | 0.011 | 0.42 | 0.020 |
| 1083 | PRDX4 | 10549 | peroxiredoxin 4 | 0.78 | 0.010 | 2.00 | 0.000 |
| 1084 | PREP | 5550 | prolyl endopeptidase | 0.79 | 0.016 | 2.04 | 0.005 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1085 | PRH1 | 5554 | proline-rich protein HaeIII subfamily 1 | 0.76 | 0.011 | 1.79 | 0.003 |
| 1086 | PRICKLE4 | 29964 | prickle homolog 4 (*Drosophila*) | 0.79 | 0.024 | 1.91 | 0.019 |
| 1087 | PRIM1 | 5557 | primase, DNA, polypeptide 1 (49 kDa) | 0.80 | 0.035 | 2.44 | 0.000 |
| 1088 | PRKCD | 5580 | protein kinase C, delta | 0.79 | 0.024 | 1.38 | 0.022 |
| 1089 | PRKCI | 5584 | protein kinase C, iota | 0.79 | 0.014 | 2.45 | 0.003 |
| 1090 | PRMT1 | 3276 | protein arginine methyltransferase 1 | 0.80 | 0.029 | 1.64 | 0.044 |
| 1091 | PRO2012 | 55478 | uncharacterized protein PRO2012 | 0.77 | 0.011 | 0.86 | 0.045 |
| 1092 | PROC | 5624 | protein C (inactivator of coagulation factors Va and VIIIa) | 0.79 | 0.019 | 0.73 | 0.042 |
| 1093 | PROL1 | 58503 | proline rich, lacrimal 1 | 0.81 | 0.032 | 0.74 | 0.010 |
| 1094 | PRPF18 | 8559 | pre-mRNA processing factor 18 | 0.82 | 0.037 | 2.09 | 0.017 |
| 1095 | PRPF4 | 9128 | pre-mRNA processing factor 4 | 0.74 | 0.008 | 1.81 | 0.025 |
| 1096 | PRR14 | 78994 | proline rich 14 | 0.80 | 0.021 | 0.51 | 0.029 |
| 1097 | PSMA1 | 5682 | proteasome (prosome, macropain) subunit, alpha type, 1 | 0.77 | 0.009 | 2.33 | 0.005 |
| 1098 | PSMA2 | 5683 | proteasome (prosome, macropain) subunit, alpha type, 2 | 0.78 | 0.010 | 1.94 | 0.010 |
| 1099 | PSMA3 | 5684 | proteasome (prosome, macropain) subunit, alpha type, 3 | 0.75 | 0.005 | 1.74 | 0.010 |
| 1100 | PSMA4 | 5685 | proteasome (prosome, macropain) subunit, alpha type, 4 | 0.78 | 0.007 | 2.27 | 0.009 |
| 1101 | PSMA7 | 5688 | proteasome (prosome, macropain) subunit, alpha type, 7 | 0.79 | 0.020 | 1.69 | 0.006 |
| 1102 | PSMB3 | 5691 | proteasome (prosome, macropain) subunit, beta type, 3 | 0.80 | 0.033 | 1.70 | 0.003 |
| 1103 | PSMB5 | 5693 | proteasome (prosome, macropain) subunit, beta type, 5 | 0.77 | 0.016 | 2.13 | 0.002 |
| 1104 | PSMB7 | 5695 | proteasome (prosome, macropain) subunit, beta type, 7 | 0.78 | 0.010 | 1.93 | 0.011 |
| 1105 | PSMC3 | 5702 | proteasome (prosome, macropain) 26S subunit, ATPase, 3 | 0.82 | 0.032 | 1.56 | 0.022 |
| 1106 | PSMC3IP | 29893 | PSMC3 interacting protein | 0.78 | 0.018 | 0.69 | 0.039 |
| 1107 | PSMC6 | 5706 | proteasome (prosome, macropain) 26S subunit, ATPase, 6 | 0.78 | 0.016 | 1.58 | 0.031 |
| 1108 | PSMD10 | 5716 | proteasome (prosome, macropain) 26S subunit, non-ATPase, 10 | 0.77 | 0.007 | 2.27 | 0.001 |
| 1109 | PSMD12 | 5718 | proteasome (prosome, macropain) 26S subunit, non-ATPase, 12 | 0.79 | 0.018 | 1.93 | 0.003 |
| 1110 | PSMD14 | 10213 | proteasome (prosome, macropain) 26S subunit, non-ATPase, 14 | 0.78 | 0.012 | 2.24 | 0.005 |
| 1111 | PSMD2 | 5708 | proteasome (prosome, macropain) 26S subunit, non-ATPase, 2 | 0.80 | 0.025 | 2.42 | 0.001 |
| 1112 | PSMD3 | 5709 | proteasome (prosome, macropain) 26S subunit, non-ATPase, 3 | 0.78 | 0.015 | 1.34 | 0.012 |
| 1113 | PSMD4 | 5710 | proteasome (prosome, macropain) 26S subunit, non-ATPase, 4 | 0.80 | 0.025 | 1.79 | 0.032 |
| 1114 | PSMD6 | 9861 | proteasome (prosome, macropain) 26S subunit, non-ATPase, 6 | 0.80 | 0.019 | 2.09 | 0.013 |
| 1115 | PSMD7 | 5713 | proteasome (prosome, macropain) 26S subunit, non-ATPase, 7 | 0.78 | 0.010 | 2.22 | 0.003 |
| 1116 | PTBP3 | 9991 | polypyrimidine tract binding protein 3 | 0.81 | 0.033 | 1.59 | 0.035 |
| 1117 | PTCH1 | 5727 | patched 1 | 0.81 | 0.035 | 0.58 | 0.013 |
| 1118 | PTGER3 | 5733 | prostaglandin E receptor 3 (subtype EP3) | 0.81 | 0.026 | 0.73 | 0.020 |
| 1119 | PTK2 | 5747 | protein tyrosine kinase 2 | 0.81 | 0.043 | 1.50 | 0.021 |
| 1120 | PTN | 5764 | pleiotrophin | 0.78 | 0.012 | 0.64 | 0.002 |
| 1121 | PTPN18 | 26469 | protein tyrosine phosphatase, non-receptor type 18 (brain-derived) | 0.82 | 0.042 | 0.55 | 0.050 |
| 1122 | PTPRD | 5789 | protein tyrosine phosphatase, receptor type, D | 0.80 | 0.033 | 0.62 | 0.013 |
| 1123 | PTPRF | 5792 | protein tyrosine phosphatase, receptor type, F | 0.78 | 0.013 | 0.62 | 0.040 |
| 1124 | PTPRT | 11122 | protein tyrosine phosphatase, receptor type, T | 0.82 | 0.047 | 0.85 | 0.041 |
| 1125 | PTPRZ1 | 5803 | protein tyrosine phosphatase, receptor-type, Z polypeptide 1 | 0.79 | 0.021 | 0.83 | 0.014 |
| 1126 | PTRF | 284119 | polymerase I and transcript release factor | 0.81 | 0.030 | 0.73 | 0.043 |
| 1127 | PTRH2 | 51651 | peptidyl-tRNA hydrolase 2 | 0.77 | 0.015 | 1.66 | 0.001 |
| 1128 | PTS | 5805 | 6-pyruvoyltetrahydropterin synthase | 0.80 | 0.026 | 1.89 | 0.022 |
| 1129 | PTTG1 | 9232 | pituitary tumor-transforming 1 | 0.80 | 0.017 | 2.08 | 0.000 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1130 | PTTG3P | 26255 | pituitary tumor-transforming 3, pseudogene | 0.76 | 0.012 | 1.50 | 0.002 |
| 1131 | PURA | 5813 | purine-rich element binding protein A | 0.81 | 0.045 | 0.59 | 0.041 |
| 1132 | PURG | 29942 | purine-rich element binding protein G | 0.79 | 0.023 | 0.80 | 0.013 |
| 1133 | PWP1 | 11137 | PWP1 homolog (S. cerevisiae) | 0.79 | 0.020 | 2.10 | 0.022 |
| 1134 | PYCRL | 65263 | pyrroline-5-carboxylate reductase-like | 0.80 | 0.031 | 1.19 | 0.032 |
| 1135 | QPCT | 25797 | glutaminyl-peptide cyclotransferase | 0.82 | 0.029 | 1.36 | 0.002 |
| 1136 | RAB11A | 8766 | RAB11A, member RAS oncogene family | 0.80 | 0.022 | 1.79 | 0.046 |
| 1137 | RAB11FIP1 | 80223 | RAB11 family interacting protein 1 (class I) | 0.81 | 0.042 | 1.27 | 0.018 |
| 1138 | RAB26 | 25837 | RAB26, member RAS oncogene family | 0.77 | 0.009 | 0.65 | 0.043 |
| 1139 | RABIF | 5877 | RAB interacting factor | 0.79 | 0.030 | 2.38 | 0.002 |
| 1140 | RACGAP1 | 29127 | Rac GTPase activating protein 1 | 0.77 | 0.013 | 1.75 | 0.000 |
| 1141 | RAD23A | 5886 | RAD23 homolog A (S. cerevisiae) | 0.79 | 0.014 | 1.96 | 0.002 |
| 1142 | RAD23B | 5887 | RAD23 homolog B (S. cerevisiae) | 0.76 | 0.009 | 1.84 | 0.016 |
| 1143 | RAD51AP1 | 10635 | RAD51 associated protein 1 | 0.80 | 0.015 | 1.46 | 0.007 |
| 1144 | RAD51C | 5889 | RAD51 paralog C | 0.77 | 0.015 | 1.42 | 0.047 |
| 1145 | RAD54B | 25788 | RAD54 homolog B (S. cerevisiae) | 0.78 | 0.021 | 1.63 | 0.001 |
| 1146 | RAG2 | 5897 | recombination activating gene 2 | 0.81 | 0.034 | 0.88 | 0.027 |
| 1147 | RAI2 | 10742 | retinoic acid induced 2 | 0.82 | 0.043 | 0.82 | 0.037 |
| 1148 | RALA | 5898 | v-ral simian leukemia viral oncogene homolog A (ras related) | 0.77 | 0.007 | 2.50 | 0.000 |
| 1149 | RAMP3 | 10268 | receptor (G protein-coupled) activity modifying protein 3 | 0.82 | 0.044 | 0.72 | 0.049 |
| 1150 | RANBP1 | 5902 | RAN binding protein 1 | 0.79 | 0.021 | 1.53 | 0.033 |
| 1151 | RANBP9 | 10048 | RAN binding protein 9 | 0.82 | 0.043 | 1.59 | 0.033 |
| 1152 | RAP1GDS1 | 5910 | RAP1, GTP-GDP dissociation stimulator 1 | 0.78 | 0.018 | 1.57 | 0.009 |
| 1153 | RAP2A | 5911 | RAP2A, member of RAS oncogene family | 0.78 | 0.011 | 1.65 | 0.020 |
| 1154 | RASL12 | 51285 | RAS-like, family 12 | 0.80 | 0.032 | 0.58 | 0.003 |
| 1155 | RASSF9 | 9182 | Ras association (RalGDS/AF-6) domain family (N-terminal) member 9 | 0.81 | 0.040 | 0.78 | 0.017 |
| 1156 | RBM3 | 5935 | RNA binding motif (RNP1, RRM) protein 3 | 0.78 | 0.016 | 0.48 | 0.012 |
| 1157 | RBM5 | 10181 | RNA binding motif protein 5 | 0.80 | 0.029 | 0.47 | 0.001 |
| 1158 | RBPMS | 11030 | RNA binding protein with multiple splicing | 0.77 | 0.008 | 0.62 | 0.002 |
| 1159 | RBX1 | 9978 | ring-box 1, E3 ubiquitin protein ligase | 0.76 | 0.012 | 1.57 | 0.018 |
| 1160 | RC3H2 | 54542 | ring finger and CCCH-type domains 2 | 0.76 | 0.003 | 2.46 | 0.000 |
| 1161 | RECQL4 | 9401 | RecQ protein-like 4 | 0.81 | 0.040 | 1.28 | 0.003 |
| 1162 | RELN | 5649 | reelin | 0.78 | 0.017 | 0.72 | 0.003 |
| 1163 | REPS1 | 85021 | RALBP1 associated Eps domain containing 1 | 0.82 | 0.036 | 0.79 | 0.020 |
| 1164 | RERE | 473 | arginine-glutamic acid dipeptide (RE) repeats | 0.78 | 0.016 | 0.47 | 0.008 |
| 1165 | RFC2 | 5982 | replication factor C (activator 1) 2, 40 kDa | 0.78 | 0.012 | 1.74 | 0.014 |
| 1166 | RFC4 | 5984 | replication factor C (activator 1) 4, 37 kDa | 0.78 | 0.014 | 1.83 | 0.019 |
| 1167 | RFC5 | 5985 | replication factor C (activator 1) 5, 36.5 kDa | 0.80 | 0.027 | 1.91 | 0.012 |
| 1168 | RFNG | 5986 | RFNG O-fucosylpeptide 3-beta-N-acetylglucosaminyltransferase | 0.78 | 0.014 | 0.47 | 0.008 |
| 1169 | RGL1 | 23179 | ral guanine nucleotide dissociation stimulator-like 1 | 0.79 | 0.032 | 0.56 | 0.010 |
| 1170 | RGPD3 | 84220 | RANBP2-like and GRIP domain containing 3 | 0.80 | 0.029 | 0.54 | 0.008 |
| 1171 | RGS5 | 8490 | regulator of G-protein signaling 5 | 0.81 | 0.046 | 0.75 | 0.021 |
| 1172 | RHBDD3 | 25807 | rhomboid domain containing 3 | 0.82 | 0.043 | 1.75 | 0.045 |
| 1173 | RHBDF1 | 64285 | rhomboid 5 homolog 1 (Drosophila) | 0.77 | 0.005 | 0.59 | 0.010 |
| 1174 | RHOA | 387 | ras homolog family member A | 0.81 | 0.042 | 0.48 | 0.003 |
| 1175 | RIC3 | 79608 | RIC3 acetylcholine receptor chaperone | 0.78 | 0.014 | 0.75 | 0.006 |
| 1176 | RIOK3 | 8780 | RIO kinase 3 | 0.79 | 0.019 | 0.67 | 0.029 |
| 1177 | RIPK2 | 8767 | receptor-interacting serine-threonine kinase 2 | 0.80 | 0.027 | 1.78 | 0.022 |
| 1178 | RIT1 | 6016 | Ras-like without CAAX 1 | 0.75 | 0.006 | 1.91 | 0.005 |
| 1179 | RITA1 | 84934 | RBPJ interacting and tubulin associated 1 | 0.76 | 0.015 | 1.47 | 0.037 |
| 1180 | RLN2 | 6019 | relaxin 2 | 0.77 | 0.008 | 0.60 | 0.000 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1181 | RMDN1 | 51115 | regulator of microtubule dynamics 1 | 0.82 | 0.050 | 1.61 | 0.006 |
| 1182 | RMI1 | 80010 | RecQ mediated genome instability 1 | 0.81 | 0.030 | 1.70 | 0.009 |
| 1183 | RNASEH2A | 10535 | ribonuclease H2, subunit A | 0.79 | 0.022 | 1.69 | 0.012 |
| 1184 | RNASEL | 6041 | ribonuclease L (2',5'-oligoisoadenylate synthetase-dependent) | 0.78 | 0.019 | 0.70 | 0.015 |
| 1185 | RNF13 | 11342 | ring finger protein 13 | 0.75 | 0.006 | 2.76 | 0.001 |
| 1186 | RNF139 | 11236 | ring finger protein 139 | 0.77 | 0.016 | 2.62 | 0.000 |
| 1187 | RNF40 | 9810 | ring finger protein 40, E3 ubiquitin protein ligase | 0.79 | 0.015 | 0.52 | 0.014 |
| 1188 | RNF41 | 10193 | ring finger protein 41, E3 ubiquitin protein ligase | 0.78 | 0.015 | 1.24 | 0.041 |
| 1189 | RNF6 | 6049 | ring finger protein (C3H2C3 type) 6 | 0.80 | 0.020 | 1.49 | 0.050 |
| 1190 | RNF7 | 9616 | ring finger protein 7 | 0.78 | 0.025 | 2.00 | 0.014 |
| 1191 | RNU86 | 6122 | RNA, U86 small nucleolar | 0.79 | 0.020 | 0.55 | 0.014 |
| 1192 | ROBO1 | 6091 | roundabout, axon guidance receptor, homolog 1 (Drosophila) | 0.79 | 0.014 | 1.28 | 0.048 |
| 1193 | ROPN1B | 152015 | rhophilin associated tail protein 1B | 0.80 | 0.026 | 0.80 | 0.035 |
| 1194 | RORC | 6097 | RAR-related orphan receptor C | 0.80 | 0.020 | 0.67 | 0.033 |
| 1195 | RPA2 | 6118 | replication protein A2, 32 kDa | 0.76 | 0.013 | 0.47 | 0.009 |
| 1196 | RPAP3 | 79657 | RNA polymerase II associated protein 3 | 0.78 | 0.015 | 1.68 | 0.016 |
| 1197 | SNORA70 | 26778 | small nucleolar RNA, H/ACA box 70 | 0.80 | 0.026 | 0.49 | 0.006 |
| 1198 | RPL12 | 6136 | ribosomal protein L12 | 0.81 | 0.043 | 0.58 | 0.018 |
| 1199 | SNORD68 | 606500 | small nucleolar RNA, C/D box 68 | 0.80 | 0.034 | 0.61 | 0.023 |
| 1200 | RPL13AP5 | 26816 | ribosomal protein L13a pseudogene 5 | 0.77 | 0.014 | 0.41 | 0.001 |
| 1201 | RPL13A | 23521 | ribosomal protein L13a | 0.81 | 0.046 | 0.62 | 0.008 |
| 1202 | RPL17 | 6139 | ribosomal protein L17 | 0.81 | 0.036 | 0.76 | 0.010 |
| 1203 | RPL22 | 6146 | ribosomal protein L22 | 0.78 | 0.018 | 0.59 | 0.033 |
| 1204 | RPL23A | 6147 | ribosomal protein L23a | 0.76 | 0.007 | 0.52 | 0.006 |
| 1205 | SNORD42A | 26809 | small nucleolar RNA, C/D box 42A | 0.75 | 0.006 | 0.36 | 0.001 |
| 1206 | RPL27 | 6155 | ribosomal protein L27 | 0.70 | 0.001 | 0.27 | 0.000 |
| 1207 | SNORA45A | 619562 | small nucleolar RNA, H/ACA box 45A | 0.78 | 0.016 | 0.36 | 0.001 |
| 1208 | RPL29 | 6159 | ribosomal protein L29 | 0.79 | 0.020 | 0.48 | 0.005 |
| 1209 | RPL3 | 6122 | ribosomal protein L3 | 0.75 | 0.008 | 0.42 | 0.000 |
| 1210 | RPL31 | 6160 | ribosomal protein L31 | 0.78 | 0.021 | 0.39 | 0.000 |
| 1211 | RPL32 | 6161 | ribosomal protein L32 | 0.80 | 0.027 | 0.40 | 0.002 |
| 1212 | RPL34 | 6164 | ribosomal protein L34 | 0.82 | 0.043 | 0.56 | 0.003 |
| 1213 | RPL36 | 25873 | ribosomal protein L36 | 0.82 | 0.047 | 0.59 | 0.010 |
| 1214 | RPL37A | 6168 | ribosomal protein L37a | 0.72 | 0.003 | 0.39 | 0.001 |
| 1215 | RPL38 | 6169 | ribosomal protein L38 | 0.77 | 0.008 | 0.45 | 0.006 |
| 1216 | RPL39 | 6170 | ribosomal protein L39 | 0.74 | 0.005 | 0.26 | 0.000 |
| 1217 | RPL41 | 6171 | ribosomal protein L41 | 0.72 | 0.003 | 0.29 | 0.000 |
| 1218 | SNORD21 | 6125 | small nucleolar RNA, C/D box 21 | 0.78 | 0.018 | 0.53 | 0.004 |
| 1219 | RPL6 | 6128 | ribosomal protein L6 | 0.76 | 0.009 | 0.42 | 0.004 |
| 1220 | RPL7 | 6129 | ribosomal protein L7 | 0.78 | 0.012 | 0.55 | 0.013 |
| 1221 | SNORD36B | 26820 | small nucleolar RNA, C/D box 36B | 0.80 | 0.029 | 0.49 | 0.005 |
| 1222 | RPL9 | 6133 | ribosomal protein L9 | 0.75 | 0.006 | 0.46 | 0.004 |
| 1223 | RPLP0 | 6175 | ribosomal protein, large, P0 | 0.78 | 0.014 | 0.55 | 0.028 |
| 1224 | RPLP1 | 6176 | ribosomal protein, large, P1 | 0.76 | 0.010 | 0.32 | 0.000 |
| 1225 | SNORA52 | 619565 | small nucleolar RNA, H/ACA box 52 | 0.81 | 0.034 | 0.42 | 0.000 |
| 1226 | RPP21 | 56658 | ribonuclease P/MRP 21 kDa subunit | 0.78 | 0.017 | 2.31 | 0.004 |
| 1227 | RPP40 | 10799 | ribonuclease P/MRP 40 kDa subunit | 0.79 | 0.022 | 2.20 | 0.012 |
| 1228 | RPS10 | 6204 | ribosomal protein S10 | 0.79 | 0.020 | 0.56 | 0.012 |
| 1229 | RPS11 | 6205 | ribosomal protein S11 | 0.81 | 0.040 | 0.34 | 0.001 |
| 1230 | RPS14 | 6208 | ribosomal protein S14 | 0.77 | 0.016 | 0.29 | 0.000 |
| 1231 | RPS15 | 6209 | ribosomal protein S15 | 0.80 | 0.028 | 0.39 | 0.001 |
| 1232 | RPS16 | 6217 | ribosomal protein S16 | 0.81 | 0.038 | 0.45 | 0.004 |
| 1233 | RPS18 | 6222 | ribosomal protein S18 | 0.75 | 0.007 | 0.40 | 0.001 |
| 1234 | RPS2 | 6187 | ribosomal protein S2 | 0.76 | 0.007 | 0.34 | 0.000 |
| 1235 | RPS20 | 6224 | ribosomal protein S20 | 0.77 | 0.012 | 0.56 | 0.019 |
| 1236 | RPS21 | 6227 | ribosomal protein S21 | 0.79 | 0.019 | 0.54 | 0.014 |
| 1237 | RPS23 | 6228 | ribosomal protein S23 | 0.72 | 0.002 | 0.24 | 0.000 |
| 1238 | RPS24 | 6229 | ribosomal protein S24 | 0.79 | 0.022 | 0.56 | 0.037 |
| 1239 | RPS25 | 6230 | ribosomal protein S25 | 0.80 | 0.042 | 0.30 | 0.000 |
| 1240 | RPS27 | 6232 | ribosomal protein S27 | 0.78 | 0.014 | 0.34 | 0.000 |
| 1241 | RPS27A | 6233 | ribosomal protein S27a | 0.80 | 0.035 | 0.47 | 0.000 |
| 1242 | RPS28 | 6234 | ribosomal protein S28 | 0.74 | 0.004 | 0.51 | 0.001 |
| 1243 | RPS29 | 6235 | ribosomal protein S29 | 0.78 | 0.023 | 0.31 | 0.000 |
| 1244 | RPS2P45 | 80052 | ribosomal protein S2 pseudogene 45 | 0.78 | 0.009 | 0.83 | 0.008 |
| 1245 | RPS3 | 6188 | ribosomal protein S3 | 0.79 | 0.017 | 0.61 | 0.006 |
| 1246 | RPS3A | 6189 | ribosomal protein S3A | 0.74 | 0.006 | 0.38 | 0.000 |
| 1247 | RPS4X | 6191 | ribosomal protein S4, X-linked | 0.75 | 0.007 | 0.42 | 0.001 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1248 | RPS6 | 6194 | ribosomal protein S6 | 0.75 | 0.009 | 0.43 | 0.000 |
| 1249 | RPS6KA2 | 6196 | ribosomal protein S6 kinase, 90 kDa, polypeptide 2 | 0.79 | 0.030 | 0.59 | 0.044 |
| 1250 | RPS6KB1 | 6198 | ribosomal protein S6 kinase, 70 kDa, polypeptide 1 | 0.81 | 0.029 | 1.45 | 0.048 |
| 1251 | RPS6KC1 | 26750 | ribosomal protein S6 kinase, 52 kDa, polypeptide 1 | 0.78 | 0.008 | 3.11 | 0.000 |
| 1252 | RPS | 6202 | ribosomal protein S8 | 0.74 | 0.006 | 0.58 | 0.004 |
| 1253 | RRM2 | 6241 | ribonucleotide reductase M2 | 0.77 | 0.010 | 1.50 | 0.004 |
| 1254 | RRN3P1 | 730092 | RNA polymerase I transcription factor homolog (S. cerevisiae) pseudogene 1 | 0.79 | 0.014 | 0.60 | 0.005 |
| 1255 | RRP15 | 51018 | ribosomal RNA processing 15 homolog (S. cerevisiae) | 0.76 | 0.010 | 1.61 | 0.009 |
| 1256 | RRP7A | 27341 | ribosomal RNA processing 7 homolog A (S. cerevisiae) | 0.77 | 0.015 | 1.43 | 0.034 |
| 1257 | RRP7B | 91695 | ribosomal RNA processing 7 homolog B (S. cerevisiae) | 0.76 | 0.008 | 0.53 | 0.002 |
| 1258 | RSAD2 | 91543 | radical S-adenosyl methionine domain containing 2 | 0.74 | 0.003 | 1.40 | 0.007 |
| 1259 | RSF1 | 51773 | remodeling and spacing factor 1 | 0.81 | 0.035 | 1.35 | 0.032 |
| 1260 | RTCA | 8634 | RNA 3'-terminal phosphate cyclase | 0.77 | 0.010 | 1.50 | 0.036 |
| 1261 | RUFY1 | 80230 | RUN and FYVE domain containing 1 | 0.78 | 0.016 | 0.40 | 0.028 |
| 1262 | RUFY2 | 55680 | RUN and FYVE domain containing 2 | 0.80 | 0.024 | 0.73 | 0.005 |
| 1263 | RUNX1T1 | 862 | runt-related transcription factor 1; translocated to, 1 (cyclin D-related) | 0.77 | 0.014 | 0.61 | 0.019 |
| 1264 | S100P | 6286 | S100 calcium binding protein P | 0.81 | 0.028 | 1.24 | 0.000 |
| 1265 | SAFB2 | 9667 | scaffold attachment factor B2 | 0.80 | 0.031 | 0.55 | 0.034 |
| 1266 | SALL2 | 6297 | spalt-like transcription factor 2 | 0.79 | 0.017 | 0.63 | 0.029 |
| 1267 | SAMHD1 | 25939 | SAM domain and HD domain 1 | 0.74 | 0.003 | 1.46 | 0.022 |
| 1268 | SAR1B | 51128 | secretion associated, Ras related GTPase 1B | 0.78 | 0.011 | 1.46 | 0.024 |
| 1269 | SCFD1 | 23256 | sec1 family domain containing 1 | 0.75 | 0.004 | 3.31 | 0.000 |
| 1270 | SCN4A | 6329 | sodium channel, voltage-gated, type IV, alpha subunit | 0.81 | 0.029 | 1.34 | 0.036 |
| 1271 | SCUBE2 | 57758 | signal peptide, CUB domain, EGF-like 2 | 0.82 | 0.033 | 0.87 | 0.043 |
| 1272 | SDF2L1 | 23753 | stromal cell-derived factor 2-like 1 | 0.77 | 0.013 | 1.49 | 0.033 |
| 1273 | SDS | 10993 | serine dehydratase | 0.81 | 0.038 | 1.59 | 0.026 |
| 1274 | SEC24D | 9871 | SEC24 family member D | 0.75 | 0.007 | 1.95 | 0.005 |
| 1275 | SEC31B | 25956 | SEC31 homolog B (S. cerevisiae) | 0.78 | 0.013 | 0.72 | 0.027 |
| 1276 | SEC61G | 23480 | Sec61 gamma subunit | 0.78 | 0.019 | 1.94 | 0.009 |
| 1277 | SEC62 | 7095 | SEC62 homolog (S. cerevisiae) | 0.77 | 0.008 | 2.22 | 0.001 |
| 1278 | SELP | 6403 | selectin P (granule membrane protein 140 kDa, antigen CD62) | 0.75 | 0.009 | 0.42 | 0.000 |
| 1279 | SEMA3G | 56920 | sema domain, immunoglobulin domain (Ig), short basic domain, secreted, (semaphorin) 3G | 0.77 | 0.010 | 0.41 | 0.000 |
| 1280 | SEMA6D | 80031 | sema domain, transmembrane domain (TM), and cytoplasmic domain, (semaphorin) 6D | 0.76 | 0.006 | 0.63 | 0.001 |
| 1281 | SERPINB8 | 5271 | serpin peptidase inhibitor, clade B (ovalbumin), member 8 | 0.80 | 0.022 | 1.51 | 0.023 |
| 1282 | SESN1 | 27244 | sestrin 1 | 0.81 | 0.035 | 0.38 | 0.000 |
| 1283 | SF3B1 | 23451 | splicing factor 3b, subunit 1, 155 kDa | 0.79 | 0.026 | 0.50 | 0.023 |
| 1284 | SFI1 | 9814 | Sfi1 homolog, spindle assembly associated (yeast) | 0.80 | 0.018 | 0.57 | 0.014 |
| 1285 | SFRP1 | 6422 | secreted frizzled-related protein 1 | 0.81 | 0.041 | 0.64 | 0.000 |
| 1286 | SGCB | 6443 | sarcoglycan, beta (43 kDa dystrophin-associated glycoprotein) | 0.78 | 0.012 | 1.77 | 0.006 |
| 1287 | SGK2 | 10110 | serum/glucocorticoid regulated kinase 2 | 0.73 | 0.003 | 0.55 | 0.003 |
| 1288 | SGSM2 | 9905 | small G protein signaling modulator 2 | 0.76 | 0.006 | 0.54 | 0.007 |
| 1289 | SH2B1 | 25970 | SH2B adaptor protein 1 | 0.72 | 0.002 | 0.50 | 0.000 |
| 1290 | SH2D3A | 10045 | SH2 domain containing 3A | 0.75 | 0.007 | 0.58 | 0.029 |
| 1291 | SHC2 | 25759 | SHC (Src homology 2 domain containing) transforming protein 2 | 0.78 | 0.012 | 0.61 | 0.012 |
| 1292 | SHH | 6469 | sonic hedgehog | 0.82 | 0.048 | 0.76 | 0.013 |
| 1293 | SHMT2 | 6472 | serine hydroxymethyltransferase 2 (mitochondrial) | 0.81 | 0.038 | 1.63 | 0.038 |
| 1294 | SIK3 | 23387 | SIK family kinase 3 | 0.82 | 0.049 | 0.53 | 0.004 |
| 1295 | SIN3B | 23309 | SIN3 transcription regulator family member B | 0.78 | 0.016 | 0.48 | 0.003 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1296 | SIX1 | 6495 | SIX homeobox 1 | 0.80 | 0.028 | 1.26 | 0.008 |
| 1297 | SKA1 | 220134 | spindle and kinetochore associated complex subunit 1 | 0.79 | 0.025 | 1.35 | 0.012 |
| 1298 | SKP1 | 6500 | S-phase kinase-associated protein 1 | 0.76 | 0.007 | 0.46 | 0.014 |
| 1299 | SLBP | 7884 | stem-loop binding protein | 0.80 | 0.036 | 2.56 | 0.001 |
| 1300 | SLC10A3 | 8273 | solute carrier family 10, member 3 | 0.77 | 0.012 | 1.19 | 0.044 |
| 1301 | SLC13A1 | 6561 | solute carrier family 13 (sodium/sulfate symporter), member 1 | 0.81 | 0.038 | 0.82 | 0.019 |
| 1302 | SLC19A3 | 80704 | solute carrier family 19 (thiamine transporter), member 3 | 0.79 | 0.025 | 0.77 | 0.015 |
| 1303 | SLC1A5 | 6510 | solute carrier family 1 (neutral amino acid transporter), member 5 | 0.80 | 0.024 | 1.48 | 0.030 |
| 1304 | SLC22A18 | 5002 | solute carrier family 22, member 18 | 0.80 | 0.024 | 0.66 | 0.012 |
| 1305 | SLC22A18AS | 5003 | solute carrier family 22 (organic cation transporter), member 18 antisense | 0.81 | 0.040 | 0.71 | 0.020 |
| 1306 | SLC22A5 | 6584 | solute carrier family 22 (organic cation/carnitine transporter), member 5 | 0.75 | 0.007 | 0.51 | 0.021 |
| 1307 | SLC25A1 | 6576 | solute carrier family 25 (mitochondrial carrier; citrate transporter), member 1 | 0.81 | 0.033 | 1.57 | 0.028 |
| 1308 | SLC25A12 | 8604 | solute carrier family 25 (aspartate/glutamate carrier), member 12 | 0.81 | 0.043 | 0.48 | 0.011 |
| 1309 | SLC25A23 | 79085 | solute carrier family 25 (mitochondrial carrier; phosphate carrier), member 23 | 0.78 | 0.021 | 1.54 | 0.016 |
| 1310 | SLC25A32 | 81034 | solute carrier family 25 (mitochondrial folate carrier), member 32 | 0.81 | 0.033 | 1.81 | 0.004 |
| 1311 | SLC25A37 | 51312 | solute carrier family 25 (mitochondrial iron transporter), member 37 | 0.79 | 0.016 | 0.47 | 0.000 |
| 1312 | SLC26A2 | 1836 | solute carrier family 26 (anion exchanger), member 2 | 0.80 | 0.024 | 1.36 | 0.045 |
| 1313 | SLC2A10 | 81031 | solute carrier family 2 (facilitated glucose transporter), member 10 | 0.81 | 0.036 | 1.37 | 0.023 |
| 1314 | SLC2A6 | 11182 | solute carrier family 2 (facilitated glucose transporter), member 6 | 0.77 | 0.010 | 1.24 | 0.035 |
| 1315 | SLC30A9 | 10463 | solute carrier family 30 (zinc transporter), member 9 | 0.78 | 0.023 | 2.24 | 0.005 |
| 1316 | SLC33A1 | 9197 | solute carrier family 33 (acetyl-CoA transporter), member 1 | 0.79 | 0.020 | 1.97 | 0.008 |
| 1317 | SLC35A5 | 55032 | solute carrier family 35, member A5 | 0.78 | 0.016 | 1.55 | 0.036 |
| 1318 | SLC35B1 | 10237 | solute carrier family 35, member B1 | 0.80 | 0.032 | 1.85 | 0.003 |
| 1319 | SLC35E1 | 79939 | solute carrier family 35, member E1 | 0.77 | 0.010 | 0.78 | 0.041 |
| 1320 | SLC35E2 | 9906 | solute carrier family 35, member E2 | 0.79 | 0.019 | 0.53 | 0.004 |
| 1321 | SLC35E3 | 55508 | solute carrier family 35, member E3 | 0.81 | 0.042 | 1.37 | 0.026 |
| 1322 | SLC35F2 | 54733 | solute carrier family 35, member F2 | 0.78 | 0.016 | 0.60 | 0.021 |
| 1323 | SLC37A4 | 2542 | solute carrier family 37 (glucose-6-phosphate transporter), member 4 | 0.81 | 0.035 | 0.49 | 0.011 |
| 1324 | SLC44A1 | 23446 | solute carrier family 44 (choline transporter), member 1 | 0.81 | 0.034 | 0.83 | 0.035 |
| 1325 | SLC4A1AP | 22950 | solute carrier family 4 (anion exchanger), member 1, adaptor protein | 0.80 | 0.026 | 2.41 | 0.034 |
| 1326 | SLC6A10P | 6535 | solute carrier family 6 (neurotransmitter transporter), member 10, pseudogene | 0.79 | 0.021 | 1.25 | 0.039 |
| 1327 | SLC6A5 | 9152 | solute carrier family 6 (neurotransmitter transporter), member 5 | 0.76 | 0.011 | 0.78 | 0.017 |
| 1328 | SLC7A10 | 56301 | solute carrier family 7 (neutral amino acid transporter light chain, asc system), member 10 | 0.78 | 0.018 | 0.79 | 0.047 |
| 1329 | SLC7A2 | 6542 | solute carrier family 7 (cationic amino acid transporter, y+ system), member 2 | 0.81 | 0.030 | 0.85 | 0.040 |
| 1330 | SLC7A5 | 8140 | solute carrier family 7 (amino acid transporter light chain, L system), member 5 | 0.81 | 0.028 | 1.30 | 0.015 |
| 1331 | SLC8B1 | 80024 | solute carrier family 8 (sodium/lithium/calcium exchanger), member B1 | 0.80 | 0.026 | 0.59 | 0.001 |
| 1332 | SLC9A3 | 6550 | solute carrier family 9, subfamily A (NHE3, cation proton antiporter 3), member 3 | 0.77 | 0.019 | 1.77 | 0.002 |
| 1333 | SLCO2A1 | 6578 | solute carrier organic anion transporter family, member 2A1 | 0.80 | 0.031 | 0.57 | 0.036 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1334 | SMARCA2 | 6595 | SWI/SNF related, matrix associated, actin dependent regulator of chromatin, subfamily a, member 2 | 0.79 | 0.028 | 0.45 | 0.002 |
| 1335 | SMARCE1 | 6605 | SWI/SNF related, matrix associated, actin dependent regulator of chromatin, subfamily e, member 1 | 0.81 | 0.046 | 1.59 | 0.032 |
| 1336 | SMC2 | 10592 | structural maintenance of chromosomes 2 | 0.78 | 0.011 | 1.95 | 0.004 |
| 1337 | SMC4 | 10051 | structural maintenance of chromosomes 4 | 0.80 | 0.019 | 1.67 | 0.007 |
| 1338 | SMC5 | 23137 | structural maintenance of chromosomes 5 | 0.83 | 0.046 | 1.77 | 0.015 |
| 1339 | SMG7-AS1 | 284649 | SMG7 antisense RNA 1 | 0.77 | 0.018 | 1.48 | 0.009 |
| 1340 | SMG8 | 55181 | SMG8 nonsense mediated mRNA decay factor | 0.81 | 0.037 | 1.66 | 0.041 |
| 1341 | SMS | 6611 | spermine synthase | 0.78 | 0.019 | 2.13 | 0.000 |
| 1342 | SNAI1 | 6615 | snail family zinc finger 1 | 0.81 | 0.036 | 1.34 | 0.015 |
| 1343 | SNAP29 | 9342 | synaptosomal-associated protein, 29 kDa | 0.80 | 0.028 | 1.66 | 0.020 |
| 1344 | SNAPC5 | 10302 | small nuclear RNA activating complex, polypeptide 5, 19 kDa | 0.75 | 0.007 | 2.12 | 0.011 |
| 1345 | TCP1 | 677812 | t-complex 1 | 0.78 | 0.014 | 1.93 | 0.002 |
| 1346 | TBRG4 | 677795 | transforming growth factor beta regulator 4 | 0.75 | 0.003 | 1.37 | 0.003 |
| 1347 | SNRNP70 | 6625 | small nuclear ribonucleoprotein 70 kDa (U1) | 0.76 | 0.007 | 0.57 | 0.005 |
| 1348 | SNRPB2 | 6629 | small nuclear ribonucleoprotein polypeptide B | 0.78 | 0.019 | 2.17 | 0.003 |
| 1349 | SNRPC | 6631 | small nuclear ribonucleoprotein polypeptide C | 0.78 | 0.017 | 2.21 | 0.007 |
| 1350 | SNRPD3 | 6634 | small nuclear ribonucleoprotein D3 polypeptide 18 kDa | 0.79 | 0.024 | 1.45 | 0.027 |
| 1351 | SNX16 | 64089 | sorting nexin 16 | 0.80 | 0.029 | 1.36 | 0.042 |
| 1352 | SNX29P2 | 440352 | sorting nexin 29 pseudogene 2 | 0.79 | 0.018 | 0.80 | 0.000 |
| 1353 | SON | 6651 | SON DNA binding protein | 0.81 | 0.045 | 0.48 | 0.022 |
| 1354 | SORBS1 | 10580 | sorbin and SH3 domain containing 1 | 0.78 | 0.010 | 0.54 | 0.004 |
| 1355 | SORBS3 | 10174 | sorbin and SH3 domain containing 3 | 0.80 | 0.025 | 0.63 | 0.048 |
| 1356 | SORL1 | 6653 | sortilin-related receptor, L(DLR class) A repeats containing | 0.80 | 0.032 | 0.56 | 0.005 |
| 1357 | SOSTDC1 | 25928 | sclerostin domain containing 1 | 0.76 | 0.012 | 0.76 | 0.001 |
| 1358 | SPAG5 | 10615 | sperm associated antigen 5 | 0.80 | 0.028 | 1.34 | 0.031 |
| 1359 | SPAG9 | 9043 | sperm associated antigen 9 | 0.82 | 0.047 | 1.85 | 0.048 |
| 1360 | SPANXB1 | 728695 | SPANX family, member B1 | 0.79 | 0.023 | 1.15 | 0.046 |
| 1361 | SPATA6 | 54558 | spermatogenesis associated 6 | 0.82 | 0.037 | 0.55 | 0.019 |
| 1362 | SPEF1 | 25876 | sperm flagellar 1 | 0.78 | 0.012 | 0.61 | 0.021 |
| 1363 | SPEN | 23013 | spen family transcriptional repressor | 0.78 | 0.017 | 0.29 | 0.000 |
| 1364 | SPG11 | 80208 | spastic paraplegia 11 (autosomal recessive) | 0.81 | 0.031 | 0.55 | 0.020 |
| 1365 | SPG20 | 23111 | spastic paraplegia 20 (Troyer syndrome) | 0.80 | 0.037 | 0.57 | 0.012 |
| 1366 | SPPL2B | 56928 | signal peptide peptidase like 2B | 0.78 | 0.012 | 0.74 | 0.037 |
| 1367 | SPSB3 | 90864 | splA/ryanodine receptor domain and SOCS box containing 3 | 0.74 | 0.005 | 0.55 | 0.012 |
| 1368 | SPTA1 | 6708 | spectrin, alpha, erythrocytic 1 | 0.77 | 0.010 | 0.75 | 0.017 |
| 1369 | SPTSSA | 171546 | serine palmitoyltransferase, small subunit A | 0.80 | 0.029 | 1.65 | 0.027 |
| 1370 | SRP14 | 6727 | signal recognition particle 14 kDa (homologous Alu RNA binding protein) | 0.75 | 0.003 | 0.24 | 0.000 |
| 1371 | SRP19 | 6728 | signal recognition particle 19 kDa | 0.80 | 0.027 | 1.97 | 0.030 |
| 1372 | SRP54 | 6729 | signal recognition particle 54 kDa | 0.79 | 0.018 | 1.70 | 0.029 |
| 1373 | SRP72 | 6731 | signal recognition particle 72 kDa | 0.80 | 0.036 | 2.79 | 0.002 |
| 1374 | SRPK2 | 6733 | SRSF protein kinase 2 | 0.82 | 0.049 | 1.64 | 0.029 |
| 1375 | SRPRB | 58477 | signal recognition particle receptor, B subunit | 0.82 | 0.046 | 1.75 | 0.040 |
| 1376 | SRRD | 402055 | SRR1 domain containing | 0.78 | 0.017 | 1.57 | 0.047 |
| 1377 | SRRM1 | 10250 | serine/arginine repetitive matrix 1 | 0.82 | 0.046 | 0.40 | 0.004 |
| 1378 | SRRM2 | 23524 | serine/arginine repetitive matrix 2 | 0.74 | 0.004 | 0.72 | 0.014 |
| 1379 | SRSF11 | 9295 | serine/arginine-rich splicing factor 11 | 0.78 | 0.017 | 0.64 | 0.020 |
| 1380 | SRSF5 | 6430 | serine/arginine-rich splicing factor 5 | 0.77 | 0.008 | 0.48 | 0.000 |
| 1381 | SRSF8 | 10929 | serine/arginine-rich splicing factor 8 | 0.77 | 0.011 | 0.37 | 0.001 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1382 | SSB | 6741 | Sjogren syndrome antigen B (autoantigen La) | 0.79 | 0.019 | 2.10 | 0.009 |
| 1383 | SSBP1 | 6742 | single-stranded DNA binding protein 1, mitochondrial | 0.77 | 0.013 | 1.78 | 0.041 |
| 1384 | SSNA1 | 8636 | Sjogren syndrome nuclear autoantigen 1 | 0.82 | 0.050 | 1.86 | 0.016 |
| 1385 | SSSCA1 | 10534 | Sjogren syndrome/scleroderma autoantigen 1 | 0.76 | 0.012 | 1.43 | 0.005 |
| 1386 | STAG3L3 | 442578 | stromal antigen 3-like 3 | 0.78 | 0.011 | 0.72 | 0.003 |
| 1387 | STAMBP | 10617 | STAM binding protein | 0.81 | 0.035 | 3.38 | 0.001 |
| 1388 | STARD13 | 90627 | StAR-related lipid transfer (START) domain containing 13 | 0.81 | 0.034 | 0.63 | 0.026 |
| 1389 | STARD3 | 10948 | StAR-related lipid transfer (START) domain containing 3 | 0.77 | 0.013 | 1.30 | 0.035 |
| 1390 | STAT5B | 6777 | signal transducer and activator of transcription 5B | 0.76 | 0.008 | 0.32 | 0.001 |
| 1391 | STAT6 | 6778 | signal transducer and activator of transcription 6, interleukin-4 induced | 0.77 | 0.016 | 0.53 | 0.006 |
| 1392 | STAU2 | 27067 | staufen double-stranded RNA binding protein 2 | 0.82 | 0.048 | 1.43 | 0.039 |
| 1393 | STC2 | 8614 | stanniocalcin 2 | 0.77 | 0.006 | 0.81 | 0.003 |
| 1394 | STIP1 | 10963 | stress-induced phosphoprotein 1 | 0.75 | 0.005 | 1.52 | 0.004 |
| 1395 | STK25 | 10494 | serine/threonine kinase 25 | 0.80 | 0.025 | 0.57 | 0.039 |
| 1396 | STK3 | 6788 | serine/threonine kinase 3 | 0.76 | 0.012 | 1.33 | 0.021 |
| 1397 | STMN1 | 3925 | stathmin 1 | 0.78 | 0.013 | 1.51 | 0.041 |
| 1398 | STRAP | 11171 | serine/threonine kinase receptor associated protein | 0.80 | 0.027 | 2.50 | 0.009 |
| 1399 | STXBP1 | 6812 | syntaxin binding protein 1 | 0.80 | 0.027 | 0.66 | 0.007 |
| 1400 | SUGCT | 79783 | succinyl-CoA:glutarate-CoA transferase | 0.79 | 0.022 | 1.37 | 0.005 |
| 1401 | SULT1A2 | 6799 | sulfotransferase family, cytosolic, 1A, phenol-preferring, member 2 | 0.76 | 0.008 | 0.63 | 0.042 |
| 1402 | SULT4A1 | 25830 | sulfotransferase family 4A, member 1 | 0.79 | 0.020 | 0.80 | 0.045 |
| 1403 | SUMO3 | 6612 | small ubiquitin-like modifier 3 | 0.77 | 0.009 | 2.15 | 0.006 |
| 1404 | SUPT4H1 | 6827 | suppressor of Ty 4 homolog 1 (S. cerevisiae) | 0.79 | 0.026 | 1.44 | 0.042 |
| 1405 | SUV420H1 | 51111 | suppressor of variegation 4-20 homolog 1 (Drosophila) | 0.82 | 0.047 | 1.91 | 0.008 |
| 1406 | SYNM | 23336 | synemin, intermediate filament protein | 0.81 | 0.039 | 0.78 | 0.032 |
| 1407 | SYNPO | 11346 | synaptopodin | 0.80 | 0.030 | 0.65 | 0.003 |
| 1408 | SYT17 | 51760 | synaptotagmin XVII | 0.82 | 0.042 | 0.85 | 0.035 |
| 1409 | SZT2 | 23334 | seizure threshold 2 homolog (mouse) | 0.76 | 0.011 | 0.55 | 0.019 |
| 1410 | TAC1 | 6863 | tachykinin, precursor 1 | 0.81 | 0.030 | 0.84 | 0.026 |
| 1411 | TACC3 | 10460 | transforming, acidic coiled-coil containing protein 3 | 0.75 | 0.005 | 1.25 | 0.013 |
| 1412 | TAF1B | 9014 | TATA box binding protein (TBP)-associated factor, RNA polymerase I, B, 63 kDa | 0.81 | 0.036 | 1.77 | 0.015 |
| 1413 | TAF1C | 9013 | TATA box binding protein (TBP)-associated factor, RNA polymerase I, C, 110 kDa | 0.79 | 0.026 | 0.70 | 0.000 |
| 1414 | TAF2 | 6873 | TAF2 RNA polymerase II, TATA box binding protein (TBP)-associated factor, 150 kDa | 0.80 | 0.027 | 1.70 | 0.007 |
| 1415 | TAGLN2 | 8407 | transgelin 2 | 0.82 | 0.037 | 1.51 | 0.019 |
| 1416 | TALDO1 | 6888 | transaldolase 1 | 0.77 | 0.010 | 1.53 | 0.024 |
| 1417 | TARS | 6897 | threonyl-tRNA synthetase | 0.76 | 0.006 | 1.77 | 0.006 |
| 1418 | TAT | 6898 | tyrosine aminotransferase | 0.77 | 0.017 | 0.85 | 0.032 |
| 1419 | TAZ | 6901 | tafazzin | 0.78 | 0.012 | 0.60 | 0.042 |
| 1420 | TBC1D30 | 23329 | TBC1 domain family, member 30 | 0.81 | 0.047 | 1.93 | 0.011 |
| 1421 | TBC1D31 | 93594 | TBC1 domain family, member 31 | 0.77 | 0.009 | 1.64 | 0.006 |
| 1422 | TBC1D9B | 23061 | TBC1 domain family, member 9B (with GRAM domain) | 0.78 | 0.014 | 0.47 | 0.038 |
| 1423 | TBCC | 6903 | tubulin folding cofactor C | 0.76 | 0.007 | 1.59 | 0.022 |
| 1424 | TBCE | 6905 | tubulin folding cofactor E | 0.82 | 0.036 | 1.89 | 0.005 |
| 1425 | TBK1 | 29110 | TANK-binding kinase 1 | 0.81 | 0.041 | 2.02 | 0.043 |
| 1426 | TBL2 | 26608 | transducin (beta)-like 2 | 0.80 | 0.026 | 1.61 | 0.049 |
| 1427 | TBX5 | 6910 | T-box 5 | 0.81 | 0.028 | 0.75 | 0.040 |
| 1428 | TCEA1 | 6917 | transcription elongation factor A (SII), 1 | 0.81 | 0.046 | 1.52 | 0.025 |
| 1429 | TCEAL2 | 140597 | transcription elongation factor A (SII)-like 2 | 0.80 | 0.022 | 0.81 | 0.043 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1430 | TCEB1 | 6921 | transcription elongation factor B (SIII), polypeptide 1 (15 kDa, elongin C) | 0.80 | 0.030 | 1.80 | 0.000 |
| 1431 | TCF7 | 6932 | transcription factor 7 (T-cell specific, HMG-box) | 0.79 | 0.020 | 0.66 | 0.015 |
| 1432 | TCF7L1 | 83439 | transcription factor 7-like 1 (T-cell specific, HMG-box) | 0.80 | 0.023 | 0.57 | 0.005 |
| 1433 | TCN1 | 6947 | transcobalamin I (vitamin B12 binding protein, R binder family) | 0.80 | 0.026 | 0.84 | 0.037 |
| 1434 | TCTN1 | 79600 | tectonic family member 1 | 0.82 | 0.028 | 0.59 | 0.014 |
| 1435 | TDP2 | 51567 | tyrosyl-DNA phosphodiesterase 2 | 0.76 | 0.007 | 1.61 | 0.035 |
| 1436 | TELO2 | 9894 | telomere maintenance 2 | 0.77 | 0.009 | 0.55 | 0.015 |
| 1437 | TENC1 | 23371 | tensin like C1 domain containing phosphatase (tensin 2) | 0.72 | 0.002 | 0.44 | 0.000 |
| 1438 | TERF1 | 7013 | telomeric repeat binding factor (NIMA-interacting) 1 | 0.82 | 0.038 | 1.59 | 0.030 |
| 1439 | TFB2M | 64216 | transcription factor B2, mitochondrial | 0.79 | 0.016 | 1.83 | 0.009 |
| 1440 | TFDP2 | 7029 | transcription factor Dp-2 (E2F dimerization partner 2) | 0.78 | 0.019 | 1.51 | 0.034 |
| 1441 | TFEC | 22797 | transcription factor EC | 0.76 | 0.004 | 1.43 | 0.038 |
| 1442 | TFIP11 | 24144 | tuftelin interacting protein 11 | 0.76 | 0.012 | 1.67 | 0.042 |
| 1443 | TFPT | 29844 | TCF3 (E2A) fusion partner (in childhood Leukemia) | 0.75 | 0.007 | 1.56 | 0.011 |
| 1444 | TGFB3 | 7043 | transforming growth factor, beta 3 | 0.80 | 0.024 | 0.59 | 0.011 |
| 1445 | TGFBR3 | 7049 | transforming growth factor, beta receptor III | 0.81 | 0.032 | 0.63 | 0.000 |
| 1446 | TGFBRAP1 | 9392 | transforming growth factor, beta receptor associated protein 1 | 0.81 | 0.039 | 0.44 | 0.030 |
| 1447 | TGOLN2 | 10618 | trans-golgi network protein 2 | 0.78 | 0.018 | 0.40 | 0.007 |
| 1448 | THNSL2 | 55258 | threonine synthase-like 2 (S. cerevisiae) | 0.79 | 0.016 | 0.56 | 0.002 |
| 1449 | THSD4 | 79875 | thrombospondin, type I, domain containing 4 | 0.77 | 0.006 | 0.72 | 0.002 |
| 1450 | TIMM17A | 10440 | translocase of inner mitochondrial membrane 17 homolog A (yeast) | 0.77 | 0.008 | 2.17 | 0.001 |
| 1451 | TIMM23 | 100287932 | translocase of inner mitochondrial membrane 23 homolog (yeast) | 0.76 | 0.008 | 1.78 | 0.018 |
| 1452 | TIMM44 | 10469 | translocase of inner mitochondrial membrane 44 homolog (yeast) | 0.78 | 0.014 | 1.82 | 0.026 |
| 1453 | TIMP2 | 7077 | TIMP metallopeptidase inhibitor 2 | 0.72 | 0.007 | 1.33 | 0.044 |
| 1454 | TIPIN | 54962 | TIMELESS interacting protein | 0.79 | 0.015 | 1.32 | 0.010 |
| 1455 | TIPRL | 261726 | TOR signaling pathway regulator | 0.77 | 0.010 | 2.03 | 0.000 |
| 1456 | TK1 | 7083 | thymidine kinase 1, soluble | 0.80 | 0.034 | 1.41 | 0.030 |
| 1457 | TLE2 | 7089 | transducin-like enhancer of split 2 | 0.78 | 0.012 | 0.67 | 0.034 |
| 1458 | TLE6 | 79816 | transducin-like enhancer of split 6 | 0.81 | 0.031 | 0.64 | 0.000 |
| 1459 | TLN2 | 83660 | talin 2 | 0.82 | 0.048 | 0.59 | 0.044 |
| 1460 | TLR6 | 10333 | toll-like receptor 6 | 0.81 | 0.029 | 0.79 | 0.035 |
| 1461 | TM2D1 | 83941 | TM2 domain containing 1 | 0.80 | 0.025 | 0.53 | 0.011 |
| 1462 | TM9SF1 | 10548 | transmembrane 9 superfamily member 1 | 0.76 | 0.012 | 2.13 | 0.007 |
| 1463 | TM9SF3 | 56889 | transmembrane 9 superfamily member 3 | 0.80 | 0.023 | 2.44 | 0.003 |
| 1464 | TMEM100 | 55273 | transmembrane protein 100 | 0.81 | 0.033 | 0.74 | 0.003 |
| 1465 | TMEM106B | 54664 | transmembrane protein 106B | 0.79 | 0.025 | 1.53 | 0.026 |
| 1466 | TMEM132A | 54972 | transmembrane protein 132A | 0.79 | 0.033 | 1.44 | 0.028 |
| 1467 | TMEM14A | 28978 | transmembrane protein 14A | 0.78 | 0.012 | 1.61 | 0.022 |
| 1468 | TMEM165 | 55858 | transmembrane protein 165 | 0.80 | 0.028 | 1.55 | 0.037 |
| 1469 | TMEM183A | 92703 | transmembrane protein 183A | 0.77 | 0.013 | 2.12 | 0.002 |
| 1470 | TMEM184C | 55751 | transmembrane protein 184C | 0.78 | 0.016 | 1.79 | 0.040 |
| 1471 | TMEM187 | 8269 | transmembrane protein 187 | 0.80 | 0.028 | 1.78 | 0.009 |
| 1472 | TMEM194A | 23306 | transmembrane protein 194A | 0.80 | 0.022 | 1.59 | 0.036 |
| 1473 | TMEM259 | 91304 | transmembrane protein 259 | 0.80 | 0.027 | 0.64 | 0.038 |
| 1474 | TMEM33 | 55161 | transmembrane protein 33 | 0.78 | 0.014 | 2.04 | 0.005 |
| 1475 | TMEM70 | 54968 | transmembrane protein 70 | 0.79 | 0.024 | 1.72 | 0.003 |
| 1476 | TMEM97 | 27346 | transmembrane protein 97 | 0.80 | 0.040 | 1.51 | 0.004 |
| 1477 | TMPO | 7112 | thymopoietin | 0.78 | 0.013 | 1.62 | 0.006 |
| 1478 | TMPRSS3 | 64699 | transmembrane protease, serine 3 | 0.80 | 0.036 | 0.82 | 0.020 |
| 1479 | TMPRSS6 | 164656 | transmembrane protease, serine 6 | 0.78 | 0.014 | 0.63 | 0.009 |
| 1480 | TMUB2 | 79089 | transmembrane and ubiquitin-like domain containing 2 | 0.80 | 0.019 | 0.52 | 0.015 |
| 1481 | TNFAIP2 | 7127 | tumor necrosis factor, alpha-induced protein 2 | 0.78 | 0.017 | 0.70 | 0.034 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1482 | TNFRSF25 | 8718 | tumor necrosis factor receptor superfamily, member 25 | 0.78 | 0.016 | 0.66 | 0.044 |
| 1483 | TNIK | 23043 | TRAF2 and NCK interacting kinase | 0.80 | 0.033 | 0.63 | 0.040 |
| 1484 | TNS1 | 7145 | tensin 1 | 0.77 | 0.015 | 0.57 | 0.001 |
| 1485 | TNXA | 7146 | tenascin XA (pseudogene) | 0.80 | 0.028 | 0.76 | 0.005 |
| 1486 | TOMM70A | 9868 | translocase of outer mitochondrial membrane 70 homolog A (*S. cerevisiae*) | 0.79 | 0.036 | 3.41 | 0.000 |
| 1487 | TOP2A | 7153 | topoisomerase (DNA) II alpha 170 kDa | 0.80 | 0.029 | 1.51 | 0.000 |
| 1488 | TOR1B | 27348 | torsin family 1, member B (torsin B) | 0.79 | 0.016 | 3.10 | 0.001 |
| 1489 | TP53 | 7157 | tumor protein p53 | 0.82 | 0.043 | 0.58 | 0.025 |
| 1490 | TP63 | 8626 | tumor protein p63 | 0.74 | 0.006 | 0.56 | 0.001 |
| 1491 | TP73-AS1 | 57212 | TP73 antisense RNA 1 | 0.79 | 0.026 | 0.39 | 0.003 |
| 1492 | TPCN1 | 53373 | two pore segment channel 1 | 0.76 | 0.009 | 0.64 | 0.024 |
| 1493 | TPRKB | 51002 | TP53RK binding protein | 0.78 | 0.011 | 1.77 | 0.027 |
| 1494 | TRA2A | 29896 | transformer 2 alpha homolog (*Drosophila*) | 0.78 | 0.013 | 0.61 | 0.035 |
| 1495 | TRAF2 | 7186 | TNF receptor-associated factor 2 | 0.81 | 0.032 | 1.29 | 0.035 |
| 1496 | TRAK1 | 22906 | trafficking protein, kinesin binding 1 | 0.80 | 0.028 | 0.57 | 0.023 |
| 1497 | TRAM1 | 23471 | translocation associated membrane protein 1 | 0.80 | 0.035 | 1.61 | 0.045 |
| 1498 | TRAPPC2 | 6399 | trafficking protein particle complex 2 | 0.77 | 0.012 | 1.67 | 0.005 |
| 1499 | TRIAP1 | 51499 | TP53 regulated inhibitor of apoptosis 1 | 0.81 | 0.040 | 2.38 | 0.019 |
| 1500 | TRIM13 | 10206 | tripartite motif containing 13 | 0.80 | 0.028 | 0.44 | 0.025 |
| 1501 | TRIM29 | 23650 | tripartite motif containing 29 | 0.75 | 0.012 | 0.70 | 0.002 |
| 1502 | TRIP13 | 9319 | thyroid hormone receptor interactor 13 | 0.80 | 0.026 | 1.79 | 0.003 |
| 1503 | TRMT12 | 55039 | tRNA methyltransferase 12 homolog (*S. cerevisiae*) | 0.80 | 0.037 | 2.76 | 0.000 |
| 1504 | TROVE2 | 6738 | TROVE domain family, member 2 | 0.80 | 0.016 | 2.24 | 0.001 |
| 1505 | TRPM2 | 7226 | transient receptor potential cation channel, subfamily M, member 2 | 0.81 | 0.042 | 1.81 | 0.014 |
| 1506 | TSC2 | 7249 | tuberous sclerosis 2 | 0.79 | 0.024 | 0.52 | 0.000 |
| 1507 | TSFM | 10102 | Ts translation elongation factor, mitochondrial | 0.82 | 0.042 | 1.78 | 0.029 |
| 1508 | TSG101 | 7251 | tumor susceptibility 101 | 0.78 | 0.015 | 1.84 | 0.021 |
| 1509 | TSKU | 25987 | tsukushi, small leucine rich proteoglycan | 0.78 | 0.027 | 1.24 | 0.040 |
| 1510 | TSPAN7 | 7102 | tetraspanin 7 | 0.80 | 0.028 | 0.73 | 0.007 |
| 1511 | TSPYL2 | 64061 | TSPY-like 2 | 0.78 | 0.019 | 0.70 | 0.018 |
| 1512 | TSR1 | 55720 | TSR1, 20S rRNA accumulation, homolog (*S. cerevisiae*) | 0.78 | 0.015 | 0.61 | 0.013 |
| 1513 | TSSK2 | 23617 | testis-specific serine kinase 2 | 0.82 | 0.048 | 1.66 | 0.030 |
| 1514 | TTC12 | 54970 | tetratricopeptide repeat domain 12 | 0.81 | 0.041 | 0.45 | 0.001 |
| 1515 | TTC19 | 54902 | tetratricopeptide repeat domain 19 | 0.78 | 0.017 | 0.52 | 0.022 |
| 1516 | TTC26 | 79989 | tetratricopeptide repeat domain 26 | 0.80 | 0.022 | 1.47 | 0.008 |
| 1517 | TTC28 | 23331 | tetratricopeptide repeat domain 28 | 0.77 | 0.009 | 0.39 | 0.002 |
| 1518 | TTI1 | 9675 | TELO2 interacting protein 1 | 0.80 | 0.044 | 1.50 | 0.035 |
| 1519 | TTK | 7272 | TTK protein kinase | 0.77 | 0.006 | 1.59 | 0.000 |
| 1520 | TTLL4 | 9654 | tubulin tyrosine ligase-like family, member 4 | 0.78 | 0.016 | 0.69 | 0.040 |
| 1521 | TUBA4B | 80086 | tubulin, alpha 4b (pseudogene) | 0.76 | 0.008 | 0.59 | 0.001 |
| 1522 | TUBB | 203068 | tubulin, beta class I | 0.78 | 0.018 | 1.75 | 0.047 |
| 1523 | TUBB3 | 10381 | tubulin, beta 3 class III | 0.81 | 0.038 | 1.71 | 0.022 |
| 1524 | TUBB4B | 10383 | tubulin, beta 4B class IVb | 0.80 | 0.026 | 1.87 | 0.013 |
| 1525 | TUBD1 | 51174 | tubulin, delta 1 | 0.77 | 0.009 | 1.64 | 0.018 |
| 1526 | TUBG2 | 27175 | tubulin, gamma 2 | 0.79 | 0.012 | 0.59 | 0.007 |
| 1527 | TXN | 7295 | thioredoxin | 0.79 | 0.015 | 2.82 | 0.000 |
| 1528 | TXNDC9 | 10190 | thioredoxin domain containing 9 | 0.79 | 0.016 | 2.97 | 0.002 |
| 1529 | TXNL4A | 10907 | thioredoxin-like 4A | 0.79 | 0.019 | 1.67 | 0.033 |
| 1530 | TXNRD1 | 7296 | thioredoxin reductase 1 | 0.78 | 0.013 | 1.75 | 0.002 |
| 1531 | UAP1 | 6675 | UDP-N-acetylglucosamine pyrophosphorylase 1 | 0.80 | 0.030 | 1.46 | 0.044 |
| 1532 | UBA2 | 10054 | ubiquitin-like modifier activating enzyme 2 | 0.78 | 0.012 | 1.93 | 0.018 |
| 1533 | UBB | 7314 | ubiquitin B | 0.82 | 0.049 | 0.48 | 0.033 |
| 1534 | UBC | 7316 | ubiquitin C | 0.79 | 0.018 | 0.42 | 0.016 |
| 1535 | UBE2A | 7319 | ubiquitin-conjugating enzyme E2A | 0.82 | 0.050 | 1.69 | 0.048 |
| 1536 | UBE2C | 11065 | ubiquitin-conjugating enzyme E2C | 0.81 | 0.041 | 1.99 | 0.000 |
| 1537 | UBE2D3 | 7323 | ubiquitin-conjugating enzyme E2D 3 | 0.79 | 0.021 | 2.52 | 0.020 |
| 1538 | UBE2J1 | 51465 | ubiquitin-conjugating enzyme E2, J1 | 0.77 | 0.007 | 1.71 | 0.050 |
| 1539 | UBE2K | 3093 | ubiquitin-conjugating enzyme E2K | 0.76 | 0.006 | 1.80 | 0.006 |
| 1540 | UBE2L3 | 7332 | ubiquitin-conjugating enzyme E2L 3 | 0.75 | 0.007 | 2.67 | 0.000 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1541 | UBE2N | 7334 | ubiquitin-conjugating enzyme E2N | 0.79 | 0.022 | 2.21 | 0.001 |
| 1542 | UBE2S | 27338 | ubiquitin-conjugating enzyme E2S | 0.76 | 0.008 | 1.44 | 0.002 |
| 1543 | UBE2V2 | 7336 | ubiquitin-conjugating enzyme E2 variant 2 | 0.81 | 0.035 | 2.11 | 0.000 |
| 1544 | UBE4B | 10277 | ubiquitination factor E4B | 0.79 | 0.025 | 0.48 | 0.032 |
| 1545 | UBFD1 | 56061 | ubiquitin family domain containing 1 | 0.77 | 0.015 | 1.71 | 0.038 |
| 1546 | UBL4A | 8266 | ubiquitin-like 4A | 0.80 | 0.024 | 1.69 | 0.015 |
| 1547 | UBL5 | 59286 | ubiquitin-like 5 | 0.78 | 0.017 | 1.86 | 0.004 |
| 1548 | UBP1 | 7342 | upstream binding protein 1 (LBP-1a) | 0.79 | 0.017 | 0.46 | 0.007 |
| 1549 | UBQLN2 | 29978 | ubiquilin 2 | 0.80 | 0.023 | 1.83 | 0.045 |
| 1550 | UBQLN4 | 56893 | ubiquilin 4 | 0.74 | 0.003 | 0.60 | 0.002 |
| 1551 | UBR4 | 23352 | ubiquitin protein ligase E3 component n-recognin 4 | 0.79 | 0.031 | 0.44 | 0.010 |
| 1552 | UCHL1 | 7345 | ubiquitin carboxyl-terminal esterase L1 (ubiquitin thiolesterase) | 0.82 | 0.049 | 1.38 | 0.038 |
| 1553 | UCHL3 | 7347 | ubiquitin carboxyl-terminal esterase L3 (ubiquitin thiolesterase) | 0.77 | 0.007 | 1.47 | 0.014 |
| 1554 | UFD1L | 7353 | ubiquitin fusion degradation 1 like (yeast) | 0.75 | 0.005 | 1.75 | 0.004 |
| 1555 | UIMC1 | 51720 | ubiquitin interaction motif containing 1 | 0.79 | 0.016 | 0.34 | 0.012 |
| 1556 | UMPS | 7372 | uridine monophosphate synthetase | 0.79 | 0.021 | 2.60 | 0.004 |
| 1557 | UQCRC2 | 7385 | ubiquinol-cytochrome c reductase core protein II | 0.81 | 0.025 | 0.47 | 0.012 |
| 1558 | URB2 | 9816 | URB2 ribosome biogenesis 2 homolog (*S. cerevisiae*) | 0.81 | 0.041 | 1.66 | 0.024 |
| 1559 | USO1 | 8615 | USO1 vesicle transport factor | 0.80 | 0.023 | 1.61 | 0.049 |
| 1560 | USP18 | 11274 | ubiquitin specific peptidase 18 | 0.76 | 0.008 | 1.29 | 0.045 |
| 1561 | USP32 | 84669 | ubiquitin specific peptidase 32 | 0.77 | 0.010 | 1.83 | 0.002 |
| 1562 | USP34 | 9736 | ubiquitin specific peptidase 34 | 0.78 | 0.013 | 0.70 | 0.032 |
| 1563 | USP46 | 64854 | ubiquitin specific peptidase 46 | 0.80 | 0.036 | 1.75 | 0.026 |
| 1564 | USP9X | 8239 | ubiquitin specific peptidase 9, X-linked | 0.79 | 0.012 | 2.71 | 0.007 |
| 1565 | UTP18 | 51096 | UTP18 small subunit (SSU) processome component homolog (yeast) | 0.79 | 0.017 | 1.49 | 0.034 |
| 1566 | UTP3 | 57050 | UTP3, small subunit (SSU) processome component, homolog (*S. cerevisiae*) | 0.79 | 0.018 | 1.47 | 0.033 |
| 1567 | VAMP1 | 6843 | vesicle-associated membrane protein 1 (synaptobrevin 1) | 0.78 | 0.015 | 0.58 | 0.003 |
| 1568 | VAMP2 | 6844 | vesicle-associated membrane protein 2 (synaptobrevin 2) | 0.78 | 0.015 | 0.52 | 0.006 |
| 1569 | VAMP7 | 6845 | vesicle-associated membrane protein 7 | 0.80 | 0.023 | 1.98 | 0.011 |
| 1570 | VBP1 | 7411 | von Hippel-Lindau binding protein 1 | 0.76 | 0.006 | 1.83 | 0.001 |
| 1571 | VDAC1 | 7416 | voltage-dependent anion channel 1 | 0.80 | 0.033 | 1.79 | 0.021 |
| 1572 | VDAC2 | 7417 | voltage-dependent anion channel 2 | 0.79 | 0.016 | 1.81 | 0.010 |
| 1573 | VIM | 7431 | vimentin | 0.81 | 0.039 | 0.70 | 0.018 |
| 1574 | VIP | 7432 | vasoactive intestinal peptide | 0.80 | 0.026 | 0.84 | 0.035 |
| 1575 | VIPAS39 | 63894 | VPS33B interacting protein, apical-basolateral polarity regulator, spe-39 homolog | 0.77 | 0.010 | 0.30 | 0.005 |
| 1576 | VIPR1 | 7433 | vasoactive intestinal peptide receptor 1 | 0.78 | 0.010 | 0.67 | 0.003 |
| 1577 | VPS11 | 55823 | vacuolar protein sorting 11 homolog (*S. cerevisiae*) | 0.81 | 0.024 | 0.46 | 0.025 |
| 1578 | VPS51 | 738 | vacuolar protein sorting 51 homolog (*S. cerevisiae*) | 0.81 | 0.036 | 0.64 | 0.047 |
| 1579 | VPS53 | 55275 | vacuolar protein sorting 53 homolog (*S. cerevisiae*) | 0.79 | 0.017 | 0.71 | 0.028 |
| 1580 | VRK1 | 7443 | vaccinia related kinase 1 | 0.80 | 0.020 | 1.47 | 0.011 |
| 1581 | VWA1 | 64856 | von Willebrand factor A domain containing 1 | 0.80 | 0.027 | 1.32 | 0.040 |
| 1582 | WASF2 | 10163 | WAS protein family, member 2 | 0.80 | 0.038 | 0.50 | 0.002 |
| 1583 | WBSCR22 | 114049 | Williams Beuren syndrome chromosome region 22 | 0.81 | 0.032 | 1.84 | 0.042 |
| 1584 | WDR19 | 57728 | WD repeat domain 19 | 0.82 | 0.039 | 0.60 | 0.013 |
| 1585 | WDR26 | 80232 | WD repeat domain 26 | 0.81 | 0.030 | 1.97 | 0.012 |
| 1586 | WDR3 | 10885 | WD repeat domain 3 | 0.80 | 0.022 | 1.84 | 0.029 |
| 1587 | WDR73 | 84942 | WD repeat domain 73 | 0.80 | 0.023 | 0.53 | 0.048 |
| 1588 | WDR78 | 79819 | WD repeat domain 78 | 0.78 | 0.014 | 0.65 | 0.033 |
| 1589 | WDTC1 | 23038 | WD and tetratricopeptide repeats 1 | 0.75 | 0.005 | 0.54 | 0.006 |
| 1590 | WDYHV1 | 55093 | WDYHV motif containing 1 | 0.80 | 0.027 | 1.81 | 0.004 |
| 1591 | WISP3 | 8838 | WNT1 inducible signaling pathway protein 3 | 0.80 | 0.021 | 0.84 | 0.021 |

TABLE 3-continued 1,635 prognostic genes for use in combination with BTN3A2 gene

| Gene No. | Gene Symbol | GENE ID | Gene Name | BTN3A2 HR | BTN3A2 p-value | prognostic gene HR | prognostic gene p-value |
|---|---|---|---|---|---|---|---|
| 1592 | WSB2 | 55884 | WD repeat and SOCS box containing 2 | 0.77 | 0.007 | 2.73 | 0.000 |
| 1593 | XDH | 7498 | xanthine dehydrogenase | 0.76 | 0.009 | 0.63 | 0.009 |
| 1594 | XPC | 7508 | xeroderma pigmentosum, complementation group C | 0.78 | 0.020 | 0.48 | 0.010 |
| 1595 | XPOT | 11260 | exportin, tRNA | 0.76 | 0.009 | 1.97 | 0.001 |
| 1596 | YIF1A | 10897 | Yip1 interacting factor homolog A (S. cerevisiae) | 0.81 | 0.031 | 1.63 | 0.016 |
| 1597 | YIPF6 | 286451 | Yip1 domain family, member 6 | 0.78 | 0.018 | 1.54 | 0.010 |
| 1598 | YKT6 | 10652 | YKT6 v-SNARE homolog (S. cerevisiae) | 0.75 | 0.009 | 1.34 | 0.048 |
| 1599 | YLPM1 | 56252 | YLP motif containing 1 | 0.80 | 0.038 | 0.40 | 0.016 |
| 1600 | YTHDF3 | 253943 | YTH domain family, member 3 | 0.81 | 0.037 | 1.91 | 0.003 |
| 1601 | ZBTB11 | 27107 | zinc finger and BTB domain containing 11 | 0.78 | 0.015 | 1.96 | 0.017 |
| 1602 | ZBTB16 | 7704 | zinc finger and BTB domain containing 16 | 0.78 | 0.018 | 0.73 | 0.001 |
| 1603 | ZBTB17 | 7709 | zinc finger and BTB domain containing 17 | 0.82 | 0.046 | 0.44 | 0.027 |
| 1604 | ZBTB25 | 7597 | zinc finger and BTB domain containing 25 | 0.78 | 0.015 | 0.66 | 0.048 |
| 1605 | ZC3H15 | 55854 | zinc finger CCCH-type containing 15 | 0.79 | 0.010 | 2.67 | 0.000 |
| 1606 | ZFHX3 | 463 | zinc finger homeobox 3 | 0.79 | 0.026 | 1.26 | 0.028 |
| 1607 | ZFHX4 | 79776 | zinc finger homeobox 4 | 0.80 | 0.031 | 0.60 | 0.027 |
| 1608 | ZFP2 | 80108 | ZFP2 zinc finger protein | 0.81 | 0.029 | 0.81 | 0.011 |
| 1609 | ZFP36L1 | 677 | ZFP36 ring finger protein-like 1 | 0.77 | 0.010 | 0.63 | 0.001 |
| 1610 | ZFYVE9 | 9372 | zinc finger, FYVE domain containing 9 | 0.79 | 0.016 | 0.52 | 0.009 |
| 1611 | ZNF141 | 7700 | zinc finger protein 141 | 0.79 | 0.021 | 0.85 | 0.044 |
| 1612 | ZNF148 | 7707 | zinc finger protein 148 | 0.80 | 0.027 | 1.73 | 0.022 |
| 1613 | ZNF160 | 90338 | zinc finger protein 160 | 0.77 | 0.008 | 0.76 | 0.015 |
| 1614 | ZNF184 | 7738 | zinc finger protein 184 | 0.76 | 0.009 | 1.44 | 0.020 |
| 1615 | ZNF202 | 7753 | zinc finger protein 202 | 0.81 | 0.035 | 0.48 | 0.042 |
| 1616 | ZNF204P | 7754 | zinc finger protein 204, pseudogene | 0.80 | 0.027 | 0.77 | 0.006 |
| 1617 | ZNF213-AS1 | 100507458 | ZNF213 antisense RNA 1 (head to head) | 0.82 | 0.046 | 0.79 | 0.008 |
| 1618 | ZNF236 | 7776 | zinc finger protein 236 | 0.73 | 0.004 | 0.57 | 0.018 |
| 1619 | ZNF286A | 57335 | zinc finger protein 286A | 0.77 | 0.011 | 0.79 | 0.022 |
| 1620 | ZNF322 | 79692 | zinc finger protein 322 | 0.75 | 0.009 | 1.68 | 0.031 |
| 1621 | ZNF385D | 79750 | zinc finger protein 385D | 0.82 | 0.043 | 0.82 | 0.011 |
| 1622 | ZNF423 | 23090 | zinc finger protein 423 | 0.82 | 0.048 | 0.71 | 0.017 |
| 1623 | ZNF446 | 55663 | zinc finger protein 446 | 0.78 | 0.012 | 0.73 | 0.014 |
| 1624 | ZNF468 | 90333 | zinc finger protein 468 | 0.80 | 0.026 | 1.54 | 0.046 |
| 1625 | ZNF480 | 147657 | zinc finger protein 480 | 0.80 | 0.034 | 1.45 | 0.047 |
| 1626 | ZNF500 | 26048 | zinc finger protein 500 | 0.77 | 0.005 | 0.54 | 0.006 |
| 1627 | ZNF562 | 54811 | zinc finger protein 562 | 0.76 | 0.007 | 0.52 | 0.013 |
| 1628 | ZNF606 | 80095 | zinc finger protein 606 | 0.80 | 0.024 | 1.93 | 0.005 |
| 1629 | ZNF611 | 81856 | zinc finger protein 611 | 0.76 | 0.008 | 0.71 | 0.019 |
| 1630 | ZNF623 | 9831 | zinc finger protein 623 | 0.80 | 0.035 | 1.94 | 0.000 |
| 1631 | ZNF629 | 23361 | zinc finger protein 629 | 0.76 | 0.008 | 0.37 | 0.010 |
| 1632 | ZNF706 | 51123 | zinc finger protein 706 | 0.80 | 0.030 | 1.72 | 0.001 |
| 1633 | ZNF767P | 79970 | zinc finger family member 767, pseudogene | 0.77 | 0.010 | 0.59 | 0.031 |
| 1634 | ZWILCH | 55055 | zwilch kinetochore protein | 0.75 | 0.006 | 1.43 | 0.010 |
| 1635 | ZWINT | 11130 | ZW10 interacting kinetochore protein | 0.82 | 0.042 | 1.46 | 0.033 |

Evaluation on Biological Functions of Prognostic Genes with Increased Prediction Accuracy Through Gene Combinations Gene Ontology (GO) analysis was used to investigate any association of the above selected 1,635 genes, which were found to improve such prediction accuracy through their combinatory use with BTN3A2 gene, with biological processes. As a result of GO analysis using relevant GO terms (such as mitotic cell cycle, cell cycle process, mitotic cell cycle phase transition, and so on), it was verified that those 1,635 genes are particularly involved in cell proliferation, as shown in the following Table 4.

TABLE 4

Gene Ontology (GO) analysis

| GO Terms—Biological process | Nos. of Genes | Adjusted p-value |
|---|---|---|
| mitotic cell cycle | 170 | 8.80E−17 |
| cell cycle process | 213 | 3.90E−16 |
| establishment of protein localization to organelle | 129 | 5.70E−16 |
| ribosome biogenesis | 82 | 2.00E−15 |
| mitotic cell cycle phase transition | 106 | 7.10E−15 |

Further, among the 213 cell-proliferation-related genes, it was confirmed via bivariate Cox analysis that a total of 159 genes (159/213, 74.6%), which are named p-genes as described above, were associated with a poor prognosis of breast as shown in the following Table 5, suggesting that each of these 159 p-genes may be used in combination with BTN3A2 gene to increase the accuracy of prognosis prediction of a cancer, particularly a breast cancer.

TABLE 5

Bivariate Cox analysis on p-genes and BTN3A2

| No | Gene Symbol | Gene ID | Gene Name | BTN3A2 HR | BTN3A2 p-value | p-gene HR | p-gene p-value |
|---|---|---|---|---|---|---|---|
| 1 | APITD1 | 378708 | apoptosis-inducing, TAF9-like domain 1 | 0.81 | 0.041 | 1.86 | 0.027 |
| 2 | BID | 637 | BH3 interacting domain death agonist | 0.77 | 0.007 | 1.72 | 0.011 |
| 3 | BUB1B | 701 | BUB1 mitotic checkpoint serine/threonine kinase B | 0.80 | 0.031 | 1.71 | 0.002 |
| 4 | BUB1 | 699 | BUB1 mitotic checkpoint serine/threonine kinase | 0.78 | 0.014 | 1.73 | 0.005 |
| 5 | CKS1B | 1163 | CDC28 protein kinase regulatory subunit 1B | 0.78 | 0.013 | 1.52 | 0.027 |
| 6 | CKS2 | 1164 | CDC28 protein kinase regulatory subunit 2 | 0.79 | 0.023 | 1.55 | 0.002 |
| 7 | DLGAP5 | 9787 | discs, large (Drosophila) homolog-associated protein 5 | 0.75 | 0.004 | 1.76 | 0.000 |
| 8 | POLA1 | 5422 | polymerase (DNA directed), alpha 1, catalytic subunit | 0.79 | 0.017 | 1.91 | 0.018 |
| 9 | POLA2 | 23649 | polymerase (DNA directed), alpha 2, accessory subunit | 0.74 | 0.006 | 1.41 | 0.010 |
| 10 | DSCC1 | 79075 | DNA replication and sister chromatid cohesion 1 | 0.80 | 0.021 | 1.93 | 0.000 |
| 11 | DNA2 | 1763 | DNA replication helicase/nuclease 2 | 0.81 | 0.034 | 1.49 | 0.047 |
| 12 | E2F8 | 79733 | E2F transcription factor 8 | 0.81 | 0.025 | 1.46 | 0.004 |
| 13 | ERCC6L | 54821 | excision repair cross-complementation group 6-like | 0.74 | 0.003 | 1.44 | 0.000 |
| 14 | FBXO5 | 26271 | F-box protein 5 | 0.74 | 0.005 | 1.49 | 0.012 |
| 15 | FANCI | 55215 | Fanconi anemia, complementation group I | 0.81 | 0.032 | 1.49 | 0.049 |
| 16 | GADD45GIP1 | 90480 | growth arrest and DNA-damage-inducible, gamma interacting protein 1 | 0.77 | 0.008 | 1.64 | 0.002 |
| 17 | GINS1 | 9837 | GINS complex subunit 1 (Psf1 homolog) | 0.82 | 0.044 | 1.42 | 0.014 |
| 18 | GINS2 | 51659 | GINS complex subunit 2 (Psf2 homolog) | 0.78 | 0.018 | 1.18 | 0.033 |
| 19 | MAD2L1 | 4085 | MAD2 mitotic arrest deficient-like 1 (yeast) | 0.77 | 0.009 | 1.57 | 0.001 |
| 20 | MAD2L1BP | 9587 | MAD2L1 binding protein | 0.79 | 0.017 | 2.01 | 0.021 |
| 21 | MIS18A | 54069 | MIS18 kinetochore protein A | 0.81 | 0.029 | 1.86 | 0.033 |
| 22 | MYBL2 | 4605 | v-myb avian myeloblastosis viral oncogene homolog-like 2 | 0.77 | 0.012 | 1.26 | 0.010 |
| 23 | NAA50 | 80218 | N(alpha)-acetyltransferase 50, NatE catalytic subunit | 0.81 | 0.030 | 1.60 | 0.037 |
| 24 | NEK2 | 4751 | NIMA-related kinase 2 | 0.80 | 0.026 | 1.45 | 0.003 |
| 25 | NSL1 | 25936 | NSL1, MIS12 kinetochore complex component | 0.78 | 0.015 | 1.96 | 0.020 |
| 26 | PBK | 55872 | PDZ binding kinase | 0.78 | 0.012 | 1.55 | 0.001 |
| 27 | RAB11A | 8766 | RAB11A, member RAS oncogene family | 0.80 | 0.022 | 1.79 | 0.046 |
| 28 | RAD51C | 5889 | RAD51 paralog C | 0.77 | 0.015 | 1.42 | 0.047 |
| 29 | RAD54B | 25788 | RAD54 homolog B (S. cerevisiae) | 0.78 | 0.021 | 1.63 | 0.001 |
| 30 | RANBP1 | 5902 | RAN binding protein 1 | 0.79 | 0.021 | 1.53 | 0.033 |
| 31 | RALA | 5898 | v-ral simian leukemia viral oncogene homolog A (ras related) | 0.77 | 0.007 | 2.50 | 0.000 |
| 32 | RACGAP1 | 29127 | Rac GTPase activating protein 1 | 0.77 | 0.013 | 1.75 | 0.000 |
| 33 | SSNA1 | 8636 | Sjogren syndrome nuclear autoantigen 1 | 0.82 | 0.050 | 1.86 | 0.016 |
| 34 | STAMBP | 10617 | STAM binding protein | 0.81 | 0.035 | 3.38 | 0.001 |
| 35 | SSSCA1 | 10534 | Sjogren syndrome/scleroderma autoantigen 1 | 0.76 | 0.012 | 1.43 | 0.005 |
| 36 | TAF2 | 6873 | TAF2 RNA polymerase II, TATA box binding protein (TBP)-associated factor, 150 kDa | 0.80 | 0.027 | 1.70 | 0.007 |
| 37 | TIPIN | 54962 | TIMELESS interacting protein | 0.79 | 0.015 | 1.32 | 0.010 |
| 38 | TIPRL | 261726 | TOR signaling pathway regulator | 0.77 | 0.010 | 2.03 | 0.000 |
| 39 | TRIAP1 | 51499 | TP53 regulated inhibitor of apoptosis 1 | 0.81 | 0.040 | 2.38 | 0.019 |
| 40 | TTK | 7272 | TTK protein kinase | 0.77 | 0.006 | 1.59 | 0.000 |
| 41 | ZWINT | 11130 | ZW10 interacting kinetochore protein | 0.82 | 0.042 | 1.46 | 0.033 |
| 42 | ASPM | 259266 | asp (abnormal spindle) homolog, microcephaly associated (Drosophila) | 0.79 | 0.011 | 1.32 | 0.002 |
| 43 | AURKA | 6790 | aurora kinase A | 0.80 | 0.024 | 1.59 | 0.002 |

TABLE 5-continued

Bivariate Cox analysis on p-genes and BTN3A2

| No | Gene Symbol | Gene ID | Gene Name | BTN3A2 HR | p-value | p-gene HR | p-value |
|---|---|---|---|---|---|---|---|
| 44 | AURKB | 9212 | aurora kinase B | 0.81 | 0.029 | 1.26 | 0.044 |
| 45 | BRD7 | 29117 | bromodomain containing 7 | 0.76 | 0.007 | 1.54 | 0.021 |
| 46 | CSNK2A1 | 1457 | casein kinase 2, alpha 1 polypeptide | 0.75 | 0.004 | 2.13 | 0.002 |
| 47 | CDC20 | 991 | cell division cycle 20 | 0.78 | 0.011 | 1.32 | 0.019 |
| 48 | CDC25C | 995 | cell division cycle 25C | 0.80 | 0.038 | 1.70 | 0.011 |
| 49 | CENPA | 1058 | centromere protein A | 0.73 | 0.002 | 2.00 | 0.000 |
| 50 | CENPE | 1062 | centromere protein E, 312 kDa | 0.78 | 0.012 | 1.33 | 0.001 |
| 51 | CENPF | 1063 | centromere protein F, 350/400 kDa | 0.79 | 0.016 | 1.64 | 0.002 |
| 52 | CENPI | 2491 | centromere protein I | 0.81 | 0.030 | 1.50 | 0.040 |
| 53 | CENPM | 79019 | centromere protein M | 0.75 | 0.005 | 1.39 | 0.001 |
| 54 | CENPN | 55839 | centromere protein N | 0.78 | 0.006 | 1.50 | 0.001 |
| 55 | CENPU | 79682 | centromere protein U | 0.79 | 0.025 | 1.77 | 0.000 |
| 56 | CEP55 | 55165 | centrosomal protein 55 kDa | 0.75 | 0.007 | 1.48 | 0.001 |
| 57 | CHEK1 | 1111 | checkpoint kinase 1 | 0.80 | 0.024 | 1.75 | 0.016 |
| 58 | CDT1 | 81620 | chromatin licensing and DNA replication factor 1 | 0.78 | 0.015 | 1.32 | 0.040 |
| 59 | C11orf80 | 79703 | chromosome 11 open reading frame 80 | 0.82 | 0.039 | 1.31 | 0.004 |
| 60 | CCNA2 | 890 | cyclin A2 | 0.82 | 0.043 | 1.70 | 0.006 |
| 61 | CCNB1 | 891 | cyclin B1 | 0.79 | 0.021 | 1.58 | 0.004 |
| 62 | CCNB2 | 9133 | cyclin B2 | 0.77 | 0.007 | 1.67 | 0.001 |
| 63 | CCNE2 | 9134 | cyclin E2 | 0.80 | 0.027 | 2.07 | 0.000 |
| 64 | CDK1 | 983 | cyclin-dependent kinase 1 | 0.76 | 0.005 | 1.56 | 0.001 |
| 65 | CDKN3 | 1033 | cyclin-dependent kinase inhibitor 3 | 0.81 | 0.037 | 2.26 | 0.000 |
| 66 | CKAP5 | 9793 | cytoskeleton associated protein 5 | 0.78 | 0.020 | 2.12 | 0.022 |
| 67 | DTL | 51514 | d.enticleless E3 ubiquitin protein ligase homolog (*Drosophila*) | 0.80 | 0.023 | 1.47 | 0.003 |
| 68 | DCTN2 | 10540 | dynactin 2 (p50) | 0.77 | 0.012 | 1.85 | 0.015 |
| 69 | DYNLT1 | 6993 | dynein, light chain, Tctex-type 1 | 0.77 | 0.010 | 2.21 | 0.003 |
| 70 | ECD | 11319 | ecdysoneless homolog (*Drosophila*) | 0.75 | 0.007 | 1.70 | 0.036 |
| 71 | ECT2 | 1894 | epithelial cell transforming 2 | 0.79 | 0.022 | 1.69 | 0.001 |
| 72 | EIF4G1 | 1981 | eukaryotic translation initiation factor 4 gamma, 1 | 0.82 | 0.043 | 1.70 | 0.033 |
| 73 | EIF4EBP1 | 1978 | eukaryotic translation initiation factor 4E binding protein 1 | 0.77 | 0.010 | 1.45 | 0.003 |
| 74 | EZR | 7430 | ezrin | 0.82 | 0.041 | 1.73 | 0.011 |
| 75 | FEN1 | 2237 | flap structure-specific endonuclease 1 | 0.77 | 0.012 | 1.77 | 0.003 |
| 76 | FOXM1 | 2305 | forkhead box M1 | 0.78 | 0.015 | 1.42 | 0.002 |
| 77 | GSK3B | 2932 | glycogen synthase kinase 3 beta | 0.79 | 0.017 | 1.99 | 0.003 |
| 78 | HMGN5 | 79366 | high mobility group nucleosome binding domain 5 | 0.83 | 0.048 | 1.50 | 0.040 |
| 79 | INTS7 | 25896 | integrator complex subunit 7 | 0.75 | 0.007 | 1.61 | 0.014 |
| 80 | KIF11 | 3832 | kinesin family member 11 | 0.78 | 0.012 | 1.61 | 0.003 |
| 81 | KIF14 | 9928 | kinesin family member 14 | 0.78 | 0.013 | 1.73 | 0.001 |
| 82 | KIF20A | 10112 | kinesin family member 20A | 0.76 | 0.011 | 1.46 | 0.005 |
| 83 | KIF23 | 9493 | kinesin family member 23 | 0.79 | 0.021 | 1.22 | 0.028 |
| 84 | KIF2C | 11004 | kinesin family member 2C | 0.78 | 0.009 | 1.90 | 0.003 |
| 85 | KIF4A | 24137 | kinesin family member 4A | 0.79 | 0.016 | 1.73 | 0.003 |
| 86 | KIFC1 | 3833 | kinesin family member C1 | 0.78 | 0.015 | 1.35 | 0.003 |
| 87 | MIF | 4282 | macrophage migration inhibitory factor (glycosylation-inhibiting factor) | 0.78 | 0.026 | 1.67 | 0.003 |
| 88 | MELK | 9833 | maternal embryonic leucine zipper kinase | 0.78 | 0.010 | 1.54 | 0.003 |
| 89 | MED1 | 5469 | mediator complex subunit 1 | 0.78 | 0.012 | 1.40 | 0.003 |
| 90 | MCM10 | 55388 | minichromosome maintenance complex component 10 | 0.79 | 0.016 | 1.39 | 0.001 |
| 91 | MCM2 | 4171 | minichromosome maintenance complex component 2 | 0.81 | 0.028 | 1.53 | 0.012 |
| 92 | MCM6 | 4175 | minichromosome maintenance complex component 6 | 0.77 | 0.013 | 1.63 | 0.020 |
| 93 | MAP2K1 | 5604 | mitogen-activated protein kinase kinase 1 | 0.77 | 0.014 | 1.99 | 0.016 |
| 94 | MSH6 | 2956 | mutS homolog 6 | 0.76 | 0.008 | 2.86 | 0.001 |
| 95 | MLF1 | 4291 | myeloid leukemia factor 1 | 0.80 | 0.027 | 1.39 | 0.041 |
| 96 | NCAPG | 64151 | non-SMC condensin I complex, subunit G | 0.76 | 0.005 | 1.98 | 0.000 |
| 97 | NUSAP1 | 51203 | nucleolar and spindle associated protein 1 | 0.79 | 0.016 | 1.73 | 0.000 |
| 98 | NUP155 | 9631 | nucleoporin 155 kDa | 0.80 | 0.031 | 1.50 | 0.048 |
| 99 | NUP93 | 9688 | nucleoporin 93 kDa | 0.75 | 0.005 | 1.17 | 0.028 |
| 100 | ORC4 | 5000 | origin recognition complex, subunit 4 | 0.78 | 0.013 | 1.55 | 0.036 |
| 101 | ORC5 | 5001 | origin recognition complex, subunit 5 | 0.77 | 0.011 | 1.86 | 0.021 |

TABLE 5-continued

Bivariate Cox analysis on p-genes and BTN3A2

| No | Gene Symbol | Gene ID | Gene Name | BTN3A2 HR | p-value | p-gene HR | p-value |
|---|---|---|---|---|---|---|---|
| 102 | PIN1 | 5300 | peptidylprolyl cis/trans isomerase, NIMA-interacting 1 | 0.75 | 0.006 | 1.26 | 0.010 |
| 103 | PIK3R4 | 30849 | phosphoinositide-3-kinase, regulatory subunit 4 | 0.78 | 0.015 | 1.90 | 0.019 |
| 104 | PTTG1 | 9232 | pituitary tumor-transforming 1 | 0.80 | 0.017 | 2.08 | 0.000 |
| 105 | PTTG3P | 26255 | pituitary tumor-transforming 3, pseudogene | 0.76 | 0.012 | 1.50 | 0.002 |
| 106 | PLK1 | 5347 | polo-like kinase 1 | 0.81 | 0.037 | 1.53 | 0.020 |
| 107 | PLK4 | 10733 | polo-like kinase 4 | 0.78 | 0.021 | 1.34 | 0.048 |
| 108 | PRIM1 | 5557 | primase, DNA, polypeptide 1 (49 kDa) | 0.80 | 0.035 | 2.44 | 0.000 |
| 109 | PA2G4 | 5036 | proliferation-associated 2G4, 38 kDa | 0.82 | 0.043 | 2.15 | 0.007 |
| 110 | LEPREL4 | 10609 | leprecan-like 4 | 0.79 | 0.029 | 1.30 | 0.046 |
| 111 | PSMC3 | 5702 | proteasome (prosome, macropain) 26S subunit, ATPase, 3 | 0.82 | 0.032 | 1.56 | 0.022 |
| 112 | PSMC6 | 5706 | proteasome (prosome, macropain) 26S subunit, ATPase, 6 | 0.78 | 0.016 | 1.58 | 0.031 |
| 113 | PSMD10 | 5716 | proteasome (prosome, macropain) 26S subunit, non-ATPase, 10 | 0.77 | 0.007 | 2.27 | 0.001 |
| 114 | PSMD12 | 5718 | proteasome (prosome, macropain) 26S subunit, non-ATPase, 12 | 0.79 | 0.018 | 1.93 | 0.003 |
| 115 | PSMD14 | 10213 | proteasome (prosome, macropain) 26S subunit, non-ATPase, 14 | 0.78 | 0.012 | 2.24 | 0.005 |
| 116 | PSMD2 | 5708 | proteasome (prosome, macropain) 26S subunit, non-ATPase, 2 | 0.80 | 0.025 | 2.42 | 0.001 |
| 117 | PSMD3 | 5709 | proteasome (prosome, macropain) 26S subunit, non-ATPase, 3 | 0.78 | 0.015 | 1.34 | 0.012 |
| 118 | PSMD4 | 5710 | proteasome (prosome, macropain) 26S subunit, non-ATPase, 4 | 0.80 | 0.025 | 1.79 | 0.032 |
| 119 | PSMD6 | 9861 | proteasome (prosome, macropain) 26S subunit, non-ATPase, 6 | 0.80 | 0.019 | 2.09 | 0.013 |
| 120 | PSMD7 | 5713 | proteasome (prosome, macropain) 26S subunit, non-ATPase, 7 | 0.78 | 0.010 | 2.22 | 0.003 |
| 121 | PSMA1 | 5682 | proteasome (prosome, macropain) subunit, alpha type, 1 | 0.77 | 0.009 | 2.33 | 0.005 |
| 122 | PSMA2 | 5683 | proteasome (prosome, macropain) subunit, alpha type, 2 | 0.78 | 0.010 | 1.94 | 0.010 |
| 123 | PSMA3 | 5684 | proteasome (prosome, macropain) subunit, alpha type, 3 | 0.75 | 0.005 | 1.74 | 0.010 |
| 124 | PSMA4 | 5685 | proteasome (prosome, macropain) subunit, alpha type, 4 | 0.78 | 0.007 | 2.27 | 0.009 |
| 125 | PSMA6 | 9692 | proteasome (prosome, macropain) subunit, alpha type, 6 | 0.76 | 0.008 | 1.67 | 0.027 |
| 126 | PSMA7 | 5688 | proteasome (prosome, macropain) subunit, alpha type, 7 | 0.79 | 0.020 | 1.69 | 0.006 |
| 127 | PSMB3 | 5691 | proteasome (prosome, macropain) subunit, beta type, 3 | 0.80 | 0.033 | 1.70 | 0.003 |
| 128 | PSMB5 | 5693 | proteasome (prosome, macropain) subunit, beta type, 5 | 0.77 | 0.016 | 2.13 | 0.002 |
| 129 | PSMB7 | 5695 | proteasome (prosome, macropain) subunit, beta type, 7 | 0.78 | 0.010 | 1.93 | 0.011 |
| 130 | PRMT1 | 3276 | protein arginine methyltransferase 1 | 0.80 | 0.029 | 1.64 | 0.044 |
| 131 | PPP2R3B | 102725016 | protein phosphatase 2, regulatory subunit B", beta | 0.83 | 0.049 | 1.24 | 0.022 |
| 132 | PPP3CA | 5530 | protein phosphatase 3, catalytic subunit, alpha isozyme | 0.82 | 0.039 | 1.52 | 0.020 |
| 133 | PRC1 | 9055 | protein regulator of cytokinesis 1 | 0.79 | 0.019 | 1.82 | 0.000 |
| 134 | RRM2 | 6241 | ribonucleotide reductase M2 | 0.77 | 0.010 | 1.50 | 0.004 |
| 135 | RPS6KB1 | 6198 | ribosomal protein S6 kinase, 70 kDa, polypeptide 1 | 0.81 | 0.029 | 1.45 | 0.048 |
| 136 | SPAG5 | 10615 | sperm associated antigen 5 | 0.80 | 0.028 | 1.34 | 0.031 |
| 137 | SKA1 | 220134 | spindle and kinetochore associated complex subunit 1 | 0.79 | 0.025 | 1.35 | 0.012 |
| 138 | STMN1 | 3925 | stathmin 1 | 0.78 | 0.013 | 1.51 | 0.041 |
| 139 | SLBP | 7884 | stem-loop binding protein | 0.80 | 0.036 | 2.56 | 0.001 |
| 140 | SMC2 | 10592 | structural maintenance of chromosomes 2 | 0.78 | 0.011 | 1.95 | 0.004 |
| 141 | SMC4 | 10051 | structural maintenance of chromosomes 4 | 0.80 | 0.019 | 1.67 | 0.007 |
| 142 | SMC5 | 23137 | structural maintenance of chromosomes 5 | 0.83 | 0.046 | 1.77 | 0.015 |
| 143 | TERF1 | 7013 | telomeric repeat binding factor (NIMA-interacting) 1 | 0.82 | 0.038 | 1.59 | 0.030 |

TABLE 5-continued

Bivariate Cox analysis on p-genes and BTN3A2

| No | Gene Symbol | Gene ID | Gene Name | BTN3A2 HR | BTN3A2 p-value | p-gene HR | p-gene p-value |
|---|---|---|---|---|---|---|---|
| 144 | TXNL4A | 10907 | thioredoxin-like 4A | 0.79 | 0.019 | 1.67 | 0.033 |
| 145 | TRIP13 | 9319 | thyroid hormone receptor interactor 13 | 0.80 | 0.026 | 1.79 | 0.003 |
| 146 | TOP2A | 7153 | topoisomerase (DNA) II alpha 170 kDa | 0.80 | 0.029 | 1.51 | 0.000 |
| 147 | TFDP2 | 7029 | transcription factor Dp-2 (E2F dimerization partner 2) | 0.78 | 0.019 | 1.51 | 0.034 |
| 148 | TACC3 | 10460 | transforming, acidic coiled-coil containing protein 3 | 0.75 | 0.005 | 1.25 | 0.013 |
| 149 | TUBB3 | 10381 | tubulin, beta 3 class III | 0.81 | 0.038 | 1.71 | 0.022 |
| 150 | TUBB4B | 10383 | tubulin, beta 4B class IVb | 0.80 | 0.026 | 1.87 | 0.013 |
| 151 | TUBB | 203068 | tubulin, beta class I | 0.78 | 0.018 | 1.75 | 0.047 |
| 152 | TSG101 | 7251 | tumor susceptibility 101 | 0.78 | 0.015 | 1.84 | 0.021 |
| 153 | UBE2C | 11065 | ubiquitin-conjugating enzyme E2C | 0.81 | 0.041 | 1.99 | 0.000 |
| 154 | UBE2L3 | 7332 | ubiquitin-conjugating enzyme E2L 3 | 0.75 | 0.007 | 2.67 | 0.000 |
| 155 | UBE2S | 27338 | ubiquitin-conjugating enzyme E2S | 0.76 | 0.008 | 1.44 | 0.002 |
| 156 | USP9X | 8239 | ubiquitin specific peptidase 9, X-linked | 0.79 | 0.012 | 2.71 | 0.007 |
| 157 | VRK1 | 7443 | vaccinia related kinase 1 | 0.80 | 0.020 | 1.47 | 0.011 |
| 158 | ZFHX3 | 463 | zinc finger homeobox 3 | 0.79 | 0.026 | 1.26 | 0.028 |
| 159 | ZWILCH | 55055 | zwilch kinetochore protein | 0.75 | 0.006 | 1.43 | 0.010 |
| 160 | MMP11 | 4320 | matrix metallopeptidase 11 (stromelysin 3) | 0.81 | 0.048 | 1.18 | 0.050 |

Combinatory Use of BTN3A2 and RRM2 gene for Prognosis Prediction

Following is the description of the combinatory use of one of the p-genes, i.e. RRM2 (Ribonucleotide Reductase M2) and BTN3A2 for the prognosis prediction of breast cancer. As shown in Table 6 below, bivariate Cox analysis indicates that BTN3A2 and RRM2 are an independent prognostic factor associated with the prognosis of breast cancer, respectively. In particular, it was confirmed that BTN3A2 is correlated with a good prognosis of breast cancer (HR<1), whereas RRM2 with a poor prognosis (HR>1).

TABLE 6

Results of Bivariate Cox analysis on BTN3A2 and RRM2 genes

| Gene | HR (Hazard Ratio) | 95% C.I. | p-value |
|---|---|---|---|
| BTN3A2 | 0.77 | 0.64 to 0.94 | 0.010 |
| RRM2 | 1.50 | 1.14 to 1.98 | 0.004 |

Figure 9:
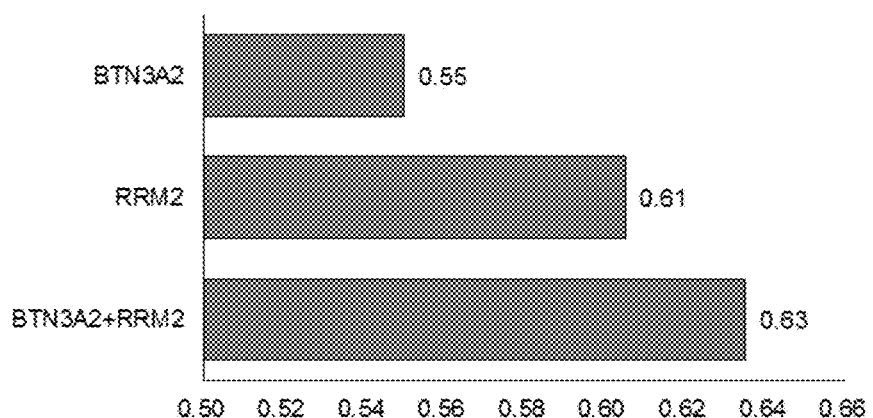
FIG. 9 shows the C-indices of BTN3A2, RRM2, and the combination of BTN3A2 and RRM2, respectively.

Further, as shown in FIG. 9, it was found that C-index (0.63) of the combination of BTN3A2 and RRM2 was larger than that of either BTN3A2 (0.55) or RRM2 (0.61) alone, suggesting that the combinatory use of the i-gene BTN3A2 and at least one p-gene would lead to an improved accuracy of the prognosis prediction.

In conclusion, these results suggest that the combinatory use of the i-genes (such as BTN3A2) with various genes may improve its prognostic performance. Particularly, such a combinatory use of the i-gene and the proliferation-related p-gene (such as RRM2) may significantly increase the prediction accuracy of survival probabilities in a breast cancer patient.

As set forth above, the present invention provides a genetic marker for early-stage breast cancer prognosis prediction and diagnosis. The genetic marker of the present invention can enable the prediction or diagnosis of the prognosis of a breast cancer patient, and thus can be favorably used to present clues for the future direction of breast cancer treatment, including the determination on whether anticancer treatment is needed.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for treating a breast cancer in a breast cancer patient, the method comprising the steps of:
   collecting a sample from the breast cancer patient;
   isolating mRNA from the sample from the breast cancer patient;
   measuring a first mRNA expression level for the mRNA of an i-gene BTN3A2 (butyrophilin, subfamily 3, member A2) and a second mRNA expression level for the mRNA of RRM2 (Ribonucleotide Reductase M2);
   normalizing the first and second mRNA expression levels to determine a normalized value;
   detecting in the breast cancer patient sample a decrease in normalized value of BTN3A2 compared to a reference breast tumor or an increased normalized value of RRM2 compared to a reference breast tumor;
   diagnosing the breast cancer patient who has a decrease in normalized value of BTN3A2 compared to a reference breast tumor sample or has an increased normalized value of RRM2 compared to a reference breast tumor sample as requiring treatment; and
   treating the diagnosed breast cancer patient by administering at least one of an anti-cancer agent, a surgery, and a radiation therapy,
   wherein the method comprises a step of using a plurality of primer pairs, wherein the plurality of the primer pairs comprises a primer pair for the i-gene BTN3A2 (butyrophilin, subfamily 3, member A2), and a primer pair for the p-gene RRM2, wherein the primer pairs are selected to amplify the i-gene and the p-gene through PCR amplification.

2. The method of claim 1, wherein the sample is a formalin-fixed paraffin-embedded (FFPE) sample of tissue containing cancer cells of the breast cancer patient.

3. The method of claim 1, wherein the step of normalizing is conducted by calculating a ratio of a mean expression level of the gene with a mean expression level of at least one standard gene selected from the group consisting of CTBP1 (C-terminal-binding protein 1), TBP (TATA-binding protein), HMBS (hydroxymethylbilane synthase), CUL1 (cullin 1), and UBQLN1 (ubiquilin-1).

* * * * *